United States Patent
DaSilva-Jardine et al.

(10) Patent No.: US 11,091,539 B2
(45) Date of Patent: Aug. 17, 2021

(54) ANTI-APOC3 ANTIBODIES AND METHODS OF USE THEREOF

(71) Applicant: STATEN BIOTECHNOLOGY B.V., Nijmegen (NL)

(72) Inventors: Paul DaSilva-Jardine, Guilford, CT (US); Hans de Haard, Oudelande (NL); James A. Landro, Cheshire, CT (US)

(73) Assignee: STATEN BIOTECHNOLOGY B.V., Nijmegen (NL)

( * ) Notice: Subject to any disclaimer, the term of this patent is extended or adjusted under 35 U.S.C. 154(b) by 100 days.

(21) Appl. No.: 16/241,407

(22) Filed: Jan. 7, 2019

(65) Prior Publication Data

US 2019/0241648 A1    Aug. 8, 2019

Related U.S. Application Data

(63) Continuation of application No. PCT/IB2017/054125, filed on Jul. 7, 2017.

(60) Provisional application No. 62/360,084, filed on Jul. 8, 2016, provisional application No. 62/491,591, filed on Apr. 28, 2017.

(51) Int. Cl.
| | |
|---|---|
| C07K 16/18 | (2006.01) |
| A61K 39/395 | (2006.01) |
| A61P 3/06 | (2006.01) |
| A61P 9/10 | (2006.01) |
| C07K 14/775 | (2006.01) |
| A61K 39/00 | (2006.01) |
| A61K 31/397 | (2006.01) |
| A61K 45/06 | (2006.01) |

(52) U.S. Cl.
CPC ............... *C07K 16/18* (2013.01); *A61P 3/06* (2018.01); *A61P 9/10* (2018.01); *A61K 31/397* (2013.01); *A61K 39/3955* (2013.01); *A61K 45/06* (2013.01); *A61K 2039/505* (2013.01); *C07K 14/775* (2013.01); *C07K 2317/22* (2013.01); *C07K 2317/33* (2013.01); *C07K 2317/34* (2013.01); *C07K 2317/622* (2013.01); *C07K 2317/76* (2013.01); *C07K 2317/92* (2013.01)

(58) Field of Classification Search
CPC .. C07K 16/18; C07K 2317/76; A61K 39/395; A61K 39/3955
See application file for complete search history.

(56) References Cited

U.S. PATENT DOCUMENTS

| | | | |
|---|---|---|---|
| 4,970,144 A | 11/1990 | Fareed et al. | |
| 6,737,056 B1 | 5/2004 | Presta | |
| 6,821,505 B2 | 11/2004 | Ward | |
| 7,083,784 B2 | 8/2006 | Dall'Acqua | |
| 7,098,036 B2 | 8/2006 | Koren et al. | |
| 7,217,797 B2 | 5/2007 | Hinton et al. | |
| 7,217,798 B2 | 5/2007 | Hinton et al. | |
| 7,662,925 B2 | 2/2010 | Lazar et al. | |
| 7,767,401 B2 | 8/2010 | Lescuyer et al. | |
| 8,030,288 B2 | 10/2011 | Berggren et al. | |
| 8,088,376 B2 | 1/2012 | Chamberlain et al. | |
| 8,163,881 B2 | 4/2012 | Ober | |
| 8,444,976 B2 | 5/2013 | Dreier et al. | |
| 8,524,231 B2 | 9/2013 | Dreier et al. | |
| 8,629,245 B2 | 1/2014 | Georgiou et al. | |
| 8,679,493 B2 | 3/2014 | Georgiou et al. | |
| 8,835,607 B2 | 9/2014 | Dreier et al. | |
| 9,221,918 B2 | 12/2015 | Dreier et al. | |
| 9,301,510 B2 | 4/2016 | McWhirter et al. | |
| 9,315,576 B2 | 4/2016 | Dreier et al. | |
| 9,346,891 B2 | 5/2016 | Dreier et al. | |
| 9,428,580 B2 | 8/2016 | Dreier et al. | |
| 9,540,437 B2 | 1/2017 | Dreier et al. | |
| 9,593,333 B2 | 3/2017 | Alexander et al. | |
| 9,926,364 B2 | 3/2018 | De Haard | |
| 10,040,870 B2 | 8/2018 | De Haard | |
| 10,538,583 B2 | 1/2020 | DaSilva-Jardine et al. | |
| 2004/0052809 A1 | 3/2004 | Mettens et al. | |
| 2008/0095762 A1 | 4/2008 | Presta | |
| 2010/0323376 A1 | 12/2010 | Contois | |
| 2014/0093496 A1 | 4/2014 | Mimoto et al. | |
| 2014/0212435 A1 | 7/2014 | Moore et al. | |
| 2014/0255398 A1 | 9/2014 | Igawa et al. | |
| 2014/0294812 A1 | 10/2014 | Lazar et al. | |
| 2015/0056182 A1 | 2/2015 | Igawa et al. | |
| 2015/0152183 A1 | 6/2015 | Chamberlain et al. | |

(Continued)

FOREIGN PATENT DOCUMENTS

| | | |
|---|---|---|
| EP | 2767548 A2 | 8/2014 |
| WO | WO 1997/034631 A1 | 9/1997 |

(Continued)

OTHER PUBLICATIONS

Benjamini et al, 1991. Immunology: A Short Course, 2nd edition, p. 40 only.*

(Continued)

*Primary Examiner* — Zachary C Howard

(74) *Attorney, Agent, or Firm* — Dechert LLP; Andrew T. Wilkins; Robin L. Brese

(57) ABSTRACT

The instant disclosure provides antibodies that specifically bind to ApoC3 (e.g., human ApoC3) and antagonize ApoC3 function. Also provided are pharmaceutical compositions comprising these antibodies, nucleic acids encoding these antibodies, expression vectors and host cells for making these antibodies, and methods of treating a subject using these antibodies.

4 Claims, 27 Drawing Sheets

Specification includes a Sequence Listing.

(56) References Cited

U.S. PATENT DOCUMENTS

| | | |
|---|---|---|
| 2015/0166654 A1 | 6/2015 | Igawa et al. |
| 2015/0218239 A1 | 8/2015 | Ulrichts et al. |
| 2016/0009792 A1 | 1/2016 | Kiernan et al. |
| 2016/0068613 A1 | 3/2016 | Regula et al. |
| 2016/0207996 A1 | 7/2016 | Ulrichts et al. |
| 2016/0264669 A1 | 9/2016 | Ultrichs et al. |
| 2017/0037118 A1 | 2/2017 | Berggren et al. |
| 2017/0037124 A1 | 2/2017 | Gusarova et al. |
| 2017/0342166 A1 | 11/2017 | Blanchetot et al. |
| 2020/0148755 A1 | 5/2020 | DaSilva-Jardine et al. |
| 2020/0216523 A1 | 7/2020 | DaSilva-Jardine et al. |
| 2020/0239555 A1 | 7/2020 | DaSilva-Jardine et al. |

FOREIGN PATENT DOCUMENTS

| | | | |
|---|---|---|---|
| WO | WO 2001/064008 A2 | 9/2001 |
| WO | WO 2003/023407 A1 | 3/2003 |
| WO | WO 2004/080375 A2 | 9/2004 |
| WO | WO 2004/081045 A2 | 9/2004 |
| WO | WO 2004/081046 A2 | 9/2004 |
| WO | WO 2004/097429 A2 | 11/2004 |
| WO | WO 2005/047327 A2 | 5/2005 |
| WO | WO 2006/053301 A2 | 5/2006 |
| WO | WO 2006/130834 A2 | 12/2006 |
| WO | WO 2009/058492 A2 | 5/2009 |
| WO | WO 2009/086320 A1 | 7/2009 |
| WO | WO 2010/001251 A2 | 1/2010 |
| WO | WO 2010/045193 A1 | 4/2010 |
| WO | WO 2010/106180 A2 | 9/2010 |
| WO | WO 2011/080350 A1 | 7/2011 |
| WO | WO 2011/111007 A2 | 9/2011 |
| WO | WO 2013/000920 A2 | 1/2013 |
| WO | WO 2013/064700 A2 | 5/2013 |
| WO | WO 2013/074598 A1 | 5/2013 |
| WO | WO 2013/100702 A1 | 7/2013 |
| WO | WO 2014/033252 A1 | 3/2014 |
| WO | WO 2014/033304 A2 | 3/2014 |
| WO | WO 2014/131008 A1 | 8/2014 |
| WO | WO 2015/032916 A1 | 3/2015 |
| WO | WO 2016/026943 A1 | 2/2016 |
| WO | WO 2017/055627 A1 | 4/2017 |
| WO | WO 2017/079748 A1 | 5/2017 |
| WO | WO 2018/007999 A1 | 1/2018 |
| WO | WO 2018/069416 A1 | 4/2018 |
| WO | WO 2018/193427 A1 | 10/2018 |
| WO | WO 2018/206748 A1 | 11/2018 |
| WO | WO 2019/087115 A1 | 5/2019 |
| WO | WO 2020/070678 A2 | 4/2020 |

OTHER PUBLICATIONS

Ferrara et al (2015. mAbs. 7(1): 32-41).*
Cobaugh et al (2008. J Mol Biol. 378(3):622-633).*
International Search Report and Written Opinion from PCT/IB2018/052780 dated Jul. 31, 2018.
International Search Report and Written Opinion from PCT/IB2018/058564 dated Feb. 15, 2019.
International Search Report and Written Opinion from PCT/IB2019/058403 dated Mar. 25, 2020.
Khetarpal et al. (2017) "A human APOC3 missense variant and monoclonal antibody accelerate apoC-III clearance and lower triglyceride-rich lipoprotein levels," Nature Medicine. 23(9):1086-1094.
Unverdorben et al. (2015) "Pharmacokinetic properties of IgG and various Fc fusion proteins in mice," MABS. 8(1):120-128.
International Search Report and Written Opinion from PCT/IB2017/054125 dated Nov. 13, 2017.

* cited by examiner

| V | E | D | P | G | M | C | V | N | T | Y | F | A | S | Q | L | H | W | K | I | R |
|---|---|---|---|---|---|---|---|---|---|---|---|---|---|---|---|---|---|---|---|---|
| E | L | D | F | Y | W | P | M | Q | I | T | G | L | S | A | V | N | H | R | C | K |
| P | E | T | P | D | F | I | S | V | A | Y | M | L | N | C | Q | K | H | R | G | W |
| D | D | E | C | T | R | S | Y | W | V | Q | P | N | A | F | G | H | I | K | L | M |
| L | I | T | L | V | M | S | F | K | Q | R | N | A | E | H | Y | D | W | C | G | P |
| D | D | E | C | F | K | M | Y | W | V | T | S | R | Q | P | N | A | G | H | I | L |
| W | E | S | D | T | W | N | F | G | Q | Y | A | V | I | M | L | H | C | P | R | K |
| F | P | E | D | T | S | G | A | N | Q | M | H | K | I | F | L | Y | V | R | C | W |
| E | P | E | D | Q | M | N | A | T | S | G | V | H | L | Y | I | F | C | K | R | W |
| S | T | I | N | Q | S | A | V | L | E | M | G | R | D | P | H | Y | K | C | F | W |
| F | Y | F | E | P | Q | L | M | T | N | V | I | H | A | S | K | R | W | D | G | C |
| K | E | P | S | D | T | M | Q | N | H | A | G | I | V | R | K | L | C | Y | F | W |
| D | E | P | I | T | D | Q | G | S | A | H | W | N | Y | R | C | L | V | F | M | K |

Figure 7C

| K | K | R | S | T | M | A | F | G | Q | E | V | N | H | I | L | P | Y | W | C | D |
|---|---|---|---|---|---|---|---|---|---|---|---|---|---|---|---|---|---|---|---|---|
| L | L | F | W | I | V | K | M | Y | Q | T | S | R | P | N | A | C | D | E | G | H |
| S | S | T | K | A | M | F | R | V | H | Q | W | Y | P | N | C | D | E | G | I | L |
| S | E | M | S | K | T | A | D | C | N | Q | V | R | I | L | H | F | Y | G | W | P |
| F | Y | L | W | K | V | N | T | S | R | Q | P | A | C | D | E | G | H | I | M |   |
| G | G | N | H | F | R | K | Y | W | V | T | S | Q | P | A | C | D | E | I | L | M |
| D | D | A | E | K | M | Q | S | R | L | C | T | N | G | I | H | V | W | Y | P | F |
| T | I | V | N | I | S | H | L | Y | W | R | Q | P | A | C | D | E | F | G | K | M |
| V | L | Y | V | F | I | A | K | M | R | H | T | W | Q | P | S | N | C | G | D | E |
| W | L | F | S | T | Y | R | K | N | A | D | G | W | E | Q | M | C | H | V | I | P |
| G | G | E | N | Q | H | D | R | S | M | K | W | C | F | T | V | P | A | Y | L | I |
| R | R | Q | E | F | M | N | G | C | K | V | S | L | P | A | D | H | W | T | Y | I |
| A | P | Q | N | A | E | G | M | R | T | S | F | C | L | V | K | H | W | I | D | Y |

```
                        SEQUENCE LISTING

<160> NUMBER OF SEQ ID NOS: 183

<210> SEQ ID NO 1
   <211> LENGTH: 79
   <212> TYPE: PRT
   <213> ORGANISM: Homo sapiens

<400> SEQUENCE: 1

Ser Glu Ala Glu Asp Ala Ser Leu Leu Ser Phe Met Gln Gly Tyr Met
   1               5                   10                  15

Lys His Ala Thr Lys Thr Ala Lys Asp Ala Leu Ser Ser Val Gln Glu
               20                  25                  30

Ser Gln Val Ala Gln Gln Ala Arg Gly Trp Val Thr Asp Gly Phe Ser
           35                  40                  45

Ser Leu Lys Asp Tyr Trp Ser Thr Val Lys Asp Lys Phe Ser Glu Phe
       50                  55                  60

Trp Asp Leu Asp Pro Glu Val Arg Pro Thr Ser Ala Val Ala Ala
   65                  70                  75

<210> SEQ ID NO 2
   <211> LENGTH: 11
   <212> TYPE: PRT
   <213> ORGANISM: Homo sapiens

<400> SEQUENCE: 2

Gly Trp Val Thr Asp Gly Phe Ser Ser Leu Lys
   1               5                   10

<210> SEQ ID NO 3
   <211> LENGTH: 10
   <212> TYPE: PRT
   <213> ORGANISM: Homo sapiens

<400> SEQUENCE: 3

Phe Ser Glu Phe Trp Asp Leu Asp Pro Glu
   1               5                   10

<210> SEQ ID NO 4
   <211> LENGTH: 5
   <212> TYPE: PRT
   <213> ORGANISM: Artificial Sequence
   <220> FEATURE:
   <223> OTHER INFORMATION: 5A11 CDRH1
```

<400> SEQUENCE: 4

Thr Arg Tyr Tyr Ala
1               5

<210> SEQ ID NO 5
<211> LENGTH: 16
<212> TYPE: PRT
<213> ORGANISM: Artificial Sequence
<220> FEATURE:
<223> OTHER INFORMATION: 5A11 CDRH2

<400> SEQUENCE: 5

Val Ile Ala Tyr Asp Gly Ser Thr Tyr Tyr Ser Pro Ser Leu Lys Ser
1               5                   10                  15

<210> SEQ ID NO 6
<211> LENGTH: 12
<212> TYPE: PRT
<213> ORGANISM: Artificial Sequence
<220> FEATURE:
<223> OTHER INFORMATION: 5A11 CDRH3

<400> SEQUENCE: 6

Val Arg Leu Ile Glu Ala Pro Tyr Glu Tyr Asp Tyr
1               5                   10

<210> SEQ ID NO 7
<211> LENGTH: 5
<212> TYPE: PRT
<213> ORGANISM: Artificial Sequence
<220> FEATURE:
<223> OTHER INFORMATION: 5E5 CDRH1

<400> SEQUENCE: 7

Thr Tyr Ser Met Arg
1               5

<210> SEQ ID NO 8
<211> LENGTH: 17
<212> TYPE: PRT
<213> ORGANISM: Artificial Sequence
<220> FEATURE:
<223> OTHER INFORMATION: 5E5 CDRH2

<400> SEQUENCE: 8

Ser Ile Ser Thr Asp Gly Gly Gly Thr Ala Tyr Arg Asp Ser Val Lys
1               5                   10                  15

Gly

<210> SEQ ID NO 9
<211> LENGTH: 5
<212> TYPE: PRT
<213> ORGANISM: Artificial Sequence
<220> FEATURE:
<223> OTHER INFORMATION: 5E5 CDRH3

<400> SEQUENCE: 9

Ala Gly Tyr Ser Asp
1               5

<210> SEQ ID NO 10
<211> LENGTH: 5
<212> TYPE: PRT
<213> ORGANISM: Artificial Sequence
<220> FEATURE:

```
<223> OTHER INFORMATION: 6A6 CDRH1

<400> SEQUENCE: 10

Ser Tyr Ala Gly Arg
1               5

<210> SEQ ID NO 11
<211> LENGTH: 16
<212> TYPE: PRT
<213> ORGANISM: Artificial Sequence
<220> FEATURE:
<223> OTHER INFORMATION: 6A6 CDRH2

<400> SEQUENCE: 11

Ser Ile Asn Ala Gly Gly Gly Ser Thr Ser Tyr Ala Asp Ser Val Lys
1               5                   10                  15

<210> SEQ ID NO 12
<211> LENGTH: 5
<212> TYPE: PRT
<213> ORGANISM: Artificial Sequence
<220> FEATURE:
<223> OTHER INFORMATION: 6A6 CDRH3

<400> SEQUENCE: 12

Asn Ser Tyr Arg Tyr
1               5

<210> SEQ ID NO 13
<211> LENGTH: 5
<212> TYPE: PRT
<213> ORGANISM: Artificial Sequence
<220> FEATURE:
<223> OTHER INFORMATION: 8F4 CDRH1

<400> SEQUENCE: 13

Ser Tyr Ser Met Tyr
1               5

<210> SEQ ID NO 14
<211> LENGTH: 17
<212> TYPE: PRT
<213> ORGANISM: Artificial Sequence
<220> FEATURE:
<223> OTHER INFORMATION: 8F4 CDRH2

<400> SEQUENCE: 14

Ala Ile Lys Thr Asp Gly Gly Ser Thr Asn Tyr Ala Asp Ser Val Lys
1               5                   10                  15

Gly

<210> SEQ ID NO 15
<211> LENGTH: 5
<212> TYPE: PRT
<213> ORGANISM: Artificial Sequence
<220> FEATURE:
<223> OTHER INFORMATION: 8F4 CDRH3

<400> SEQUENCE: 15

Gln Gly Tyr Gly Thr
1               5

<210> SEQ ID NO 16
<211> LENGTH: 5
<212> TYPE: PRT
<213> ORGANISM: Artificial Sequence
```

```
<220> FEATURE:
<223> OTHER INFORMATION: 11H1 CDRH1

<400> SEQUENCE: 16

Ser Tyr Ser Met Arg
1               5

<210> SEQ ID NO 17
<211> LENGTH: 17
<212> TYPE: PRT
<213> ORGANISM: Artificial Sequence
<220> FEATURE:
<223> OTHER INFORMATION: 11H1 CDRH2

<400> SEQUENCE: 17

Ser Ile Lys Ser Asp Gly Ser Ile Thr Ser Tyr Ala Asp Ser Val Lys
1               5                   10                  15

Gly

<210> SEQ ID NO 18
<211> LENGTH: 5
<212> TYPE: PRT
<213> ORGANISM: Artificial Sequence
<220> FEATURE:
<223> OTHER INFORMATION: 11H1 CDRH3

<400> SEQUENCE: 18

Gln Gly Tyr Ile Asn
1               5

<210> SEQ ID NO 19
<211> LENGTH: 5
<212> TYPE: PRT
<213> ORGANISM: Artificial Sequence
<220> FEATURE:
<223> OTHER INFORMATION: 5A4 CDRH1

<400> SEQUENCE: 19

His Tyr Thr Met Tyr
1               5

<210> SEQ ID NO 20
<211> LENGTH: 17
<212> TYPE: PRT
<213> ORGANISM: Artificial Sequence
<220> FEATURE:
<223> OTHER INFORMATION: 5A4 CDRH2

<400> SEQUENCE: 20

Ala Ile Ser Gly Gly Gly Asp Arg Thr Ile Tyr Thr Asp Ser Val Lys
1               5                   10                  15

Gly

<210> SEQ ID NO 21
<211> LENGTH: 5
<212> TYPE: PRT
<213> ORGANISM: Artificial Sequence
<220> FEATURE:
<223> OTHER INFORMATION: 5A4 CDRH3

<400> SEQUENCE: 21

Gln Gly Tyr Glu Tyr
1               5

<210> SEQ ID NO 22
```

```
<211> LENGTH: 5
<212> TYPE: PRT
<213> ORGANISM: Artificial Sequence
<220> FEATURE:
<223> OTHER INFORMATION: 5A7 CDRH1

<400> SEQUENCE: 22

Asn Arg Arg Tyr Ala
1               5

<210> SEQ ID NO 23
<211> LENGTH: 16
<212> TYPE: PRT
<213> ORGANISM: Artificial Sequence
<220> FEATURE:
<223> OTHER INFORMATION: 5A7 CDRH2

<400> SEQUENCE: 23

Val Ile Val Tyr Asp Gly Asn Thr His Val Ser Pro Ser Leu Arg Ser
1               5                   10                  15

<210> SEQ ID NO 24
<211> LENGTH: 12
<212> TYPE: PRT
<213> ORGANISM: Artificial Sequence
<220> FEATURE:
<223> OTHER INFORMATION: 5A7 CDRH3

<400> SEQUENCE: 24

Val Leu Leu Leu Arg Asp Pro Leu Ser Leu Asp Tyr
1               5                   10

<210> SEQ ID NO 25
<211> LENGTH: 5
<212> TYPE: PRT
<213> ORGANISM: Artificial Sequence
<220> FEATURE:
<223> OTHER INFORMATION: 8A4 CDRH1

<400> SEQUENCE: 25

Asn Tyr Ala Met Arg
1               5

<210> SEQ ID NO 26
<211> LENGTH: 17
<212> TYPE: PRT
<213> ORGANISM: Artificial Sequence
<220> FEATURE:
<223> OTHER INFORMATION: 8A4 CDRH2

<400> SEQUENCE: 26

Ser Ile Asp Ser Gly Gly Asp Arg Thr Lys Tyr Gly Asp Ser Val Lys
1               5                   10                  15

Gly

<210> SEQ ID NO 27
<211> LENGTH: 5
<212> TYPE: PRT
<213> ORGANISM: Artificial Sequence
<220> FEATURE:
<223> OTHER INFORMATION: 8A4 CDRH3

<400> SEQUENCE: 27

Gln Gly Tyr Ile Phe
1               5
```

```
<210> SEQ ID NO 28
<211> LENGTH: 5
<212> TYPE: PRT
<213> ORGANISM: Artificial Sequence
<220> FEATURE:
<223> OTHER INFORMATION: 8B4 CDRH1

<400> SEQUENCE: 28

Asn Ala Tyr Leu Tyr
1               5

<210> SEQ ID NO 29
<211> LENGTH: 17
<212> TYPE: PRT
<213> ORGANISM: Artificial Sequence
<220> FEATURE:
<223> OTHER INFORMATION: 8B4 CDRH2

<400> SEQUENCE: 29

Gly Ile Asn Pro Ala Gly Asp Gly Arg Ala Tyr Ala Thr Ser Val Lys
1               5                   10                  15

Gly

<210> SEQ ID NO 30
<211> LENGTH: 9
<212> TYPE: PRT
<213> ORGANISM: Artificial Sequence
<220> FEATURE:
<223> OTHER INFORMATION: 8B4 CDRH3

<400> SEQUENCE: 30

Ala Ser Arg Val Val Ala Tyr Asp Ser
1               5

<210> SEQ ID NO 31
<211> LENGTH: 17
<212> TYPE: PRT
<213> ORGANISM: Artificial Sequence
<220> FEATURE:
<223> OTHER INFORMATION: 8H4 CDRH2

<400> SEQUENCE: 31

Ser Ile Asn Ser Asp Gly Gly Ser Thr Lys Tyr Ser Asp Ser Val Lys
1               5                   10                  15

Gly

<210> SEQ ID NO 32
<211> LENGTH: 5
<212> TYPE: PRT
<213> ORGANISM: Artificial Sequence
<220> FEATURE:
<223> OTHER INFORMATION: 8H4 CDRH3

<400> SEQUENCE: 32

Gln Gly Tyr Thr Asp
1               5

<210> SEQ ID NO 33
<211> LENGTH: 5
<212> TYPE: PRT
<213> ORGANISM: Artificial Sequence
<220> FEATURE:
<223> OTHER INFORMATION: 10B6 CDRH1

<400> SEQUENCE: 33

Ser Tyr Ala Met Arg
```

<210> SEQ ID NO 34
<211> LENGTH: 17
<212> TYPE: PRT
<213> ORGANISM: Artificial Sequence
<220> FEATURE:
<223> OTHER INFORMATION: 10B6 CDRH2

<400> SEQUENCE: 34

Ser Ile Asn Ile Asp Gly Gly Ser Thr Arg Tyr Thr Asp Ser Val Gln
1               5                   10                  15

Gly

<210> SEQ ID NO 35
<211> LENGTH: 5
<212> TYPE: PRT
<213> ORGANISM: Artificial Sequence
<220> FEATURE:
<223> OTHER INFORMATION: 10B6 CDRH3

<400> SEQUENCE: 35

Gln Gly Tyr Ile Tyr
1               5

<210> SEQ ID NO 36
<211> LENGTH: 16
<212> TYPE: PRT
<213> ORGANISM: Artificial Sequence
<220> FEATURE:
<223> OTHER INFORMATION: 12A3 CDRH2

<400> SEQUENCE: 36

Ser Ile Asn Ile Ala Gly Ser Ser Val Val Tyr Ala Asp Ser Val Lys
1               5                   10                  15

<210> SEQ ID NO 37
<211> LENGTH: 5
<212> TYPE: PRT
<213> ORGANISM: Artificial Sequence
<220> FEATURE:
<223> OTHER INFORMATION: 12A3 CDRH3

<400> SEQUENCE: 37

Gln Gly Phe Val Tyr
1               5

<210> SEQ ID NO 38
<211> LENGTH: 5
<212> TYPE: PRT
<213> ORGANISM: Artificial Sequence
<220> FEATURE:
<223> OTHER INFORMATION: 12C3 CDRH1

<400> SEQUENCE: 38

Ser Tyr Ser Met Phe
1               5

<210> SEQ ID NO 39
<211> LENGTH: 17
<212> TYPE: PRT
<213> ORGANISM: Artificial Sequence
<220> FEATURE:
<223> OTHER INFORMATION: 12C3 CDRH2

<400> SEQUENCE: 39

Gly Ile Asn Gly Gly Gly Asp Arg Ser Asn Tyr Ala Asp Ser Val Arg
1               5                   10                  15

Asp

<210> SEQ ID NO 40
<211> LENGTH: 5
<212> TYPE: PRT
<213> ORGANISM: Artificial Sequence
<220> FEATURE:
<223> OTHER INFORMATION: 12C3 CDRH3

<400> SEQUENCE: 40

Gln Gly Tyr Ala Tyr
1               5

<210> SEQ ID NO 41
<211> LENGTH: 7
<212> TYPE: PRT
<213> ORGANISM: Artificial Sequence
<220> FEATURE:
<223> OTHER INFORMATION: 12C12 CDRH1

<400> SEQUENCE: 41

Thr Ser Tyr Tyr Ala Trp Thr
1               5

<210> SEQ ID NO 42
<211> LENGTH: 16
<212> TYPE: PRT
<213> ORGANISM: Artificial Sequence
<220> FEATURE:
<223> OTHER INFORMATION: 12C12 CDRH2

<400> SEQUENCE: 42

Ala Ile Val Tyr Asp Gly Ser Thr Phe Tyr Ser Pro Ser Leu Lys Ser
1               5                   10                  15

<210> SEQ ID NO 43
<211> LENGTH: 9
<212> TYPE: PRT
<213> ORGANISM: Artificial Sequence
<220> FEATURE:
<223> OTHER INFORMATION: 12C12 CDRH3

<400> SEQUENCE: 43

Ser Tyr Gly Leu Gly Leu Tyr Asp Leu
1               5

<210> SEQ ID NO 44
<211> LENGTH: 13
<212> TYPE: PRT
<213> ORGANISM: Homo sapiens

<400> SEQUENCE: 44

Asp Lys Phe Ser Glu Phe Trp Asp Leu Asp Pro Glu Val
1               5                   10

<210> SEQ ID NO 45
<211> LENGTH: 13
<212> TYPE: PRT
<213> ORGANISM: Homo sapiens

<400> SEQUENCE: 45

Ala Arg Gly Trp Val Thr Asp Gly Phe Ser Ser Leu Lys
1               5                   10

<210> SEQ ID NO 46
<211> LENGTH: 7
<212> TYPE: PRT
<213> ORGANISM: Artificial Sequence
<220> FEATURE:
<223> OTHER INFORMATION: linker

<400> SEQUENCE: 46

Gly Ser Gly Ser Gly Ser Gly
1               5

<210> SEQ ID NO 47
<211> LENGTH: 5
<212> TYPE: PRT
<213> ORGANISM: Artificial Sequence
<220> FEATURE:
<223> OTHER INFORMATION: 12D4 CDRH1

<400> SEQUENCE: 47

Ser Ser Asn Met Arg
1               5

<210> SEQ ID NO 48
<211> LENGTH: 17
<212> TYPE: PRT
<213> ORGANISM: Artificial Sequence
<220> FEATURE:
<223> OTHER INFORMATION: 12D4 CDRH2

<400> SEQUENCE: 48

Thr Ile Ser Pro Asp Gly Gly Lys Thr Leu Tyr Ala Asp Ser Val Lys
1               5                   10                  15

Gly

<210> SEQ ID NO 49
<211> LENGTH: 5
<212> TYPE: PRT
<213> ORGANISM: Artificial Sequence
<220> FEATURE:
<223> OTHER INFORMATION: 12D4 CDRH3

<400> SEQUENCE: 49

Ala Gly Tyr Asp Tyr
1               5

<210> SEQ ID NO 50
<211> LENGTH: 5
<212> TYPE: PRT
<213> ORGANISM: Artificial Sequence
<220> FEATURE:
<223> OTHER INFORMATION: 12E12 CDRH1

<400> SEQUENCE: 50

Asn Ile Tyr Met Ser
1               5

<210> SEQ ID NO 51
<211> LENGTH: 17
<212> TYPE: PRT
<213> ORGANISM: Artificial Sequence
<220> FEATURE:
<223> OTHER INFORMATION: 12E12 CDRH2

<400> SEQUENCE: 51

Ala Ile Asn Thr Ala Gly Thr Val Thr Tyr Tyr Ala Asp Ser Val Lys
1               5                   10                  15

Gly

<210> SEQ ID NO 52
<211> LENGTH: 4
<212> TYPE: PRT
<213> ORGANISM: Artificial Sequence
<220> FEATURE:
<223> OTHER INFORMATION: 12E12 CDRH3

<400> SEQUENCE: 52

Gly Glu Val Asp
1

<210> SEQ ID NO 53
<211> LENGTH: 5
<212> TYPE: PRT
<213> ORGANISM: Artificial Sequence
<220> FEATURE:
<223> OTHER INFORMATION: 13C7 CDRH1

<400> SEQUENCE: 53

Arg Tyr Tyr Met Ser
1               5

<210> SEQ ID NO 54
<211> LENGTH: 17
<212> TYPE: PRT
<213> ORGANISM: Artificial Sequence
<220> FEATURE:
<223> OTHER INFORMATION: 13C7 CDRH2

<400> SEQUENCE: 54

Ser Ile Tyr Lys Asp Gly Ser Asn Thr Tyr Tyr Ala Asp Ser Val Lys
1               5                   10                  15

Gly

<210> SEQ ID NO 55
<211> LENGTH: 8
<212> TYPE: PRT
<213> ORGANISM: Artificial Sequence
<220> FEATURE:
<223> OTHER INFORMATION: 13C7 CDRH3

<400> SEQUENCE: 55

Ala Leu Arg Ala Glu Tyr Asp Tyr
1               5

<210> SEQ ID NO 56
<211> LENGTH: 7
<212> TYPE: PRT
<213> ORGANISM: Artificial Sequence
<220> FEATURE:
<223> OTHER INFORMATION: 13G7 CDRH1

<400> SEQUENCE: 56

Thr Thr Ala Pro Ala Trp Gly
1               5

<210> SEQ ID NO 57
<211> LENGTH: 16
<212> TYPE: PRT
<213> ORGANISM: Artificial Sequence
<220> FEATURE:
<223> OTHER INFORMATION: 13G7 CDRH2

<400> SEQUENCE: 57

```
Val Ile Ala Phe Asp Gly Ser Ala Tyr Tyr Ser Pro Ser Leu Lys Ser
1               5                   10                  15

<210> SEQ ID NO 58
<211> LENGTH: 12
<212> TYPE: PRT
<213> ORGANISM: Artificial Sequence
<220> FEATURE:
<223> OTHER INFORMATION: 13G7 CDRH3

<400> SEQUENCE: 58

Leu Gly Gly Arg Asn Tyr Pro Pro Tyr Val Glu Leu
1               5                   10

<210> SEQ ID NO 59
<211> LENGTH: 5
<212> TYPE: PRT
<213> ORGANISM: Artificial Sequence
<220> FEATURE:
<223> OTHER INFORMATION: 14C4 CDRH1

<400> SEQUENCE: 59

Asn Tyr Asp Met Ser
1               5

<210> SEQ ID NO 60
<211> LENGTH: 17
<212> TYPE: PRT
<213> ORGANISM: Artificial Sequence
<220> FEATURE:
<223> OTHER INFORMATION: 14C4 CDRH2

<400> SEQUENCE: 60

Val Ile Asn Ser Asp Gly Asp Gly Thr Tyr Tyr Val Asp Ser Val Lys
1               5                   10                  15

Gly

<210> SEQ ID NO 61
<211> LENGTH: 5
<212> TYPE: PRT
<213> ORGANISM: Artificial Sequence
<220> FEATURE:
<223> OTHER INFORMATION: 14C4 CDRH3

<400> SEQUENCE: 61

Ala Asn Leu Gly Leu
1               5

<210> SEQ ID NO 62
<211> LENGTH: 7
<212> TYPE: PRT
<213> ORGANISM: Artificial Sequence
<220> FEATURE:
<223> OTHER INFORMATION: 14C7 CDRH1

<400> SEQUENCE: 62

Thr Asn Ser Tyr Tyr Trp Ser
1               5

<210> SEQ ID NO 63
<211> LENGTH: 16
<212> TYPE: PRT
<213> ORGANISM: Artificial Sequence
<220> FEATURE:
<223> OTHER INFORMATION: 14C7 CDRH2
```

<400> SEQUENCE: 63

Ala Ile Asp Tyr Ser Gly Asp Thr Tyr Tyr Ser Pro Ser Leu Lys Ser
1               5                   10                  15

<210> SEQ ID NO 64
<211> LENGTH: 7
<212> TYPE: PRT
<213> ORGANISM: Artificial Sequence
<220> FEATURE:
<223> OTHER INFORMATION: 14C7 CDRH3

<400> SEQUENCE: 64

Arg Ile Pro Thr Gly Glu Tyr
1               5

<210> SEQ ID NO 65
<211> LENGTH: 5
<212> TYPE: PRT
<213> ORGANISM: Artificial Sequence
<220> FEATURE:
<223> OTHER INFORMATION: 14G4 CDRH1

<400> SEQUENCE: 65

Arg Tyr Thr Met Asn
1               5

<210> SEQ ID NO 66
<211> LENGTH: 16
<212> TYPE: PRT
<213> ORGANISM: Artificial Sequence
<220> FEATURE:
<223> OTHER INFORMATION: 14G4 CDRH2

<400> SEQUENCE: 66

Ala Ile Ser Pro Asp Gly Gly Lys Thr Ile Asp Ala Asp Ser Val Lys
1               5                   10                  15

<210> SEQ ID NO 67
<211> LENGTH: 6
<212> TYPE: PRT
<213> ORGANISM: Artificial Sequence
<220> FEATURE:
<223> OTHER INFORMATION: 14G4 CDRH3

<400> SEQUENCE: 67

Gly His Asn Met Asp Tyr
1               5

<210> SEQ ID NO 68
<211> LENGTH: 5
<212> TYPE: PRT
<213> ORGANISM: Artificial Sequence
<220> FEATURE:
<223> OTHER INFORMATION: 12D7 CDRH1

<400> SEQUENCE: 68

Asp Tyr Ala Met Ser
1               5

<210> SEQ ID NO 69
<211> LENGTH: 16
<212> TYPE: PRT
<213> ORGANISM: Artificial Sequence
<220> FEATURE:
<223> OTHER INFORMATION: 12D7 CDRH2

<400> SEQUENCE: 69

```
Ala Ile Thr Ser Asn Gly Lys Arg Thr Asp Tyr Ala Glu Ser Met Lys
1               5                   10                  15

<210> SEQ ID NO 70
<211> LENGTH: 16
<212> TYPE: PRT
<213> ORGANISM: Artificial Sequence
<220> FEATURE:
<223> OTHER INFORMATION: 12D7 CDRH3

<400> SEQUENCE: 70

Gly Pro Pro His Tyr Ile Pro Ile Pro Ser Met Thr Pro Arg Asp Ser
1               5                   10                  15

<210> SEQ ID NO 71
<211> LENGTH: 15
<212> TYPE: PRT
<213> ORGANISM: Artificial Sequence
<220> FEATURE:
<223> OTHER INFORMATION: 12G8 CDRH2

<400> SEQUENCE: 71

Ala Ile Arg Trp Asn Gly Asp Thr Tyr Tyr Ala Glu Ser Met Lys
1               5                   10                  15

<210> SEQ ID NO 72
<211> LENGTH: 9
<212> TYPE: PRT
<213> ORGANISM: Artificial Sequence
<220> FEATURE:
<223> OTHER INFORMATION: 12G8 CDRH3

<400> SEQUENCE: 72

His Arg Pro Gly Gly Ala Leu Asp Thr
1               5

<210> SEQ ID NO 73
<211> LENGTH: 14
<212> TYPE: PRT
<213> ORGANISM: Artificial Sequence
<220> FEATURE:
<223> OTHER INFORMATION: 5A11 CDRL1

<400> SEQUENCE: 73

Gly Leu Ser Ser Gly Ser Val Thr Thr Arg Ser Tyr Pro Gly
1               5                   10

<210> SEQ ID NO 74
<211> LENGTH: 7
<212> TYPE: PRT
<213> ORGANISM: Artificial Sequence
<220> FEATURE:
<223> OTHER INFORMATION: 5A11 CDRL2

<400> SEQUENCE: 74

Ser Thr Ser Ser Arg His Ser
1               5

<210> SEQ ID NO 75
<211> LENGTH: 9
<212> TYPE: PRT
<213> ORGANISM: Artificial Sequence
<220> FEATURE:
<223> OTHER INFORMATION: 5A11 CDRL3

<400> SEQUENCE: 75
```

```
Ala Leu Asp Ile Gly Ser Tyr Ile Val
1               5
```

<210> SEQ ID NO 76
<211> LENGTH: 16
<212> TYPE: PRT
<213> ORGANISM: Artificial Sequence
<220> FEATURE:
<223> OTHER INFORMATION: 5E5 CDRL1

<400> SEQUENCE: 76

```
Lys Thr Ser Gln Gly Leu Val His Ser Asp Gly Lys Thr Tyr Phe Tyr
1               5                   10                  15
```

<210> SEQ ID NO 77
<211> LENGTH: 7
<212> TYPE: PRT
<213> ORGANISM: Artificial Sequence
<220> FEATURE:
<223> OTHER INFORMATION: 5E5 CDRL2

<400> SEQUENCE: 77

```
Gln Val Ser Asn Arg Ala Ser
1               5
```

<210> SEQ ID NO 78
<211> LENGTH: 9
<212> TYPE: PRT
<213> ORGANISM: Artificial Sequence
<220> FEATURE:
<223> OTHER INFORMATION: 5E5 CDRL3

<400> SEQUENCE: 78

```
Ala Gln Gly Thr Tyr Tyr Pro His Thr
1               5
```

<210> SEQ ID NO 79
<211> LENGTH: 16
<212> TYPE: PRT
<213> ORGANISM: Artificial Sequence
<220> FEATURE:
<223> OTHER INFORMATION: 6A6 CDRL1

<400> SEQUENCE: 79

```
Lys Ala Ser Gln Ser Leu Ile His Thr Asp Gly Lys Thr Tyr Leu Tyr
1               5                   10                  15
```

<210> SEQ ID NO 80
<211> LENGTH: 7
<212> TYPE: PRT
<213> ORGANISM: Artificial Sequence
<220> FEATURE:
<223> OTHER INFORMATION: 6A6 CDRL2

<400> SEQUENCE: 80

```
Gln Val Ser Ser His Glu Ser
1               5
```

<210> SEQ ID NO 81
<211> LENGTH: 9
<212> TYPE: PRT
<213> ORGANISM: Artificial Sequence
<220> FEATURE:
<223> OTHER INFORMATION: 6A6 CDRL3

<400> SEQUENCE: 81

```
Ala Gln Ala Thr Tyr Asn Pro Arg Thr
```

```
1               5

<210> SEQ ID NO 82
<211> LENGTH: 16
<212> TYPE: PRT
<213> ORGANISM: Artificial Sequence
<220> FEATURE:
<223> OTHER INFORMATION: 8F4 CDRL1

<400> SEQUENCE: 82

Lys Ala Ser Gln Ser Leu Val His Ser Asp Gly Lys Thr Tyr Leu Tyr
1               5                   10                  15

<210> SEQ ID NO 83
<211> LENGTH: 7
<212> TYPE: PRT
<213> ORGANISM: Artificial Sequence
<220> FEATURE:
<223> OTHER INFORMATION: 8F4 CDRL2

<400> SEQUENCE: 83

Gln Val Ser Asn Arg Gly Ser
1               5

<210> SEQ ID NO 84
<211> LENGTH: 9
<212> TYPE: PRT
<213> ORGANISM: Artificial Sequence
<220> FEATURE:
<223> OTHER INFORMATION: 8F4 CDRL3

<400> SEQUENCE: 84

Ala Gln Ala Thr Tyr Tyr Gly His Ser
1               5

<210> SEQ ID NO 85
<211> LENGTH: 16
<212> TYPE: PRT
<213> ORGANISM: Artificial Sequence
<220> FEATURE:
<223> OTHER INFORMATION: 11H1 CDRL1

<400> SEQUENCE: 85

Arg Ala Ser Gln Ser Leu Ile His Ser Ala Gly Lys Thr Tyr Phe Tyr
1               5                   10                  15

<210> SEQ ID NO 86
<211> LENGTH: 7
<212> TYPE: PRT
<213> ORGANISM: Artificial Sequence
<220> FEATURE:
<223> OTHER INFORMATION: 11H1 CDRL2

<400> SEQUENCE: 86

Gln Val Ser Asn Arg Glu Ser
1               5

<210> SEQ ID NO 87
<211> LENGTH: 9
<212> TYPE: PRT
<213> ORGANISM: Artificial Sequence
<220> FEATURE:
<223> OTHER INFORMATION: 11H1 CDRL3

<400> SEQUENCE: 87

Ala Gln Gly Thr Tyr Asn Pro Lys Thr
1               5
```

<210> SEQ ID NO 88
<211> LENGTH: 16
<212> TYPE: PRT
<213> ORGANISM: Artificial Sequence
<220> FEATURE:
<223> OTHER INFORMATION: 5A4 CDRL1

<400> SEQUENCE: 88

Lys Ala Ile Gln Ser Leu Val His Thr Asp Gly Lys Thr Tyr Leu Tyr
1               5                   10                  15

<210> SEQ ID NO 89
<211> LENGTH: 7
<212> TYPE: PRT
<213> ORGANISM: Artificial Sequence
<220> FEATURE:
<223> OTHER INFORMATION: 5A4 CDRL2

<400> SEQUENCE: 89

Gln Val Ser Asn Arg Gly Ser
1               5

<210> SEQ ID NO 90
<211> LENGTH: 14
<212> TYPE: PRT
<213> ORGANISM: Artificial Sequence
<220> FEATURE:
<223> OTHER INFORMATION: 5A7 CDRL1

<400> SEQUENCE: 90

Ala Gly Thr Ser Ser Asp Ile Gly Ala Tyr Asn Phe Val Ser
1               5                   10

<210> SEQ ID NO 91
<211> LENGTH: 7
<212> TYPE: PRT
<213> ORGANISM: Artificial Sequence
<220> FEATURE:
<223> OTHER INFORMATION: 5A7 CDRL2

<400> SEQUENCE: 91

Asp Ile Asp Lys Arg Ala Ser
1               5

<210> SEQ ID NO 92
<211> LENGTH: 10
<212> TYPE: PRT
<213> ORGANISM: Artificial Sequence
<220> FEATURE:
<223> OTHER INFORMATION: 5A7 CDRL3

<400> SEQUENCE: 92

Ala Ala Tyr Gly Ser Arg Asp Asn Val Val
1               5                   10

<210> SEQ ID NO 93
<211> LENGTH: 7
<212> TYPE: PRT
<213> ORGANISM: Artificial Sequence
<220> FEATURE:
<223> OTHER INFORMATION: 8A4 CDRL2

<400> SEQUENCE: 93

Gln Val Ser Asn His Glu Ser
1               5

<210> SEQ ID NO 94
<211> LENGTH: 9
<212> TYPE: PRT
<213> ORGANISM: Artificial Sequence
<220> FEATURE:
<223> OTHER INFORMATION: 8A4 CDRL3

<400> SEQUENCE: 94

Ala Gln Ala Thr Tyr Tyr Pro Leu Thr
1               5

<210> SEQ ID NO 95
<211> LENGTH: 17
<212> TYPE: PRT
<213> ORGANISM: Artificial Sequence
<220> FEATURE:
<223> OTHER INFORMATION: 8B4 CDRL1

<400> SEQUENCE: 95

Lys Ser Ser Gln Ser Val Glu Ser Gly Ser Asp Gln Lys Ser Tyr Leu
1               5                   10                  15

Asn

<210> SEQ ID NO 96
<211> LENGTH: 7
<212> TYPE: PRT
<213> ORGANISM: Artificial Sequence
<220> FEATURE:
<223> OTHER INFORMATION: 8B4 CDRL2

<400> SEQUENCE: 96

Tyr Ala Ser Thr Gln Glu Ser
1               5

<210> SEQ ID NO 97
<211> LENGTH: 9
<212> TYPE: PRT
<213> ORGANISM: Artificial Sequence
<220> FEATURE:
<223> OTHER INFORMATION: 8B4 CDRL3

<400> SEQUENCE: 97

Gln Gln Ala Tyr Ser Ala Pro Phe Thr
1               5

<210> SEQ ID NO 98
<211> LENGTH: 16
<212> TYPE: PRT
<213> ORGANISM: Artificial Sequence
<220> FEATURE:
<223> OTHER INFORMATION: 8H4 CDRL1

<400> SEQUENCE: 98

Lys Val Ser Gln Ser Leu Val His Ser Asp Gly Lys Thr Tyr Leu Tyr
1               5                   10                  15

<210> SEQ ID NO 99
<211> LENGTH: 7
<212> TYPE: PRT
<213> ORGANISM: Artificial Sequence
<220> FEATURE:
<223> OTHER INFORMATION: 8H4 CDRL2

<400> SEQUENCE: 99

Gln Val Ser Asn Arg Asp Ser
1               5

```
<210> SEQ ID NO 100
<211> LENGTH: 9
<212> TYPE: PRT
<213> ORGANISM: Artificial Sequence
<220> FEATURE:
<223> OTHER INFORMATION: 8H4 CDRL3

<400> SEQUENCE: 100

Ala Gln Gly Thr Tyr Asn Pro Tyr Thr
1               5

<210> SEQ ID NO 101
<211> LENGTH: 16
<212> TYPE: PRT
<213> ORGANISM: Artificial Sequence
<220> FEATURE:
<223> OTHER INFORMATION: 10B6 CDRL1

<400> SEQUENCE: 101

Lys Ala Ser Gln Ser Leu Val His Ser Asn Gly Val Ile Tyr Phe Tyr
1               5                   10                  15

<210> SEQ ID NO 102
<211> LENGTH: 9
<212> TYPE: PRT
<213> ORGANISM: Artificial Sequence
<220> FEATURE:
<223> OTHER INFORMATION: 10B6 CDRL3

<400> SEQUENCE: 102

Ala Gln Gly Thr Tyr Tyr Pro His Ser
1               5

<210> SEQ ID NO 103
<211> LENGTH: 16
<212> TYPE: PRT
<213> ORGANISM: Artificial Sequence
<220> FEATURE:
<223> OTHER INFORMATION: 12A3 CDRL1

<400> SEQUENCE: 103

Lys Ala Gly Arg Ser Leu Val His Ser Asp Gly Arg Thr Tyr Leu Tyr
1               5                   10                  15

<210> SEQ ID NO 104
<211> LENGTH: 7
<212> TYPE: PRT
<213> ORGANISM: Artificial Sequence
<220> FEATURE:
<223> OTHER INFORMATION: 12A3 CDRL2

<400> SEQUENCE: 104

Gln Val Ser Asn Arg Ser Ser
1               5

<210> SEQ ID NO 105
<211> LENGTH: 9
<212> TYPE: PRT
<213> ORGANISM: Artificial Sequence
<220> FEATURE:
<223> OTHER INFORMATION: 12A3 CDRL3

<400> SEQUENCE: 105

Ala Gln Gly Thr Tyr Tyr Pro Val Thr
1               5
```

<210> SEQ ID NO 106
<211> LENGTH: 7
<212> TYPE: PRT
<213> ORGANISM: Artificial Sequence
<220> FEATURE:
<223> OTHER INFORMATION: 12C3 CDRL2

<400> SEQUENCE: 106

Gln Thr Ser Asn Arg Gly Ser
1               5

<210> SEQ ID NO 107
<211> LENGTH: 9
<212> TYPE: PRT
<213> ORGANISM: Artificial Sequence
<220> FEATURE:
<223> OTHER INFORMATION: 12C3 CDRL3

<400> SEQUENCE: 107

Ala Gln Ala Thr Tyr Ser Pro His Thr
1               5

<210> SEQ ID NO 108
<211> LENGTH: 13
<212> TYPE: PRT
<213> ORGANISM: Artificial Sequence
<220> FEATURE:
<223> OTHER INFORMATION: 12C12 CDRL1

<400> SEQUENCE: 108

Thr Gly Ser Ser Ser Asn Ile Gly Asp Asn Tyr Val Asn
1               5                   10

<210> SEQ ID NO 109
<211> LENGTH: 7
<212> TYPE: PRT
<213> ORGANISM: Artificial Sequence
<220> FEATURE:
<223> OTHER INFORMATION: 12C12 CDRL2

<400> SEQUENCE: 109

Ser Asn Ser Asn Arg Ala Ser
1               5

<210> SEQ ID NO 110
<211> LENGTH: 11
<212> TYPE: PRT
<213> ORGANISM: Artificial Sequence
<220> FEATURE:
<223> OTHER INFORMATION: 12C12 CDRL3

<400> SEQUENCE: 110

Ser Ser Trp Asp Asp Ser Leu Ser Gly Val Val
1               5                   10

<210> SEQ ID NO 111
<211> LENGTH: 16
<212> TYPE: PRT
<213> ORGANISM: Artificial Sequence
<220> FEATURE:
<223> OTHER INFORMATION: 12D1 CDRL1

<400> SEQUENCE: 111

Lys Thr Ser Gln Ser Leu Thr His Ser Asp Gly Lys Thr Tyr Leu Tyr
1               5                   10                  15

```
<210> SEQ ID NO 112
<211> LENGTH: 10
<212> TYPE: PRT
<213> ORGANISM: Artificial Sequence
<220> FEATURE:
<223> OTHER INFORMATION: HA control peptide

<400> SEQUENCE: 112

Tyr Pro Tyr Asp Val Pro Asp Tyr Ala Gly
1               5                   10

<210> SEQ ID NO 113
<211> LENGTH: 9
<212> TYPE: PRT
<213> ORGANISM: Artificial Sequence
<220> FEATURE:
<223> OTHER INFORMATION: 12D1 CDRL3

<400> SEQUENCE: 113

Ala Gln Ala Thr Tyr Tyr Pro His Thr
1               5

<210> SEQ ID NO 114
<211> LENGTH: 7
<212> TYPE: PRT
<213> ORGANISM: Artificial Sequence
<220> FEATURE:
<223> OTHER INFORMATION: 12D4 CDRL2

<400> SEQUENCE: 114

Gln Val Ser Asn Gln Gly Ser
1               5

<210> SEQ ID NO 115
<211> LENGTH: 9
<212> TYPE: PRT
<213> ORGANISM: Artificial Sequence
<220> FEATURE:
<223> OTHER INFORMATION: 12D4 CDRL3

<400> SEQUENCE: 115

Ala Gln Ala Thr Tyr Ala Pro His Ser
1               5

<210> SEQ ID NO 116
<211> LENGTH: 14
<212> TYPE: PRT
<213> ORGANISM: Artificial Sequence
<220> FEATURE:
<223> OTHER INFORMATION: 12E12 CDRL1

<400> SEQUENCE: 116

Gly Leu Ser Ser Gly Ser Val Thr Ser Val Thr Tyr Pro Gly
1               5                   10

<210> SEQ ID NO 117
<211> LENGTH: 7
<212> TYPE: PRT
<213> ORGANISM: Artificial Sequence
<220> FEATURE:
<223> OTHER INFORMATION: 12E12 CDRL2

<400> SEQUENCE: 117

Asn Thr Asn Ser Arg Phe Ser
1               5

<210> SEQ ID NO 118
```

```
<211> LENGTH: 12
<212> TYPE: PRT
<213> ORGANISM: Artificial Sequence
<220> FEATURE:
<223> OTHER INFORMATION: 12E12 CDRL3

<400> SEQUENCE: 118

Ser Val Tyr Ile Gly Gly Gly Ile Tyr Pro Ala Val
1               5                   10

<210> SEQ ID NO 119
<211> LENGTH: 14
<212> TYPE: PRT
<213> ORGANISM: Artificial Sequence
<220> FEATURE:
<223> OTHER INFORMATION: 13C7 CDRL1

<400> SEQUENCE: 119

Ala Gly Thr Ser Ser Asp Ile Gly Gly Tyr Asn Tyr Val Ala
1               5                   10

<210> SEQ ID NO 120
<211> LENGTH: 7
<212> TYPE: PRT
<213> ORGANISM: Artificial Sequence
<220> FEATURE:
<223> OTHER INFORMATION: 13C7 CDRL2

<400> SEQUENCE: 120

Glu Val Asn Lys Arg Ala Ser
1               5

<210> SEQ ID NO 121
<211> LENGTH: 10
<212> TYPE: PRT
<213> ORGANISM: Artificial Sequence
<220> FEATURE:
<223> OTHER INFORMATION: 13C7 CDRL3

<400> SEQUENCE: 121

Ala Ser Tyr Arg Ser Ser Asn Ser Tyr Val
1               5                   10

<210> SEQ ID NO 122
<211> LENGTH: 11
<212> TYPE: PRT
<213> ORGANISM: Artificial Sequence
<220> FEATURE:
<223> OTHER INFORMATION: 13G7 CDRL1

<400> SEQUENCE: 122

Gln Gly Gly Ser Leu Arg Val Ser Tyr Ala His
1               5                   10

<210> SEQ ID NO 123
<211> LENGTH: 7
<212> TYPE: PRT
<213> ORGANISM: Artificial Sequence
<220> FEATURE:
<223> OTHER INFORMATION: 13G7 CDRL2

<400> SEQUENCE: 123

Asp Asp Asp Ser Arg Pro Ser
1               5

<210> SEQ ID NO 124
<211> LENGTH: 11
```

```
<212> TYPE: PRT
<213> ORGANISM: Artificial Sequence
<220> FEATURE:
<223> OTHER INFORMATION: 13G7 CDRL3

<400> SEQUENCE: 124

Gln Ser Ala Asp Ser Ser Gly Asp Asn Trp Val
1               5                   10

<210> SEQ ID NO 125
<211> LENGTH: 16
<212> TYPE: PRT
<213> ORGANISM: Artificial Sequence
<220> FEATURE:
<223> OTHER INFORMATION: 14C4 CDRL1

<400> SEQUENCE: 125

Lys Ala Thr Gln Ser Leu Val His Ser Asp Gly Lys Thr Tyr Leu Ser
1               5                   10                  15

<210> SEQ ID NO 126
<211> LENGTH: 7
<212> TYPE: PRT
<213> ORGANISM: Artificial Sequence
<220> FEATURE:
<223> OTHER INFORMATION: 14C4 CDRL3

<400> SEQUENCE: 126

Ala Gln Ala Pro Tyr Trp Thr
1               5

<210> SEQ ID NO 127
<211> LENGTH: 14
<212> TYPE: PRT
<213> ORGANISM: Artificial Sequence
<220> FEATURE:
<223> OTHER INFORMATION: 14C7 CDRL1

<400> SEQUENCE: 127

Gly Leu Asn Ser Gly Ser Val Thr Ser Ser Asn Tyr Pro Asp
1               5                   10

<210> SEQ ID NO 128
<211> LENGTH: 7
<212> TYPE: PRT
<213> ORGANISM: Artificial Sequence
<220> FEATURE:
<223> OTHER INFORMATION: 14C7 CDRL2

<400> SEQUENCE: 128

Asn Thr Asn Ser Arg His Ser
1               5

<210> SEQ ID NO 129
<211> LENGTH: 10
<212> TYPE: PRT
<213> ORGANISM: Artificial Sequence
<220> FEATURE:
<223> OTHER INFORMATION: 14C7 CDRL3

<400> SEQUENCE: 129

Ala Leu Tyr Met Gly Ser Asp Ser Val Val
1               5                   10

<210> SEQ ID NO 130
<211> LENGTH: 9
<212> TYPE: PRT
```

```
<213> ORGANISM: Artificial Sequence
<220> FEATURE:
<223> OTHER INFORMATION: 14G4 CDRL3

<400> SEQUENCE: 130

Ala Gln Ala Thr Tyr Thr Pro Arg Thr
1               5

<210> SEQ ID NO 131
<211> LENGTH: 11
<212> TYPE: PRT
<213> ORGANISM: Artificial Sequence
<220> FEATURE:
<223> OTHER INFORMATION: 12D7 CDRL1

<400> SEQUENCE: 131

Gln Gly Gly Thr Leu Gly Arg Tyr Tyr Gly Ser
1               5                   10

<210> SEQ ID NO 132
<211> LENGTH: 7
<212> TYPE: PRT
<213> ORGANISM: Artificial Sequence
<220> FEATURE:
<223> OTHER INFORMATION: 12D7 CDRL2

<400> SEQUENCE: 132

Gly Asp Asn Ser Arg Pro Ser
1               5

<210> SEQ ID NO 133
<211> LENGTH: 11
<212> TYPE: PRT
<213> ORGANISM: Artificial Sequence
<220> FEATURE:
<223> OTHER INFORMATION: 12D7 CDRL3

<400> SEQUENCE: 133

Glu Ser Phe Asp Phe Ser Gly Asn Ala Ala Val
1               5                   10

<210> SEQ ID NO 134
<211> LENGTH: 11
<212> TYPE: PRT
<213> ORGANISM: Artificial Sequence
<220> FEATURE:
<223> OTHER INFORMATION: 12G8 CDRL1

<400> SEQUENCE: 134

Gln Gly Gly Asn Phe Gly Asn Phe Tyr Ala Ser
1               5                   10

<210> SEQ ID NO 135
<211> LENGTH: 7
<212> TYPE: PRT
<213> ORGANISM: Artificial Sequence
<220> FEATURE:
<223> OTHER INFORMATION: 12G8 CDRL2

<400> SEQUENCE: 135

Lys Asp Ser Glu Arg Pro Ser
1               5

<210> SEQ ID NO 136
<211> LENGTH: 10
<212> TYPE: PRT
<213> ORGANISM: Artificial Sequence
```

```
<220> FEATURE:
<223> OTHER INFORMATION: 12G8 CDRL3

<400> SEQUENCE: 136

Gln Ser Gly Ser Ser Ser Asp Asn Val Val
1               5                   10

<210> SEQ ID NO 137
<211> LENGTH: 122
<212> TYPE: PRT
<213> ORGANISM: Artificial Sequence
<220> FEATURE:
<223> OTHER INFORMATION: 5A11 VH

<400> SEQUENCE: 137

Gln Val Gln Val Gln Glu Ser Gly Pro Gly Leu Val Lys Pro Ser Gln
1               5                   10                  15

Thr Leu Ser Leu Thr Cys Thr Val Ser Gly Val Ser Ile Thr Thr Arg
                20                  25                  30

Tyr Tyr Ala Trp Ser Trp Ile Arg Gln Pro Pro Gly Lys Gly Leu Glu
            35                  40                  45

Trp Met Gly Val Ile Ala Tyr Asp Gly Ser Thr Tyr Tyr Ser Pro Ser
    50                  55                  60

Leu Lys Ser Arg Thr Ser Ile Ser Arg Asp Thr Ser Lys Asn Gln Phe
65                  70                  75                  80

Ser Leu Gln Leu Thr Ser Val Thr Pro Glu Asp Thr Ala Val Tyr Tyr
                85                  90                  95

Cys Ala Arg Val Arg Leu Ile Glu Ala Pro Tyr Glu Tyr Asp Tyr Trp
            100                 105                 110

Gly Gln Gly Thr Gln Val Thr Val Ser Ser
        115                 120

<210> SEQ ID NO 138
<211> LENGTH: 114
<212> TYPE: PRT
<213> ORGANISM: Artificial Sequence
<220> FEATURE:
<223> OTHER INFORMATION: 5E5 VH

<400> SEQUENCE: 138

Gln Leu Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Gly Thr Tyr
                20                  25                  30

Ser Met Arg Trp Val Arg Gln Val Pro Arg Lys Ala Leu Glu Trp Val
            35                  40                  45

Ser Ser Ile Ser Thr Asp Gly Gly Thr Ala Tyr Arg Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Asn Leu Lys Pro Glu Asp Thr Ala Ile Tyr Tyr Cys
                85                  90                  95

Val Ile Ala Gly Tyr Ser Asp Trp Gly Gln Gly Thr Gln Val Thr Val
            100                 105                 110

Ser Ser

<210> SEQ ID NO 139
<211> LENGTH: 114
<212> TYPE: PRT
```

<213> ORGANISM: Artificial Sequence
<220> FEATURE:
<223> OTHER INFORMATION: 6A6 VH

<400> SEQUENCE: 139

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Gly Arg Trp Val Arg Gln Pro Gly Lys Gly Leu Glu Trp Val
        35                  40                  45

Ser Ser Ile Asn Ala Gly Gly Ser Thr Ser Tyr Ala Asp Ser Val
50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Pro Glu Asp Thr Ala Lys Tyr Tyr Cys
            85                  90                  95

Thr Gln Asn Ser Tyr Arg Tyr Trp Gly Gln Gly Thr Arg Val Ala Val
            100                 105                 110

Ser Ser
```

<210> SEQ ID NO 140
<211> LENGTH: 114
<212> TYPE: PRT
<213> ORGANISM: Artificial Sequence
<220> FEATURE:
<223> OTHER INFORMATION: 8F4 VH

<400> SEQUENCE: 140

```
Gln Leu Gln Leu Val Glu Ser Gly Gly Gly Leu Val Gln Pro Gly Gly
1               5                   10                  15

Ser Leu Arg Leu Ser Cys Ala Ala Ser Gly Phe Ala Phe Ser Ser Tyr
            20                  25                  30

Ser Met Tyr Trp Val Arg Gln Ala Pro Gly Lys Gly Leu Glu Arg Val
        35                  40                  45

Ala Ala Ile Lys Thr Asp Gly Gly Ser Thr Asn Tyr Ala Asp Ser Val
50                  55                  60

Lys Gly Arg Phe Thr Val Ser Arg Asp Asn Ala Lys Asn Thr Leu Tyr
65                  70                  75                  80

Leu Gln Met Asn Ser Leu Lys Ser Glu Asp Thr Ala Val Tyr Tyr Cys
            85                  90                  95

Val Ile Gln Gly Tyr Gly Thr Trp Gly Gln Gly Thr Val Thr Val
            100                 105                 110

Ser Ser
```

<210> SEQ ID NO 141
<211> LENGTH: 114
<212> TYPE: PRT
<213> ORGANISM: Artificial Sequence
<220> FEATURE:
<223> OTHER INFORMATION: 11H1 VH

<400> SEQUENCE: 141

```
Glu Leu Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ser Met Arg Trp Val Arg Gln Ala Pro Gly Lys Gly Leu Glu Trp Leu
```

```
                 35                  40                  45
Ser Ser Ile Lys Ser Asp Gly Ser Ile Thr Ser Tyr Ala Asp Ser Val
 50                  55                  60

Lys Gly Arg Phe Thr Met Ser Arg Asp Asn Ala Lys Asn Thr Leu Tyr
 65                  70                  75                  80

Leu Gln Met Asn Ser Leu Lys Ser Glu Asp Thr Ala Met Tyr Tyr Cys
                 85                  90                  95

Thr Asn Gln Gly Tyr Ile Asn Trp Gly Gln Gly Thr Val Thr Val
                100                 105                 110

Ser Ser

<210> SEQ ID NO 142
<211> LENGTH: 114
<212> TYPE: PRT
<213> ORGANISM: Artificial Sequence
<220> FEATURE:
<223> OTHER INFORMATION: 5A4 VH

<400> SEQUENCE: 142

Gln Leu Gln Leu Val Glu Ser Gly Gly Gly Leu Val Gln Pro Gly Gly
 1               5                  10                  15

Ser Leu Arg Leu Ser Cys Val Ala Ser Gly Phe Ala Phe Ser His Tyr
                 20                  25                  30

Thr Met Tyr Trp Val Arg Gln Ala Pro Val Arg Gly Leu Glu Arg Val
                 35                  40                  45

Ser Ala Ile Ser Gly Gly Gly Asp Arg Thr Ile Tyr Thr Asp Ser Val
 50                  55                  60

Lys Gly Arg Phe Thr Ile Ser Arg Asp Asn Ala Ala Asn Ala Leu Tyr
 65                  70                  75                  80

Leu Gln Met Asn Ser Leu Gln Pro Glu Asp Thr Ala Val Tyr Tyr Cys
                 85                  90                  95

Val Ala Gln Gly Tyr Glu Tyr Trp Gly Gln Gly Thr Arg Val Thr Val
                100                 105                 110

Ser Ser

<210> SEQ ID NO 143
<211> LENGTH: 122
<212> TYPE: PRT
<213> ORGANISM: Artificial Sequence
<220> FEATURE:
<223> OTHER INFORMATION: 5A7 VH

<400> SEQUENCE: 143

Glu Val Gln Val Gln Glu Ser Gly Pro Gly Leu Val Lys Pro Ser Gln
 1               5                  10                  15

Thr Leu Ser Leu Thr Cys Thr Val Ser Gly Ala Ser Ile Thr Asn Arg
                 20                  25                  30

Arg Tyr Ala Trp Thr Trp Ile Arg Gln Pro Pro Gly Lys Gly Leu Glu
                 35                  40                  45

Trp Met Gly Val Ile Val Tyr Asp Gly Asn Thr His Val Ser Pro Ser
 50                  55                  60

Leu Arg Ser Arg Thr Ser Ile Ser Arg Asp Thr Ser Lys Asn Gln Phe
 65                  70                  75                  80

Ser Leu Gln Leu Ser Ser Leu Thr Pro Glu Asp Thr Ala Val Tyr Tyr
                 85                  90                  95

Cys Ala Arg Val Leu Leu Leu Arg Asp Pro Leu Ser Leu Asp Tyr Trp
                100                 105                 110
```

```
Gly Gln Gly Thr Gln Val Thr Val Ser Ser
        115                 120

<210> SEQ ID NO 144
<211> LENGTH: 114
<212> TYPE: PRT
<213> ORGANISM: Artificial Sequence
<220> FEATURE:
<223> OTHER INFORMATION: 8A4 VH

<400> SEQUENCE: 144

Gln Val Gln Leu Val Glu Ser Gly Gly Gly Leu Val Gln Pro Gly Gly
1               5                   10                  15

Ser Leu Lys Val Ser Cys Thr Ala Ser Gly Phe Thr Phe Asn Asn Tyr
            20                  25                  30

Ala Met Arg Trp Val Arg Gln Ala Glu Gly Lys Gly Leu Glu Trp Val
        35                  40                  45

Ser Ser Ile Asp Ser Gly Gly Asp Arg Thr Lys Tyr Gly Asp Ser Val
    50                  55                  60

Lys Gly Arg Phe Ser Ile Ser Arg Asp Asn Ala Lys Asn Thr Val Tyr
65                  70                  75                  80

Leu Gln Met Asp Ala Leu Lys Pro Glu Asp Thr Gly Val Tyr Tyr Cys
                85                  90                  95

Val Ser Gln Gly Tyr Ile Phe Trp Gly Gln Gly Ala Val Thr Val
            100                 105                 110

Ser Ser

<210> SEQ ID NO 145
<211> LENGTH: 118
<212> TYPE: PRT
<213> ORGANISM: Artificial Sequence
<220> FEATURE:
<223> OTHER INFORMATION: 8B4 VH

<400> SEQUENCE: 145

Glu Leu Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Ala
            20                  25                  30

Tyr Leu Tyr Trp Val Arg Gln Val Pro Gly Lys Gly Leu Glu Trp Val
        35                  40                  45

Ser Gly Ile Asn Pro Ala Gly Asp Gly Arg Ala Tyr Ala Thr Ser Val
    50                  55                  60

Lys Gly Arg Phe Thr Ile Ser Arg Asp Asn Ala Lys Asn Thr Leu Tyr
65                  70                  75                  80

Leu Gln Met Asn Thr Leu Glu Ser Asp Asp Thr Ala Val Tyr Tyr Cys
                85                  90                  95

Ala Thr Ala Ser Arg Val Val Ala Tyr Asp Ser Trp Gly Gln Gly Thr
            100                 105                 110

Gln Val Thr Val Ser Ser
        115

<210> SEQ ID NO 146
<211> LENGTH: 114
<212> TYPE: PRT
<213> ORGANISM: Artificial Sequence
<220> FEATURE:
<223> OTHER INFORMATION: 8H4 VH
```

<400> SEQUENCE: 146

| Glu | Leu | Gln | Leu | Val | Glu | Ser | Gly | Gly | Gly | Leu | Val | Gln | Pro | Gly | Arg |
|---|---|---|---|---|---|---|---|---|---|---|---|---|---|---|---|
| 1 | | | | 5 | | | | | 10 | | | | | 15 | |

| Ser | Leu | Arg | Leu | Ser | Cys | Ala | Ala | Ser | Gly | Phe | Thr | Phe | Ser | Ser | Tyr |
| | | | 20 | | | | | 25 | | | | | 30 | | |

| Ser | Met | Arg | Trp | Val | Arg | Gln | Thr | Pro | Gly | Lys | Gly | Leu | Glu | Trp | Val |
| | | 35 | | | | | 40 | | | | | 45 | | | |

| Thr | Ser | Ile | Asn | Ser | Asp | Gly | Gly | Ser | Thr | Lys | Tyr | Ser | Asp | Ser | Val |
| 50 | | | | | 55 | | | | | 60 | | | | | |

| Lys | Gly | Arg | Phe | Thr | Ile | Ser | Arg | Asp | Asn | Ala | Lys | Asn | Thr | Leu | Tyr |
| 65 | | | | | 70 | | | | | 75 | | | | | 80 |

| Leu | Gln | Met | Asn | Asn | Val | Lys | Pro | Glu | Asp | Thr | Ala | Ile | Tyr | Tyr | Cys |
| | | | | 85 | | | | | 90 | | | | | 95 | |

| Ala | Ile | Gln | Gly | Tyr | Thr | Asp | Trp | Gly | Gln | Gly | Thr | Gln | Val | Thr | Val |
| | | | 100 | | | | | 105 | | | | | 110 | | |

Ser Ser

<210> SEQ ID NO 147
<211> LENGTH: 114
<212> TYPE: PRT
<213> ORGANISM: Artificial Sequence
<220> FEATURE:
<223> OTHER INFORMATION: 10B6 VH

<400> SEQUENCE: 147

| Glu | Val | Gln | Leu | Val | Glu | Ser | Gly | Gly | Gly | Leu | Val | Gln | Pro | Gly | Gly |
|---|---|---|---|---|---|---|---|---|---|---|---|---|---|---|---|
| 1 | | | | 5 | | | | | 10 | | | | | 15 | |

| Ser | Leu | Arg | Leu | Ser | Cys | Ala | Ala | Ser | Gly | Phe | Thr | Phe | Ser | Ser | Tyr |
| | | | 20 | | | | | 25 | | | | | 30 | | |

| Ala | Met | Arg | Trp | Val | Arg | Gln | Ala | Pro | Gly | Lys | Gly | Leu | Glu | Trp | Ile |
| | | 35 | | | | | 40 | | | | | 45 | | | |

| Ser | Ser | Ile | Asn | Ile | Asp | Gly | Gly | Ser | Thr | Arg | Tyr | Thr | Asp | Ser | Val |
| 50 | | | | | 55 | | | | | 60 | | | | | |

| Gln | Gly | Arg | Phe | Thr | Val | Ser | Arg | Asp | Asn | Ala | Lys | Asn | Thr | Leu | Tyr |
| 65 | | | | | 70 | | | | | 75 | | | | | 80 |

| Leu | Gln | Met | Asn | Asn | Leu | Lys | Pro | Glu | Asp | Thr | Gly | Ile | Tyr | Tyr | Cys |
| | | | | 85 | | | | | 90 | | | | | 95 | |

| Thr | Ile | Gln | Gly | Tyr | Ile | Tyr | Trp | Gly | Gln | Gly | Thr | Gln | Val | Thr | Val |
| | | | 100 | | | | | 105 | | | | | 110 | | |

Ser Ser

<210> SEQ ID NO 148
<211> LENGTH: 114
<212> TYPE: PRT
<213> ORGANISM: Artificial Sequence
<220> FEATURE:
<223> OTHER INFORMATION: 12A3 VH

<400> SEQUENCE: 148

| Glu | Leu | Gln | Leu | Val | Glu | Ser | Gly | Gly | Gly | Leu | Val | Gln | Ser | Gly | Gly |
|---|---|---|---|---|---|---|---|---|---|---|---|---|---|---|---|
| 1 | | | | 5 | | | | | 10 | | | | | 15 | |

| Ser | Leu | Arg | Leu | Ser | Cys | Ala | Ala | Ser | Gly | Phe | Thr | Phe | Ser | Asn | Tyr |
| | | | 20 | | | | | 25 | | | | | 30 | | |

| Ala | Met | Arg | Trp | Val | Arg | Gln | Ala | Pro | Gly | Gly | Arg | Leu | Glu | Trp | Val |
| | | 35 | | | | | 40 | | | | | 45 | | | |

| Ser | Ser | Ile | Asn | Ile | Ala | Gly | Ser | Val | Val | Tyr | Ala | Asp | Ser | Val |
| 50 | | | | | 55 | | | | | 60 | | | | | |

```
Lys Gly Arg Phe Thr Ile Ser Arg Asp Asn Ala Lys Asn Thr Leu Tyr
 65                  70                  75                  80

Leu Gln Met Asn Ser Leu Lys Ser Glu Asp Thr Ala Val Tyr Tyr Cys
                 85                  90                  95

Ala Met Gln Gly Phe Val Tyr Trp Gly Gln Gly Thr Val Thr Val
            100                 105                 110

Ser Ser

<210> SEQ ID NO 149
<211> LENGTH: 114
<212> TYPE: PRT
<213> ORGANISM: Artificial Sequence
<220> FEATURE:
<223> OTHER INFORMATION: 12C3 VH

<400> SEQUENCE: 149

Glu Leu Gln Leu Val Glu Ser Gly Gly Leu Val Gln Pro Gly Gly
 1               5                  10                  15

Ser Leu Arg Leu Ser Cys Ala Ala Ser Gly Phe Thr Phe Ser Ser Tyr
                20                  25                  30

Ser Met Phe Trp Val Arg Gln Ser Pro Gly Lys Gly Leu Glu Arg Val
             35                  40                  45

Ser Gly Ile Asn Gly Gly Asp Arg Ser Asn Tyr Ala Asp Ser Val
 50                  55                  60

Arg Asp Arg Phe Thr Ile Ser Arg Asp Asn Ala Lys Asn Thr Leu Tyr
 65                  70                  75                  80

Leu Gln Met Asn Ser Leu Lys Ser Glu Asp Thr Ala Val Tyr Tyr Cys
                 85                  90                  95

Val Ile Gln Gly Tyr Ala Tyr Trp Gly Gln Gly Thr Val Thr Val
            100                 105                 110

Ser Ser

<210> SEQ ID NO 150
<211> LENGTH: 119
<212> TYPE: PRT
<213> ORGANISM: Artificial Sequence
<220> FEATURE:
<223> OTHER INFORMATION: 12C12

<400> SEQUENCE: 150

Glu Val Gln Val Gln Glu Ser Gly Pro Gly Leu Val Lys Pro Ser Gln
 1               5                  10                  15

Thr Leu Ser Leu Thr Cys Thr Val Ser Gly Gly Ser Ile Thr Thr Ser
                20                  25                  30

Tyr Tyr Ala Trp Thr Trp Ile Arg Gln Pro Pro Gly Lys Gly Leu Glu
             35                  40                  45

Trp Val Gly Ala Ile Val Tyr Asp Gly Ser Thr Phe Tyr Ser Pro Ser
 50                  55                  60

Leu Lys Ser Arg Thr Ser Ile Ser Arg Asp Thr Ser Lys Ser Gln Phe
 65                  70                  75                  80

Ser Leu Gln Leu Ser Ser Val Thr Pro Glu Asp Thr Ala Val Tyr Tyr
                 85                  90                  95

Cys Ala Arg Ser Tyr Gly Leu Gly Leu Tyr Asp Leu Trp Gly Gln Gly
            100                 105                 110

Thr Gln Val Thr Val Ser Ser
            115
```

```
<210> SEQ ID NO 151
<211> LENGTH: 107
<212> TYPE: PRT
<213> ORGANISM: Artificial Sequence
<220> FEATURE:
<223> OTHER INFORMATION: 12G8 VL

<400> SEQUENCE: 151

Gln Ala Val Leu Thr Gln Pro Ser Ala Val Ser Val Ser Leu Gly Gln
1               5                   10                  15

Thr Ala Arg Ile Thr Cys Gln Gly Gly Asn Phe Gly Asn Phe Tyr Ala
            20                  25                  30

Ser Trp Tyr Gln Gln Lys Pro Gly Gln Ala Pro Val Leu Val Ile Tyr
        35                  40                  45

Lys Asp Ser Glu Arg Pro Ser Gly Ile Pro Glu Arg Phe Ser Gly Ser
    50                  55                  60

Ser Ser Gly Asp Thr Ala Thr Leu Thr Ile Ser Gly Ala Gln Ala Glu
65                  70                  75                  80

Asp Glu Ala Asp Tyr Tyr Cys Gln Ser Gly Ser Ser Asp Asn Val
                85                  90                  95

Val Phe Gly Gly Gly Thr His Leu Thr Val Leu
            100                 105

<210> SEQ ID NO 152
<211> LENGTH: 114
<212> TYPE: PRT
<213> ORGANISM: Artificial Sequence
<220> FEATURE:
<223> OTHER INFORMATION: 12D4 VH

<400> SEQUENCE: 152

Gln Leu Gln Leu Val Glu Ser Gly Gly Gly Leu Val Gln Pro Gly Gly
1               5                   10                  15

Ser Leu Arg Val Ser Cys Ala Ala Ser Gly Phe Thr Phe Ser Ser Ser
            20                  25                  30

Asn Met Arg Trp Val Arg Gln Val Ser Gly Lys Gly Leu Glu Trp Val
        35                  40                  45

Ser Thr Ile Ser Pro Asp Gly Gly Lys Thr Leu Tyr Ala Asp Ser Val
    50                  55                  60

Lys Gly Arg Phe Thr Ile Ser Arg Asp Asn Ala Lys Asn Thr Leu His
65                  70                  75                  80

Leu Gln Met Val Ser Leu Lys Pro Glu Asp Thr Ala Leu Tyr Tyr Cys
                85                  90                  95

Val Lys Ala Gly Tyr Asp Tyr Trp Gly Gln Gly Thr Gln Val Thr Val
            100                 105                 110

Ser Ser

<210> SEQ ID NO 153
<211> LENGTH: 113
<212> TYPE: PRT
<213> ORGANISM: Artificial Sequence
<220> FEATURE:
<223> OTHER INFORMATION: 12E12 VH

<400> SEQUENCE: 153

Glu Val Gln Leu Val Glu Ser Gly Gly Asp Leu Val Gln Pro Gly Gly
1               5                   10                  15

Ser Leu Arg Val Ser Cys Ala Ala Ser Gly Leu Thr Phe Ser Asn Ile
            20                  25                  30
```

```
Tyr Met Ser Trp Val Arg Gln Ala Pro Gly Lys Gly Leu Glu Trp Val
        35                  40                  45

Ser Ala Ile Asn Thr Ala Gly Thr Val Thr Tyr Tyr Ala Asp Ser Val
 50                  55                  60

Lys Gly Arg Phe Thr Ile Ser Arg Asp Asn Ala Lys Asn Thr Leu Tyr
 65                  70                  75                  80

Leu Gln Met Asn Ser Leu Lys Pro Glu Asp Thr Ala His Tyr Tyr Cys
                 85                  90                  95

Thr Thr Gly Glu Val Asp Trp Gly Lys Gly Thr Leu Val Thr Val Ser
                100                 105                 110

Ser

<210> SEQ ID NO 154
<211> LENGTH: 117
<212> TYPE: PRT
<213> ORGANISM: Artificial Sequence
<220> FEATURE:
<223> OTHER INFORMATION: 13C7 VH

<400> SEQUENCE: 154

Gln Leu Gln Leu Val Glu Ser Gly Gly Gly Leu Val Gln Pro Gly Gly
 1               5                  10                  15

Ser Leu Arg Leu Ser Cys Ala Ala Ser Gly Gly Thr Phe Ser Arg Tyr
                 20                  25                  30

Tyr Met Ser Trp Val Arg Gln Ala Pro Gly Lys Gly Leu Glu Trp Val
        35                  40                  45

Ser Ser Ile Tyr Lys Asp Gly Ser Asn Thr Tyr Tyr Ala Asp Ser Val
 50                  55                  60

Lys Gly Arg Phe Thr Ile Ser Arg Asp Asn Ala Lys Asn Thr Leu Tyr
 65                  70                  75                  80

Leu Gln Met Asn Ser Leu Lys Ser Glu Asp Thr Ala Val Tyr Tyr Cys
                 85                  90                  95

Ala Lys Ala Leu Arg Ala Glu Tyr Asp Tyr Trp Gly Gln Gly Thr Gln
                100                 105                 110

Val Thr Val Ser Ser
            115

<210> SEQ ID NO 155
<211> LENGTH: 122
<212> TYPE: PRT
<213> ORGANISM: Artificial Sequence
<220> FEATURE:
<223> OTHER INFORMATION: 13G7 VH

<400> SEQUENCE: 155

Gln Val Gln Leu Gln Glu Ser Gly Pro Gly Leu Val Lys Pro Ser Gln
 1               5                  10                  15

Thr Leu Ser Leu Thr Cys Thr Val Ser Gly Gly Ser Ile Ser Thr Thr
                 20                  25                  30

Ala Pro Ala Trp Gly Trp Ile Arg Gln Ser Pro Gly Lys Gly Leu Asp
        35                  40                  45

Trp Met Ala Val Ile Ala Phe Asp Gly Ser Ala Tyr Tyr Ser Pro Ser
 50                  55                  60

Leu Lys Ser Arg Thr Leu Ile Ser Arg Asp Thr Ser Lys Asn Gln Phe
 65                  70                  75                  80

Ser Leu Gln Leu Ser Ser Val Thr Pro Glu Asp Thr Ala Val Tyr Tyr
                 85                  90                  95
```

```
Cys Ala Arg Leu Gly Gly Arg Asn Tyr Pro Pro Tyr Val Glu Leu Trp
            100                 105                 110

Gly Gln Gly Thr Leu Val Thr Val Ser Ser
        115                 120

<210> SEQ ID NO 156
<211> LENGTH: 114
<212> TYPE: PRT
<213> ORGANISM: Artificial Sequence
<220> FEATURE:
<223> OTHER INFORMATION: 14C4 VH

<400> SEQUENCE: 156

Gln Leu Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Gly Asn Tyr
            20                  25                  30

Asp Met Ser Trp Val Arg Gln Ala Pro Gly Lys Gly Pro Glu Trp Val
        35                  40                  45

Ser Val Ile Asn Ser Asp Gly Asp Thr Tyr Tyr Val Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Pro Glu Asp Arg Ala Val Tyr Tyr Cys
                85                  90                  95

Ala Ile Ala Asn Leu Gly Leu Trp Gly Gln Gly Thr Leu Val Thr Val
            100                 105                 110

Ser Ser

<210> SEQ ID NO 157
<211> LENGTH: 117
<212> TYPE: PRT
<213> ORGANISM: Artificial Sequence
<220> FEATURE:
<223> OTHER INFORMATION: 14C7 VH

<400> SEQUENCE: 157

Gln Val Gln Val Gln Glu Ser Gly Pro Gly Leu Val Lys Pro Ser Gln
1               5                   10                  15

Thr Leu Ser Leu Thr Cys Thr Val Ser Gly Gly Ser Ile Thr Thr Asn
            20                  25                  30

Ser Tyr Tyr Trp Ser Trp Ile Arg Gln Pro Pro Gly Lys Gly Leu Glu
        35                  40                  45

Trp Met Gly Ala Ile Asp Tyr Ser Gly Asp Thr Tyr Tyr Ser Pro Ser
    50                  55                  60

Leu Lys Ser Arg Thr Ser Ile Ser Arg Asp Thr Ser Lys Asn Gln Phe
65                  70                  75                  80

Thr Leu Gln Leu Thr Ser Val Thr Pro Glu Asp Thr Ala Val Tyr Tyr
                85                  90                  95

Cys Val Ser Arg Ile Pro Thr Gly Glu Tyr Trp Gly Gln Gly Thr Gln
            100                 105                 110

Val Thr Val Ser Ser
        115

<210> SEQ ID NO 158
<211> LENGTH: 115
<212> TYPE: PRT
<213> ORGANISM: Artificial Sequence
```

```
<220> FEATURE:
<223> OTHER INFORMATION: 14G4 VH

<400> SEQUENCE: 158

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Ala Phe Ser Arg Tyr
            20                  25                  30

Thr Met Asn Trp Val Arg Gln Ala Pro Gly Lys Gly Leu Glu Trp Leu
        35                  40                  45

Ser Ala Ile Ser Pro Asp Gly Gly Lys Thr Ile Asp Ala Asp Ser Val
    50                  55                  60

Lys Gly Ala Phe Ala Ser Ser Arg Asp Asn Thr Met Asn Thr Leu Tyr
65                  70                  75                  80

Leu Asp Met Asn Ser Leu Lys Pro Glu Asp Ala Ala Val Tyr Tyr Cys
                85                  90                  95

Val Ala Gly His Asn Met Asp Tyr Trp Gly Lys Gly Ile Leu Val Thr
            100                 105                 110

Val Ser Ser
        115

<210> SEQ ID NO 159
<211> LENGTH: 125
<212> TYPE: PRT
<213> ORGANISM: Artificial Sequence
<220> FEATURE:
<223> OTHER INFORMATION: 12D7 VH

<400> SEQUENCE: 159

Glu Leu Gln Leu Val Glu Ser Gly Gly Asp Leu Val Gln Pro Gly Gly
1               5                   10                  15

Ser Leu Arg Leu Ser Cys Ala Ala Ser Gly Phe Thr Phe Asp Asp Tyr
            20                  25                  30

Ala Met Ser Trp Val Arg Gln Ala Pro Gly Lys Gly Leu Glu Trp Val
        35                  40                  45

Ser Ala Ile Thr Ser Asn Gly Lys Arg Thr Asp Tyr Ala Glu Ser Met
    50                  55                  60

Lys Gly Arg Phe Thr Ile Ser Arg Asp Asn Ser Lys Asn Thr Leu Tyr
65                  70                  75                  80

Leu Glu Met Asn Ser Leu Lys Ser Glu Asp Thr Ala Val Tyr Tyr Cys
                85                  90                  95

Thr Lys Gly Pro Pro His Tyr Ile Pro Ile Pro Ser Met Thr Pro Arg
            100                 105                 110

Asp Ser Trp Gly Gln Gly Thr Gln Val Thr Val Ser Ser
        115                 120                 125

<210> SEQ ID NO 160
<211> LENGTH: 117
<212> TYPE: PRT
<213> ORGANISM: Artificial Sequence
<220> FEATURE:
<223> OTHER INFORMATION: 12G8 VH

<400> SEQUENCE: 160

Gln Leu Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asp Asp Tyr
            20                  25                  30
```

```
Ala Met Ser Trp Val Arg Gln Ala Pro Gly Lys Gly Leu Glu Trp Val
             35                  40                  45

Ser Ala Ile Arg Trp Asn Gly Asp Thr Tyr Tyr Ala Glu Ser Met Lys
 50                  55                  60

Gly Arg Phe Asp Met Ser Arg Asp Asn Ala Lys Asn Thr Leu Tyr Leu
 65                  70                  75                  80

Gln Met Asn Ser Leu Lys Ser Glu Asp Thr Ala Val Tyr Tyr Cys Ala
                 85                  90                  95

Lys His Arg Pro Gly Gly Ala Leu Asp Thr Trp Gly Gln Gly Thr Leu
                100                 105                 110

Val Thr Val Ser Ser
            115
```

<210> SEQ ID NO 161
<211> LENGTH: 109
<212> TYPE: PRT
<213> ORGANISM: Artificial Sequence
<220> FEATURE:
<223> OTHER INFORMATION: 5A11 VL

<400> SEQUENCE: 161

```
Gln Ala Val Val Thr Gln Glu Pro Ser Leu Ser Val Ser Pro Gly Gly
 1               5                  10                  15

Thr Val Thr Leu Thr Cys Gly Leu Ser Ser Gly Ser Val Thr Thr Arg
                 20                  25                  30

Ser Tyr Pro Gly Trp Phe Gln Gln Thr Pro Gly Gln Ala Pro Arg Ser
             35                  40                  45

Leu Ile His Ser Thr Ser Ser Arg His Ser Gly Ile Pro Thr Arg Phe
 50                  55                  60

Ser Gly Ser Ile Ser Gly Asn Lys Ala Ala Leu Thr Ile Thr Gly Ala
 65                  70                  75                  80

Gln Pro Glu Asp Glu Ala Asp Tyr Tyr Cys Ala Leu Asp Ile Gly Ser
                 85                  90                  95

Tyr Ile Val Phe Gly Gly Gly Thr His Leu Thr Val Leu
                100                 105
```

<210> SEQ ID NO 162
<211> LENGTH: 112
<212> TYPE: PRT
<213> ORGANISM: Artificial Sequence
<220> FEATURE:
<223> OTHER INFORMATION: 5E5 VL

<400> SEQUENCE: 162

```
Ala Thr Met Leu Thr Gln Ser Pro Gly Ser Leu Ser Val Val Pro Gly
 1               5                  10                  15

Glu Ser Ala Ser Ile Ser Cys Lys Thr Ser Gln Gly Leu Val His Ser
                 20                  25                  30

Asp Gly Lys Thr Tyr Phe Tyr Trp Phe Leu Gln Lys Pro Gly Gln Ser
             35                  40                  45

Pro Gln Gln Leu Ile Tyr Gln Val Ser Asn Arg Ala Ser Gly Val Pro
 50                  55                  60

Asp Arg Phe Thr Gly Ser Gly Ser Gly Thr Asp Phe Thr Leu Lys Ile
 65                  70                  75                  80

Ser Gly Val Lys Ala Glu Asp Ala Gly Val Tyr Tyr Cys Ala Gln Gly
                 85                  90                  95

Thr Tyr Tyr Pro His Thr Phe Gly Ser Gly Thr Arg Leu Glu Ile Lys
                100                 105                 110
```

<210> SEQ ID NO 163
<211> LENGTH: 112
<212> TYPE: PRT
<213> ORGANISM: Artificial Sequence
<220> FEATURE:
<223> OTHER INFORMATION: 6A6 VL

<400> SEQUENCE: 163

Asp Val Leu Thr Gln Thr Pro Gly Ser Leu Ser Val Val Pro Gly
1               5                   10                  15

Glu Ser Ala Ser Ile Ser Cys Lys Ala Ser Gln Ser Leu Ile His Thr
            20                  25                  30

Asp Gly Lys Thr Tyr Leu Tyr Trp Leu Leu Gln Lys Pro Gly Gln Arg
        35                  40                  45

Pro Gln Leu Leu Ile Tyr Gln Val Ser His Glu Ser Gly Val Pro
    50                  55                  60

Asp Arg Phe Thr Gly Ser Gly Ser Gly Thr Asp Phe Thr Leu Lys Ile
65                  70                  75                  80

Ser Gly Val Lys Ala Glu Asp Ala Gly Val Tyr Tyr Cys Ala Gln Ala
                85                  90                  95

Thr Tyr Asn Pro Arg Thr Phe Gly Gln Gly Thr Lys Leu Glu Ile Lys
            100                 105                 110

<210> SEQ ID NO 164
<211> LENGTH: 112
<212> TYPE: PRT
<213> ORGANISM: Artificial Sequence
<220> FEATURE:
<223> OTHER INFORMATION: 8F4 VL

<400> SEQUENCE: 164

Asp Leu Val Leu Thr Gln Ile Pro Gly Ser Leu Ser Val Val Pro Gly
1               5                   10                  15

Glu Ser Ala Ser Ile Ser Cys Lys Ala Ser Gln Ser Leu Val His Ser
            20                  25                  30

Asp Gly Lys Thr Tyr Leu Tyr Trp Leu Leu Gln Lys Pro Gly Gln Ser
        35                  40                  45

Pro Gln Arg Leu Ile Tyr Gln Val Ser Asn Arg Gly Ser Gly Val Pro
    50                  55                  60

Asp Arg Phe Thr Gly Ser Gly Ser Gly Thr Asp Phe Thr Leu Lys Ile
65                  70                  75                  80

Ser Gly Val Glu Ala Glu Asp Ala Gly Val Tyr Tyr Cys Ala Gln Ala
                85                  90                  95

Thr Tyr Tyr Gly His Ser Phe Gly Ser Gly Thr Arg Leu Glu Ile Lys
            100                 105                 110

<210> SEQ ID NO 165
<211> LENGTH: 112
<212> TYPE: PRT
<213> ORGANISM: Artificial Sequence
<220> FEATURE:
<223> OTHER INFORMATION: 11H1 VL

<400> SEQUENCE: 165

Ala Thr Met Leu Thr Gln Ser Pro Gly Ser Leu Thr Ile Val Pro Gly
1               5                   10                  15

Glu Ser Ala Ser Ile Ser Cys Arg Ala Ser Gln Ser Leu Ile His Ser
            20                  25                  30

```
Ala Gly Lys Thr Tyr Phe Tyr Trp Leu Leu Gln Lys Pro Gly Gln Arg
            35                  40                  45

Pro Gln Leu Leu Ile Tyr Gln Val Ser Asn Arg Glu Ser Gly Val Pro
 50                  55                  60

Asp Arg Phe Thr Gly Ser Gly Ser Gly Thr Asp Phe Thr Leu Lys Ile
 65                  70                  75                  80

Ser Gly Val Lys Ala Glu Asp Ala Gly Val Tyr Tyr Cys Ala Gln Gly
                85                  90                  95

Thr Tyr Asn Pro Lys Thr Phe Gly Gln Gly Thr Lys Leu Glu Ile Lys
                100                 105                 110
```

<210> SEQ ID NO 166
<211> LENGTH: 112
<212> TYPE: PRT
<213> ORGANISM: Artificial Sequence
<220> FEATURE:
<223> OTHER INFORMATION: 5A4 VL

<400> SEQUENCE: 166

```
Ala Thr Met Leu Thr Gln Ser Pro Gly Ser Leu Ser Val Val Pro Gly
  1               5                  10                  15

Glu Ser Ala Ser Ile Ser Cys Lys Ala Ile Gln Ser Leu Val His Thr
             20                  25                  30

Asp Gly Lys Thr Tyr Leu Tyr Trp Phe Leu Gln Lys Pro Gly Gln Ser
            35                  40                  45

Pro Gln Arg Leu Ile Tyr Gln Val Ser Asn Arg Gly Ser Gly Val Pro
 50                  55                  60

Asp Arg Phe Thr Gly Ser Gly Ser Gly Thr Asp Phe Thr Leu Lys Ile
 65                  70                  75                  80

Ser Gly Val Lys Ala Glu Asp Ala Gly Val Tyr Tyr Cys Ala Gln Gly
                85                  90                  95

Thr Tyr Ser Ser Lys Thr Phe Gly Gln Gly Thr Lys Leu Glu Ile Lys
                100                 105                 110
```

<210> SEQ ID NO 167
<211> LENGTH: 110
<212> TYPE: PRT
<213> ORGANISM: Artificial Sequence
<220> FEATURE:
<223> OTHER INFORMATION: 5A7 VL

<400> SEQUENCE: 167

```
Ser Ser Ala Leu Thr Gln Pro Pro Ser Met Ser Gly Thr Leu Gly Lys
  1               5                  10                  15

Thr Leu Thr Ile Ser Cys Ala Gly Thr Ser Ser Asp Ile Gly Ala Tyr
             20                  25                  30

Asn Phe Val Ser Trp Tyr Gln Gln Leu Pro Gly Thr Ala Pro Lys Leu
            35                  40                  45

Leu Ile Tyr Asp Ile Asp Lys Arg Ala Ser Gly Ile Pro Asp Arg Phe
 50                  55                  60

Ser Gly Ser Lys Ser Gly Asn Thr Ala Ser Leu Ser Ile Ser Gly Leu
 65                  70                  75                  80

Gln Ser Glu Asp Glu Ala Asp Tyr Tyr Cys Ala Ala Tyr Gly Ser Arg
                85                  90                  95

Asp Asn Val Val Phe Gly Gly Gly Thr His Leu Thr Val Leu
                100                 105                 110
```

<210> SEQ ID NO 168

```
<211> LENGTH: 112
<212> TYPE: PRT
<213> ORGANISM: Artificial Sequence
<220> FEATURE:
<223> OTHER INFORMATION: 8A4 VL

<400> SEQUENCE: 168

Ala Thr Met Leu Thr Gln Ser Pro Gly Ser Leu Ser Val Val Pro Gly
1               5                   10                  15

Glu Ser Ala Ser Ile Ser Cys Lys Ala Ser Gln Ser Leu Val His Ser
            20                  25                  30

Asp Gly Lys Thr Tyr Leu Tyr Trp Leu Leu Gln Lys Pro Gly Gln Arg
        35                  40                  45

Pro Gln Leu Leu Ile Tyr Gln Val Ser Asn His Glu Ser Gly Val Pro
    50                  55                  60

Asp Arg Phe Thr Gly Ser Gly Ser Gly Thr Asp Tyr Thr Leu Lys Ile
65                  70                  75                  80

Ser Gly Val Lys Ala Glu Asp Ala Gly Val Tyr Tyr Cys Ala Gln Ala
                85                  90                  95

Thr Tyr Tyr Pro Leu Thr Phe Gly Gln Gly Thr Lys Val Glu Leu Lys
            100                 105                 110

<210> SEQ ID NO 169
<211> LENGTH: 113
<212> TYPE: PRT
<213> ORGANISM: Artificial Sequence
<220> FEATURE:
<223> OTHER INFORMATION: 8B4 VL

<400> SEQUENCE: 169

Glu Ile Val Leu Thr Gln Ser Pro Ser Ser Val Thr Ala Ser Val Gly
1               5                   10                  15

Glu Lys Val Thr Ile Asn Cys Lys Ser Ser Gln Ser Val Glu Ser Gly
            20                  25                  30

Ser Asp Gln Lys Ser Tyr Leu Asn Trp Tyr Gln Arg Pro Gly Gln Gln
        35                  40                  45

Ser Pro Arg Leu Leu Ile Tyr Tyr Ala Ser Thr Gln Glu Ser Gly Ile
    50                  55                  60

Pro Asp Arg Phe Ser Gly Ser Gly Ser Thr Thr Asp Phe Thr Leu Thr
65                  70                  75                  80

Ile Ser Ser Val Gln Pro Glu Asp Ala Ala Val Tyr Tyr Cys Gln Gln
                85                  90                  95

Ala Tyr Ser Ala Pro Phe Thr Phe Gly Gln Gly Thr Lys Val Glu Leu
            100                 105                 110

Lys

<210> SEQ ID NO 170
<211> LENGTH: 112
<212> TYPE: PRT
<213> ORGANISM: Artificial Sequence
<220> FEATURE:
<223> OTHER INFORMATION: 8H4 VL

<400> SEQUENCE: 170

Asp Val Val Leu Thr Gln Thr Pro Gly Ser Leu Ser Val Val Pro Gly
1               5                   10                  15

Glu Ser Ala Ser Ile Ser Cys Lys Val Ser Gln Ser Leu Val His Ser
            20                  25                  30

Asp Gly Lys Thr Tyr Leu Tyr Trp Leu Leu Gln Lys Pro Gly Gln Ser
```

```
                35                  40                  45
Pro Gln Arg Leu Ile Tyr Gln Val Ser Asn Arg Asp Ser Gly Val Pro
        50                  55                  60

Asp Arg Phe Thr Gly Ser Gly Ser Gly Thr Asp Phe Thr Leu Lys Ile
65                  70                  75                  80

Ser Gly Val Lys Ala Glu Asp Ala Gly Val Tyr Tyr Cys Ala Gln Gly
                85                  90                  95

Thr Tyr Asn Pro Tyr Thr Phe Gly Ser Gly Thr Arg Leu Glu Ile Lys
            100                 105                 110
```

<210> SEQ ID NO 171
<211> LENGTH: 112
<212> TYPE: PRT
<213> ORGANISM: Artificial Sequence
<220> FEATURE:
<223> OTHER INFORMATION: 10B6 VL

<400> SEQUENCE: 171

```
Ala Thr Met Leu Thr Gln Ser Pro Gly Ser Leu Ser Ile Val Pro Gly
1               5                   10                  15

Glu Ser Ala Ser Ile Ser Cys Lys Ala Ser Gln Ser Leu Val His Ser
            20                  25                  30

Asn Gly Val Ile Tyr Phe Tyr Trp Leu Leu Gln Lys Pro Gly Gln Ser
        35                  40                  45

Pro Gln Arg Leu Ile Tyr Gln Val Ser Asn Arg Asp Ser Gly Val Pro
        50                  55                  60

Asp Arg Phe Thr Gly Ser Gly Ser Gly Thr Asp Phe Thr Leu Lys Ile
65                  70                  75                  80

Ser Gly Val Lys Ala Glu Asp Ala Gly Val Tyr Tyr Cys Ala Gln Gly
                85                  90                  95

Thr Tyr Tyr Pro His Ser Phe Gly Ser Gly Thr Arg Leu Gln Ile Lys
            100                 105                 110
```

<210> SEQ ID NO 172
<211> LENGTH: 112
<212> TYPE: PRT
<213> ORGANISM: Artificial Sequence
<220> FEATURE:
<223> OTHER INFORMATION: 12A3 VL

<400> SEQUENCE: 172

```
Asp Val Val Leu Thr Gln Thr Pro Gly Ser Leu Ser Val Val Pro Gly
1               5                   10                  15

Glu Ser Ala Asn Ile Ser Cys Lys Ala Gly Arg Ser Leu Val His Ser
            20                  25                  30

Asp Gly Arg Thr Tyr Leu Tyr Trp Leu Leu Gln Lys Pro Gly Gln Ser
        35                  40                  45

Pro Gln Arg Leu Ile Tyr Gln Val Ser Asn Arg Ser Ser Gly Val Pro
        50                  55                  60

Asp Arg Phe Thr Gly Ser Gly Ser Gly Thr Asp Phe Thr Leu Lys Ile
65                  70                  75                  80

Thr Gly Val Lys Ala Glu Asp Ala Gly Val Tyr Tyr Cys Ala Gln Gly
                85                  90                  95

Thr Tyr Tyr Pro Val Thr Phe Gly Gln Gly Thr Lys Val Glu Leu Lys
            100                 105                 110
```

<210> SEQ ID NO 173
<211> LENGTH: 112

```
<212> TYPE: PRT
<213> ORGANISM: Artificial Sequence
<220> FEATURE:
<223> OTHER INFORMATION: 12C3 VL

<400> SEQUENCE: 173

Asp Val Val Leu Thr Gln Thr Pro Ala Ser Leu Ser Val Pro Gly
1               5                   10                  15

Glu Ser Ala Ser Ile Ser Cys Lys Ala Ser Gln Ser Leu Val His Ser
                20                  25                  30

Asp Gly Lys Thr Tyr Leu Tyr Trp Leu Leu Gln Lys Pro Gly Gln Ser
            35                  40                  45

Pro Gln Arg Leu Ile Tyr Gln Thr Ser Asn Arg Gly Ser Gly Val Pro
    50                  55                  60

Asp Arg Phe Thr Gly Ser Gly Ser Gly Thr Asp Phe Thr Leu Asp Ile
65                  70                  75                  80

Ser Gly Val Lys Ala Glu Asp Ala Gly Val Tyr Tyr Cys Ala Gln Ala
                85                  90                  95

Thr Tyr Ser Pro His Thr Phe Gly Ser Gly Thr Arg Leu Glu Ile Lys
            100                 105                 110

<210> SEQ ID NO 174
<211> LENGTH: 110
<212> TYPE: PRT
<213> ORGANISM: Artificial Sequence
<220> FEATURE:
<223> OTHER INFORMATION: 12C12 VL

<400> SEQUENCE: 174

Gln Ala Val Leu Thr Gln Pro Pro Ser Val Ser Gly Ser Pro Gly Gln
1               5                   10                  15

Lys Phe Thr Ile Ser Cys Thr Gly Ser Ser Ser Asn Ile Gly Asp Asn
                20                  25                  30

Tyr Val Asn Trp Tyr Gln His Leu Pro Gly Thr Ala Pro Lys Leu Leu
            35                  40                  45

Ile Tyr Ser Asn Ser Asn Arg Ala Ser Gly Val Pro Asp Arg Phe Ser
    50                  55                  60

Gly Ser Lys Ser Gly Ser Ser Ala Ser Leu Thr Ile Thr Gly Leu Gln
65                  70                  75                  80

Ala Glu Asp Glu Ala Asp Tyr Tyr Cys Ser Ser Trp Asp Asp Ser Leu
                85                  90                  95

Ser Gly Val Val Phe Gly Gly Gly Thr His Leu Thr Val Leu
            100                 105                 110

<210> SEQ ID NO 175
<211> LENGTH: 116
<212> TYPE: PRT
<213> ORGANISM: Artificial Sequence
<220> FEATURE:
<223> OTHER INFORMATION: 12D1 VL

<400> SEQUENCE: 175

Ser Ala Leu Asp Val Val Leu Thr Gln Thr Pro Gly Ser Leu Ser Val
1               5                   10                  15

Val Pro Gly Glu Ser Ala Ser Ile Ser Cys Lys Thr Ser Gln Ser Leu
                20                  25                  30

Thr His Ser Asp Gly Lys Thr Tyr Leu Tyr Trp Leu Leu Gln Lys Pro
            35                  40                  45

Gly Gln Ser Pro Gln Arg Leu Ile Tyr Gln Val Ser Asn Arg Gly Ser
```

```
                    50                  55                  60
Gly Val Pro Asp Arg Phe Thr Gly Ser Gly Ser Gly Thr Asp Phe Thr
 65                  70                  75                  80

Leu Lys Ile Ser Gly Val Lys Ala Glu Asp Ala Gly Met Tyr Tyr Cys
                     85                  90                  95

Ala Gln Ala Thr Tyr Tyr Pro His Thr Phe Gly Ser Gly Ser Arg Leu
                100                 105                 110

Glu Ile Glu Arg
            115

<210> SEQ ID NO 176
<211> LENGTH: 112
<212> TYPE: PRT
<213> ORGANISM: Artificial Sequence
<220> FEATURE:
<223> OTHER INFORMATION: 12D4 VL

<400> SEQUENCE: 176

Ala Thr Met Leu Thr Gln Ser Pro Gly Ser Leu Ser Val Val Pro Gly
  1               5                  10                  15

Glu Ser Ala Ser Ile Ser Cys Lys Ala Ser Gln Ser Leu Val His Ser
                 20                  25                  30

Asp Gly Lys Thr Tyr Leu Tyr Trp Leu Leu Gln Lys Pro Gly Gln Ser
             35                  40                  45

Pro Gln Arg Leu Ile Tyr Gln Val Ser Asn Gln Gly Ser Gly Val Pro
 50                  55                  60

Asp Arg Phe Thr Gly Ser Gly Ser Gly Thr Asp Phe Thr Leu Lys Ile
 65                  70                  75                  80

Ser Gly Val Lys Ala Glu Asp Ala Gly Val Tyr Tyr Cys Ala Gln Ala
                 85                  90                  95

Thr Tyr Ala Pro His Ser Phe Gly Ser Gly Thr Arg Leu Glu Ile Lys
                100                 105                 110

<210> SEQ ID NO 177
<211> LENGTH: 112
<212> TYPE: PRT
<213> ORGANISM: Artificial Sequence
<220> FEATURE:
<223> OTHER INFORMATION: 12E12 VL

<400> SEQUENCE: 177

Gln Thr Val Val Thr Gln Glu Pro Ser Leu Ser Val Ser Pro Gly Gly
  1               5                  10                  15

Thr Val Thr Leu Thr Cys Gly Leu Ser Ser Gly Ser Val Thr Ser Val
                 20                  25                  30

Thr Tyr Pro Gly Trp Tyr Gln Gln Lys Pro Gly Gln Ala Pro Arg Thr
             35                  40                  45

Leu Ile Tyr Asn Thr Asn Ser Arg Phe Ser Val Pro Asn Arg Phe
 50                  55                  60

Ser Gly Ser Ile Ser Gly Asn Lys Ala Ala Leu Thr Ile Thr Gly Ala
 65                  70                  75                  80

Leu Pro Glu Asp Glu Ala Asp Tyr Tyr Cys Ser Val Tyr Ile Gly Gly
                 85                  90                  95

Gly Ile Tyr Pro Ala Val Phe Gly Gly Gly Thr His Leu Thr Val Leu
                100                 105                 110

<210> SEQ ID NO 178
<211> LENGTH: 110
```

-continued

```
<212> TYPE: PRT
<213> ORGANISM: Artificial Sequence
<220> FEATURE:
<223> OTHER INFORMATION: 13C7 VL

<400> SEQUENCE: 178

Asn Phe Met Leu Thr Gln Pro Pro Ser Val Ser Gly Thr Leu Gly Lys
1               5                   10                  15

Thr Val Thr Ile Ser Cys Ala Gly Thr Ser Ser Asp Ile Gly Gly Tyr
            20                  25                  30

Asn Tyr Val Ala Trp Tyr Gln Gln Leu Pro Gly Thr Ala Pro Lys Leu
        35                  40                  45

Leu Ile Ser Glu Val Asn Lys Arg Ala Ser Gly Ile Pro Asp Arg Phe
    50                  55                  60

Ser Gly Ser Lys Ser Gly Asn Thr Ala Ser Leu Ser Ile Ser Gly Leu
65                  70                  75                  80

Gln Ser Glu Asp Glu Ala Asp Tyr Tyr Cys Ala Ser Tyr Arg Ser Ser
                85                  90                  95

Asn Ser Tyr Val Phe Gly Gly Gly Thr Lys Leu Thr Val Leu
            100                 105                 110

<210> SEQ ID NO 179
<211> LENGTH: 108
<212> TYPE: PRT
<213> ORGANISM: Artificial Sequence
<220> FEATURE:
<223> OTHER INFORMATION: 13G7 VL

<400> SEQUENCE: 179

Gln Pro Val Leu Thr Gln Pro Pro Ala Leu Ser Val Thr Leu Gly Gln
1               5                   10                  15

Thr Ala Lys Ile Thr Cys Gln Gly Gly Ser Leu Arg Val Ser Tyr Ala
            20                  25                  30

His Trp Tyr Gln Gln Lys Pro Gly Gln Ala Pro Val Leu Val Ser Tyr
        35                  40                  45

Asp Asp Asp Ser Arg Pro Ser Gly Ile Pro Glu Arg Phe Ser Gly Ser
    50                  55                  60

Gly Ser Gly Ala Thr Ala Thr Leu Thr Ile Ser Gly Ala Gln Ala Glu
65                  70                  75                  80

Asp Glu Gly Asp Tyr Tyr Cys Gln Ser Ala Asp Ser Ser Gly Asp Asn
                85                  90                  95

Trp Val Phe Gly Gly Gly Thr His Leu Thr Val Leu
            100                 105

<210> SEQ ID NO 180
<211> LENGTH: 110
<212> TYPE: PRT
<213> ORGANISM: Artificial Sequence
<220> FEATURE:
<223> OTHER INFORMATION: 14C4 VL

<400> SEQUENCE: 180

Ala Thr Met Leu Thr Gln Ser Pro Gly Ser Leu Ser Val Val Pro Gly
1               5                   10                  15

Glu Ser Ala Ser Ile Ser Cys Lys Ala Thr Gln Ser Leu Val His Ser
            20                  25                  30

Asp Gly Lys Thr Tyr Leu Ser Trp Leu Leu Gln Lys Pro Gly Gln Ser
        35                  40                  45

Pro Gln Arg Leu Ile Tyr Gln Val Ser Asn Arg Gly Ser Gly Val Pro
```

Asp Arg Phe Thr Gly Ser Gly Ser Gly Thr Asp Phe Thr Leu Lys Ile
65                  70                  75                  80

Ser Gly Val Lys Ala Glu Asp Ala Gly Val Tyr Tyr Cys Ala Gln Ala
                85                  90                  95

Pro Tyr Trp Thr Phe Gly Gln Gly Thr Lys Leu Glu Ile Lys
            100                 105                 110

<210> SEQ ID NO 181
<211> LENGTH: 110
<212> TYPE: PRT
<213> ORGANISM: Artificial Sequence
<220> FEATURE:
<223> OTHER INFORMATION: 14C7 VL

<400> SEQUENCE: 181

Gln Thr Val Val Thr Gln Glu Pro Ser Leu Ser Val Ser Pro Gly Gly
1               5                   10                  15

Thr Val Thr Leu Thr Cys Gly Leu Asn Ser Gly Ser Val Thr Ser Ser
                20                  25                  30

Asn Tyr Pro Asp Trp Tyr Gln Gln Thr Pro Gly Gln Ala Pro Arg Leu
            35                  40                  45

Leu Ile Tyr Asn Thr Asn Ser Arg His Ser Gly Val Pro Ser Arg Phe
50                  55                  60

Ser Gly Ser Ile Ser Gly Asn Lys Ala Ala Leu Thr Ile Thr Gly Ala
65                  70                  75                  80

Gln Pro Glu Asp Glu Ala Asp Tyr Tyr Cys Ala Leu Tyr Met Gly Ser
                85                  90                  95

Asp Ser Val Val Phe Gly Gly Gly Thr His Leu Thr Val Leu
            100                 105                 110

<210> SEQ ID NO 182
<211> LENGTH: 112
<212> TYPE: PRT
<213> ORGANISM: Artificial Sequence
<220> FEATURE:
<223> OTHER INFORMATION: 14G4 VL

<400> SEQUENCE: 182

Asp Val Val Leu Thr Gln Thr Pro Gly Ser Leu Ser Val Val Pro Gly
1               5                   10                  15

Glu Ser Ala Ser Ile Ser Cys Lys Ala Ser Gln Ser Leu Val His Ser
                20                  25                  30

Asp Gly Lys Thr Tyr Leu Tyr Trp Leu Leu Gln Lys Pro Gly Gln Ser
            35                  40                  45

Pro Gln Arg Leu Ile Tyr Gln Val Ser Asn Gly Ser Gly Val Pro
    50                  55                  60

Asp Arg Phe Thr Gly Ser Gly Ser Gly Thr Asp Phe Thr Leu Lys Ile
65                  70                  75                  80

Ser Gly Val Lys Ala Glu Asp Ala Gly Val Tyr Tyr Cys Ala Gln Ala
                85                  90                  95

Thr Tyr Thr Pro Arg Thr Phe Gly Gln Gly Thr Thr Leu Glu Val Lys
            100                 105                 110

<210> SEQ ID NO 183
<211> LENGTH: 108
<212> TYPE: PRT
<213> ORGANISM: Artificial Sequence
<220> FEATURE:

```
<223> OTHER INFORMATION: 12D7 VL

<400> SEQUENCE: 183

Ser Ser Ala Leu Thr Gln Pro Ser Ala Val Ser Val Ser Leu Gly Gln
1               5                   10                  15

Thr Ala Arg Ile Thr Cys Gln Gly Gly Thr Leu Gly Arg Tyr Tyr Gly
            20                  25                  30

Ser Trp Tyr Gln Gln Lys Pro Ala Gln Ala Pro Val Leu Leu Ile Tyr
        35                  40                  45

Gly Asp Asn Ser Arg Pro Ser Gly Ile Pro Glu Arg Phe Ser Gly Ser
    50                  55                  60

Lys Ser Gly Asp Thr Ala Thr Leu Thr Ile Ser Gly Thr Gln Ala Glu
65                  70                  75                  80

Asp Glu Ala Asp Tyr Tyr Cys Glu Ser Phe Asp Phe Ser Gly Asn Ala
                85                  90                  95

Ala Val Phe Gly Gly Gly Thr His Leu Thr Val Leu
                100                 105
```

ANTI-APOC3 ANTIBODIES AND METHODS OF USE THEREOF

RELATED APPLICATIONS

This application is a continuation of International Patent Application No. PCT/IB2017/054125, filed Jul. 7, 2017, which claims the benefit of U.S. Provisional Application Nos. 62/360,084, filed Jul. 8, 2016; and 62/491,591, filed Apr. 28, 2017, each of which is incorporated by reference herein in its entirety.

FIELD

The instant disclosure relates to antibodies that specifically bind to ApoC3 (e.g., human ApoC3) and methods of using the same.

BACKGROUND

Elevated blood triglyceride levels (hypertriglyceridemia) are a causal factor for atherosclerosis, and increase the risk of cardiovascular events, such as cardiovascular death, angina, myocardial infarction, and stroke.

ApoC3 is a protein that circulates at very high concentrations (greater than 10 μM) in the blood, mostly bound to triglyceride rich lipoprotein (TRL), TRL remnants, and high density lipoprotein. ApoC3 appears to be an important regulator of blood triglyceride levels. For example, ApoC3 levels in humans have been shown to positively correlate with blood triglyceride levels, with elevated ApoC3 levels being associated with hypertriglyceridemia. In addition, ApoC3 has been shown to inhibit the activity of lipoprotein lipase (an enzyme that hydrolyses triglycerides in TRL) and also to inhibit hepatic uptake of TRL remnants, both of which cause elevation of blood triglyceride levels.

There are several approved therapies for the treatment hypertriglyceridemia (e.g., fibrates, niacin, and omega-3 fatty acids). However, these therapies are only modestly effective at lowering plasma triglycerides. Accordingly, there is a need in the art for improved therapies for lowering plasma triglycerides.

SUMMARY

The instant disclosure provides antibodies (e.g., isolated antibodies) that specifically bind to ApoC3 (e.g., human ApoC3) and inhibit ApoC3 function. Also provided are pharmaceutical compositions comprising these antibodies, nucleic acids encoding these antibodies, expression vectors and host cells for making these antibodies, and methods of treating a subject using these antibodies. In certain embodiments, the anti-ApoC3 antibodies disclosed herein can attenuate the ability of ApoC3 to inhibit TRL uptake by hepatocytes. Accordingly, the disclosed anti-ApoC3 antibodies are useful for the treatment and prevention of hypertriglyceridemia and associated diseases (e.g., cardiovascular disease and pancreatitis).

Accordingly, in one aspect, the instant disclosure provides an antibody that specifically binds to ApoC3 and attenuates the ability of ApoC3 to inhibit hepatocyte uptake of very low density lipoprotein (VLDL). In certain embodiments, the antibody is capable of inhibiting post-prandial lipemia in a subject. In certain embodiments, the antibody is capable of increasing the rate of clearance of ApoB from the blood in a subject. In certain embodiments, the antibody is capable of reducing the level of ApoB in the blood in a subject. In certain embodiments, the antibody attenuates the ability of ApoC3 to inhibit lipoprotein lipase-mediated lipolysis of VLDL. In certain embodiments, the antibody inhibits the binding of ApoC3 to a lipid. In certain embodiments, the antibody is capable of binding to lipid-bound ApoC3.

Several, distinct types of anti-ApoC3 antibody are disclosed herein, each binding to a different, novel epitope of ApoC3 and having different functional properties. For example, in certain embodiments, the anti-ApoC3 antibodies disclosed herein bind to an epitope within the amino acid sequence set forth in SEQ ID NO:3 [FSEFWDLDPE], and are capable of binding to lipid-bound ApoC3. Alternatively, in certain embodiments, the anti-ApoC3 antibodies disclosed herein bind to an epitope within the amino acid sequence set forth in SEQ ID NO:2 [GWVTDGFSSLK], and inhibit the binding of ApoC3 to a lipid.

Accordingly, in another aspect, the instant disclosure provides an antibody that specifically binds to ApoC3, wherein the antibody binds to an epitope within the amino acid sequence set forth in SEQ ID NO:2 [GWVTDGFSSLK]. In certain embodiments, the epitope comprises at least one of the amino acids at positions 1, 4, 6, 7, 9 or 10 of SEQ ID NO: 2. In certain embodiments, the epitope comprises the amino acids at positions 4 and 9 of SEQ ID NO: 2. In certain embodiments, the epitope comprises the amino acids at positions 4, 6 and 9 of SEQ ID NO: 2. In certain embodiments, the epitope comprises the amino acids at positions 1, 4, 6 and 9 of SEQ ID NO: 2. In certain embodiments, the epitope comprises the amino acids at positions 1, 4, 6, 7, 9 and 10 of SEQ ID NO: 2. In certain embodiments, the antibody attenuates the ability of ApoC3 to inhibit lipoprotein lipase-mediated lipolysis of VLDL. In certain embodiments, the antibody inhibits the binding of ApoC3 to a lipid.

In another aspect, the instant disclosure provides an antibody that specifically binds to ApoC3, wherein the antibody binds to an epitope within the amino acid sequence set forth in SEQ ID NO:3 [FSEFWDLDPE]. In certain embodiments, the epitope comprises at least one of the amino acids at position 2, 5, 6, 8, or 10 of SEQ NO:3. In certain embodiments, the epitope comprises the amino acids at positions 5 and 6 of SEQ ID NO:3. In certain embodiments, the epitope comprises the amino acids at positions 2, 5, 6, and 8 of SEQ ID NO:3. In certain embodiments, the epitope comprises the amino acids at position 10 of SEQ ID NO:3. In certain embodiments, the epitope comprises the amino acids at positions 6, 8, and 10 of SEQ ID NO:3. In certain embodiments, the epitope comprises the amino acids at positions 6 and 8 of SEQ ID NO:3. In certain embodiments, the antibody is capable of binding to lipid-bound ApoC3. In certain embodiments, the antibody attenuates the ability of ApoC3 to inhibit hepatocyte uptake of very low density lipoprotein (VLDL). In certain embodiments, the antibody is capable of inhibiting post-prandial lipemia in a subject. In certain embodiments, the antibody is capable of increasing the rate of clearance of ApoB from the blood in a subject. In certain embodiments, the antibody is capable of reducing the level of ApoB in the blood in a subject.

In another aspect, the instant disclosure provides an antibody that specifically binds to ApoC3, comprising a heavy chain variable region having complementarity determining regions CDRH1, CDRH2 and CDRH3, and a light chain variable region having complementarity determining regions CDRL1, CDRL2 and CDRL3, wherein CDRH1, CDRH2, CDRH3; CDRL1, CDRL2, and CDRL3 comprise the amino acid sequences set forth in SEQ ID NOs: 4, 5, 6, 73, 74, and 75; 7, 8, 9, 76, 77, and 78; 10, 11, 12, 79, 80, and 81; 13, 14, 15, 82, 83, and 84; 16, 17, 18, 85, 86, and 87; 19, 20, 21, 88, 83, and 89; 22, 23, 24, 90, 91; and 92; 25, 26, 27; 82; 93, and 94; 28, 29, 30, 95, 96, and 97; 16, 31; 32, 98, 99, and 100; 33, 34, 35, 101, 99, and 102; 25, 36, 37, 103, 104, and 105; 38, 39, 40, 82, 106, and 107; 41, 42, 43, 108, 109, and 110; 7, 8, 9, 111, 83, and 113; 47, 48, 49, 82, 114, and 115; 50, 51, 52, 116, 117, and 118; 53, 54, 55, 119, 120, and 121; 56, 57, 58, 122, 123, and 124; 59, 60, 61, 125, 83, and 126; 62, 63, 64, 127, 128, and 129; 65, 66, 67, 82, 114, and 130; 68, 69, 70, 131, 132, and 133; or 68, 71, 72, 124, 135, and 136, respectively.

In another aspect, the instant disclosure provides an antibody that specifically binds to ApoC3, the antibody comprising a heavy chain variable region comprising an amino acid sequence selected from the group consisting of SEQ ID NOs: 137-160. In another aspect, the instant disclosure provides an antibody that specifically binds to ApoC3, the antibody comprising a light chain variable region comprising an amino acid sequence selected from the group consisting of SEQ ID NOs: 161-183 and 151. In another aspect, the instant disclosure provides an antibody that specifically binds to ApoC3, the antibody comprising a heavy chain variable region and a light chain variable region, wherein the heavy chain variable region and the light chain variable region, respectively, comprise the amino acid sequences set forth in SEQ ID NOs: 137 and 161, 138 and 162, 139 and 163, 140 and 164, 141 and 165, 142 and 166, 143 and 167, 144 and 168, 145 and 169, 146 and 170, 147 and 171, 148 and 172, 149 and 173, 150 and 174, 138 and 175, 152 and 176, 153 and 177, 154 and 178, 155 and 179, 156 and 180, 157 and 181, 158 and 182, 159 and 183, or 160 and 151.

In another aspect, the instant disclosure provides an antibody that competes for binding to ApoC3 with an antibody comprising a heavy chain variable region having complementarity determining regions CDRH1, CDRH2 and CDRH3, and a light chain variable region having complementarity determining regions CDRL1, CDRL2 and CDRL3, wherein CDRH1, CDRH2, CDRH3, CDRL1, CDRL2, and CDRL3 comprise the amino acid sequences set forth in SEQ NOs: 4, 5, 6, 73, 74, and 75; 7, 8, 9, 76, 77, and 78; 10, 11, 12, 79, 80, and 81; 13, 14, 15, 82, 83, and 84; 16, 17, 18, 85, 86, and 87; 19, 20, 21, 88, 83, and 89; 22, 23, 24, 90, 91, and 92; 25, 26, 27, 82, 93, and 94; 28, 29, 30, 95, 96, and 97; 16, 31, 32, 98, 99, and 100; 33, 34, 35, 101, 99, and 102; 25, 36, 37, 103, 104, and 105; 38, 39, 40, 82, 106, and 107; 41, 42, 43, 108, 109, and 110; 7, 8, 9, 111, 83, and 113; 47, 48, 49, 82, 114, and 115; 50, 51, 52, 116, 117, and 118; 53, 54, 55, 119, 120, and 121; 56, 57, 58, 122, 123, and 124; 59, 60, 61, 125, 83, and 126; 62, 63, 64, 127, 128, and 129; 65, 66, 67, 82, 114, and 130; 68, 69, 70, 131, 132, and 133; or 68, 71, 72, 124, 135, and 136, respectively.

In another aspect, the instant disclosure provides an antibody that competes for binding to ApoC3 with an antibody comprising a heavy chain variable region comprising an amino acid sequence selected from the group consisting of SEQ ID NOs: 137-160. In another aspect, the instant disclosure provides an antibody that competes for binding to ApoC3 with an antibody comprising a light chain variable region comprising an amino acid sequence selected from the group consisting of SEQ ID NOs: 161-183 and 151. In another aspect, the instant disclosure provides an antibody that competes for binding to ApoC3 with an antibody comprising a heavy chain variable region and a light chain variable region, wherein the heavy chain variable region and the light chain variable region, respectively, comprise the amino acid sequences set forth in SEQ ID NOs: 137 and 161, 138 and 162, 139 and 163, 140 and 164, 141 and 165, 142 and 166, 143 and 167, 144 and 168, 145 and 169, 146 and 170, 147 and 171, 148 and 172, 149 and 173, 150 and 174, 138 and 175, 152 and 176, 153 and 177, 154 and 178, 155 and 179, 156 and 180, 157 and 181, 158 and 182, 159 and 183, or 160 and 151.

In another aspect, the instant disclosure provides an antibody that binds to the same epitope of ApoC3 as an antibody comprising a heavy chain variable region having complementarity determining regions CDRH1, CDRH2 and CDRH3, and a light chain variable region having complementarity determining regions CDRL1, CDRL2 and CDRL3, wherein CDRH1, CDRH2, CDRH3, CDRL1, CDRL2, and CDRL3 comprise the amino acid sequences set forth in SEQ NOs: 4, 5, 6, 73, 74, and 75; 7, 8, 9, 76, 77, and 78; 10, 11, 12, 79, 80, and 81; 13, 14, 15, 82, 83, and 84; 16, 17, 18, 85, 86, and 87; 19, 20, 21, 88, 83, and 89; 22, 23, 24, 90, 91, and 92; 25, 26, 27, 82, 93, and 94; 28, 29, 30, 95, 96, and 97; 16, 31, 32, 98, 99, and 100; 33, 34, 35, 101, 99, and 102; 25, 36, 37, 103, 104, and 105; 38, 39, 40, 82, 106, and 107; 41, 42, 43, 108, 109, and 110; 7, 8, 9, 111, 83, and 113; 47, 48, 49, 82, 114, and 115; 50, 51, 52, 116, 117, and 118; 53, 54, 55, 119, 120, and 121; 56, 57, 58, 122, 123, and 124; 59, 60, 61, 125, 83, and 126; 62, 63, 64, 127, 128, and 129; 65, 66, 67, 82, 114, and 130; 68, 69, 70, 131, 132, and 133; or 68, 71, 72, 124, 135, and 136, respectively.

In another aspect, the instant disclosure provides an antibody that binds to the same epitope of ApoC3 as an antibody comprising a heavy chain variable region comprising an amino acid sequence selected from the group consisting of SEQ ID NOs: 137-160. In another aspect, the instant disclosure provides an antibody that binds to the same epitope of ApoC3 as an antibody comprising a light chain variable region comprising an amino acid sequence selected from the group consisting of SEQ ID NOs: 161-183 and 151. In another aspect, the instant disclosure provides an antibody that binds to the same epitope of ApoC3 as an antibody comprising a heavy chain variable region and a light chain variable region, wherein the heavy chain variable region and the light chain variable region, respectively, comprise the amino acid sequences set forth in SEQ ID NOs: 137 and 161, 138 and 162, 139 and 163, 140 and 164, 141 and 165, 142 and 166, 143 and 167, 144 and 168, 145 and 169, 146 and 170, 147 and 171, 148 and 172, 149 and 173, 150 and 174, 138 and 175, 152 and 176, 153 and 177, 154 and 178, 155 and 179, 156 and 180, 157 and 181, 158 and 182, 159 and 183, or 160 and 151.

In certain embodiments, the antibody disclosed herein attenuates the ability of ApoC3 to inhibit hepatocyte uptake of very low density lipoprotein (VLDL). In certain embodiments, the antibody is capable of inhibiting post-prandial lipemia in a subject. In certain embodiments, the antibody is capable of increasing the rate of clearance of ApoB from the blood in a subject. In certain embodiments, the antibody is capable of reducing the level of ApoB in the blood in a subject. In certain embodiments, the antibody attenuates the ability of ApoC3 to inhibit lipoprotein lipase-mediated lipolysis of VLDL. In certain embodiments, the antibody inhibits the binding of ApoC3 to a lipid. In certain embodiments, the antibody is capable of binding to lipid-bound ApoC3.

In another aspect, the instant application provides a pharmaceutical composition comprising an antibody as disclosed herein and a pharmaceutically acceptable carrier.

In another aspect, the instant application provides a polynucleotide (e.g., an isolated polynucleotide) encoding the heavy chain variable region or the light chain variable region of an antibody as disclosed herein. In another aspect, the instant application provides an expression vector comprising the polynucleotide. In another aspect, the instant application provides a host cell comprising the expression vector. In another aspect, the instant application provides a method for producing an antibody that binds to ApoC3, the method comprising culturing the host cell under conditions that allow expression of the antibody.

In another aspect, the instant application provides a method for inhibiting the activity of ApoC3 in the blood of a subject, the method comprising administering to the subject an effective amount of an antibody or pharmaceutical composition as disclosed herein. In another aspect, the instant application provides a method for reducing triglyceride levels in the blood of a subject, the method comprising administering to the subject an effective amount of an antibody or pharmaceutical composition as disclosed herein. In another aspect, the instant application provides a method for inhibiting post-prandial lipemia in a subject, the method comprising administering to the subject an effective amount of an antibody or pharmaceutical composition as disclosed herein. In another aspect, the instant application provides a method for treating hypertriglyceridemia in a subject, the method comprising administering to the subject an effective amount of an antibody or pharmaceutical composition as disclosed herein. In another aspect, the instant application provides a method for treating chylomicronemia in a subject, the method comprising administering to the subject an effective amount of an antibody or pharmaceutical composition as disclosed herein.

In another aspect, the instant application provides a method for reducing the risk of cardiovascular disease in a subject with hypertriglyceridemia, the method comprising administering to the subject an effective amount of an antibody or pharmaceutical composition as disclosed herein. In certain embodiments, the cardiovascular disease is myocardial infarction. In certain embodiments, the cardiovascular disease is angina. In certain embodiments, the cardiovascular disease is stroke. In certain embodiments, the cardiovascular disease is atherosclerosis.

In certain embodiments, the antibody reduces the levels of chylomicron or chylomicron remnants in the blood of the subject.

In certain embodiments, the subject is receiving an additional lipid lowering agent. In certain embodiments, the additional lipid lowering agent is an HMG-CoA reductase inhibitor. In certain embodiments, the HMG-CoA reductase inhibitor is atorvastatin, fluvastatin, lovastatin, pitavastatin, pravastatin, rosuvastatin or simvastatin. In certain embodiments, the additional lipid lowering agent is a PCSK9 inhibitor. In certain embodiments, the PCSK9 inhibitor is alirocumab, evolocumab, or bococizumab. In certain embodiments, the additional lipid lowering agent is ezetimibe. In certain embodiments, the additional lipid lowering agent is a combination of ezetimibe and an HMG-CoA reductase inhibitor. In certain embodiments, the additional lipid lowering agent is a combination of ezetimibe, an HMG-CoA reductase inhibitor, and a PCSK9 inhibitor.

BRIEF DESCRIPTION OF THE DRAWINGS

FIGS. 24-2C are a set of graphs showing binding of ApoC3 to VLDL in the presence of anti-ApoC3 antibodies. In FIG. 2C, liposome was captured on a Biacore L1 chip, ApoC3 was injected at t=1800 s, and 5E5 and 6A6 were injected at t=4400s. SPR signal was measured.

FIGS. 7A-7C are a set of graphs showing epitope substitution scanning of 5E5 (FIG. 7A), 6A6 (FIG. 7B) and 14C7 (FIG. 7C). In FIGS. 7A-7B, an array of ApoC3 peptides having the 13 amino acids DKFSEFWDLDPEV (SEQ ID NO: 44) with single amino acid mutations replacing each amino acid with the other 19 L-amino acids was synthesized. Binding of the indicated anti-ApoC3 antibody with the peptides was measured. Substitution matrices depicting the relative binding affinity of wild-type and mutant ApoC3 peptides were generated from the binding affinity data. In FIG. 7C, An array of ApoC3 peptides having 13 amino acids ARGWVTDGFSSLK (SEQ ID NO: 45) with single amino acid mutations replacing each amino acid with the other 19 L-amino acids was synthesized. Binding of the 14C7 anti-ApoC3 antibody with the peptides was measured. A substitution matrix depicting the relative binding affinity of wild-type and mutant ApoC3 peptides was generated from the binding affinity data. In each of FIGS. 7A-7C, the first column represents the sequence of the wild-type ApoC3 peptide (SEQ ID NO: 185 or 186) from bottom to top. Amino acid substitutions at each position as denoted in the first column are placed in the order of binding affinity from higher (left) to lower (right). For each row from left to right, the intensity of shade decreases to a lowest point and then increases. To the left of the lowest point, the intensity of shade correlates positively with the binding affinity; to the right of the lowest point, the intensity of shade correlates negatively with the binding affinity.

FIG. 10C shows the concentrations of human Apoc3 in the plasma. FIGS. 10A-10B are graphed as percent difference from negative isotype control, and FIG. 10D is graphed as percentage change relative to the respective baseline level measured from a blood sample collected immediately before the administration of the antibodies.

DETAILED DESCRIPTION

Figure 1:
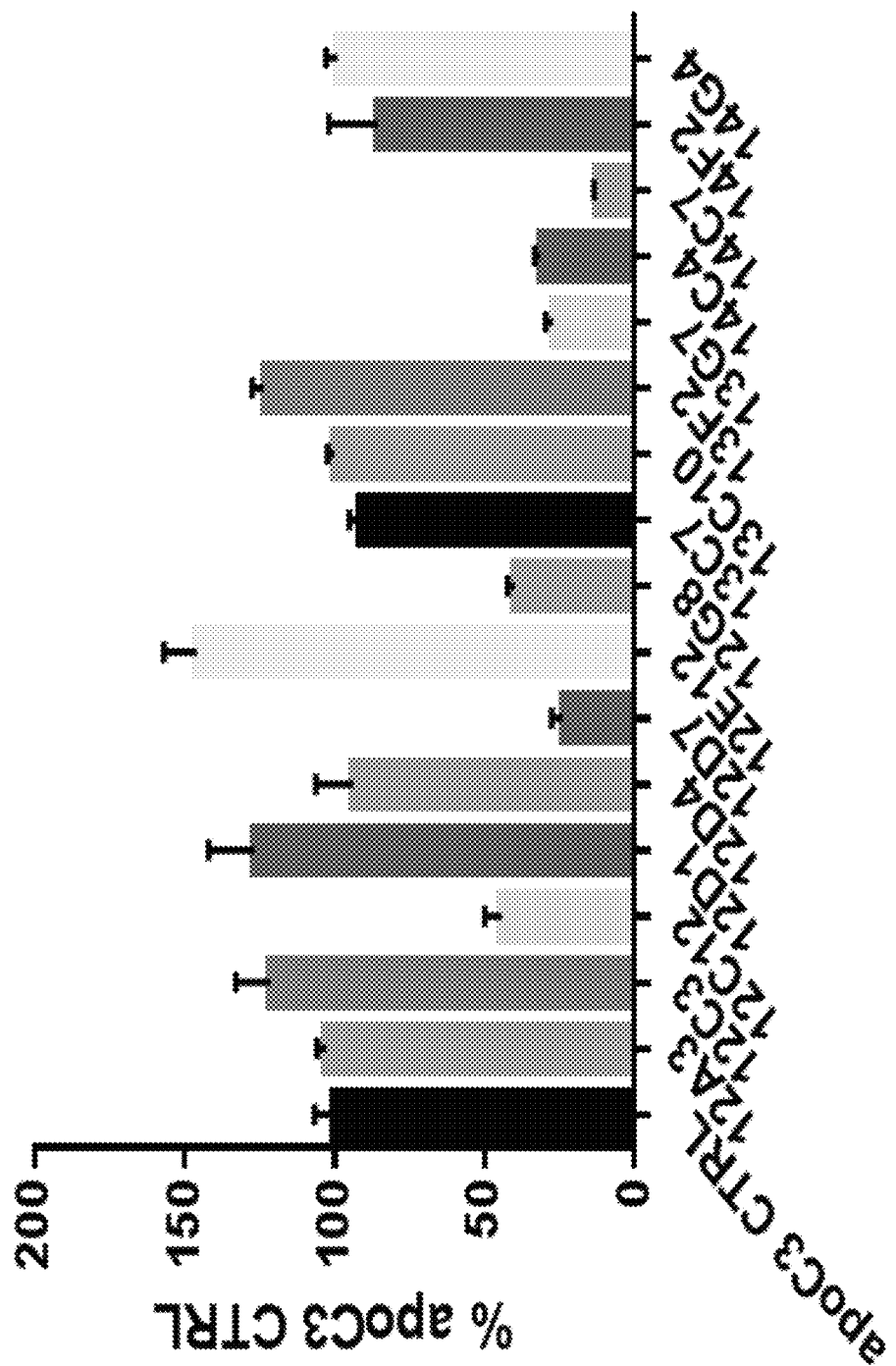
FIG. 1 is a graph showing the interference of ApoC3 antibodies on the binding of ApoC3 to dimyristoylphosphatidyl choline (DMPC). An ELISA microplate was coated with DMPC and incubated with ApoC3 mixed with test anti-ApoC3 antibodies. The amount of ApoC3 that remained attached to the plate was measured with a biotinylated anti-ApoC3 polyclonal goat antibody following standard steps of an ELISA colorimetric assay.

The instant disclosure provides antibodies that specifically bind to ApoC3 (e.g., human ApoC3) and inhibit ApoC3 function. Also provided are pharmaceutical compositions comprising these antibodies, nucleic acids encoding these antibodies, expression vectors and host cells for making these antibodies, and methods of treating a subject using these antibodies. In certain embodiments, the anti-ApoC3 antibodies disclosed herein can attenuate the ability of ApoC3 to inhibit TRL uptake by hepatocytes. Accordingly, the disclosed anti-ApoC3 antibodies are useful for the treatment and prevention of hypertriglyceridemia and associated diseases (e.g., cardiovascular disease and pancreatitis).

Several, distinct types of anti-ApoC3 antibody are disclosed herein, each binding to a different, novel epitope of ApoC3 and having different functional properties. For example, in certain embodiments, the anti-ApoC3 antibodies disclosed herein bind to an epitope within the amino acid sequence set forth in SEQ ID NO:3 [FSEFWDLDPE], and are capable of binding to lipid-bound ApoC3. Alternatively, in certain embodiments, the anti-ApoC3 antibodies disclosed herein bind to an epitope within the amino acid sequence set forth in SEQ ID NO:2 [GWVTDGFSSLK], and inhibit the binding of ApoC3 to a lipid.

1. Definitions

As used herein, the term "ApoC3" refers to Apolipoprotein C3 protein. In certain embodiments, the ApoC3 is human ApoC3. An exemplary human ApoC3 amino acid sequence is set forth in RefSeq accession number NP_000031.1. The mature amino acid sequence of NP_900031.1 is as follows: SEAEDASLLSFMQGYM-KHATKTAKDALSSVQESQVAQQARGWVTDGFSS-IKDYWS TVKDKFSEFWDLDPEVRPTSAVAA (SEQ ID NO: 1).

As used herein, the terms "antibody" and "antibodies" include full length antibodies, antigen-binding fragments of full length antibodies, and molecules comprising antibody CDRs, VH regions or VL regions. Examples of antibodies include monoclonal antibodies, recombinantly produced antibodies, monospecific antibodies, multispecific antibodies (including bispecific antibodies), human antibodies, humanized antibodies, chimeric antibodies, immunoglobulins, synthetic antibodies, tetrameric antibodies comprising two heavy chain and two light chain molecules, an antibody light chain monomer, an antibody heavy chain monomer, an antibody light chain dimer, an antibody heavy chain dialer, an antibody light chain-antibody heavy chain pair, intrabodies, heteroconjugate antibodies, single domain antibodies, monovalent antibodies, single chain antibodies or single-chain Fvs (scFv), scFv-Fcs, camelid antibodies (e.g., llama antibodies), camelized antibodies, affybodies, Fab fragments, F(ab')$_2$ fragments, disulfide-linked Fvs (sdFv), anti-idiotypic (anti-Id) antibodies (including, e.g., anti-anti-Id antibodies), and antigen-binding fragments of any of the above. In certain embodiments, antibodies described herein refer to polyclonal antibody populations. Antibodies can be of any type (e.g., IgG, IgE, IgM, IgD, IgA or IgY), any class (e.g., IgG$_1$, IgG$_2$, IgG$_3$, IgG$_4$, IgA$_1$ or IgA$_2$), or any subclass (e.g., IgG$_{2a}$ or IgG$_{2b}$) of immunoglobulin molecule. In certain embodiments, antibodies described herein are IgG antibodies, or a class (e.g., human IgG$_1$ or IgG$_4$) or subclass thereof. In a specific embodiment, the antibody is a humanized monoclonal antibody.

As used herein, the term "isolated antibody" refers to an antibody that has been identified and separated and/or recovered from at least one component of its natural environment. The term "isolated antibody" includes an antibody in situ within a recombinant host cell.

As used herein, the term "CDR" or "complementarity determining region" means the noncontiguous antigen combining sites found within the variable region of both heavy and light chain polypeptides. These particular regions have been described by Kabat et al., J. Biol. Chem. 252, 6609-6616 (1977) and Kabat et al., Sequences of protein of immunological interest. (1991), by Chothia et al., J. Mol. Biol. 196:901-917 (1987), and by MacCallum et al., J. Mol. Biol. 262:732-745 (1996), all of which are incorporated by reference in their entireties, where the definitions include overlapping or subsets of amino acid residues when compared against each other. In certain embodiments, the term "CDR" is a CDR as defined by Kabat et al., J. Biol. Chem. 252, 6609-6616 (1977) and Kabat et al., Sequences of protein of immunological interest. (1991). CDRH1, CDRH2 and CDRH3 denote the heavy chain CDRs, and CDRL1, CDRL2 and CDRL3 denote the light chain CDRs.

As used herein, the term "framework (FR) amino acid residues" refers to those amino acids in the framework region of an immunoglobulin chain. The term "framework region" or "FR region" as used herein, includes the amino acid residues that are part of the variable region, but are not part of the CDRs (e.g., using the Kabat definition of CDRs).

As used herein, the terms "variable region" and "variable domain" are used interchangeably and are common in the art. The variable region typically refers to a portion of an antibody, generally, a portion of a light or heavy chain, typically about the amino-terminal 110 to 120 amino acids or 110 to 125 amino acids in the mature heavy chain and about 90 to 115 amino acids in the mature light chain, which differ extensively in sequence among antibodies and are used in the binding and specificity of a particular antibody for its particular antigen. The variability in sequence is concentrated in those regions called complementarity determining regions (CDRs) while the more highly conserved regions in the variable domain are called framework regions (FR). Without wishing to be bound by any particular mechanism or theory, it is believed that the CDRs of the light and heavy chains are primarily responsible for the interaction and specificity of the antibody with antigen. In certain embodiments, the variable region is a human variable region. In certain embodiments, the variable region comprises rodent or murine CDRs and human framework regions (FRs), in particular embodiments, the variable region is a primate (e.g., non-human primate) variable region. In certain embodiments, the variable region comprises rodent or murine CDRs and primate (e.g., non-human primate) framework regions (FRs).

The terms "VL" and "VL domain" are used interchangeably to refer to the light chain variable region of an antibody.

The terms "VH" and "VH domain" are used interchangeably to refer to the heavy chain variable region of an antibody.

As used herein, the terms "constant region" and "constant domain" are interchangeable and are common in the art. The constant region is an antibody portion, e.g., a carboxyl terminal portion of a light or heavy chain which is not directly involved in binding of an antibody to antigen but which can exhibit various effector functions, such as interaction with the Fc receptor. The constant region of an immunoglobulin molecule generally has a more conserved amino acid sequence relative to an immunoglobulin variable domain.

As used herein, the term "heavy chain" when used in reference to an antibody can refer to any distinct type, e.g., alpha (α), delta (δ), epsilon (ε), gamma (γ), and mu (μ), based on the amino acid sequence of the constant domain, which give rise to IgA, IgD, IgE, IgG, and IgM classes of antibodies, respectively, including subclasses of IgG, e.g., $IgG_1$, $IgG_2$, $IgG_3$, and $IgG_4$.

As used herein, the term "light chain" when used in reference to an antibody can refer to any distinct type, e.g., kappa (κ) or lambda (λ) based on the amino acid sequence of the constant domains. Light chain amino acid sequences are well known in the art. In specific embodiments, the light chain is a human light chain.

As used herein, the term "specifically binds to" refers to the ability of an antibody to bind to an antigen with an dissociation constant (Kd) of less than about $1 \times 10^{-6}$ M, $1 \times 10^{-7}$ M, $1 \times 10^{-8}$ M, $1 \times 10^{-9}$ M, $1 \times 10^{-10}$ M, $1 \times 10^{-11}$ M, $1 \times 10^{-12}$ M, or less, or bind to an antigen with an affinity that is at least two-fold greater than its affinity for a nonspecific antigen.

As used herein, an "epitope" refers to a localized region of an antigen to which an antibody can specifically bind. An epitope can be, for example, contiguous amino acids of a polypeptide (a linear or contiguous epitope) or an epitope can, for example, be formed from two or more non-contiguous regions of a polypeptide or polypeptides (a conformational, non-linear, discontinuous, or non-contiguous epitope). In certain embodiments, the epitope to which an antibody binds can be determined by, e.g., NMR spectroscopy, X-ray diffraction crystallography studies, ELISA assays, hydrogen/deuteriwn exchange coupled with mass spectrometry (e.g., liquid chromatography electrospray mass spectrometry), peptide scanning assays, or mutagenesis mapping (e.g., site-directed mutagenesis mapping).

As used herein, the term "treat," "treating," and "treatment" refer to therapeutic or preventative measures described herein. The methods of "treatment" employ administration of an anti-ApoC3 antibody to a subject having a disease or disorder, or predisposed to having such a disease or disorder, in order to prevent, cure, delay, reduce the severity of, reduce the risk of developing, or ameliorate one or more symptoms of the disease or disorder or recurring disease or disorder, or in order to prolong the survival of a subject beyond that expected in the absence of such treatment.

As used herein, the term "effective amount" in the context of the administration of a therapy to a subject refers to the amount of a therapy that achieves a desired prophylactic or therapeutic effect.

As used herein, the term "subject" includes any human or non-human animal.

As used herein, the term "or" means and/or.

As used herein, the terms "about" and "approximately," when used to modify a numeric value or numeric range, indicate that deviations of 5% to 10% above and 5% to 10% below the value or range remain within the intended meaning of the recited value or range.

2. Anti-ApoC3 Antibodies

The instant disclosure provides antibodies (e.g., isolated antibodies) that specifically bind to ApoC3 (e.g., human ApoC3) and inhibit ApoC3 function.

In certain embodiments, the anti-ApoC3 antibodies bind to ApoC3 protein of a mammal. In certain embodiments, the anti-ApoC3 antibodies bind to human ApoC3. In certain embodiments, the anti-ApoC3 antibodies bind to *Macaca fascicularis* (cynomologus monkey) ApoC3. In certain embodiments, the anti-ApoC3 antibodies bind to murine ApoC3.

In certain embodiments, the anti-ApoC3 antibodies disclosed herein attenuate the ability of ApoC3 to inhibit hepatocyte uptake of TRL (e.g., VLDL) or TRL remnants (in vivo or in vitro). In certain embodiments, the anti-ApoC3 antibodies disclosed herein attenuate the ability of ApoC3 to inhibit hepatocyte uptake of TRL (e.g., VLDL) or TRL remnants by at least 5%, 10%, 15%, 20%, 25%, 30%, 35%, 40%, 45%, 50%, 55%, 60%, 65%, 70%, 75%, 80%, 85%, 90%, 95%, 98%, or 99%, as assessed by methods described herein or by methods known to one of skill in the art. In certain embodiments, the anti-ApoC3 antibodies disclosed herein attenuate the ability of ApoC3 to inhibit hepatocyte uptake of TRL (e.g., VLDL) or TRL remnants by at least about 1.1 fold, 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold, as assessed by methods described herein or by methods known to one of skill in the art.

In certain embodiments, the antibodies disclosed herein are capable of inhibiting post-prandial lipemia in a subject when administered to the subject prior to, during, or after a meal. In certain embodiments, the anti-ApoC3 antibodies disclosed herein are capable of inhibiting post-prandial lipemia in the subject by at least 5%, 10%, 15%, 20%, 25%, 30%, 35%, 40%, 45%, 50%, 55%, 60%, 65%, 70%, 75%, 80%, 85%, 90%, 95%, 98%, or 99%, as assessed by methods described herein or by methods known to one of skill in the art. In certain embodiments, the anti-ApoC3 antibodies disclosed herein are capable of inhibiting post-prandial lipemia in the subject by at least about 1.1 fold, 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold, as assessed by methods described herein or by methods known to one of skill in the art.

In certain embodiments, the antibodies disclosed herein are capable of reducing the levels of post-prandial chylomicron or chylomicron remnants in a subject when administered to the subject prior to, during, or after a meal. In certain embodiments, the anti-ApoC3 antibodies disclosed herein are capable of reducing the levels of post-prandial chylomicron or chylomicron remnants in a subject by at least 5%, 10%, 15%, 20%, 25%, 30%, 35%, 40%, 45%, 50%, 55%, 60%, 65%, 70%, 75%. 80%, 85%, 90%, 95%, 98%, or 99%, as assessed by methods described herein or by methods known to one of skill in the art. In certain embodiments, the anti-ApoC3 antibodies disclosed herein are capable of reducing the levels of post-prandial chylomicron or chylomicron remnants in a subject by at least about 1.1 fold, 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold, as assessed by methods described herein or by methods known to one of skill in the art.

In certain embodiments, the isolated antibodies disclosed herein are capable of increasing the rates of clearance of ApoC3 and/or ApoB (e.g., ApoB48 and/or ApoB100) from the blood in a subject. In certain embodiments, the anti-ApoC3 antibodies are capable of increasing the rates of clearance of ApoC3 and/or ApoB (e.g., ApoB48 and/or ApoB100) from the blood in a subject by at least 5%, 10%, 15%, 20%, 25%, 30%, 35%, 40%, 45%, 50%, 55%, 60%, 65%, 70%, 75%, 80%, 85%, 90%, 95%, 98%, or 99%, as assessed by methods disclosed herein or by methods known to one of skill in the art. In certain embodiments, the anti-ApoC3 antibodies disclosed herein are capable of increasing the rates of clearance of ApoC3 and/or ApoB (e.g., ApoB48 and/or ApoB100) from the blood in a subject by at least about 1.1 fold, 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold, as assessed by methods disclosed herein or by methods known to one of skill in the art. Methods for assessing the clearance of ApoC3 and/or ApoB (e.g., ApoB48 and/or ApoB100) include without limitation the isotope tracer techniques, wherein the isotope can be either radioactive or stable.

In certain embodiments, the isolated antibodies disclosed herein are capable of reducing the levels of ApoC3 and/or ApoB (e.g., ApoB48 and/or ApoB100) in the blood in a subject. In certain embodiments, the anti-ApoC3 antibodies are capable of reducing the levels of ApoC3 and/or ApoB (e.g., ApoB48 and/or ApoB100) in the blood in a subject by at least 5%, 10%, 15%, 20%, 25%, 30%, 35%, 40%, 45%, 50%, 55%, 60%, 65%, 70%, 75%, 80%, 85%, 90%, 95%, 98%, or 99%, as assessed by methods disclosed herein or by methods known to one of skill in the art. In certain embodiments, the anti-ApoC3 antibodies disclosed herein are capable of reducing the levels of ApoC3 and/or ApoB (e.g., ApoB48 and/or ApoB100) in the blood in a subject by at least about 1.1 fold, 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold, as assessed by methods disclosed herein or by methods known to one of skill in the art. In certain embodiments, the reduction in the levels of ApoC3 and/or ApoB ApoB48 and/or ApoB100) in the blood in the subject is maintained for at least 1, 2, 3, 4, 5, 6, 7, 8, 9, 10, 12, 15, 18, 24, 30, 36, 42, or 48 hours.

In certain embodiments, the antibodies disclosed herein attenuate the ability of ApoC3 to inhibit lipoprotein lipase-mediated lipolysis of TRL (e.g., VLDL). In certain embodiments, the anti-ApoC3 antibodies disclosed herein attenuate the ability of ApoC3 to inhibit lipoprotein lipase-mediated lipolysis of TRL (e.g., VLDL) by at least 5%, 10%, 15%, 20%, 25%, 30%, 5%, 40%, 45%, 50%, 55%, 65%, 70%, 75%, 85%, 90%, 95%, 98%, or 99%, as assessed by methods described herein or by methods known to one of skill in the art. In certain embodiments, the anti-ApoC3 antibodies disclosed herein attenuate the ability of ApoC3 to inhibit lipoprotein lipase-mediated lipolysis of TRL (e.g., VLDL) by at least about 1.1 fold, 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold, as assessed by methods described herein or h methods known to one of skill in the art. In certain embodiments, the anti-ApoC3 antibodies disclosed herein attenuate the ability of ApoC3 to inhibit lipoprotein lipase-mediated lipolysis of TRL (e.g., VLDL) by at least 50% at the concentration of 1, 2, 3, 4, or 5 µM.

In certain embodiments, the antibodies disclosed herein inhibit the binding of ApoC3 to a lipid or a lipoprotein. In certain embodiments, the lipid comprises a fatty acid chain. In certain embodiments, the lipid comprises a phosphatidyl group. In certain embodiments, the lipid comprises a phosphatidylcholine (e.g., DMPC), a phosphatidylserine, a phosphatidylethanolamine, a phosphatidylinositol or a phosphatidylglycerol. In certain embodiments, the lipid is a triglyceride. In certain embodiments, the lipoprotein is a TRL (e.g., VLDL) or a TRL remnant. In certain embodiments, the anti-ApoC3 antibodies disclosed inhibit the binding of ApoC3 to lipids and lipoproteins (e.g., triglyceride, TRL (e.g., VLDL) or TRL remnants) by at least 5%, 10%, 15%, 20%, 25%, 30%, 35%, 40%, 45%, 50%, 55%, 60%, 65%, 70%, 75%, 80%, 85%, 90%, 95%, 98%, or 99%, as assessed by methods described herein or by methods known to one of skill in the art. In certain embodiments, the anti-ApoC3 antibodies disclosed herein attenuate the binding of ApoC3 to lipids and lipoproteins (e.g., triglyceride, TRL (e.g., VLDL) or TRL remnants) by at least about 1.1 fold, 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold, as assessed by methods described herein or by methods known to one of skill in the art.

In certain embodiments, the antibodies disclosed herein are capable of binding to lipid-bound ApoC3 (e.g., ApoC3 bound to triglyceride, TRL (e.g., VLDL) or TRL remnants), as assessed by methods described herein (e.g., in Example 3) or by methods known to one of skill in the art.

The antibodies disclosed herein can have one or more, two or more, three or more, four or more, five or more, six or more, seven of more, or all of the characteristics as set forth in the foregoing embodiments. For example, in certain embodiments, the antibodies disclosed herein attenuate the ability of ApoC3 to inhibit hepatocyte uptake of TRL (e.g., VLDL) or TRL remnants by at least about 10%, 20%, 30%, 40%, 50%, 60%, 70%, 80%, 90%, 95%, or 99%, and attenuate the ability of ApoC3 to inhibit lipoprotein lipase-mediated lipolysis of TRL (e.g., VLDL) or TRL remnants by at least 50% at the concentration of 1, 2, 3, 4, or 5 µM. In certain embodiments, the antibodies disclosed herein attenuate the ability of ApoC3 to inhibit hepatocyte uptake of TRL (e.g., VLDL) or TRL remnants by at least about 10%, 20%, 30%, 40%, 50%, 60%, 70%, 80%, 90%, 95%, or 99%, and are capable of binding to lipid-bound ApoC3 (e.g., ApoC3 bound to triglyceride, TRL (e.g., VLDL) or TRL remnants.

Any suitable assays can be used to measure the foregoing functional activities of the antibodies disclosed herein. Exemplary assays include, but are not limited to, the functional assays disclosed in the Examples herein.

The amino acid sequences of exemplary anti-ApoC3 antibodies are set forth in Tables 1-4, herein.

TABLE 1

Heavy chain CDR amino acid sequences of exemplary anti-ApoC3 antibodies.

| VH clone | CDRH1 | SEQ ID NO: | CDRH2 | SEQ ID NO: | CDRH3 | SEQ ID NO: |
|---|---|---|---|---|---|---|
| 5A11 | TRYYA | 4 | VIAYDGSTYYSPSLKS | 5 | VRLIEAPYEYDY | 6 |
| 5E5 | TYSMR | 7 | SISTDGGGTAYRDSVKG | 8 | AGYSD | 9 |
| 6A6 | SYAGR | 10 | SINAGGGSTSYADSVK | 11 | NSYRY | 12 |
| 8F4 | SYSMY | 13 | AIKTDGGSTNYADSVK | 14 | QGYGT | 15 |
| 11H1 | SYSMR | 16 | SIKSDGSITSYADSVKG | 17 | QGYIN | 18 |
| 5A4 | HYTMY | 19 | AISGGGDRTIYTDSVKG | 20 | QGYEY | 21 |
| 5A7 | NRRYA | 22 | VIVYDGNTHVSPSLRS | 23 | VLLLRDPLSLDY | 24 |
| 8A4 | NYAMR | 25 | SIDSGGDRTKYGDSVKG | 26 | QGYIF | 27 |
| 8B4 | NAYLY | 28 | GINPAGDGRAYATSVKG | 29 | ASRVVAYDS | 30 |
| 8H4 | SYSMR | 16 | SINSDGGSTKISDSVKG | 31 | QGYTD | 32 |
| 10B6 | SYAMR | 33 | SINIDGGSTRYTDSVQG | 34 | QGYIY | 35 |
| 12A3 | NYAMR | 25 | SINIAGSSVVYADSVK | 36 | QGFVY | 37 |
| 12C3 | SYSMF | 38 | GINGGGDRSNYADSVRD | 39 | QGYAY | 40 |
| 12C12 | TSYYAWT | 41 | AIVYDGSTFYSPSLKS | 42 | SYGLGLYDL | 43 |
| 12D1 | TYSMR | 7 | SISTDGGGTAYRDSVKG | 8 | AGYSD | 9 |
| 12D4 | SSNMR | 47 | TISPDGGKTLYADSVKG | 48 | AGYDY | 49 |
| 12E12 | NIYMS | 50 | AINTAGTVTYYADSVKG | 51 | GEVD | 52 |
| 13C7 | RYYMS | 53 | SIYKDGSNTYADSVKG | 54 | ALRAEYDY | 55 |
| 13G7 | TTAPAWG | 56 | VIAFDGSAYYSPSLKS | 57 | LGGRNYPPYVEL | 58 |
| 14C4 | NYDMS | 59 | VINSDGDGTYYVDSVKG | 60 | ANLGL | 61 |
| 14C7 | TNSYYWS | 62 | AIDYSGDTYYSPSLKS | 63 | RIPTGEY | 64 |
| 14G4 | RYTMN | 65 | AISPDGGKTIDADSVK | 66 | GHNMDY | 67 |
| 12D7 | DYAMS | 68 | AITSNGKRTDYAESMK | 69 | GPPHYIPIPSMTPRDS | 70 |
| 12G8 | DYAMS | 68 | AIRWNGDTYYAESMK | 71 | HRPGGALDT | 72 |

TABLE 2

Light chain CDR amino acid sequences of exemplary anti-ApoC3 antibodies

| VL clone | CDRL1 | SEQ ID NO: | CDRL2 | SEQ ID NO: | CDRL3 | SEQ ID NO: |
|---|---|---|---|---|---|---|
| 5A11 | GLSSGSVTTRSYPG | 73 | STSSRHS | 74 | ALDIGSYIV | 75 |
| 5E5 | KTSQGLVHSDGKTYFY | 76 | QVSNRAS | 77 | AQGTYYPHT | 78 |
| 6A6 | KASQSLIHTDGKTYLY | 79 | QVSSHES | 80 | AQATYNPRT | 81 |
| 8F4 | KASQSLVHSDGKTYLY | 82 | QVSNRGS | 83 | AQATYYGHS | 84 |
| 11H1 | RASQSLIHSAGKTYFY | 85 | QVSNRES | 86 | AQGTYNPKT | 87 |
| 5A4 | KAIQSLVHTDGKTYLY | 88 | QVSNRGS | 83 | AQGTYSSKT | 89 |
| 5A7 | AGTSSDIGAYNFVS | 90 | DIDKRAS | 91 | AAYGSRDNVV | 92 |
| 8A4 | KASQSLVHSDGKTYLY | 82 | QVSNHES | 93 | AQATYYPLT | 94 |
| 8B4 | KSSQSVESGSDQKSYLN | 95 | YASTQES | 96 | QQAYSAPFT | 97 |
| 8H4 | KVSQSLVHSDGKTYLY | 98 | QVSNRDS | 99 | AQGTYNPYT | 100 |
| 10B6 | KASQSLVHSNGVIYFY | 101 | QVSNRDS | 99 | AQGTYYPHS | 102 |
| 12A3 | KAGRSLVHSDGRTYLY | 103 | QVSNRSS | 104 | AQGTYYPVT | 105 |
| 12C3 | KASQSLVHSDGKTYLY | 82 | QTSNRGS | 106 | AQATYSPHT | 107 |
| 12C12 | TGSSSNIGDNYVN | 108 | SNSNRAS | 109 | SSWDDSLSGVV | 110 |
| 12D1 | KTSQSLTHSDGKTYLY | 111 | QVSNRGS | 83 | AQATYYPHT | 113 |
| 12D4 | KASQSLVHSDGKTYLY | 82 | QVSNQGS | 114 | AQATYAPHS | 115 |
| 12E12 | GLSSGSVTSVTYPG | 116 | NTNSRFS | 117 | SVYIGGGIYPAV | 118 |
| 13C7 | AGTSSDIGGYNYVA | 119 | EVNKRAS | 120 | ASYRSSNSYV | 121 |
| 13G7 | QGGSLRVSYAH | 122 | DDDSRPS | 123 | QSADSSGDNWV | 124 |
| 14C4 | KATQSLVHSDGKTYLS | 125 | QVSNRGS | 83 | AQAPYWT | 126 |
| 14C7 | GLNSGSVTSSNYPD | 127 | NTNSRHS | 128 | ALYMGSDSVV | 129 |
| 14G4 | KASQSLVHSDGKTYLY | 82 | QVSNQGS | 114 | AQATYTPRT | 130 |
| 12D7 | QGGTLGRYYGS | 131 | GDNSRPS | 132 | ESFDFSGNAAV | 133 |
| 12G8 | QGGNFGNFYAS | 134 | KDSERPS | 135 | QSGSSSDNVV | 136 |

TABLE 3

VH amino acid sequences of exemplary anti-ApoC3 antibodies.

| VH clone | Amino acid Sequence | SEQ ID NO |
|---|---|---|
| 5A11 | QVQVQESGPGLVKPSQTLSLTCTVSGVSITTRYYAWSWIRQPPG KGLEWMGVIAYDGSTYYSPSLKSRTSISRDTSKNQFSLQLTSVTP EDTAVYYCARVRLIEAPYEYDYWGQGTQVTSS | 137 |
| 5E5 | QLQLVESGGGLVQPGGSLRLSCAASGFTFGTYSMRWVRQVPRK ALEWVSSISTDGGGTAYRDSVKGRFTISRDNAKNTLYLQMNNL KPEDTAIYYCVIAGYSDWGQGTQVTSS | 138 |
| 6A6 | EVQLVESGGGLVQPGGSLRLSCAASGFTFSSYAGRWVRQVPGK GLEWVSSINAGGGSTSYADSVKGRFTISRDNAKNTLYLQMNSLK PEDTAKYYCTQNSYRYWGQGTRVAVSS | 139 |
| 8F4 | QLQLVESGGGLVQPGGSLRLSCAASGFAFSSYSMYWVRQAPGK GLERVAAIKTDGGSTNYADSVKGRFTVSRDNAKNTLYLQMNSL KSEDTAVYYCVIQGYGTWGQGTQVTSS | 140 |

TABLE 3-continued

VH amino acid sequences of exemplary anti-ApoC3 antibodies.

| VH clone | Amino acid Sequence | SEQ ID NO |
|---|---|---|
| 11H1 | ELQLVESGGGLVQPGGSLRLSCAASGFTFSSYSMRWVRQAPGK GLEWLSSIKSDGSITSYADSVKGRFTMSRDNAKNTLYLQMNSLK SEDTAMYYCTNQGYINWGQGTQVTVSS | 141 |
| 5A4 | QLQLVESGGGLVQPGGSLRLSCVASGFAFSHYTMYWVRQAPVR GLERVSAISGGGDRTIYTDSVKGRFTISRDNAANALYLQMNSLQ PEDTAVYYCVAQGYEYWGQGTRNTVSS | 142 |
| 5A7 | EVQVQESGPGLVKPSQTLSLTCTVSGASITNRRYAWTWIRQPPG KGLEWMGVIVYDGNTHVSPSLRSRTSISRDTSKNQFSLQLSSLTP EDTAVYYCARVLLLRDPLSLDYWGQGTQVTVSS | 143 |
| 8A4 | QVQLVESGGGLVQPGGSLKVSCTASGFTFNNYAMRWVRQAEG KGLEWVSSIDSGGDRTKYGDSVKGRFSISRDNAKNTVYLQMDA LKPEDTGVYYCVSQGYIFWGQGAQVTVSS | 144 |
| 8B4 | ELQLVESGGGLVQPGGSLRLSCAASGFTFSNAYLYWVRQVPGK GLEWVSGINPAGDGRAYATSVKGRFTISRDNAKNTLYLQMNTL ESDDTAVYYCATASRVVAYDSWGQGTQVTVSS | 145 |
| 8H4 | ELQLVESGGGLVQPGRSLRLSCAASGFTFSSYSMRWVRQTPGKG LEWVTSINSDGGSTKYSDSVKGRFTISRDNAKNTLYLQMNNVKP EDTAIYYCAIQGYTDWGQGTQVTVSS | 146 |
| 10B6 | EVQLVESGGGLVQPGGSLRLSCAASGFTFSSYAMRWVRQAPGK GLEWISSINIDGGSTRYTDSVQGRFTVSRDNAKNTLYLQMNNLK PEDTGIYYCTIQGYIYWGQGTQVTVSS | 147 |
| 12A3 | ELQLVESGGGLVQSGGSLRLSCAASGFTFSNYAMRWVRQAPGG RLEWVSSINIAGSSVVYADSVKGRFTISRDNAKNTLYLQMNSLK SEDTAVYYCAMQGFVYWGQGTQVTVSS | 148 |
| 12C3 | ELQLVESGGGLVQPGGSLRLSCAASGFTFSSYSMFWVRQSPGKG LERVSGINGGGDRSNYADSVRDRFTISRDNAKNTLYLQMNSLKS EDTAVYYCVIQGYAYWGQGTQVTVSS | 149 |
| 12C12 | EVQVQESGPGLVKPSQTLSLTCTVSGGSITTSYYAWTWIRQPPG KGLEWVGAIVYDGSTFYSPSLKSRTSISRDTSKSQFSLQLSSVTPE DTAVYYCARSYGLGLYDLWGQGTQVTVSS | 150 |
| 12D1 | QLQLVESGGGLVQPGGSLRLSCAASGFTFGTYSMRWVRQVPRK ALEWVSSISTDGGGTAYRDSVKGRFTISRDNAKNTLYLQMNNL KPEDTAIYYCVIAGYSDWGQGTQVTVSS | 138 |
| 12D4 | QLQLVESGGGLVQPGGSLRVSCAASGFTFSSSNMRWVRQVSGK GLEWVSTISPDGGKTLYADSVKGRFTISRDNAKNTLHLQMVSLK PEDTALYYCVKAGYDVWGQGTQVTVSS | 152 |
| 12E12 | EVQLVESGGDLVQPGGSLRVSCAASGLTFSNIYMSWVRQAPGK GLEWVSAINTAGTVTYYADSVKGRFTISRDNAKNTLYLQMNSL KPEDTAHYYCTTGEVDWGKGTLVTVSS | 153 |
| 13C7 | QLQLVESGGGLVQPGGSLRLSCAASGGTFSRYYMSWVRQAPGK GLEWVSSIYKDGSNTYYADSVKGRFTISRDNAKNTLYLQMNSL KSEDTAVYYCAKALRAEYDYWGQGTQVTVSS | 154 |
| 13G7 | QVQLQESGPGLVKPSQTLSLTCTVSGGSISTTAPAWGWIRQSPG KGLDWMAVIAFDGSAYYSPSLKSRTLISRDTSKNQFSLQLSSVTP EDTAVYYCARLGGRNYPPYVELWGQGTLVTVSS | 155 |
| 14C4 | QLQLVESGGGLVQPGGSLRLSCAASGFTFGNYDMSWVRQAPGK GPEWVSVINSDGDGTYYVDSVKGRFTISRDNAKNTLYLQMNSL KPEDRAVYYCAIANLGLWGQGTLVTVSS | 156 |
| 14C7 | QVQVQESGPGLVKPSQTLSLTCTVSGGSITTNSYYWSWIRQPPG KGLEWMGAIDYSGDTYYSPSLKSRTSISRDTSKNQFTLQLTSVTP EDTAVYYCVSRIPTGEYWGQGTQVTVSS | 157 |
| 14G4 | QVQLVESGGGLVQPGGSLRLSCAASGFAFSRYTMNWVRQAPGK GLEWLSAISPDGGKTIDADSVKGAFASSRDNTMNTLYLDMNSL KPEDAAVYYCVAGHNMDYWGKGILVTVSS | 158 |
| 12D7 | ELQLVESGGDLVQPGGSLRLSCAASGFTFDDYAMSWVRQAPGK GLEWVSAITSNGKRTDYAESMKGRFTISRDNSKNTLYLEMNSLK SEDTAVYYCTKGPPHYIPIPSMTPRDSWGQGTQVTVSS | 159 |

TABLE 3-continued

VH amino acid sequences of exemplary anti-ApoC3 antibodies.

| VH clone | Amino acid Sequence | SEQ ID NO |
|---|---|---|
| 12G8 | QLQLVESGGGLVQPGGSLRLSCAASGFTFDDYAMSWVRQAPGK GLEWVSAIRWNGDTYYAESMKGRFDMSRDNAKNTLYLQMNSL KSEDTAVYYCAKHRPGGALDTWGQGTLVTVSS | 160 |

TABLE 4

VL amino acid sequences of exemplary anti-ApoC3 antibodies.

| VL clone | Amino acid Sequence | SEQ ID NO |
|---|---|---|
| 5A11 | QAVVTQEPSLSVSPGGTVTLTCGLSSGSVTTRSYPGWFQQTPGQ APRSLIHSTSSRHSGIPTRFSGSISGNKAALTITGAQPEDEADYYC ALDIGSYIVFGGGTHLTVL | 161 |
| 5E5 | ATMLTQSPGSLSVVPGESASISCKTSQGLVHSDGKTYFYWFLQK PGQSPQQLIYQVSNRASGVPDRFTGSGSGTDFTLKISGVKAEDA GVYYCAQGTYYPHTFGSGTRLEIK | 162 |
| 6A6 | DVVLTQTPGSLSVVPGESASISCKASQSLIHTDGKTYLYWLLQKP GQRPQLLIYQVSSHESGVPDRFTGSGSGTDFTLKISGVKAEDAGV YYCAQATYNPRTFGQGTKLEIK | 163 |
| 8F4 | DLVLTQIPGSLSVVPGESASISCKASQSLVHSDGKTYLYWLLQKP GQSPQRLIYQVSNRGSGVPDRFTGSGSGTDFTLKISGVEAEDAG VYYCAQATYYGHSFGSGTRLEIK | 164 |
| 11H1 | ATMLTQSPGSLTIVPGESASISCRASQSLIHSAGKTYFYWLLQKP GQRPQLLIYQVSNRESGVPDRFTGSGSGTDFTLKISGVKAEDAG VYYCAQGTYNPKTFGQGTKLEIK | 165 |
| 5A4 | ATMLTQSPGSLSVVPGESASISCKAIQSLVHTDGKTYLYWFLQK PGQSPQRLIYQVSNRGSGVPDRFTGSGSGTDFTLKISGVKAEDAG VYYCAQGTYSSKTFGQGTKLEIK | 166 |
| 5A7 | SSALTQPPSMSGTLGKTLTISCAGTSSDIGAYNFVSWYQQLPGTA PKLLIYDIDKRASGIPDRFSGSKSGNTASLSISGLQSEDEADYYCA AYGSRDNVVFGGGTHLTVL | 167 |
| 8A4 | ATMLTQSPGSLSVVPGESASISCKASQSLVHSDGKTYLYWLLQK PGQRPQLLIYQVSNHESGVPDRFTGSGSGTDYTLKISGVKAEDA GVYYCAQATYYPLTFGQGTKVELK | 168 |
| 8B4 | EIVLTQSPSSVTASVGEKVTINCKSSQSVESGSDQKSYLNWYQQ RPGQSPRLLIYYASTQESGIPDRFSGSGSTTDFTLTISSVQPEDAA VYYCQQAYSAPFTFGQGTKVELK | 169 |
| 8H4 | DVVLTQTPGSLSVVPGESASISCKVSQSLVHSDGKTYLYWLLQK PGQSPQRLIYQVSNRDSGVPDRFTGSGSGTDFTLKISGVKAEDAG VYYCAQGTYNPYTFGSGTRLEIK | 170 |
| 10B6 | ATMLTQSPGSLSIVPGESASISCKASQSLVHSNGVIYFYWLLQKP GQSPQRLIYQVSNRDSGVPDRFTGSGSGTDFTLKISGVKAEDAG VYYCAQGTYYPHSFGSGTRLQIK | 171 |
| 12A3 | DVVLTQTPGSLSVVPGESANISCKAGRSLVHSDGRTYLYWLLQK PGQSPQRLIYQVSNRSSGVPDRFTGSGSGTDFTLKITGVKAEDAG VYYCAQGTYYPVTFGQGTKVELK | 172 |
| 12C3 | DVVLTQTPASLSVVPGESASISCKASQSLVHSDGKTYLYWLLQK PGQSPQRLIYQTSNRGSGVPDRFTGSGSGTDFTLDISGVKAEDAG VYYCAQATYSPHTFGSGTRLEIK | 173 |
| 12C12 | QAVLTQPPSVSGSPGQKFTISCTGSSSNIGDNYVNWYQHLPGTAP KLLIYSNSNRASGVPDRFSGSKSGSSASLTITGLQAEDEADYYCS SWDDSLSGVVFGGGTHLTVL | 174 |
| 12D1 | SALDVVLTQTPGSLSVVPGESASISCKTSQSLTHSDGKTYLYWLL QKPGQSPQRLIYQVSNRGSGVPDRFTGSGSGTDFTLKISGVKAED AGMYYCAQATYYPHTFGSGSRLEIER | 175 |

TABLE 4-continued

VL amino acid sequences of exemplary anti-ApoC3 antibodies.

| VL clone | Amino acid Sequence | SEQ ID NO |
|---|---|---|
| 12D4 | ATMLTQSPGSLSVVPGESASISCKASQSLVHSDGKTYLYWLLQK PGQSPQRLIYQVSNQGSGVPDRFTGSGSGTDFTLKISGVKAEDA GVYYCAQATYAPHSFGSGTRLEIK | 176 |
| 12E12 | QTVVTQEPSLSVSPGGTVTLTCGLSSGSVTSVTYPGWYQQKPGQ APRTLIYNTNSRFSGVPNRFSGSISGNKAALTITGALPEDEADYY CSVYIGGGIYPAVFGGGTHLTVL | 177 |
| 13C7 | NFMLTQPPSVSGTLGKTVTISCAGTSSDIGGYNYVAWYQQLPGT APKLLISEVNKRASGIPDRFSGSKSGNTASLSISGLQSEDEADYYC ASYRSSNSYVFGGGTKLTVL | 178 |
| 13G7 | QPVLTQPPALSVTLGQTAKITCQGGSLRVSYAHWYQQKPGQAP VLVSYDDDSRPSGIPERFSGSGSGATATLTISGAQAEDEGDYYCQ SADSSGDNWVFGGGTHLTVL | 179 |
| 14C4 | ATMLTQSPGSLSVVPGESASISCKATQSLVHSDGKTYLSWLLQK PGQSPQRLIYQVSNRGSGVPDRFTGSGSGTDFTLKISGVKAEDAG VYYCAQAPYWTFGQGTKLEIK | 180 |
| 14C7 | QTVVTQEPSLSVSPGGTVTLTCGLNSGSVTSSNYPDWYQQTPGQ APRLLIYNTNSRHSGVPSRFSGSISGNKAALTITGAQPEDEADYY CALYMGSDSVVFGGGTHLTVL | 181 |
| 14G4 | DVVLTQTPGSLSVVPGESASISCKASQSLVHSDGKTYLYWLLQK PGQSPQRLIYQVSNQGSGVPDRFTGSGSGTDFTLKISGVKAEDA GVYYCAQATYTPRTFGQGTTLEVK | 182 |
| 12D7 | SSALTQPSAVSVSLGQTARITCQGGTLGRYYGSWYQQKPAQAP VLLIYGDNSRPSGIPERFSGSKSGDTATLTISGTQAEDEADYYCES FDFSGNAAVFGGGTHLTVL | 183 |
| 12G8 | QAVLTQPSAVSVSLGQTARITCQGGNFGNFYASWYQQKPGQAP VLVIYKDSERPSGIPERFSGSSSGDTATLTISGAQAEDEADYYCQS GSSSDNVVFGGGTHLTVL | 151 |

In one aspect, the instant disclosure provides an isolated antibody that specifically binds to ApoC3 (e.g, human ApoC3), the antibody comprising a VH domain comprising one, two, or all three of the CDRs of a VH domain set forth in Table 3 herein. In certain embodiments, the antibody comprises the CDRH1 of one of VH domains set forth in Table 3. In certain embodiments, the antibody comprises the CDRH2 of one of the VH domains set forth in Table 3. In certain embodiments, the antibody comprises the CDRH3 of one of the VH domains set forth in Table 3.

In another aspect, the instant disclosure provides an isolated antibody that specifically binds to ApoC3 (e.g., human ApoC3), the antibody comprising a VL domain comprising one, two, or all three of the CDRs of a VL domain disclosed in Table 4 herein. In certain embodiments, the antibody comprises the CDRH1 of one of VL domains set forth in Table 4. In certain embodiments, the antibody comprises the CDRH2 of one of the VL domains set forth in Table 4. In certain embodiments, the antibody comprises the CDRH3 of one of the VL domains set forth in Table 4.

In certain embodiments, the CDRs of an antibody can be determined according to Kabat et al., J. Biol. Chem. 252, 6609-6616 (1977) and Kabat et al., Sequences of protein of immunological interest (1991). In certain embodiments, the light chain CDRs of an antibody are determined according to Kabat and the heavy chain CDRs of an antibody are determined according to MacCallum (supra).

In certain embodiments, the CDRs of an antibody can be determined according to the Chothia numbering scheme, which refers to the location of immunoglobulin structural loops (see, e.g., Chothia C & Lesk A M, (1987), J Mol Biol 196: 901-917; Al-Lazikani B et al., (1997) J Mol Biol 273: 927-948; Chothia. C et al., (1992) J Mol Biol 227: 799-817; Tramontano A et al., (1990) J Mol Biol 215(1): 175-82; and U.S. Pat. No. 7,709,226). Typically, when using the Kabat numbering convention, the Chothia CDRH1 loop is present at heavy chain amino acids 26 to 32, 33, or 34, the Chothia CDRH2 loop is present at heavy chain amino acids 52 to 56, and the Chothia CDRH3 loop is present at heavy chain amino acids 95 to 102, while the Chothia CDRL1 loop is present at light chain amino acids 24 to 34, the Chothia CDRL2 loop is present at light chain amino acids 50 to 56, and the Chothia CDRL3 loop is present at light chain amino acids 89 to 97. The end of the Chothia CDRH1 loop when numbered using the Kabat numbering convention varies between H32 and H34 depending on the length of the loop (this is because the Kabat numbering scheme places the insertions at H35A and H35B; if neither 35A nor 35B is present, the loop ends at 32; if only 35A is present, the loop ends at 33; if both 35A and 35B are present, the loop ends at 34).

In certain embodiments, the CDRs of an antibody can be determined according to the IMGT numbering system as described in Lefranc M-P, (1999) The Immunologist 7: 132-136 and Lefranc M-P et al., (1999) Nucleic Acids Res 27: 209-212. According to the IMGT numbering scheme, CDRH1 is at positions 26 to 35, CDRH2 is at positions 51 to 57, CDRH3 is at positions 93 to 102, CDRL1 is at positions 27 to 32, CDRL2 is at positions 50 to 52, and CDRL3 is at positions 89 to 97.

In certain embodiments, the CDRs of an antibody can be determined according to the AbM numbering scheme, which refers to AbM hypervariahie regions, which represent a compromise between the Kabat CDRs and Chothia structural loops, and are used by Oxford Molecular's AbM antibody modeling software (Oxford Molecular Group, Inc.).

In certain embodiments, the CDRs of an antibody can be determined according to MacCallum R M et al., (1996) J Mol Biol 262: 732-745. See also, e.g., Martin A, "Protein Sequence and Structure Analysis of Antibody Variable Domains," in *Antibody Engineering*, Kontermann and Dübel, eds., Chapter 31, pp. 422-439, Springer-Verlag, Berlin (2001).

In certain embodiments, the instant disclosure provides an isolated antibody that specifically binds to ApoC3 (e.g., human ApoC3), wherein the antibody comprises a heavy chain variable region comprising the CDRH1, CDRH2, and CDRH3 region amino acid sequences of a VH domain set forth in Table 3, and a light chain variable region comprising the CDRL1, CDRL2, and CDRL3 region amino acid sequences of a VL domain set forth in Table 4, wherein each CDR is independently defined in accordance with the Kabat, Chothia, IMGT, MacCallum, or AbM definition of a CDR, as disclosed herein.

In another aspect, the instant disclosure provides an isolated antibody that specifically binds to ApoC3 (e.g., human ApoC3), the antibody comprising:
(a) a CDRH1 comprising the amino acid sequence of SEQ ID NO: 4, 7, 10, 13, 16, 19, 22, 25, 28, 33, 38, 41, 47, 50, 53, 56, 62, 65, or 68; or
(b) a CDRH2 comprising the amino acid sequence of SEQ ID NO: 5, 8, 11, 14, 17, 20, 23, 26, 29, 31, 34, 36, 39, 42, 48, 51, 54, 57, 60, 63, 66, 69, or 71; or
(c) a CDRH3 comprising the amino acid sequence of SEQ ID NO: 6, 9, 12, 15, 18, 21, 24, 27, 30, 32, 35, 37, 40, 43, 49, 52, 55, 58, 61, 64, 67, 70, or 72; or
(d) a CDRL1 comprising the amino acid sequence of SEQ ID NO: 73, 76, 79, 82, 85, 88, 90, 95, 98, 101, 103, 108, 111, 116, 119, 122, 125, 127, 131, or 134; or
(e) a CDRL2 comprising the amino acid sequence of SEQ ID NO: 74, 77, 80, 83, 86, 91, 93, 96, 99, 104, 106, 109, 114, 117, 120, 123, 128, 132, or 135; or
(f) a CDRL3 comprising the amino acid sequence of SEQ ID NO: 75, 78, 81, 84, 87, 89, 92, 94, 97, 100, 102, 105, 107, 110, 113, 115, 118, 121, 124, 126, 129, 130, 133, or 136.

In another aspect, the instant disclosure provides an isolated antibody that specifically binds to ApoC3 (e.g., human ApoC3), wherein the antibody comprises a VH domain comprising the CDRH1, CDRH2 and CDRH3 amino acid sequences set forth in SEQ ID NOs: 4, 5, and 6; 7, 8, and 9; 10, 11, and 12; 13, 14, and 15; 16, 17, and 18; 19, 20, and 21; 22, 23, and 24; 25, 26, and 27; 28, 29, and 30; 16, 31, and 32; 33, 34, and 35; 25, 36, and 37; 38, 39, and 40; 41, 42, and 43; 47, 48, and 49; 50, 51, and 52; 53, 54, and 55; 56, 57, and 58; 59, 60, and 61; 62, 63, and 64; 65, 66, and 67; 68, 69, and 70; or 68, 71, and 72; respectively. In certain embodiments, the instant disclosure provides an isolated antibody that specifically binds to ApoC3 (e.g., human ApoC3), wherein the antibody comprises a VH domain comprising the CDRH1, CDRH2 and CDRH3 amino acid sequences set forth in SEQ ID NOs: 7, 8, and 9, respectively. In certain embodiments, the instant disclosure provides an isolated antibody that specifically binds to ApoC3 (e.g., human ApoC3), wherein the antibody comprises a VH domain comprising the CDRH1, CDRH2 and CDRH3 amino acid sequences set forth in SEQ ID NOs: 10, 11, and 12, respectively. In certain embodiments, the instant disclosure provides an isolated antibody that specifically binds to ApoC3 (e.g., human ApoC3), wherein the antibody comprises a VH domain comprising the CDRH1, CDRH2 and CDRH3 amino acid sequences set forth in SEQ ID NOs: 62, 63 and 64, respectively.

In another aspect, the instant disclosure provides an isolated antibody that specifically binds to ApoC3 (e.g., human ApoC3), wherein the antibody comprises a VL domain comprising the CDRL1, CDRL2 and CDRL3 amino acid sequences set forth in SEQ NOs: 73, 74, and 75; 76, 77, and 78; 79, 80, and 81; 82, 83, and 84; 85, 86, and 87; 88, 83, and 89; 90, 91, and 92; 82, 93, and 94; 95, 96, and 97; 98, 99, and 100; 101, 99, and 102; 103, 104, and 105; 82, 106, and 107; 108, 109, and 110; 111, 83, and 113; 82, 114, and 115; 116, 117, and 118; 119, 120, and 121; 122, 123, and 124; 125, 83, and 126; 127, 128, and 129; 82, 114, and 130; 131, 132, and 133; or 124, 135, and 136, respectively. In certain embodiments, the instant disclosure provides an isolated antibody that specifically binds to ApoC3 (e.g., human ApoC3), wherein the antibody comprises a VL domain comprising the CDRL1, CDRL2 and CDRL3 amino acid sequences set forth in SEQ ID NOs: 76, 77, and 78, respectively. In certain embodiments, the instant disclosure provides an isolated antibody that specifically binds to ApoC3 (e.g., human ApoC3), wherein the antibody comprises a VL domain comprising the CDRL1, CDRL2 and CDRL3 amino acid sequences set forth in SEQ ID NOs: 79, 80 and 81, respectively. In certain embodiments, the instant disclosure provides an isolated antibody that specifically binds to ApoC3 (e.g., human ApoC3), wherein the antibody comprises a VL domain comprising the CDRL1, CDRL2 and CDRL3 amino acid sequences set forth in SEQ ID NOs: 62, 63 and 64, respectively.

In another aspect, the instant disclosure provides an isolated antibody that specifically binds to ApoC3 (e.g., human ApoC3), wherein the antibody comprises a heavy chain variable region comprising CDRH1, CDRH2, and CDRH3 regions, and a light chain variable region comprising CDRL1, CDRL2, and CDRL3 regions, wherein the CDRH1, CDRH2, CDRH3, CDRL1, CDRL2, and CDRL3 regions comprise the amino acid sequences set forth in SEQ ID NOs: 4, 5, 6, 73, 74, and 75; 7, 8, 9, 76, 77, and 78; 10, 11, 12, 79, 80, and 81; 13, 14, 15, 82, 83, and 84; 16, 17, 18, 85, 86, and 87; 19, 20, 21, 88, 83, and 89; 22; 23, 24, 90, 91, and 92; 25, 26, 27, 82, 93, and 94; 28, 29, 30, 95, 96, and 97; 16, 31, 32, 98, 99, and 100; 33, 34, 35, 101, 99, and 102; 25, 36, 37, 103, 104, and 105; 38, 39, 40, 82, 106, and 107; 41, 42, 43, 108, 109, and 110; 7, 8, 9, 111, 83, and 113; 47, 48, 49, 82, 114, and 115; 50, 51, 52, 116, 117, and 118; 53, 54, 55, 119, 120, and 121; 56, 57, 58, 122, 123, and 124; 59, 60, 61, 125, 83, and 126; 62, 63, 64, 127, 128, and 129; 65, 66, 67, 82, 114, and 130; 68, 69, 70, 131, 132, and 133; or 68, 71, 72, 124, 135, and 136, respectively. In certain embodiments, the instant disclosure provides an isolated antibody that specifically binds to ApoC3 (e.g., human ApoC3), wherein the antibody comprises a heavy chain variable region comprising CDRH1, CDRH2, and CDRH3 regions, and a light chain variable region comprising CDRL1, CDRL2, and CDRL3 regions, wherein the CDRH1, CDRH2, CDRH3, CDRL1, CDRL2, and CDRL3 regions comprise the amino acid sequences set forth in SEQ ID NOs: 7, 8, 9, 76, 77, and 78, respectively. In certain embodiments, the instant disclosure provides an isolated antibody that specifically binds to ApoC3 (e.g., human ApoC3), wherein the antibody comprises a heavy chain variable region comprising CDRH1, CDRH2, and CDRH3 regions, and a light chain variable region comprising CDRL1, CDRL2, and CDRL3 regions, wherein the CDRH1, CDRH2, CDRH3, CDRL1, CDRL2, and CDRL3 regions comprise the amino acid sequences set forth in SEQ ID NOs: 10, 11, 12, 79, 80 and 81, respectively. In certain embodiments, the instant disclosure provides an isolated antibody that specifically binds to ApoC3 (e.g., human ApoC3), wherein the antibody comprises a heavy chain variable region comprising CDRH1, CDRH2, and CDRH3 regions, and a light chain variable region comprising CDRL1, CDRL2, and CDRL3 regions, wherein the CDRH1, CDRH2, CDRH3, CDRL1, CDRL2, and CDRL3 regions comprise the amino acid sequences set forth in SEQ ID NOs: 62, 63, 64, 127, 128, and 129, respectively.

In another aspect, the instant disclosure provides an isolated antibody that specifically binds to ApoC3 (e.g., human ApoC3), comprising a heavy chain variable region comprising an amino acid sequence that is at least 75%, 80%, 85%, 90%, 95%, or 100% (e.g., at least 86, 87, 88, 89, 90, 91, 92, 93, 94, 9.5, 96, 97, 98 or 99%) identical to the amino acid sequence set forth in SEQ ID NO: 137, 138, 139, 140, 141, 142, 143, 144, 145, 146, 147, 148, 149, 150, 152, 153, 154, 155, 156, 157, 158, 159, or 160. In certain embodiments, the antibody comprises a heavy chain variable region having the amino acid sequence set forth in SEQ ID NO: 137, 138, 139, 140, 141, 142, 143, 144, 145, 146, 147, 148, 149, 150, 152, 153, 154, 155, 156, 157, 158, 159, or 160. In certain embodiments, the antibody comprises a heavy chain variable region having the amino acid sequence set forth in SEQ ID NO: 138. In certain embodiments, the antibody comprises a heavy chain variable region having the amino acid sequence set forth in SEQ ID NO: 139. In certain embodiments, the antibody comprises a heavy chain variable region having the amino acid sequence set forth in SEQ ID NO: 157.

In another aspect, the instant disclosure provides an isolated antibody that specifically binds to ApoC3 (e.g., human ApoC3), comprising a light chain variable region comprising an amino acid sequence that is at least 75%, 80%, 85%, 90%, 95%, or 100% (e.g., at least 86, 87, 88, 89, 90, 91, 92, 93, 94, 95, 96, 97, 98 or 99%) identical to the amino acid sequence set forth in SEQ ID NO: 161, 162, 163, 164, 165, 166, 167, 168, 169, 170, 171, 172, 173, 174, 175, 176, 177, 178, 179, 180, 181, 182, 183, or 151. In certain embodiments, the antibody comprises a light chain variable region having the amino acid sequence set forth in SEQ ID NO: 161, 162, 163, 164, 165, 166, 167, 168, 169, 170, 171, 172, 173, 174, 175, 176, 177, 178, 179, 180, 181, 182, 183, or 151. In certain embodiments, the antibody comprises a light chain having the amino acid sequence set forth in SEQ ID NO: 162. In certain embodiments, the antibody comprises a light chain having the amino acid sequence set forth in SEQ ID NO: 163. In certain embodiments, the antibody comprises a light chain having the amino acid sequence set forth in SEQ ID NO: 181.

In another aspect, the instant disclosure provides an isolated antibody that specifically binds to ApoC3 (e.g., human ApoC3), comprising a heavy chain variable region comprising an amino acid sequence that is at least 75%, 80%, 85%, 90%, 95%, or 100% (e.g., at least 86, 87, 88, 89, 90, 91, 92, 93, 94, 95, 96, 97, 98 or 99%) identical to the amino acid sequence set forth in SEQ ID NO: 137, 138, 139, 140, 141, 142, 143, 144, 145, 146, 147, 148, 149, 150, 152, 153, 154, 155, 156, 157, 158, 159, or 160, and a light chain variable region comprising an amino acid sequence that is at least 75%, 80%, 85%, 90%, 95%, or 100% (e.g., at least 86, 87, 88, 89, 90, 91, 92, 93, 94, 95, 96, 97, 98 or 99%) identical to the amino acid sequence set forth in SEQ ID NO: 161, 162, 163, 164, 165, 166, 167, 168, 169, 170, 171, 172, 173, 174, 175, 176, 177, 178, 179, 180, 181, 182, 183, or 151. In certain embodiments, the antibody comprises a heavy chain variable region having the amino acid sequence set forth in SEQ ID NO: 137, 138, 139, 140, 141, 142, 143, 144, 145, 146, 147, 148, 149, 150, 152, 153, 154, 155, 156, 157, 158, 159, or 160, and a light chain variable region having the amino acid sequence set forth in SEQ ID NO: 161, 162, 163, 164, 165, 166, 167, 168, 169, 170, 171, 172, 173, 174, 175, 176, 177, 178, 179, 180, 181, 182, 183, or 151. In certain embodiments, the antibody comprises a heavy chain variable region and light chain variable region having the amino acid sequences set forth in SEQ ID NOs: 137 and 161, 138 and 162, 139 and 163, 140 and 164, 141 and 165, 142 and 166, 143 and 167, 144 and 168, 145 and 169, 146 and 170, 147 and 171, 148 and 172, 149 and 173, 150 and 174, 138 and 175, 152 and 176, 153 and 177, 154 and 178, 155 and 179, 156 and 180, 157 and 181, 158 and 182, 159 and 183, or 160 and 151, respectively. In certain embodiments, the antibody comprises a heavy chain variable region and light chain variable region having the amino acid sequences set forth in SEQ ID NO: 138 and 163, respectively. In certain embodiments, the antibody comprises a heavy chain variable region and light chain variable region having the amino acid sequences set forth in SEQ ID NO: 139 and 163, respectively. In certain embodiments, the antibody comprises a heavy chain variable region and light chain variable region having the amino acid sequences set forth in SEQ ID NO: 157 and 181, respectively.

In another aspect, the instant disclosure provides an isolated antibody that binds to the same or an overlapping epitope of ApoC3 (e.g., an epitope of human ApoC3) as an antibody described herein, e.g., an antibody comprising the heavy and light chain variable region amino acid sequences set forth in SEQ ID NOs: 137 and 161, 138 and 162, 139 and 163, 140 and 164, 141 and 165, 142 and 166, 143 and 167, 144 and 168, 145 and 169, 146 and 170, 147 and 171, 148 and 172, 149 and 173, 150 and 174, 138 and 175, 152 and 176, 153 and 177, 154 and 178, 155 and 179, 156 and 180, 157 and 181, 158 and 182, 159 and 183, or 160 and 151, respectively. The epitope of an antibody can be determined by, e.g., NMR spectroscopy, surface plasmon resonance (BIAcore®), X-ray diffraction crystallography studies, ELISA assays, hydrogen/deuterium exchange coupled with mass spectrometry (e.g., liquid chromatography electrospray mass spectrometry), peptide scanning assays, or mutagenesis mapping (e.g., site-directed mutagenesis mapping).

In another aspect, the instant disclosure provides an isolated antibody that competes for binding to ApoC3 (e.g., human ApoC3) with an antibody comprising the heavy and light chain variable region amino acid sequences set forth in SEQ ID NOs: 137 and 161, 138 and 162, 139 and 163, 140 and 164, 141 and 165, 142 and 166, 143 and 167, 144 and 168, 145 and 169, 146 and 170, 147 and 171, 148 and 172, 149 and 173, 150 and 174, 138 and 175, 152 and 176, 153 and 177, 154 and 178, 155 and 179, 156 and 180, 157 and 181, 158 and 182, 159 and 183, or 160 and 151, respectively. Competitive binding can be determined in an assay in which the immunoglobulin under test inhibits specific binding of a reference antibody to a common antigen, such as ApoC3 (e.g., human ApoC3). Numerous types of competitive binding assays are known, for example: solid phase direct or indirect radioimmunoassay (RIA), solid phase direct or indirect enzyme immunoassay (EIA), sandwich competition assay (see Stahli C et al., (1983) Methods Enzymol 9: 242-253); solid phase direct biotin-avidin EIA (see Kirkland T N et al., (1986) J Immunol 137: 3614-9); solid phase direct labeled assay, solid phase direct labeled sandwich assay (see Harlow E & Lane D, (1988) Antibodies: A Laboratory Manual, Cold Spring Harbor Press); solid phase direct label RIA using I-125 label (see Morel G A et al., (1988) Mol Immunol 25(1): 7-15); solid phase direct biotin-avidin EIA (Cheung R C et al., (1990) Virology 176: 546-52); and direct labeled RIA. (Moldenhauer G et al., (1990) Scand J Immunol 32: 77-82). Typically, such an assay involves the use of purified ApoC3 (e.g., human ApoC3) bound to a solid surface or cells bearing either of these, an unlabeled test immunoglobulin and a labeled reference immunoglobulin. Competitive inhibition can be measured by determining the amount of label bound to the solid surface or cells in the presence of the test immunoglobulin. Usually the test immunoglobulin is present in excess. Usually, when a competing antibody is present in excess, it will inhibit specific binding of a reference antibody to a common antigen by at least 50-55%, 55-60%, 60-65%, 65-70%, 70-75% or more. A competition binding assay can be configured in a large number of different formats using either labeled antigen or labeled antibody. In a common version of this assay, the antigen is immobilized on a 96-well plate. The ability of unlabeled antibodies to block the binding of labeled antibodies to the antigen is then measured using radioactive or enzyme labels. For further details see, for example, Wagener C et al., (1983) J Immunol 130: 2308-2315; Wagener C et al., (1984) J Immunol Methods 68: 269-274; Kuroki M et al., (1990) Cancer Res 50: 4872-4879; Kuroki M et al., (1992) Immunol Invest 21: 523-538; Kuroki M et al., (1992) Hybridoma 11: 391-407 and Antibodies: A Laboratory Manual, Ed Harlow E & Lane D editors supra, pp. 386-389.

In certain embodiments, the instant disclosure provides an isolated antibody that binds to an epitope of ApoC3 within the amino acid sequence FSEFWDLDPE (SEQ ID NO: 3). In certain embodiments, the epitope comprises at least one amino acid within SEQ ID NO: 3, and optionally comprises one or more amino acids from SEQ ID NO: 1 contiguous to SEQ ID NO: 3. In certain embodiments, the epitope comprises at least one of the amino acid at position 2, 5, 6, 8, or 10 of SEQ ID NO:3. In certain embodiments, the epitope comprises at least two of the amino acid at position 2, 5, 6, 8, or 10 of SEQ ID NO:3. In certain embodiments, the epitope comprises at least three of the amino acid at position 2, 5, 6, 8, or 10 of SEQ NO:3. In certain embodiments, the epitope comprises at least four of the amino acid at position 2, 5, 6, 8, or 10 of SEQ ID NO:3. In certain embodiments, the epitope comprises the amino acids at positions 5 and 6 of SEQ ID NO:3. In certain embodiments, the epitope comprises the amino acids at positions 2, 5 and 6 of SEQ ID NO:3. In certain embodiments, the epitope comprises the amino acids at positions 2, 5 and 8 of SEQ ID NO:3. In certain embodiments, the epitope comprises the amino acids at positions 2, 5, 6, and 8 of SEQ ID NO:3. In certain embodiments, the epitope comprises the amino acid at position 10 of SEQ ID NO:3. In certain embodiments, the epitope comprises the amino acids at positions 6 and 10 of SEQ ID NO:3. In certain embodiments, the epitope comprises the amino acids at positions 8 and 10 of SEQ ID NO:3. In certain embodiments, the epitope comprises the amino acids at positions 6 and 8 of SEQ ID NO:3. In certain embodiments, the epitope comprises the amino acids at positions 6, 8 and 10 of SEQ ID NO:3. In certain embodiments, the instant disclosure provides an isolated antibody that competes for binding to ApoC3 (e.g., human ApoC3) with an antibody comprising the heavy and light chain variable region amino acid sequences set forth in SEQ ID NOs: 138 and 162; or 139 and 163, respectively. In certain embodiments, the antibody comprises a heavy chain variable region having complementarity determining regions CDRH1, CDRH2 and CDRH3, and a light chain variable region having complementarity determining regions CDRL1, CDRL2 and CDRL3, wherein CDRH1, CDRH2, CDRH3, CDRL1, CDRL2, and CDRL3 comprise the amino acid sequences set forth in SEQ ID NOs: 7, 8, 9, 76, 77, and 78; or 10, 11, 12, 79, 80, and 81, respectively. In certain embodiments, the heavy chain variable region and light chain variable region comprise the amino acid sequences set forth in SEQ ID NOs: 138 and 162; or 139 and 163, respectively. Such antibodies optionally further have one or more, two or more, three or more, four or more, five or more, six or more, or all of the following characteristics: (a) the antibodies are capable of binding to lipid-bound ApoC3 (e.g., ApoC3 bound to triglyceride, TRL (e.g., VLDL) or TRL remnants); (b) the antibodies are not capable of attenuating the ability of ApoC3 to inhibit lipoprotein lipase-mediated lipolysis of TRL VLDL) (e.g., the antibodies attenuate the ability of ApoC3 to inhibit lipoprotein lipase-mediated lipolysis of TRL (e.g., VLDL) by less than 50% at the concentration of 1, 2, 3, 4, 5, 6, 7, 8, 9, or 10 µM); (c) the antibodies are capable of attenuating the ability of ApoC3 to inhibit hepatocyte uptake of TRL (e.g., VLDL) or TRL remnants by at least about 10%, 20%, 30%, 40%, 50%, 60%, 70%, 80%, 90%, 95%, or 99%; (d) the antibodies are capable of inhibiting post-prandial lipemia in a subject (e.g., inhibiting the increased level of post-prandial triglyceride in the serum of the subject by at least 10%, 20%, 30%, 40%, 50%, 60%, 70%, or 80%) when administered to the subject prior to, during, or after a meal; (e) the antibodies are capable of reducing the levels of post-prandial chylomicron or chylomicron remnants in a subject when administered to the subject prior to, during, or after a meal; (f) the antibodies are capable of increasing the rate of clearance of ApoC3 and/or ApoB from the blood in a subject; (g) the antibodies are capable of reducing the level of ApoC3 in the blood in a subject by at least 10%, 20%, 30%, 40%, 50%, 60%, 70%, or 80%; and (h) the antibodies are capable of reducing the level of ApoB in the blood in a subject by at least 10%, 20%, 30%, 40%, 50%, 60%, 70%, or 80%, wherein the characteristics are assessed by methods described herein or by methods known to one of skill in the art.

In certain embodiments, the instant disclosure provides an isolated antibody that binds to an epitope of ApoC3 within the amino acid sequence GWVTDGFSSLK (SEQ ID NO: 2). In certain embodiments, the epitope comprises at least one amino acid within SEQ ID NO: 2, and optionally comprises one or more amino acids from SEQ ID NO: 1 contiguous to SEQ ID NO: 2. In certain embodiments, the epitope comprises at least one of the amino acid at position 1, 4, 6, 7, 9 or 10 of SEQ ID NO: 2. In certain embodiments, the epitope comprises at least two of the amino acid at position 1, 4, 6, 7, 9 or 10 of SEQ ID NO: 2. In certain embodiments, the epitope comprises at least three of the amino acid at position 1, 4, 6, 7, 9 or 10 of SEQ ID NO: 2. In certain embodiments, the epitope comprises at least four of the amino acid at position 1, 4, 6, 7, 9 or 10 of SEQ ID NO: 2, In certain embodiments, the epitope comprises at least five of the amino acid at position 1, 4, 6, 7, 9 or 10 of SEQ ID NO: 2. In certain embodiments, the epitope comprises the amino acids at positions 4 and 9 of SEQ ID NO:2. In certain embodiments, the epitope comprises the amino acids at positions 4, 6 and 9 of SEQ ID NO: 2. In certain embodiments, the epitope comprises the amino acids at positions 1, 4 and 6 of SEQ ID NO: 2. In certain embodiments, the epitope comprises the amino acids at positions 1, 4, 6 and 9 of SEQ ID NO: 2. In certain embodiments, the epitope comprises the amino acids at positions 1, 4, 6, 9 and 10 of SEQ ID NO: 2. In certain embodiments, the epitope comprises the amino acids at positions 1, 4, 6, 7 and 9 of SEQ ID NO: 2. In certain embodiments, the epitope comprises the amino acids at positions 1, 4, 6, 7, 9 and 10 of SEQ ID NO: 2. In certain embodiments, the instant disclosure provides an isolated antibody that competes for binding to ApoC3 (e.g., human ApoC3) with an antibody comprising the heavy and light chain variable region amino acid sequences set forth in SEQ ID NOs: 157 and 181, respectively. In certain embodiments, the antibody comprises a heavy chain variable region having complementarity determining regions CDRH1, CDRH2 and CDRH3, and a light chain variable region having complementarity determining regions CDRL1, CDRL2 and CDRL3, wherein CDRH1, CDRH2, CDRH3, CDRL1, CDRL2, and CDRL3 comprise the amino acid sequences set forth in SEQ ID NOs: 62, 63, 64, 127, 128, and 129, respectively. In certain embodiments, the heavy chain variable region and light chain variable region comprise the amino acid sequences set forth in SEQ ID NOs: 157 and 181, respectively. Such antibodies optionally further have one or more, two or more, three or more, four or more, five or more, six or more, or all of the following characteristics: (a) the antibodies are capable of attenuating the ability of ApoC3 to inhibit lipoprotein lipase-mediated lipolysis of TRL (e.g., VLDL) by at least 50% at the concentration of 1, 2, 3, 4, or 5 µM; (b) the antibodies are capable of inhibiting the binding of ApoC3 to lipids and lipoproteins (e.g., triglyceride, TRL (e.g., VLDL) or TRL remnants) by at least 70% 80%, 90%, 95%, 96%, 97%, 98%, or 99%; (c) the antibodies are capable of attenuating the ability of ApoC3 to inhibit hepatocyte uptake of TRL (e.g., VLDL) or TRL remnants by at least about 10%, 20%, 30%, 40%, 50%, 60%, 70%, 80%, 90%, 95%, or 99%; (d) the antibodies are capable of inhibiting post-prandial lipemia in a subject when administered to the subject prior to, during, or after a meal; (e) the antibodies are capable of reducing the levels of post-prandial chylomicron or chylomicron remnants in a subject when administered to the subject prior to, during, or after a meal; (f) the antibodies are capable of increasing the rate of clearance of ApoC3 and/or ApoB from the blood in a subject; and (g) the antibodies are capable of reducing the level of ApoC3 and/or ApoB in the blood in a subject, wherein the characteristics are assessed by methods described herein or by methods known to one of skill in the art.

Any Ig constant region can be used in the antibodies disclosed herein. In certain embodiments, the Ig region is a human IgG, IgE, IgM, IgD, IgA, or IgY immunoglobulin molecule, any class (e.g., $IgG_1$, $IgG_2$, $IgG_3$, $IgG_4$, $IgA_1$, and $IgA_2$), or any subclass (e.g., $IgG_{2a}$ and $IgG_{2b}$) of immunoglobulin molecule.

3. Methods of Use

ApoC3 inhibits TRL (e.g., VLDL) and TRL remnant uptake and clearance by hepatocytes and inhibits lipoprotein lipase-mediated lipolysis of TRL (e.g., VLDL), thereby functioning to increase triglyceride levels in the blood of a subject. In certain embodiments, the anti-ApoC3 antibodies disclosed herein can attenuate the ability of ApoC3 to inhibit TRL (e.g., VLDL) and TRL remnant uptake and clearance by hepatocytes or attenuate the ability of ApoC3 to inhibit lipoprotein lipase-mediated lipolysis of TRL (e.g., VLDL). Accordingly, in certain embodiments, the instant disclosure provides a method for inhibiting the activity of ApoC3 in the blood of a subject, the method comprising administering to the subject an effective amount of an anti-ApoC3 antibody or pharmaceutical composition disclosed herein. In certain embodiments, the activity of ApoC3 is inhibition of TRL (e.g., VLDL) and TRL remnants uptake and clearance by hepatocytes. In certain embodiments, the activity of ApoC3 is inhibition of lipoprotein lipase-mediated lipolysis of TRL. In certain embodiments, the activity of ApoC3 is inhibition of TRL (e.g., VLDL) and TRL remnants uptake and clearance by hepatocytes and inhibition of lipoprotein lipase-mediated lipolysis of TRL.

The anti-ApoC3 antibodies disclosed herein are useful for increasing the rate of clearance of ApoC3 and/or ApoB (e.g., ApoB48 and/or ApoB100) from the blood in a subject. Accordingly, in certain embodiments, the instant disclosure provides a method for increasing the rate of clearance of ApoC3 and/or ApoB (e.g., ApoB48 and/or ApoB100) from the blood in a subject, the method comprising administering to the subject an effective amount of an anti-ApoC3 antibody or pharmaceutical composition disclosed herein.

The anti-ApoC3 antibodies disclosed herein are useful for reducing the level of ApoC3 and/or ApoB ApoB48 and/or ApoB100) in the blood of a subject. Accordingly, in certain embodiments, the instant disclosure provides a method for reducing the level of ApoC3 and/or ApoB (e.g., ApoB48 and/or ApoB100) in the blood of a subject, the method comprising administering to the subject an effective amount of an anti-ApoC3 antibody or pharmaceutical composition disclosed herein. In certain embodiments, the method reduces the level of ApoC3 and/or ApoB (e.g., ApoB48 and/or ApoB100) in the blood of a subject by at least 5%, 10%, 15%, 20%, 25%, 30%, 35%, 40%, 45%, 50%, 55%, 60%, 65%, 70%, 75%, 80%, 85%, 90%, 95%, 98%, or 99%, as assessed by methods disclosed herein or by methods known to one of skill in the art. In certain embodiments, the method reduces the levels of ApoC3 and/or ApoB (e.g., ApoB48 and/or ApoB100) in the blood in a subject by at least about 1.1 fold, 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold, as assessed by methods disclosed herein or by methods known to one of skill in the art. In certain embodiments, the reduction in the levels of ApoC3 and/or ApoB (e.g., ApoB48 and/or ApoB100) in the blood in the subject is maintained for at least 1, 2, 3, 4, 5, 6, 7, 8, 9, 10, 12, 15, 18, 24, 30, 36, 42, or 48 hours.

The disclosed anti-ApoC3 antibodies are useful for reducing triglyceride levels in the blood of a subject. Accordingly, in certain embodiments, the instant disclosure provides a method for reducing triglyceride levels in the blood of a subject, the method comprising administering to the subject an effective amount of an anti-ApoC3 antibody or pharmaceutical composition disclosed herein.

The disclosed anti-ApoC3 antibodies are useful for the treatment of hypertriglyceridemia. Accordingly, in certain embodiments, the instant disclosure provides a method for treating hypertriglyceridemia in a subject, the method comprising administering to the subject an effective amount of an anti-ApoC3 antibody or pharmaceutical composition disclosed herein. In certain embodiments, the instant disclosure provides a method for treating chylomicronemia in a subject, the method comprising administering to the subject an effective amount of an anti-ApoC3 antibody or pharmaceutical composition disclosed herein. In certain embodiments, the instant disclosure provides a method for treating chylomicronemia syndrome in a subject, the method comprising administering to the subject an effective amount of an anti-ApoC3 antibody or pharmaceutical composition disclosed herein.

The disclosed anti-ApoC3 antibodies are useful for the treatment and prevention of post-prandial lipemia in a subject. Accordingly, in certain embodiments, the instant disclosure provides a method for inhibiting post-prandial lipemia in a subject, the method comprising administering to the subject an effective amount of an anti-ApoC3 antibody or pharmaceutical composition disclosed herein. The anti-ApoC3 antibody can be administered to the subject prior to, during, or after a meal.

Without wishing to be bound by theory, Applicants believe that, in certain embodiments, the antibodies disclosed herein are capable of reducing the levels of post-prandial chylomicron or chylomicron remnants in a subject when administered to the subject prior to, during, or after a meal. Accordingly, in certain embodiments, the instant disclosure provides a method for reducing the levels of post-prandial chylomicron or chylomicron remnants in a subject, the method comprising administering to the subject an effective amount of an anti-ApoC3 antibody or pharmaceutical composition disclosed herein. The anti-ApoC3 antibody can be administered to the subject prior to, during, or after a meal.

The reduction of triglyceride levels in blood in patients with hypertriglyceridemia may reduce the risk of development of pancreatitis. Accordingly, in certain embodiments, the instant disclosure provides a method for reducing the risk of pancreatitis in a subject with hypertriglyceridemia, the method comprising administering to the subject an effective amount of an anti-ApoC3 antibody or pharmaceutical composition disclosed herein The disclosed anti-ApoC3 antibodies are useful for reducing the risk of cardiovascular disease in a subject. Accordingly, in certain embodiments, the instant disclosure provides a method for reducing the risk of cardiovascular disease in a subject with hypertriglyceridemia, the method comprising administering to the subject an effective amount of an anti-ApoC3 antibody or pharmaceutical composition disclosed herein. The risk of developing any cardiovascular disease associated with or caused by hypertriglyceridemia or excessive post prandial lipemia can be reduced by administration of an anti-ApoC3 antibody or pharmaceutical composition disclosed herein. Cardiovascular disease for which the risk can be reduced include without limitation coronary artery disease, atherosclerosis, angina, myocardial infarction, and stroke.

The anti-ApoC3 antibody or pharmaceutical composition disclosed herein can be administered either alone or in combination an additional therapeutic agent. In certain embodiments, the additional therapeutic agent is another lipid lowering agent. Any one or more lipid lowering agent can be used in combination with an anti-ApoC3 antibody or pharmaceutical composition disclosed herein. Suitable lipid lowering agents include without limitation HMG-CoA reductase inhibitors (e.g., atorvastatin, fluvastatin, lovastatin, pitavastatin, pravastatin, rosuvastatin or simvastatin), fibrates, niacin, bile acid sequestrants (e.g., cholestyramine, colestipol, and colesevelam), inhibitors of dietary cholesterol absorption (e.g., ezetimibe), microsomal triglyceride transfer protein (MTP) inhibitors (e.g., lomitapide), phytosterols, pancreatic lipase inhibitors (e.g., orlistat), cholesteryl ester transfer protein inhibitors, squalene synthase inhibitors (e.g., TAK-475, zaragozic acid, and RPR 107393), ApoA-1 Milano, succinobucol (AGI-1067), Apoprotein-B inhibitors (e.g., Mipomersen), proprotein convertase subtilisin/kexin type 9 (PCSK9) inhibitors (e.g, alirocumab, evolocumab, and bococizumab), and any combinations thereof. In certain embodiments, the additional lipid lowering agent is a combination of ezetimibe and an HMG-CoA reductase inhibitor. In certain embodiments, the lipid lowering agent is a combination of ezetimibe, an HMG-CoA reductase inhibitor, and a PCSK9 inhibitor.

An anti-ApoC3 antibody or pharmaceutical composition disclosed herein may be delivered to a subject by a variety of routes. These include, but are not limited to, parenteral, intradermal, intramuscular, intraperitoneal, intravenous, and subcutaneous routes. In certain embodiments, the antibody or pharmaceutical composition described herein is delivered subcutaneously or intravenously.

The amount of an anti-ApoC3 antibody or pharmaceutical composition disclosed herein which will be effective in the treatment or prevention of a condition will depend on the nature of the disease, and can be empirically determined by standard clinical techniques. The precise dose to be employed in a composition will also depend on the route of administration, and the seriousness of the infection or disease caused by it, and should be decided according to the judgment of the practitioner and each subject's circumstances. For example, effective doses may also vary depending upon means of administration, target site, physiological state of the patient (including age, body weight and health), whether the patient is human or an animal, other medications administered, or whether treatment is prophylactic or therapeutic. Usually, the patient is a human but non-human mammals including transgenic mammals can also be treated. Treatment dosages are optimally titrated to optimize safety and efficacy.

An anti-ApoC3 antibody described herein can also be used to assay ApoC3 (e.g., human ApoC3) protein levels in a biological sample using classical immunohistological methods known to those of skill in the art, including immunoassays, such as the enzyme linked immunosorbent assay (ELISA), immunoprecipitation, or Western blotting. Suitable antibody assay labels are known in the art and include enzyme labels, such as, glucose oxidase; radioisotopes, such as iodine ($^{125}$I, $^{121}$I), carbon ($^{14}$C), sulfur ($^{35}$S), tritium ($^{3}$H), indium ($^{121}$In), and technetium ($^{99}$Tc); luminescent labels, such as luminol; and fluorescent labels, such as fluorescein and rhodamine, and biotin. Such labels can be used to label an antibody described herein. Alternatively, a second antibody that recognizes an anti-ApoC3 antibody described herein can be labeled and used in combination with an anti-ApoC3 antibody to detect ApoC3 (e.g., human ApoC3) protein levels.

Assaying for the expression level of ApoC3 (e.g., human ApoC3) protein is intended to include qualitatively or quantitatively measuring or estimating the level of ApoC3 (e.g., human ApoC3) protein in a first biological sample either directly (e.g, by determining or estimating absolute protein level) or relatively (e.g, by comparing to the disease associated protein level in a second biological sample). ApoC3 (e.g., human ApoC3) polypeptide expression level in the first biological sample can be measured or estimated and compared to a standard ApoC3 (e.g., human ApoC3) protein level, the standard being taken from a second biological sample obtained from an individual not having the disorder or being determined by averaging levels from a population of individuals not having the disorder. As will be appreciated in the art, once the "standard" ApoC3 (e.g., human ApoC3) polypeptide level is known, it can be used repeatedly as a standard for comparison.

As used herein, the term "biological sample" refers to any biological sample obtained from a subject, cell line, tissue, or other source of cells potentially expressing ApoC3 (e.g., human ApoC3). Methods for obtaining tissue biopsies and body fluids from animals (e.g., humans) are well known in the art. Biological samples include peripheral mononuclear blood cells.

An anti-ApoC3 antibody described herein can be used for prognostic, diagnostic, monitoring and screening applications, including in vitro and in vivo applications well known and standard to the skilled artisan and based on the present description. Prognostic, diagnostic, monitoring and screening assays and kits for in vitro assessment and evaluation of immune system status or immune response may be utilized to predict, diagnose and monitor to evaluate patient samples including those known to have or suspected of having elevated ApoC3 activity. In one embodiment, an anti-ApoC3 antibody can be used in immunohistochemistry of biopsy samples. In another embodiment, an anti-ApoC3 antibody can be used to detect levels of ApoC3 (e.g., human ApoC3), which levels can then be linked to certain disease symptoms. Anti-ApoC3 antibodies described herein may carry a detectable or functional label. When fluorescence labels are used, currently available microscopy and fluorescence-activated cell sorter analysis (FACS) or combination of both methods procedures known in the art may be utilized to identify and to quantitate the specific binding members. Anti-ApoC3 antibodies described herein may carry a fluorescence label. Exemplary fluorescence labels include, for example, reactive and conjugated probes e.g. Aminocoumarin, Fluorescein and Texas red, Alexa Fluor dyes, Cy dyes and DyLight dyes. An anti-ApoC3 antibody may carry a radioactive label, such as the isotopes $^{3}H$, $^{14}C$, $^{32}P$, $^{35}S$, $^{36}Cl$, $^{51}Cr$, $^{57}Co$, $^{58}Co$, $^{59}Fe$, $^{67}Cu$, $^{90}Y$, $^{99}Tc$, $^{111}In$, $^{117}Lu$, $^{121}I$, $^{124}I$, $^{125}I$, $^{131}I$, $^{198}Au$, $^{211}At$, $^{213}Bi$, $^{225}Ac$ and $^{186}Re$. When radioactive labels are used, currently available counting procedures known in the art may be utilized to identify and quantitate the specific binding of anti-ApoC3 antibody to ApoC3 (e.g., human ApoC3). In the instance where the label is an enzyme, detection may be accomplished by any of the presently utilized colorimetric, spectrophotometric, fluorospectrophotometric, arnperornetric or gasometric techniques as known in the art. This can be achieved by contacting a sample or a control sample with an anti-ApoC3 antibody under conditions that allow for the formation of a complex between the antibody and ApoC3 (e.g., human ApoC3). Any complexes formed between the antibody and ApoC3 (e.g., human ApoC3) are detected and compared in the sample and the control. The antibodies described herein can also be used to purify ApoC3 (e.g., human ApoC3) via immunoaffinity purification. Also included herein is an assay system which may be prepared in the form of a test kit for the quantitative analysis of the extent of the presence of, for instance, ApoC3 (e.g., human ApoC3). The system or test kit may comprise a labeled component, e.g., a labeled ApoC3 antibody, and one or more additional immunochemical reagents.

4. Pharmaceutical Compositions

Provided herein are pharmaceutical compositions comprising an anti-ApoC3 antibody described herein having the desired degree of purity in a physiologically acceptable carrier, excipient or stabilizer (Remington's Pharmaceutical Sciences (1990) Mack Publishing Co., Easton, Pa.). Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); or non-ionic surfactants such as TWEEN™, PLURONICS™ or polyethylene glycol (PEG).

In a specific embodiment, pharmaceutical compositions comprise an anti-ApoC3 antibody described herein, and optionally one or more additional prophylactic or therapeutic agents, in a pharmaceutically acceptable carrier. In a specific embodiment, pharmaceutical compositions comprise an effective amount of an antibody described herein, and optionally one or more additional prophylactic or therapeutic agents, in a pharmaceutically acceptable carrier. In some embodiments, the antibody is the only active ingredient included in the pharmaceutical composition. Pharmaceutical compositions described herein can be useful in inhibiting ApoC3 activity and treating a condition, such as cancer or an infectious disease.

Pharmaceutically acceptable carriers used in parenteral preparations include aqueous vehicles, nonaqueous vehicles, antimicrobial agents, isotonic agents, buffers, antioxidants, local anesthetics, suspending and dispersing agents, emulsifying agents, sequestering or chelating agents and other pharmaceutically acceptable substances. Examples of aqueous vehicles include Sodium Chloride Injection, Ringers Injection, Isotonic Dextrose Injection, Sterile Water Injection, Dextrose and Lactated Ringers Injection. Nonaqueous parenteral vehicles include fixed oils of vegetable origin, cottonseed oil, corn oil, sesame oil and peanut oil. Antimicrobial agents in bacteriostatic or fungistatic concentrations can be added to parenteral preparations packaged in multiple-dose containers which include phenols or cresols, mercurials, benzyl alcohol, chlorobutanol, methyl and propyl p-hydroxybenzoic acid esters, thimerosal, benzalkonium chloride and benzethonium chloride. Isotonic agents include sodium chloride and dextrose. Buffers include phosphate and citrate. Antioxidants include sodium bisulfate. Local anesthetics include procaine hydrochloride. Suspending and dispersing agents include sodium carboxymethylcelluose, hydroxypropyl methylcellulose and polyvinylpyrrolidone. Emulsifying agents include Polysorbate 80 (TWEEN® 80). A sequestering or chelating agent of metal ions includes EDTA. Pharmaceutical carriers also include ethyl alcohol, polyethylene glycol and propylene glycol for water miscible vehicles; and sodium hydroxide, hydrochloric acid, citric acid or lactic acid for pH adjustment.

A pharmaceutical composition may be formulated for any e of administration to a subject. Specific examples of routes of administration include intranasal, oral, pulmonary, transdermal, intradermal, and parenteral. Parenteral administration, characterized by either subcutaneous, intramuscular or intravenous injection, is also contemplated herein. Injectables can be prepared in conventional forms, either as liquid solutions or suspensions, solid forms suitable for solution or suspension in liquid prior to injection, or as emulsions. The injectables, solutions and emulsions also contain one or more excipients. Suitable excipients are, for example, water, saline, dextrose, glycerol or ethanol. In addition, if desired, the pharmaceutical compositions to be administered can also contain minor amounts of non-toxic auxiliary substances such as wetting or emulsifying agents, pH buffering agents, stabilizers, solubility enhancers, and other such agents, such as for example, sodium acetate, sorbitan monolaurate, triethanolamine oleate and cyclodextrins.

Preparations for parenteral administration of an antibody include sterile solutions ready for injection, sterile dry soluble products, such as lyophilized powders, ready to be combined with a solvent just prior to use, including hypodermic tablets, sterile suspensions ready for injection, sterile dry insoluble products ready to be combined with a vehicle just prior to use and sterile emulsions. The solutions may be either aqueous or nonaqueous.

If administered intravenously, suitable carriers include physiological saline or phosphate buffered saline (PBS), and solutions containing thickening and solubilizing agents, such as glucose, polyethylene glycol, and polypropylene glycol and mixtures thereof.

Topical mixtures comprising an antibody are prepared as described for the local and systemic administration. The resulting mixture can be a solution, suspension, emulsions or the like and can be formulated as creams, gels, ointments, emulsions, solutions, elixirs, lotions, suspensions, tinctures, pastes, foams, aerosols, irrigations, sprays, suppositories, bandages, dermal patches or any other formulations suitable for topical administration.

An anti-ApoC3 antibody described herein can be formulated as an aerosol for topical application, such as by inhalation (see, e.g., U.S. Pat. Nos. 4,044,126, 4,414,209 and 4,364,923, which describe aerosols for delivery of a steroid useful for treatment of inflammatory diseases, particularly asthma). These formulations for administration to the respiratory tract can be in the form of an aerosol or solution for a nebulizer, or as a microfine powder for insufflations, alone or in combination with an inert carrier such as lactose. In such a case, the particles of the formulation will, in one embodiment, have diameters of less than 50 microns, in one embodiment less than 10 microns.

An anti-ApoC3 antibody described herein can be formulated for local or topical application, such as for topical application to the skin and mucous membranes, such as in the eye, in the form of gels, creams, and lotions and for application to the eye or for intracisternal or intraspinal application. Topical administration is contemplated for transdermal delivery and also for administration to the eyes or mucosa, or for inhalation therapies. Nasal solutions of the antibody alone or in combination with other pharmaceutically acceptable excipients can also be administered.

Transdermal patches, including iontophoretic and electrophoretic devices, are well known to those of skill in the art, and can be used to administer an antibody. For example, such patches are disclosed in U.S. Pat. Nos. 6,267,983, 6,261,595, 6,256,533, 6,167,301, 6,024,975, 6,010715, 5,985,317, 5,983,134, 5,948,433, and 5,860,957.

In certain embodiments, a pharmaceutical composition comprising an described herein is a lyophilized powder, which can be reconstituted for administration as solutions, emulsions and other mixtures. It may also be reconstituted and formulated as solids or gels. The lyophilized powder is prepared by dissolving an antibody described herein, or a pharmaceutically acceptable derivative thereof, in a suitable solvent. In some embodiments, the lyophilized powder is sterile. The solvent may contain an excipient which improves the stability or other pharmacological component of the powder or reconstituted solution, prepared from the powder. Excipients that may be used include, but are not limited to, dextrose, sorbitol, fructose, corn syrup, xylitol, glycerin, glucose, sucrose or other suitable agent. The solvent may also contain a buffer, such as citrate, sodium or potassium phosphate or other such buffer known to those of skill in the art at, in one embodiment, about neutral pH. Subsequent sterile filtration of the solution followed by lyophilization under standard conditions known to those of skill in the art provides the desired formulation. In one embodiment, the resulting solution will be apportioned into vials for lyophilization. Each vial will contain a single dosage or multiple dosages of the compound. The lyophilized powder can be stored under appropriate conditions, such as at about 4° C. to room temperature. Reconstitution of this lyophilized powder with water for injection provides a formulation for use in parenteral administration. For reconstitution, the lyophilized powder is added to sterile water or other suitable carrier. The precise amount depends upon the selected compound. Such amount can be empirically determined.

The anti-ApoC3 antibodies described herein and other compositions provided herein can also be formulated to be targeted to a particular tissue, receptor, or other area of the body of the subject to be treated. Many such targeting methods are well known to those of skill in the art. All such targeting methods are contemplated herein for use in the instant compositions. For non-limiting examples of targeting methods, see, e.g., U.S. Pat. Nos. 6,316,652, 6,274,552, 6,271,359, 6,253,872, 6,139,865, 6,131,570, 6,120,751, 6,071,495, 6,060,082, 6,048,736, 6,039,975, 6,004,534, 5,985,307, 5,972,366, 5,900,252, 5,840,674, 5,759,542 and 5,709,874.

The compositions to be used for in vivo administration can be sterile. This is readily accomplished by filtration through, e.g., sterile filtration membranes.

5. Polynucleotides, Vectors and Methods of Producing Anti-ApoC3 Antibodies

In another aspect, provided herein are polynucleotides comprising a nucleotide sequence encoding an anti-ApoC3 antibody described herein (e.g., a light chain variable region or heavy chain variable region), and vectors, e.g., vectors comprising such polynucleotides for recombinant expression in host cells (e.g., *E. coli* and mammalian cells).

As used herein, an "isolated" polynucleotide or nucleic acid molecule is one which is separated from other nucleic acid molecules which are present in the natural source (e.g., in a mouse or a human) of the nucleic acid molecule. Moreover, an "isolated" nucleic acid molecule, such as a cDNA molecule, can be substantially free of other cellular material, or culture medium when produced by recombinant techniques, or substantially free of chemical precursors or other chemicals when chemically synthesized. For example, the language "substantially free" includes preparations of polynucleotide or nucleic acid molecule having less than about 15%, 10%, 5%, 2%, 1%, 0.5%, or 0.1% (in particular less than about 10%) of other material, e.g., cellular material, culture medium, other nucleic acid molecules, chemical precursors or other chemicals. In a specific embodiment, a nucleic acid molecule(s) encoding an antibody described herein is isolated or purified.

In particular aspects, provided herein are polynucleotides comprising nucleotide sequences encoding antibodies, which specifically bind to a ApoC3 (e.g., human ApoC3) polypeptide and comprises an amino acid sequence as described herein, as well as antibodies which compete with such antibodies for binding to a ApoC3 (e.g., human ApoC3)

polypeptide (e.g., in a dose-dependent manner), or which binds to the same epitope as that of such antibodies.

In certain aspects, provided herein are polynucleotides comprising a nucleotide sequence encoding the light chain or heavy chain of an antibody described herein. The polynucleotides can comprise nucleotide sequences encoding the VH, VL or CDRs of antibodies described herein (see, e.g., Tables 1-4 herein)

Also provided herein are polynucleotides encoding an anti-ApoC3 antibody that are optimized, e.g., by codon/RNA optimization, replacement with heterologous signal sequences, and elimination of mRNA instability elements. Methods to generate optimized nucleic acids encoding an anti-ApoC3 antibody (e.g., light chain, heavy chain, VH domain, or VL domain) for recombinant expression by introducing codon changes or eliminating inhibitory regions in the mRNA can be carried out by adapting the optimization methods described in, e.g, U.S. Pat. Nos. 5,965,726; 6,174,666; 6,291,664; 6,414,132; and 6,794,498, accordingly. For example, potential splice sites and instability elements (e.g, A/T or A/U rich elements) within the RNA can be mutated without altering the amino acids encoded by the nucleic acid sequences to increase stability of the RNA for recombinant expression. The alterations utilize the degeneracy of the genetic code, e.g., using an alternative codon for an identical amino acid. In some embodiments, it can be desirable to alter one or more codons to encode a conservative mutation, e.g., a similar amino acid with similar chemical structure and properties or function as the original amino acid. Such methods can increase expression of an anti-ApoC3 by at least 1 fold, 2 fold, 3 fold, 4 fold, 5 fold, 10 fold, 20 fold, 30 fold, 40 fold, 50 fold, 60 fold, 70 fold, 80 fold, 90 fold, or 100 fold or more relative to the expression of an anti-ApoC3 antibody encoded by polynucleotides that have not been optimized.

In certain embodiments, an optimized polynucleotide sequence encoding an anti-ApoC3 antibody described herein (e.g., VL domain or VH domain) can hybridize to an antisense (e.g., complementary) polynucleotide of an unoptimized polynucleotide sequence encoding an anti-ApoC3 antibody described herein (e.g, VL domain or VH domain). In specific embodiments, an optimized nucleotide sequence encoding an anti-ApoC3 antibody described herein or a fragment hybridizes under high stringency conditions to antisense polynucleotide of an unoptimized polynucleotide sequence encoding an anti-ApoC3 antibody described herein. In a specific embodiment, an optimized nucleotide sequence encoding an anti-ApoC3 antibody described herein hybridizes under high stringency, intermediate or lower stringency hybridization conditions to an antisense polynucleotide of an unoptimized nucleotide sequence encoding an anti-ApoC3 antibody described herein. Information regarding hybridization conditions has been described, see, e.g., U.S. Patent Application Publication No. US 2005/0048549 (e.g., paragraphs 72-73), which is incorporated herein by reference.

The polynucleotides can be obtained, and the nucleotide sequence of the polynucleotides determined, by any method known in the art. Nucleotide sequences encoding antibodies described herein, e.g., antibodies described in Table 1, and modified versions of these antibodies can be determined using methods well known in the art, i.e., nucleotide codons known to encode particular amino acids are assembled in such a way to generate a nucleic acid that encodes the antibody. Such a polynucleotide encoding the antibody can be assembled from chemically synthesized oligonucleotides (e.g., as described in Kutmeier G et al., (1994), Bioiechniques 17: 242-6), which, briefly, involves the synthesis of overlapping oligonucleotides containing portions of the sequence encoding the antibody, annealing and ligating of those oligonucleotides, and then amplification of the ligated oligonucleotides by PCR.

Alternatively, a polynucleotide encoding an antibody described herein can be generated from nucleic acid from a suitable source (e.g., a hybridoma) using methods well known in the art (e.g., PCR and other molecular cloning methods). For example, PCR amplification using synthetic primers hybridizable to the 3' and 5' ends of a known sequence can be performed using genomic DNA obtained from hybridoma cells producing the antibody of interest. Such PCR amplification methods can be used to obtain nucleic acids comprising the sequence encoding the light chain or heavy chain of an antibody. Such PCR amplification methods can be used to obtain nucleic acids comprising the sequence encoding the variable light chain region or the variable heavy chain region of an antibody. The amplified nucleic acids can be cloned into vectors for expression in host cells and for further cloning, for example, to generate chimeric and humanized antibodies.

If a clone containing a nucleic acid encoding a particular antibody is not available, but the sequence of the antibody molecule is known, a nucleic acid encoding the immunoglobulin can be chemically synthesized or obtained from a suitable source (e.g., an antibody cDNA library or a cDNA library generated from, or nucleic acid, preferably poly A+ RNA, isolated from, any tissue or cells expressing the antibody, such as hybridoma cells selected to express an antibody described herein) by PCR amplification using synthetic primers hybridizable to the 3' and 5' ends of the sequence or by cloning using an oligonucleotide probe specific for the particular gene sequence to identify, e.g., a cDNA clone from a cDNA library that encodes the antibody. Amplified nucleic acids generated by PCR can then be cloned into replicable cloning vectors using any method well known in the art.

DNA encoding anti-ApoC3 (e.g., human ApoC3) antibodies described herein can be readily isolated and sequenced using conventional procedures (e.g., by using oligonucleotide probes that are capable of binding specifically to genes encoding the heavy and light chains of the anti-ApoC3 (e.g., human ApoC3) antibodies). Hybridoma cells can serve as a source of such DNA. Once isolated, the DNA can be placed into expression vectors, which are then transfected into host cells such as E. coli cells, simian COS cells, Chinese hamster ovary (CHO) cells (e.g., CHO cells from the CHO GS System™ (Lonza)), or myeloma cells that do not otherwise produce immunoglobulin protein, to obtain the synthesis of anti-ApoC3 (e.g., human ApoC3) antibodies in the recombinant host cells.

To generate whole antibodies, PCR primers including VH or VL nucleotide sequences, a restriction site, and a flanking sequence to protect the restriction site can be used to amplify the VH or VL sequences in scFv clones. Utilizing cloning techniques known to those of skill in the art, the PCR amplified VH domains can be cloned into vectors expressing a heavy chain constant region, e.g., the human gamma 4 constant region, and the PCR amplified VL domains can be cloned into vectors expressing a light chain constant region, e.g., human kappa or lambda constant regions. In certain embodiments, the vectors for expressing the VH or VL domains comprise an EF-1α promoter, a secretion signal, a cloning site for the variable region, constant domains, and a selection marker such as neomycin. The VH and VL domains can also be cloned into one vector expressing the necessary constant regions. The heavy chain conversion vectors and light chain conversion vectors are then co-transfected into cell lines to generate stable or transient cell lines that express full-length antibodies, e.g., IgG, using techniques known to those of skill in the art.

The DNA also can be modified, for example, by substituting the coding sequence for human heavy and light chain constant domains in place of the murine sequences, or by covalently joining to the immunoglobulin coding sequence all or part of the coding sequence for a non-immunoglobulin polypeptide.

Also provided are polynucleotides that hybridize under high stringency, intermediate or lower stringency hybridization conditions to polynucleotides that encode an antibody described herein. In specific embodiments, polynucleotides described herein hybridize under high stringency, intermediate or lower stringency hybridization conditions to polynucleotides encoding a VH domain or VL domain provided herein.

Hybridization conditions have been described in the art and are known to one of skill in the art. For example, hybridization under stringent conditions can involve hybridization to filter-bound DNA in 6× sodium chloride/sodium citrate (SSC) at about 45° C. followed by one or more washes in 0.2×SSC/0.1% SDS at about 50-65° C.; hybridization under highly stringent conditions can involve hybridization to filter-bound nucleic acid in 6×SSC at about 45° C. followed by one or more washes in 0.1×SSC/0.2% SDS at about 68° C. Hybridization under other stringent hybridization conditions are known to those of skill in the art and have been described, see, for example, Ausubel F M et al., eds., (1989) Current Protocols in Molecular Biology, Vol. I, Green Publishing Associates, Inc. and John Wiley & Sons, Inc., New York at pages 6.3.1-6.3.6 and 2.10.3.

In certain aspects, provided herein are cells (e.g., host cells) expressing (e.g., recombinantly) antibodies described herein which specifically bind to ApoC3 (e.g., human ApoC3) and related polynucleotides and expression vectors. Provided herein are vectors (e.g., expression vectors) comprising polynucleotides comprising nucleotide sequences encoding anti-ApoC3 (e.g., human ApoC3) antibodies or a fragment for recombinant expression in host cells, preferably in mammalian cells. Also provided herein are host cells comprising such vectors for recombinantly expressing anti-ApoC3 (e.g., human ApoC3) antibodies described herein (e.g., hwnan or hwnanized antibody). In a particular aspect, provided herein are methods for producing an antibody described herein, comprising expressing such antibody from a host cell.

Recombinant expression of an antibody described herein (e.g., a full-length antibody, heavy or light chain of an antibody, or a single chain antibody described herein) that specifically binds to ApoC3 (e.g., human ApoC3) involves construction of an expression vector containing a polynucleotide that encodes the antibody. Once a polynucleotide encoding an antibody molecule, heavy or light chain of an antibody, (e.g., heavy or light chain variable regions) described herein has been obtained, the vector for the production of the antibody molecule can be produced by recombinant DNA technology using techniques well known in the art. Thus, methods for preparing a protein by expressing a polynucleotide containing an antibody or antibody fragment (e.g., light chain or heavy chain) encoding nucleotide sequence are described herein. Methods which are well known to those skilled in the art can be used to construct expression vectors containing antibody or antibody fragment (e.g., light chain or heavy chain) coding sequences and appropriate transcriptional and translational control signals. These methods include, for example, in vitro recombinant DNA techniques, synthetic techniques, and in vivo genetic recombination. Also provided are replicable vectors comprising a nucleotide sequence encoding an antibody molecule described herein, a heavy or light chain of an antibody, a heavy or light chain variable region of an antibody, or a heavy or light chain CDR, operably linked to a promoter. Such vectors can, for example, include the nucleotide sequence encoding the constant region of the antibody molecule (see, e.g., international Publication Nos. WO 86/05807 and WO 89/01036; and U.S. Pat. No. 5,122,464) and variable regions of the antibody can be cloned into such a vector for expression of the entire heavy, the entire light chain, or both the entire heavy and light chains.

An expression vector can be transferred to a cell (e.g., host cell) by conventional techniques and the resulting cells can then be cultured by conventional techniques to produce an antibody described herein. Thus, provided herein are host cells containing a polynucleotide encoding an antibody described herein, or a heavy or light chain thereof, or fragment thereof, or a single chain antibody described herein, operably linked to a promoter for expression of such sequences in the host cell. In certain embodiments, for the expression of double-chained antibodies, vectors encoding both the heavy and light chains, individually, can be co-expressed in the host cell for expression of the entire immunoglobulin molecule, as detailed below. In certain embodiments, a host cell contains a vector comprising a polynucleotide encoding both the heavy chain and light chain of an antibody described herein. In specific embodiments, a host cell contains two different vectors, a first vector comprising a polynucleotide encoding a heavy chain or a heavy chain variable region of an antibody described herein, or a fragment thereof, and a second vector comprising a polynucleotide encoding a light chain or a light chain variable region of an antibody described herein, or a fragment thereof. In other embodiments, a first host cell comprises a first vector comprising a polynucleotide encoding a heavy chain or a heavy chain variable region of an antibody described herein, or a fragment thereof, and a second host cell comprises a second vector comprising a polynucleotide encoding a light chain or a light chain variable region of an antibody described herein. In specific embodiments, a heavy chain/heavy chain variable region expressed by a first cell associated with a light chain/light chain variable region of a second cell to form an anti-ApoC3 antibody described herein. In certain embodiments, provided herein is a population of host cells comprising such first host cell and such second host cell.

In a particular embodiment, provided herein is a population of vectors comprising a first vector comprising a polynucleotide encoding a light chain/light chain variable region of an anti-ApoC3 antibody described herein, and a second vector comprising a polynucleotide encoding a heavy chain/heavy chain variable region of an anti-ApoC3 antibody described herein.

A variety of host-expression vector systems can be utilized to express antibody molecules described herein (see, e.g., U.S. Pat. No. 5,807,715). Such host-expression systems represent vehicles by which the coding sequences of interest can be produced and subsequently purified, but also represent cells which can, when transformed or transfected with the appropriate nucleotide coding sequences, express an antibody molecule described herein in situ. These include but are not limited to microorganisms such as bacteria (e.g., E. coli and B. subtilis) transformed with recombinant bacteriophage DNA, plasmid DNA or cosmid DNA expression vectors containing antibody coding sequences; yeast (e.g., *Saccharomyces Pichia*) transformed with recombinant yeast expression vectors containing antibody coding sequences; insect cell systems infected with recombinant virus expression vectors (e.g., baculovirus) containing antibody coding sequences; plant cell systems (e.g., green algae such as *Chlamydomonas reinhardtii*) infected with recombinant virus expression vectors (e.g., cauliflower mosaic virus, CaMV; tobacco mosaic virus, TMV) or transformed with recombinant plasmid expression vectors (e.g., Ti plasmid) containing antibody coding sequences; or mammalian cell systems (e.g, COS (e.g., COS1 or COS), CHO, BHK, MDCK, HEK 293, NS0, PER.C6, VERO, CRL7O3O, HsS78Bst, HeLa, and NIH 3T3, HEK-293T, HepG2, SP210, R1.1, B-W, L-M, BSC1, BSC40, YB/20 and BMT10 cells) harboring recombinant expression constructs containing promoters derived from the genome of mammalian cells (e.g., metallothionein promoter) or from mammalian viruses (e.g., the adenovirus late promoter; the vaccinia virus 7.5K promoter). In a specific embodiment, cells for expressing antibodies described herein are CHO cells, for example CHO cells from the CHO GS System™ (Lonza). In a particular embodiment, cells for expressing antibodies described herein are human cells, e.g, hwnan cell lines. In a specific embodiment, a mammalian expression vector is pOptiVEC™ or pcDNA3.3. In a particular embodiment, bacterial cells such as *Escherichia coli*, or eukaryotic cells (e.g., mammalian cells), especially for the expression of whole recombinant antibody molecule, are used for the expression of a recombinant antibody molecule. For example, mammalian cells such as Chinese hamster ovary (CHO) cells, in conjunction with a vector such as the major intermediate early gene promoter element from human cytomegalovirus is an effective expression system for antibodies (Foecking M K & Hofstetter H (1986) Gene 45: 101-5; and Cockett M I et al., (1990) Biotechnology 8(7): 662-7). In certain embodiments, antibodies described herein are produced by CHO cells or NS0 cells. In a specific embodiment, the expression of nucleotide sequences encoding antibodies described herein which specifically bind ApoC3 (e.g., human ApoC3) is regulated by a constitutive promoter, inducible promoter or tissue specific promoter.

In bacterial systems, a number of expression vectors can be advantageously selected depending upon the use intended for the antibody molecule being expressed. For example, when a large quantity of such an antibody is to be produced, for the generation of pharmaceutical compositions of an antibody molecule, vectors which direct the expression of high levels of fusion protein products that are readily purified can be desirable. Such vectors include, but are not limited to, the *E. coli* expression vector pUR278 (Ruether U & Mueller-Hill B (1983) EMBO J 2: 1791-1794), in which the antibody coding sequence can be ligated individually into the vector in frame with the lac Z coding region so that a fusion protein is produced; pIN vectors (Inouye S & Inouye M (1985) Nuc Acids Res 13: 3101-3109; Van Heeke G & Schuster S M (1989) J Biol Chem 24: 5503-5509); and the like. For example, pGEX vectors can also be used to express foreign polypeptides as fusion proteins with glutathione 5-transferase (GST). In general, such fusion proteins are soluble and can easily be purified from lysed cells by adsorption and binding to matrix glutathione agarose beads followed by elution in the presence of free glutathione. The pGEX vectors are designed to include thrombin or factor Xa protease cleavage sites so that the cloned target gene product can be released from the GST moiety.

In an insect system, *Autographa californica* nuclear polyhedrosis virus (AcNPV), for example, can be used as a vector to express foreign genes. The virus grows in *Spodoptera frugiperda* cells. The antibody coding sequence can be cloned individually into non-essential regions (for example the polyhedrin gene) of the virus and placed under control of an AcNPV promoter (for example the polyhedrin promoter).

In mammalian host cells, a number of viral-based expression systems can be utilized. In cases where an adenovirus is used as an expression vector, the antibody coding sequence of interest can be ligated to an adenovirus transcription/translation control complex, e.g., the late promoter and tripartite leader sequence. This chimeric gene can then be inserted in the adenovirus genome by in vitro or in vivo recombination. Insertion in a non-essential region of the viral genome (e.g., region E1 or E3) will result in a recombinant virus that is viable and capable of expressing the antibody molecule in infected hosts (e.g., see Logan J & Shenk T (1984) PNAS 81(12): 3655-9). Specific initiation signals can also be required for efficient translation of inserted antibody coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression can be enhanced by the inclusion of appropriate transcription enhancer elements, transcription terminators, etc. (see, e.g., Bitter G et al. (1987) Methods Enzymol. 153: 516-544).

In addition, a host cell strain can be chosen which modulates the expression of the inserted sequences, or modifies and processes the gene product in the specific fashion desired. Such modifications (e.g., glycosylation) and processing (e.g., cleavage) of protein products can be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product can be used. Such mammalian host cells include but are not limited to CHO, VERO, BHK, Hela, MDCK, HEK 293, NTH 3T3, W138, B483, Hs578T, HTB2, BT2O and T47D, NS0 (a murine myeloma cell line that does not endogenously produce any immunoglobulin chains), CRL7O3O, COS (e.g., COS1 or COS), PER.C6, VERO, HsS78Bst, HEK-293T, HepG2, SP210, R1.1, B-W, L-M, BSC1, BSC40, YB/20, BMT10 and HsS78Bst cells. In certain embodiments, anti-ApoC3 (e.g., human ApoC3) antibodies described herein are produced in mammalian cells, such as CHO cells.

In a specific embodiment, the antibodies described herein have reduced fucose content or no fucose content. Such antibodies can be produced using techniques known one skilled in the art. For example, the antibodies can be expressed in cells deficient or lacking the ability of to fucosylate. In a specific example, cell lines with a knockout of both alleles of α1,6-fucosyltransferase can be used to produce antibodies with reduced fucose content. The Potelligent® system (Lonza) is an example of such a system that can be used to produce antibodies with reduced fucose content.

For long-term, high-yield production of recombinant proteins, stable expression cells can be generated. For example, cell lines which stably express an anti-ApoC3 antibody described herein can be engineered. In specific embodiments, a cell provided herein stably expresses a light chain/light chain variable region and a heavy chain/heavy chain variable region which associate to form an antibody described herein.

In certain aspects, rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA/polynucleotide, engineered cells can be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method can advantageously be used to engineer cell lines which express an anti-ApoC3 antibody described herein. Such engineered cell lines can be particularly useful in screening and evaluation of compositions that interact directly or indirectly with the antibody molecule.

A number of selection systems can be used, including but not limited to the herpes simplex virus thymidine kinase (Wigler M et al., (1977) Cell 11(1): 223-32), hypoxanthine-guanine phosphoribosyltransferase (Szyhalska E H & Szybalski W (1962) PNAS 48(12): 2026-2034) and adenine phosphoribosyltransferase (Lowy I et al., (1980) Cell 22(3): 817-23) genes in tk-, hgprt- or aprt-cells, respectively. Also, antimetabolite resistance can be used as the basis of selection for the following genes: dhfr, which confers resistance to methotrexate (Wigler M et al., (1980) PNAS 77(6): 3567-70; O'Hare K et al., (1981) PNAS 78: 1527-31); gpt, which confers resistance to mycophenolic acid (Mulligan R C & Berg P (1981) PNAS 78(4): 2072-6); neo, which confers resistance to the aminoglycoside G-418 (Wu G Y & Wu C H (1991) Biotherapy 3: 87-95; Tolstoshev P (1993) Ann Rev Pharmacol Toxicol 32: 573-596; Mulligan R C (1993) Science 260: 9'26-932; and Morgan R A & Anderson W F (1993) Ann Rev Biochem 62: 191-217; Nabel G J & Feigner P L (1993) Trends Biotechnol 11(5): 211-5); and hygro, which confers resistance to hygromycin (Santerre R F et al., (1984) Gene 30(1-3): 147-56). Methods commonly known in the art of recombinant DNA technology can be routinely applied to select the desired recombinant clone and such methods are described, for example, in Ausubel F M et al., (eds.), Current Protocols in Molecular Biology, John Wiley & Sons, NY (1993); Kriegler M, Gene Transfer and Expression, A Laboratory Manual, Stockton Press, NY (1990); and in Chapters 12 and 13, Dracopoli N C et al., (eds.), Current Protocols in Human Genetics, John Wiley & Sons, NY (1994); Colbere-Garapin F et al., (1981) J Mol Biol 150: 1-14, which are incorporated by reference herein in their entireties.

The expression levels of an antibody molecule can be increased by vector amplification (for a review, see Bebbington C R & Hentschel C C G. The use of vectors based on gene amplification for the expression of cloned genes in mammalian cells in DNA cloning, Vol. 3 (Academic Press, New York, 1987)). When a marker in the vector system expressing antibody is amplifiable, increase in the level of inhibitor present in culture of host cell will increase the number of copies of the marker gene. Since the amplified region is associated with the antibody gene, production of the antibody will also increase (Crouse G F et al., (1983) Mol Cell Biol 3: 257-66).

The host cell can be co-transfected with two or more expression vectors described herein, the first vector encoding a heavy chain derived polypeptide and the second vector encoding a light chain derived polypeptide. The two vectors can contain identical selectable markers which enable equal expression of heavy and light chain polypeptides. The host cells can be co-transfected with different amounts of the two or more expression vectors. For example, host cells can be transfected with any one of the following ratios of a first expression vector and a second expression vector: 1:1, 1:2, 1:3, 1:4, 1:5, 1:6, 1:7, 1:8, 1:9, 1:10, 1:12, 1:15, 1:20, 1:25, 1:30, 1:35, 1:40, 1:45, or 1:50.

Alternatively, a single vector can be used which encodes, and is capable of expressing, both heavy and light chain polypeptides. In such situations, the light chain should be placed before the heavy chain to avoid an excess of toxic free heavy chain (Proudfoot N J (1986) Nature 322: 562-565; and Köhler G (1980) PNAS 77: 2197-2199). The coding sequences for the heavy and light chains can comprise cDNA or genomic DNA. The expression vector can be monocistronic or muiticistronic. A muiticistronic nucleic acid construct can encode 2, 3, 4, 5, 6, 7, 8, 9, 10 or more, or in the range of 2-5, 5-10 or 10-20 genes/nucleotide sequences. For example, a bicistronic nucleic acid construct can comprise in the following order a promoter, a first gene (e.g., heavy chain of an antibody described herein), and a second gene and (e.g., light chain of an antibody described herein). In such an expression vector, the transcription of both genes can be driven by the promoter, whereas the translation of the mRNA from the first gene can be by a cap-dependent scanning mechanism and the translation of the mRNA from the second gene can be by a cap-independent mechanism, e.g., by an IRES.

Once an antibody molecule described herein has been produced by recombinant expression, it can be purified by any method known in the art for purification of an immunoglobulin molecule, for example, by chromatography (e.g., ion exchange, affinity, particularly by affinity for the specific antigen after Protein A, and sizing column chromatography), centrifugation, differential solubility, or by any other standard technique for the purification of proteins. Further, the antibodies described herein can be fused to heterologous polypeptide sequences described herein or otherwise known in the art to facilitate purification.

In specific embodiments, an antibody described herein is isolated or purified. Generally, an isolated antibody is one that is substantially free of other antibodies with different antigenic specificities than the isolated antibody. For example, in a particular embodiment, a preparation of an antibody described herein is substantially free of cellular material or chemical precursors. The language "substantially free of cellular material" includes preparations of an antibody in which the antibody is separated from cellular components of the cells from which it is isolated or recombinantly produced. Thus, an antibody that is substantially free of cellular material includes preparations of antibody having less than about 30%, 20%, 10%, 5%, 2%, 1%, 0.5%, or 0.1% (by dry weight) of heterologous protein (also referred to herein as a "contaminating protein") or variants of an antibody, for example, different post-translational modified forms of an antibody or other different versions of an antibody (e.g., antibody fragments). When the antibody is recombinantly produced, it is also generally substantially free of culture medium, i.e., culture medium represents less than about 20%, 10%, 2%, 0.5%, or 0.1% of the volume of the protein preparation. When the antibody is produced by chemical synthesis, it is generally substantially free of chemical precursors or other chemicals, i.e., it is separated from chemical precursors or other chemicals which are involved in the synthesis of the protein. Accordingly, such preparations of the antibody have less than about 30%, 20%, 10%, or 5% (by dry weight) of chemical precursors or compounds other than the antibody of interest. In a specific embodiment, antibodies described herein are isolated or purified.

Antibodies that specifically bind to ApoC3 (e.g., human ApoC3) can be produced by any method known in the art for the synthesis of antibodies, for example, by chemical synthesis or by recombinant expression techniques. The methods described herein employs, unless otherwise indicated, conventional techniques in molecular biology, microbiology, genetic analysis, recombinant DNA, organic chemistry, biochemistry, PCR, oligonucleotide synthesis and modification, nucleic acid hybridization, and related fields within the skill of the art. These techniques are described, for example, in the references cited herein and are fully explained in the literature. See, e.g., Maniatis T et al., (1982) Molecular Cloning: A Laboratory Manual, Cold Spring Harbor Laboratory Press; Sambrook J et al., (1989). Molecular Cloning: A Laboratory Manual, Second Edition, Cold Spring Harbor Laboratory Press; Sambrook J et al., (2001) Molecular Cloning: A Laboratory Manual, Cold Spring Harbor Laboratory Press, Cold Spring Harbor, N.Y.; Ausubel F M et al., Current Protocols in Molecular Biology, John Wiley & Sons (1987 and annual updates); Current Protocols in Immunology, John Wiley & Sons (1987 and annual updates) Gait (ed.) (1984) Oligonucleotide Synthesis: A Practical Approach, IRL Press; Eckstein (ed.) (1991) Oligonucleotides and Analogues: A Practical Approach, IRL. Press; Birren B et al., (eds.) (1999) Genome Analysis: A Laboratory Manual, Cold Spring Harbor Laboratory Press.

In a specific embodiment, an antibody described herein is an antibody (e.g, recombinant antibody) prepared, expressed, created or isolated by any means that involves creation, e.g., via synthesis, genetic engineering of DNA sequences. In certain embodiments, such antibody comprises sequences (e.g., DNA sequences or amino acid sequences) that do not naturally exist within the antibody germline repertoire of an animal or mammal (e.g., human) in vivo.

In one aspect, provided herein is a method of making an antibody which specifically binds to ApoC3 (e.g., human ApoC3) comprising culturing a cell or host cell described herein. In a certain aspect, provided herein is a method of making an antibody which specifically binds to ApoC3 (e.g., human ApoC3) comprising expressing (e.g., recombinantly expressing) the antibody using a cell or host cell described herein (e.g., a cell or a host cell comprising polynucleotides encoding an antibody described herein). In a particular embodiment, the cell is an isolated cell. In a particular embodiment, the exogenous polynucleotides have been introduced into the cell. In a particular embodiment, the method further comprises the step of purifying the antibody obtained from the cell or host cell.

Methods for producing polyclonal antibodies are known in the art (see, for example, Chapter 11 in: Short Protocols in Molecular Biology, (2002) 5th Ed., Ausubel F M et al., eds., John Wiley and Sons, New York).

Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow E &. Lane D, Antibodies: A Laboratory Manual, (Cold Spring Harbor Laboratory Press, 2nd ed. 1988); Hammerling G J et al., in: Monoclonal Antibodies and T-Cell Hybridomas 563 681 (Elsevier, N.Y., 1981). The term "monoclonal antibody" as used herein is not limited to antibodies produced through hybridoma technology. For example, monoclonal antibodies can be produced recombinantly from host cells exogenously expressing an antibody described herein, for example, light chain or heavy chain of such antibody.

In specific embodiments, a "monoclonal antibody," as used herein, is an antibody produced by a single cell (e.g., hybridoma or host cell producing a recombinant antibody), wherein the antibody specifically binds to ApoC3 (e.g., human ApoC3) as determined, e.g., by ELISA or other antigen-binding or competitive binding assay known in the art or in the examples provided herein. In particular embodiments, a monoclonal antibody can be a chimeric antibody or a humanized antibody. In certain embodiments, a monoclonal antibody is a monovalent antibody or multivalent (e.g., bivalent) antibody. In particular embodiments, a monoclonal antibody is a monospecific or multispecific antibody (e.g., hispecific antibody). Monoclonal antibodies described herein can, for example, be made by the hybridoma method as described in Kohler G & Milstein C (1975) Nature 256: 495 or can, e.g., be isolated from phage libraries using the techniques as described herein, for example. Other methods for the preparation of clonal cell lines and of monoclonal antibodies expressed thereby are well known in the art (see, for example, Chapter 11 in: Short Protocols in Molecular Biology, (2002) 5th Ed., Ausubel F M et al., supra)

Methods for producing and screening for specific antibodies using hybridoma technology are routine and well known in the art. For example, in the hybridoma method, a mouse or other appropriate host animal, such as a sheep, goat, rabbit, rat, hamster or macaque monkey, is immunized to elicit lymphocytes that produce or are capable of producing antibodies that will specifically bind to the protein (e.g., ApoC3 (e.g., human ApoC3)) used for immunization. Alternatively, lymphocytes may be immunized in vitro. Lymphocytes then are fused with myeloma cells using a suitable fusing agent, such as polyethylene glycol, to form a hybridoma cell (Goding J W (Ed), Monoclonal Antibodies: Principles and Practice, pp. 59-103 (Academic Press, 1986)). Additionally, a RIMMS (repetitive immunization multiple sites) technique can be used to immunize an animal (Kilpatrick K E et al., (1997) Hybridoma 16:381-9, incorporated by reference in its entirety).

In some embodiments, mice (or other animals, such as rats, monkeys, donkeys, pigs, sheep, hamster, or dogs) can be immunized with an antigen (e.g., ApoC3 (e.g., human ApoC3)) and once an immune response is detected, e.g., antibodies specific for the antigen are detected in the mouse serum, the mouse spleen is harvested and splenocytes isolated. The splenocytes are then fused by well-known techniques to any suitable myeloma cells, for example cells from cell line SP20 available from the American Type Culture Collection (ATCC®) (Manassas, Va.), to form hybridomas. Hybridomas are selected and cloned by limited dilution. In certain embodiments, lymph nodes of the immunized mice are harvested and fused with NS0 myeloma cells.

The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Specific embodiments employ myeloma cells that fuse efficiently, support stable high-level production of antibody by the selected antibody-producing cells, and are sensitive to a medium such as HAT medium. Among these myeloma cell lines are murine myeloma lines, such as NS0 cell line or those derived from MOPC-21 and MPC-11 mouse tumors available from the Salk Institute Cell Distribution Center, San Diego, Calif., USA, and SP-2 or X63-Ag8.653 cells available from the American Type Culture Collection, Rockville, Md., USA. Human myeloma and mouse-human heteromyeloma cell lines also have been described for the production of human monoclonal antibodies (Kozbor D (1984) J Immunol 133: 3001-5; Brodeur et cit., Monoclonal Antibody Production Techniques and Applications, pp. 51-63 (Marcel Dekker, Inc., New York, 1987)), Culture medium in which hybridoma cells are growing is assayed for production of monoclonal antibodies directed against ApoC3 (e.g., human ApoC3). The binding specificity of monoclonal antibodies produced by hybridoma cells is determined by methods known in the art, for example, immunoprecipitation or by an in vitro binding assay, such as radioimmunoassay (RIA) or enzyme-linked immunoabsorbent assay (ELISA).

After hybridoma cells are identified that produce antibodies of the desired specificity, affinity, or activity, the clones may be subcloned by limiting dilution procedures and grown by standard methods (Goding J W (Ed), Monoclonal Antibodies: Principles and Practice, supra). Suitable culture media for this purpose include, for example, D-MEM or RPMI 1640 medium. In addition, the hybridoma cells may be grown in vivo as ascites tumors in an animal.

The monoclonal antibodies secreted by the subclones are suitably separated from the culture medium, ascites fluid, or serum by conventional immunoglobulin purification procedures such as, for example, protein A-Sepharose, hydroxylapatite chromatography, gel electrophoresis, dialysis, or affinity chromatography.

Antibodies described herein include antibody fragments which recognize specific ApoC3 (e.g., human ApoC3) and can be generated by any technique known to those of skill in the art. For example, Fab and F(ab')$_2$ fragments described herein can be produced by proteolytic cleavage of immunoglobulin molecules, using enzymes such as papain (to produce Fab fragments) or pepsin (to produce F(ab')$_2$ fragments). A Fab fragment corresponds to one of the two identical arms of an antibody molecule and contains the complete light chain paired with the VH and CH1 domains of the heavy chain. A F(ab')$_2$ fragment contains the two antigen-binding arms of an antibody molecule linked by disulfide bonds in the hinge region.

Further, the antibodies described herein can also be generated using various phage display methods known in the art. In phage display methods, functional antibody domains are displayed on the surface of phage particles which carry the polynucleotide sequences encoding them. In particular, DNA sequences encoding VH and VL domains are amplified from animal cDNA libraries e.g., human or murine cDNA libraries of affected tissues). The DNA encoding the VH and VL domains are recombined together with a scFv linker by PCR and cloned into a phagemid vector. The vector is electroporated in E. coli and the E. coli is infected with helper phage. Phage used in these methods are typically filamentous phage including fd and M13, and the VH and VL domains are usually recombinantly fused to either the phage gene III or gene VIII. Phage expressing an antigen binding domain that binds to a particular antigen can be selected or identified with antigen, e.g., using labeled antigen or antigen bound or captured to a solid surface or bead. Examples of phage display methods that can be used to make the antibodies described herein include those disclosed in Brinkman U et al., (1995) J Immunol Methods 182: 41-50; Ames R S et al., (1995) J Immunol Methods 184: 177-186; Kettleborough C A et al., (1994) Eur J Immunol 24: 952-958; Persic L et al., (1997) Gene 187: 9-18; Burton D R & Barbas C F (1994) Advan Immunol 57: 191-280; PCT Application No. PCT/GB91/001134; International Publication Nos. WO 90/02809, WO 91/10737, WO 92/01047, WO 92/18619, WO 93/1 1236, WO 95/15982, WO 95/20401, and WO 97/13844; and U.S. Pat. Nos. 5,698,426, 5,223,409, 5,403,484, 5,580,717, 5,427,908, 5,750,753; 5,821,047, 5,571,698, 5,427,908, 5,516,637; 5,780,225, 5,658,727, 5,733,743 and 5,969,108.

As described in the above references, after phage selection, the antibody coding regions from the phage can be isolated and used to generate whole antibodies, including human antibodies, or any other desired antigen binding fragment, and expressed in any desired host, including mammalian cells, insect cells, plant cells, yeast, and bacteria, e.g., as described below. Techniques to recombinantly produce antibody fragments such as Fab, Fab' and F(ab')$_2$ fragments can also be employed using methods known in the art such as those disclosed in PCT publication No. WO 92/22324; Mullinax R L et al., (1992) BioTechniques 12(6): 864-9; Sawai H et al., (1995) Am J Reprod Immunol 34: 26-34; and Better M et al., (1988) Science 240: 1041-1043.

In certain embodiments, to generate whole antibodies, PCR primers including VH or VL nucleotide sequences, a restriction site, and a flanking sequence to protect the restriction site can be used to amplify the VH or VL sequences from a template, e.g., scFv clones, Utilizing cloning techniques known to those of skill in the art, the PCR amplified VH domains can be cloned into vectors expressing a VH constant region, and the PCR amplified VL domains can be cloned into vectors expressing a VL constant region, e.g., human kappa or lambda constant regions. The VH and VL domains can also be cloned into one vector expressing the necessary constant regions. The heavy chain conversion vectors and light chain conversion vectors are then co-transfected into cell lines to generate stable or transient cell lines that express full-length antibodies, e.g., IgG, using techniques known to those of skill in the art.

A chimeric antibody is a molecule in which different portions of the antibody are derived from different immunoglobulin molecules. For example, a chimeric antibody can contain a variable region of a mouse or rat monoclonal antibody fused to a constant region of a human antibody. Methods for producing chimeric antibodies are known in the art. See, e.g., Morrison S L (1985) Science 229: 1202-7; Oi V T & Morrison S L (1986) BioTechniques 4: 214-221; Gillies S D et al., (1989) J Immunol Methods 125: 191-202; and U.S. Pat. Nos. 5,807,715, 4,816,567, 4,816,397, and 6,331,415.

A humanized antibody is capable of binding to a predetermined antigen and which comprises a framework region having substantially the amino acid sequence of a human immunoglobulin and CDRs having substantially the amino acid sequence of a non-human immunoglobulin (e.g., a murine immunoglobulin). In particular embodiments, a humanized antibody also comprises at least a portion of an immunoglobulin constant region (Fc), typically that of a human immunoglobulin. The antibody also can include the CH1, hinge, CH2, CH3, and CH4 regions of the heavy chain. A humanized antibody can be selected from any class of immunoglobulins, including IgM, IgG, IgD, IgA and IgE, and any isotype, including $IgG_1$, $IgG_2$, $IgG_3$ and $IgG_4$. Humanized antibodies can be produced using a variety of techniques known in the art, including but not limited to, CDR-grafting (European Patent No. EP 239400; International Publication No. WO 91/09967; and U.S. Pat. Nos. 5,225,539, 5,530,101, and 5,585,089), veneering or resurfacing (European Patent Nos. EP 592106 and EP 519596; Padlan E A (1991) Mol Immunol 28(4/5): 489-498; Studnicka G M et al., (1994) Prot Engineering 7(6): 805-814; and Roguska M A et al., (1994) PNAS 91: 969-973), chain shuffling (U.S. Pat. No. 5,565,332), and techniques disclosed in, e.g., U.S. Pat. Nos. 6,407,213, 5,766,886, International Publication No. WO 93/17105; Tan P et al., (2002) J Immunol 169: 1119-25; Caldas C et al., (2000) Protein Eng. 13(5): 353-60; Morea V et al, (2000) Methods 20(3): 267-79; Baca M et al., (1997) J Biol Chem 272(16): 10678-84; Roguska M A et al., (1996) Protein Eng 9(10): 895 904; Couto J R et al., (1995) Cancer Res. 55 (23 Supp): 5973s-5977s; Couto J R et al., (1995) Cancer Res 55(8): 1717-22; Sandhu J S (1994) Gene 150(2): 409-10 and Pedersen J T et al., (1994) J Mol Biol 235(3): 959-73. See also U.S. Application Publication No. US 2005/0042664 A1 (Feb. 24, 2005), which is incorporated by reference herein in its entirety.

Methods for making multispecific (e.g., bispecific antibodies) have been described, see, for example, U.S. Pat. Nos. 7,951,917; 7,183,076; 8,227,577; 5,837,242; 5,989,830; 5,869,620; 6,132,992 and 8,586,713.

Single domain antibodies, for example, antibodies lacking the light chains, can be produced by methods well known in the art. See Riechmann L & Muyldermans S (1999) J Immunol 231: 25-38; Nuttall S D et al., (2000) Curr Biotechnol 1(3): 253-263; Muyldermans 5, (2001) J Biotechnol 74(4): 277-302; U.S. Pat. No. 6,005,079; and International Publication Nos. WO 94/04678, WO 94/25591 and WO 01/44301.

Further, antibodies that specifically bind to a ApoC3 (e.g., human ApoC3) antigen can, in turn, be utilized to generate anti-idiotype antibodies that "mimic" an antigen using techniques well known to those skilled in the art. (See, e.g., Greenspan N S & Bona C A (1989) FASEB J 7(5): 437-444; and Nissinoff A (1991) J Immunol 147(8): 2429-2438).

In particular embodiments, an antibody described herein, which binds to the same epitope of ApoC3 (e.g., human ApoC3) as an anti-ApoC3 antibody described herein, is a human antibody. In particular embodiments, an antibody described herein, which competitively blocks (e.g., in a dose-dependent manner) any one of the antibodies described herein, from binding to ApoC3 (e.g., human ApoC3), is a human antibody. Human antibodies can be produced using any method known in the art. For example, transgenic mice which are incapable of expressing functional endogenous immunoglobulins, but which can express human immunoglobulin genes, can be used. In particular, the human heavy and light chain immunoglobulin gene complexes can be introduced randomly or by homologous recombination into mouse embryonic stem cells. Alternatively, the human variable region, constant region, and diversity region can be introduced into mouse embryonic stem cells in addition to the human heavy and light chain genes. The mouse heavy and light chain immunoglobulin genes can be rendered non-functional separately or simultaneously with the introduction of human immunoglobulin loci by homologous recombination. In particular, homozygous deletion of the $J_H$ region prevents endogenous antibody production. The modified embryonic stem cells are expanded and microinjected into blastocysts to produce chimeric mice. The chimeric mice are then bred to produce homozygous offspring which express human antibodies. The transgenic mice are immunized in the normal fashion with a selected antigen, e.g., all or a portion of an antigen (e.g., ApoC3 (e.g., human ApoC3)). Monoclonal antibodies directed against the antigen can be obtained from the immunized, transgenic mice using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg N & Huszar D (1995) Int Rev Immunol 13:65-93. For a detailed discussion of this technology for producing human antibodies and human monoclonal antibodies and protocols for producing such antibodies, see, e.g., International Publication Nos. WO 98/24893, WO 96/34096 and WO 96/33735; and U.S. Pat. Nos. 5,413,923, 5,625,126, 5,633,425, 5,569,825, 5,661,016, 5,545,806, 5,814,318 and 5,939,598. Examples of mice capable of producing human antibodies include the Xenomouse™ (Abgenix, Inc.: U.S. Pat. Nos. 6,075,181 and 6,150,184), the HuAb-Mouse™ (Mederex, Inc./Gen Pharm; U.S. Pat. Nos. 5,545,806 and 5,569, 825), the Trans Chromo Mouse™ (Kirin) and the KM Mouse™ (Medarex/Kirin).

Human antibodies which specifically bind to ApoC3 (e.g., human ApoC3) can be made by a variety of methods known in the art including phage display methods described above using antibody libraries derived from human immunoglobulin sequences. See also U.S. Pat. Nos. 4,444,887, 4,716,111, and 5,885,793; and international Publication Nos. WO 98/46645, WO 98/50433, WO 98/24893, WO 98/16654, WO 96/34096, WO 96/33735, and WO 91/10741.

In some embodiments, human antibodies can be produced using mouse-human hybridomas. For example, human peripheral blood lymphocytes transformed with Epstein-Barr virus (EBV) can be fused with mouse myeloma cells to produce mouse-human hybridomas secreting human monoclonal antibodies, and these mouse-human hybridomas can be screened to determine ones which secrete human monoclonal antibodies that specifically bind to a target antigen ApoC3 (e.g., human ApoC3)). Such methods are known and are described in the art, see, e.g., Shinmoto H et al (2004) Cytotechnology 46: 19-23; Naganawa et al., (2005) Human Antibodies 14: 27-31.

6. Kits

Also provided, are kits comprising one or more antibodies described herein, or pharmaceutical composition or conjugates thereof. In a specific embodiment, provided herein is a pharmaceutical pack or kit comprising one or more containers filled with one or more of the ingredients of the pharmaceutical compositions described herein, such as one or more antibodies provided herein. In some embodiments, the kits contain a pharmaceutical composition described herein and any prophylactic or therapeutic agent, such as those described herein. Optionally associated with such container(s) can be a notice in the form prescribed by a governmental agency regulating the manufacture, use or sale of pharmaceuticals or biological products, which notice reflects approval by the agency of manufacture, use or sale for human administration.

Also provided, are kits that can be used in the above methods. In one embodiment, a kit comprises an antibody described herein, preferably a purified antibody, in one or more containers. In a specific embodiment, kits described herein contain a substantially isolated ApoC3 (e.g., human ApoC3) antigen as a control. In another specific embodiment, the kits described herein further comprise a control antibody which does not react with a ApoC3 (e.g., human ApoC3) antigen. In another specific embodiment, kits described herein contain one or more elements for detecting the binding of an antibody to a ApoC3 (e.g., human ApoC3) antigen (e.g., the antibody can be conjugated to a detectable substrate such as a fluorescent compound, an enzymatic substrate, a radioactive compound or a luminescent compound, or a second antibody which recognizes the first antibody can be conjugated to a detectable substrate). In specific embodiments, a kit provided herein can include a recombinantly produced or chemically synthesized ApoC3 (e.g., human ApoC3) antigen. The ApoC3 (e.g., human ApoC3) antigen provided in the kit can also be attached to a solid support. In a more specific embodiment, the detecting means of the above described kit includes a solid support to which a ApoC3 (e.g., human ApoC3) antigen is attached. Such a kit can also include a non-attached reporter-labeled anti-human antibody or anti-mouse/rat antibody. In this embodiment, binding of the antibody to the ApoC3 (e.g., human ApoC3) antigen can be detected by binding of the said reporter-labeled antibody.

EXAMPLES

The examples in this Section are provided to further elucidate the advantages and features of the present application, but are not intended to limit the scope of the application. The examples are for illustrative purposes only.

Example 1

Construction of Anti-ApoC3 Antibody Phage Display Library from Immunized Animals This example describes initial construction of an anti-ApoC3 antibody library. Human ApoC3 (huApoC3) protein purified from human serum was obtained from Athens Research and Technology. This huApoC3 protein was used in this example as well as in certain of the following examples. HuApoC3 was complexed with dimyristoylphosphatidyl choline (DMPC) liposomes to closely mimic physiologically relevant conformations. Two llamas were immunized with 6 doses of huApoC3 with Freund's incomplete adjuvant by intramuscular injection following the procedures described by Klarenbeek and colleagues (Klarenbeek et al., Protein Eng Des Sel (2016) 29(4):123-133), which is incorporated by reference herein in its entirety. The immunization schedule included weekly injection with first two doses of 100 µg huApoC3 each and four more doses of 50 µg huApoC3 each, followed by two booster doses of 50 µtg huApoC3 each. Peripheral blood lymphocytes were isolated from a blood sample of the immunized llamas after boosting. Total RNA was extracted and used as a template for the preparation of a cDNA library amplified with random primers. Antibody repertoires were amplified and clones as scFv phage display libraries as was described earlier (Van der Woning et al., DNA immunization combined with sav phage display identifies antagonistic GCGR specific antibodies and reveals new epitopes on the small extracellular loops. (2016) mAbs, 8(6):1126-35, which is incorporated by reference herein in its entirety).

The phage display library was selected on coated huApoC3 in the biopanning procedure or alternatively with biotinylated ApoC3 captured on coated streptavidin. Phages were eluted at pH 5.5 to select antibody clones that lost affinity to huApoC3 under acidic conditions. After 3 rounds of selection, single colonies were prepared and subject to antibody screening as set forth in Example 2.

Example 2

Screening for Anti-ApoC3 Monoclonal Antibodies

This example describes screening of the scFv phage display library prepared in Example 1 for antibodies that bind to ApoC3. Two ELISA-based screening methods were adopted, one with purified ApoC3 directly coated on plates, the other with biotinylated ApoC3 captured by streptavidin which was coated on plates. Each method revealed a number of antibody clones that have affinity to ApoC3. There was significant overlap between the clones identified from these two assays, while the difference may reflect dissimilarities in conformation of ApoC3 protein and exposure of epitopes under the two conditions.

2.1 Analysis of Affinity to Directly Coated ApoC3

The antibody clones selected from the scFv phage display library constructed in Example 1 were analyzed by an ELISA assay with purified huApoC3 (Athens Research and Technology) directly coated on plates. Human native ApoC3 at a concentration of 1-10 µg/ml (100 µl/well) diluted in phosphate buffer saline (PBS) pH 7.4 was incubated in Microtiter Immunoassay Maxisorp 96-well plates (NUNC cat #456537 or similar) overnight at 4° C. The coated plates were washed three times with 250 µl/well PBS containing Tween-20 at 0.05% (v/v) (PBS-T) to remove the excess of the unbound antigen. After washing, 250 µl 4% (m/v) dried skimmed milk solution prepared in PBS was added to each coated well for blocking and the plates were incubated for 1 to 2 hours at room temperature on a plate shaker (TinaMax 1000 or Heidolph). After blocking, the plates were washed three times to remove the excess of the blocking solution with 250 µl/well PBS-T. The antibody fragments (scFv) from crude periplasmic extracts (P.E.) (diluted 1:5 in PBS to a final volume of 100 µl) were allowed to bind to the immobilized antigen four 1 hour at room temperature on a plate shaker. Unbound soluble scFvs in the P.E. were removed by washing the plates 5 times with 250 µl/well PBS-T. For detection, 100 µl per well of an anti c-myc horseradish peroxidase (HRP)-conjugated monoclonal Ab (Bethyl; cat #: A190-105P or similar) recognizing the c-myc tag fused to the C-terminus of the scFv antibody fragment was used at 1:5000 dilution in 1% (m/v) dried skimmed milk solution. After 1 hour incubation at room temperature, the plates were washed consecutively 3 times with 250 µl/well PBS-T and 3 times with 250 µl/well PBS. Spectrophotometric detection was used to monitor the oxidization of 3,3',5, 5'-tetramethylbenzidine (TMB, eBioscience, cat #:00-4201-56) as catalyzed by the HRP enzyme conjugate. Reaction was stopped by adding 100 µl per well of 0.5 M $H_2SO_4$. The absorbance of the end-product is measured at 450 nm using a Microplate spectrophotometer. Binding specificity was determined based on the Absorbance values compared to control wells having received a blank P.E.

30 antibodies were identified to have affinity to huApoC3. The clones giving the strongest signals are 8B4, 8A4, 8H4, 1D5, 12E12, 6A6, 10B6, 4H1, 5A7, 8F4, 5C11, 7D9, 5A8, 9A4, 4C2, 5A4, 12C3 and 5E5. The sequence of the VH and VL of some of these clones are listed in Tables 1-4.

2.2 Analysis of Affinity to Captured Biotinylated ApoC3

The antibody clones selected from the scFv phage display library constructed in Example 1 were analyzed by a ELISA assay with biotinylated ApoC3 captured by streptavidin which was coated on plates. Neutravidin (Fisher Scientific LDAcat #: W9995L) diluted in PBS (pH 7.4) at a concentration of 2-5 µg/ml (100 µl/well) was incubated in Microtiter Immunoassay Maxisorp 96-well plates (NUNC cat #:1456537 or similar) at 4° C. overnight. The coated plates were washed three times with 250 µl/well PBS-T to remove the excess of the unbound neutravidin. After washing, 250 µl 1% (m/v) of casein solution prepared in PBS was added to each coated well for blocking, and the plates were incubated for 1 to 2 hours at room temperature on a plate shaker (TitraMax 1000, Heidolph or similar). After blocking, the plates were washed three times to remove the excess of the blocking solution with 250 µl/well PBS-T. Biotin groups were introduced at random sites of human native ApoC3 protein (Athens Research and Technology). The biotinylated ApoC3 diluted at a concentration of 1 to 5 nM (100 µl per well) in 0.1 casein in PBS was incubated in the coated and blocked plates for 1 hour at room temperature for capture of ApoC3 antigen. The unbound antigen was removed by washing the plates 5 times with 250 µl/well PBS-T. The antibody fragments (scFv) from crude P.E. (diluted 1:5 in PBS to a final volume 100 µl) were allowed to bind to the captured antigen during 1 hour incubation at room temperature. The unbound soluble scFv fragments were removed by washing the plates 5 times with 250 µl/well PBS-T. For detection, 100 µl per well of an anti c-myc horseradish peroxidase (HRP)-conjugated monoclonal Ab (Bethyl; cat #: A190-105P or similar) recognizing the c-myc tag fused to the C-terminus of the scFv antibody fragment was used at 1:5000 dilution in 1% (m/v) dried skimmed milk solution. After 1 hour incubation at room temperature, the plates were washed consecutively 3 times with 250 µl/well PBS-T and 3 times with 250 µl/well PBS. Spectrophotometric detection was used to monitor the oxidization of TMB as catalyzed by the HRP enzyme conjugate. Reaction was stopped by adding 100 µl per well of 0.5 M $H_2SO_4$. The absorbance of the end-product is measured at 450 nm using a Microplate spectrophotometer. Binding specificity was determined based on the Absorbance values compared to control wells having received a blank P.E.

17 antibodies were identified to have affinity to huApoC3. The clones giving the strongest absorbance at 450 nm are 12E12, 12C3, 13C10, 13G7, 12G8, 14C4, 13F2, 13C7, 14G4, 12D7, 14C7, 12A3 and 12E3. The sequences of the VH and VL of some of the clones are listed in Tables 1-4.

2.3 Biacore SPR Assay

This example describes characterization of anti-ApoC3 antibodies regarding their affinity to ApoC3 under neutral conditions using an SPR-based assay using a Biacore 3000 instrument (Biacore AB). Native huApoC3 protein was immobilized on a CM5 chip. The immobilization was performed in accordance with the method provided by Biacore using the NHS/EDC kit (Biacore AB): after activation of the chip, a solution of 60 µg/ml of human ApoC3 in 10 mM acetate buffer with pH of 4.5 was prepared and injected until the surface density reached approximately 1000 RU. Capturing of the human ApoC3 on the streptavidin coated chip (SA) was performed at pH 7.4 in accordance with a method provided by Biacore via injection of 20 µl 10 µg/ml biotinylated human ApoC3 thereby reaching the surface density of approximately 500 RU. 60 µL of test antibody in 1-100 nM range diluted in HBS-EP buffer (GE, cat # BR-1008-26; 0.010 M HEPES, 0.150M NaCl, 3 mM EDTA, 0.05% (v/v) surfactant P20, pH 7.4) was injected and passed through the flow cells at a flow rate of 30 µl/min, followed by an off-rate wash at pH7.4 or pH5.5 for 5 min. After the dissociation, the flow cell surfaces were regenerated by injecting 10 µl of 10 mM MOH/1 M NaCl and 10 µl of 10 mM glycine at pH1.5. The resulting sensorgrams were analyzed using the BIAevaluation 4.1 software using Langmuir 1:1 binding model to derive binding kinetics. Data was zero adjusted and the reference cell sensorgrams were subtracted.

A number of scFv-Fc antibodies were examined in this assay. The association rate (ka), dissociation rate (kd), analyte binding capacity (Rmax), equilibrium association constant (KA) and equilibrium dissociation constant (KD) of these antibodies are shown in Table 5.

Table 5. Biacore affinity measurement results

TABLE 5

Biacore affinity measurement results

| Clone ID | ka (1/Ms) | kd (1/s) | Rmax (RU) | KA (1/M) | KD (M) |
|---|---|---|---|---|---|
| 1D5 | 1.15E+06 | 3.34E−04 | 2130 | 3.43E+09 | 2.91E−10 |
| 1G4 | 5.82E+05 | 0.0115 | 694 | 5.07E+07 | 1.97E−08 |
| 4C2 | 2.06E+05 | 2.55E−04 | 2450 | 8.07E+08 | 1.24E−09 |
| 4H1 | 3.91E+05 | 1.03E−04 | 2320 | 3.80E+09 | 2.63E−10 |
| 5A4 | 1.06E+06 | 3.51E−04 | 1260 | 3.02E+09 | 3.31E−10 |
| 5A7 | 1.35E+06 | 6.47E−04 | 460 | 2.08E+09 | 4.80E−10 |
| 5A11 | 1.44E+06 | 6.68E−04 | 412 | 2.15E+09 | 4.65E−10 |
| 5C11 | 7.39E+04 | 7.82E−04 | 429 | 9.44E+07 | 1.06E−08 |
| 5E5 | 2.60E+05 | 4.37E−04 | 764 | 5.94E+08 | 1.68E−09 |
| 5E7 | 5.16E+05 | 9.16E−04 | 204 | 5.63E+08 | 1.78E−09 |
| 6A6 | 1.19E+06 | 1.86E−04 | 1140 | 6.41E+09 | 1.56E−10 |
| 7A9 | 2.59E+06 | 6.70E−04 | 516 | 3.87E+09 | 2.58E−10 |
| 7D9 | 5.99E+04 | 9.64E−04 | 230 | 6.21E+07 | 1.61E−08 |
| 8A4 | 3.00E+05 | 7.02E−05 | 581 | 4.27E+09 | 2.34E−10 |
| 8B7 | 2.81E+06 | 6.75E−04 | 516 | 4.16E+09 | 2.40E−10 |
| 8F4 | 1.63E+05 | 9.44E−05 | 811 | 1.72E+09 | 5.81E−10 |
| 8H4 | 1.87E+05 | 7.44E−05 | 1030 | 2.52E+09 | 3.97E−10 |
| 10B6 | 1.71E+05 | 6.64E−05 | 620 | 2.58E+09 | 3.88E−10 |
| 11H1 | 1.22E+05 | 2.07E−04 | 935 | 5.89E+08 | 1.70E−09 |
| 14C7* | 8.20E+04 | 5.61E−05 | 358 | 1.46E+09 | 6.84E−10 |

*This clone was examined in an IgG1 format.

Example 3

Lipid Competition Assays

This example describes characterization of anti-ApoC3 antibodies regarding whether they compete with lipid for binding to ApoC3. A ELISA-based assay was first conducted to identify antibodies that did or did not abrogate lipid binding. To further validate the results, a surface plasmon resonance (SPR)-based assay was then conducted with certain clones.

3.1 ELISA-Based Assay

An ELISA-based lipid competition assay was performed to determine whether the anti-ApoC3 antibodies identified from Examples 2 interfered with the interaction between huApoC3 protein with lipid immobilized on ELISA plates. Briefly, stock solutions of 1,2-Dimyristoyl-sn-glycero-3-phosphocholine (Avanti Polar Lipids DMPC; 14:0 PC) in chloroform were diluted in a mixture of methanol chloroform:water (2.0:1.0:0.8). 5 µg of DMPC was dispensed into each well of a Greiner U-bottom high bind plate (#850345) and the chloroform, methanol and water solvent was allowed to evaporate for a minimum of 3 hours at room temperature. Wells were blocked in 200 µL buffer consisting of fat-free milk powder dissolved in PBS (referred to herein as "clear milk PBS") overnight at 4° C. Each test antibody was mixed with native ApoC3 protein purified from human serum (Athens Research and Technology). 50 µL of the mixed solution was dispensed into the DMPC-coated microliter plate, and the plate was rotated at 300 rpm at room temperature for 2 hours. The plate was washed 4 times with 200 µL PBS. 50 µL of a biotinylated anti-apoC3 polyclonal goat antibody (Abcam # ab21024) dissolved in clear milk PBS was added and the plate was rotated at 300 rpm at room temperature for 1 hour. The plate was washed once with 200 µL PBS and 50 µL of a streptavidin-HRP solution (Abcam #34028; diluted 100-fold in PBS) was added. The plate was rotated at 300 rpm at room temperature for 30 minutes. Wells were washed 4 times with 200 µL PBS. 80 µL TMB ELISA development reagent (Thermo Ultra-TMB ELISA #34028) was added and the chromogenic reaction was stopped by 50 uL 0.5 N HCL after the color developed. Absorbance at 450 nm was read and data was analyzed using 4-parameter logistic function (GraphPad Prism 6).

As shown in FIG. 1, clones 12C12, 12D7, 12G8, 13G7, 14C4 and 14C7 inhibited the binding of lipid to huApoC3, whereas clones 12A3, 12C3, 12D1, 12D4, 12E12, 13C7, 13C10, 13F2, 14F2 and 14G4 did not.

3.2 SPR-Based VLDL Binding Assay

Figure 2A:
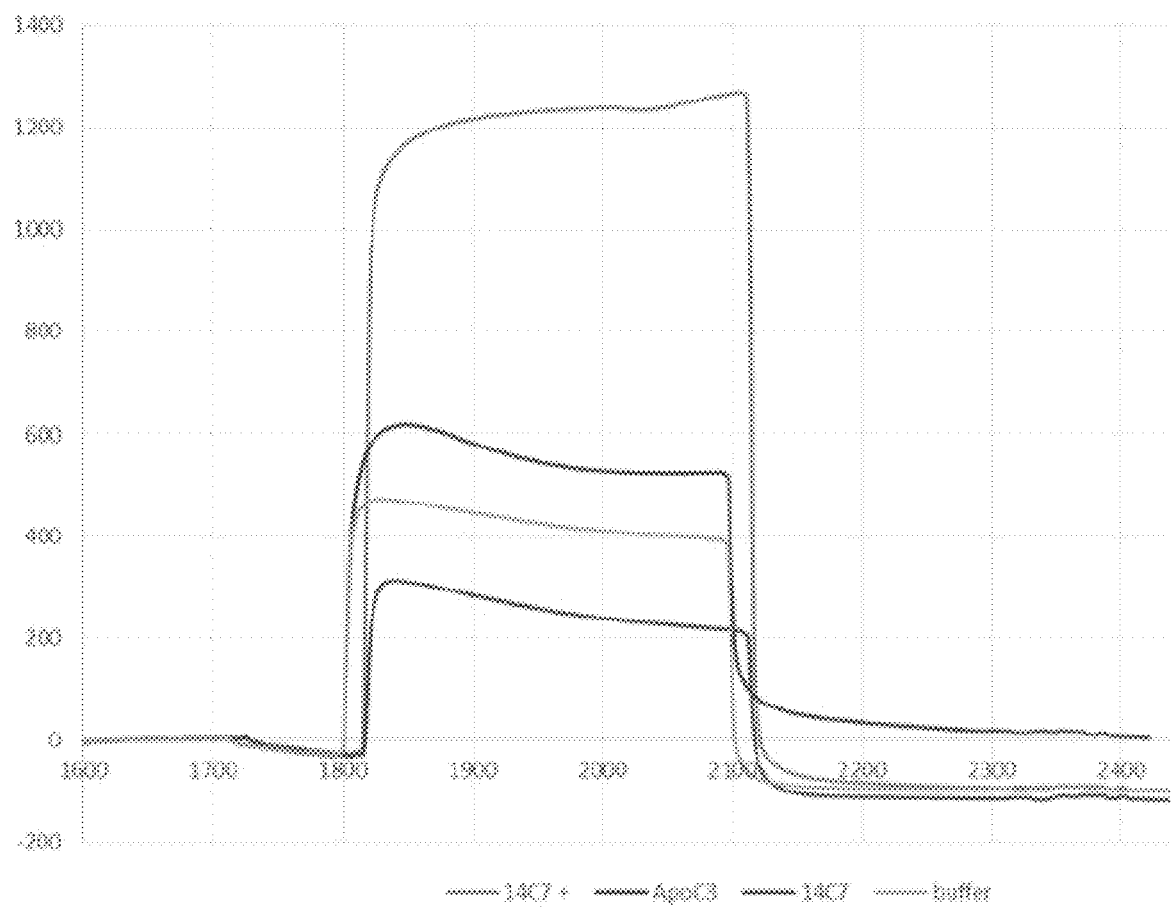
In FIGS. 2A-2B. VLDL was immobilized on a surface for surface plasmon resonance (SPR) assay. ApoC3 alone ("ApoC3"), 14C7 alone ("14C7"), or ApoC3 and 14C7 ("14C7 +") (FIG. 2A); or ApoC3 alone ("ApoC3"), 5E5 alone ("5E5"), 6A6 alone ("6A6"), ApoC3 and 5E5 ("5E5 +"), or ApoC3 and 6A6 ("6A6+") (FIG. 2B) was injected at t=1800 s and buffer was injected at t=2100 s to remove unbound molecules.

An SPR-based lipid competition assay was performed to confirm whether selected anti-ApoC3 antibodies, namely 14C7, 5E5 and 6A6 in the scFv-Fc format, competed with lipid for ApoC3 binding. VLDL liposomes were immobilized on a L1 sensor chip (Biacore, Uppsala, Sweden) as was described by Mendoza-Barbera and colleagues (Mendoza-Barbera et al., J Lipid Res 2013). As shown in FIG. 2A, injection of 10 µg/ml ApoC3 with a flow rate of 10 µl/min at t=1800 s generated an increased binding signal as compared to the negative controls where buffer or 14C7 mAb was injected, indicating that ApoC3 was incorporated into the immobilized VLDL liposomes. Injection of buffer at t=2100 s led to a reduction of the signal, but the signal remained above the baseline as compared to the negative controls, suggesting that ApoC3 was incorporated into the VLDL liposomes. In comparison, when a mixture of pre-incubated 10 µg/ml ApoC3 and 10 µg/ml 14C7 antibody was injected at t=1800 s (indicated as "14C7+"), an initial increase of binding signal was observed, but upon buffer injection at t=2100 s the response returned to the background level as for the negative controls, suggesting that 14C7 interfered with stable interaction between ApoC3 and lipid.

Figure 2B:
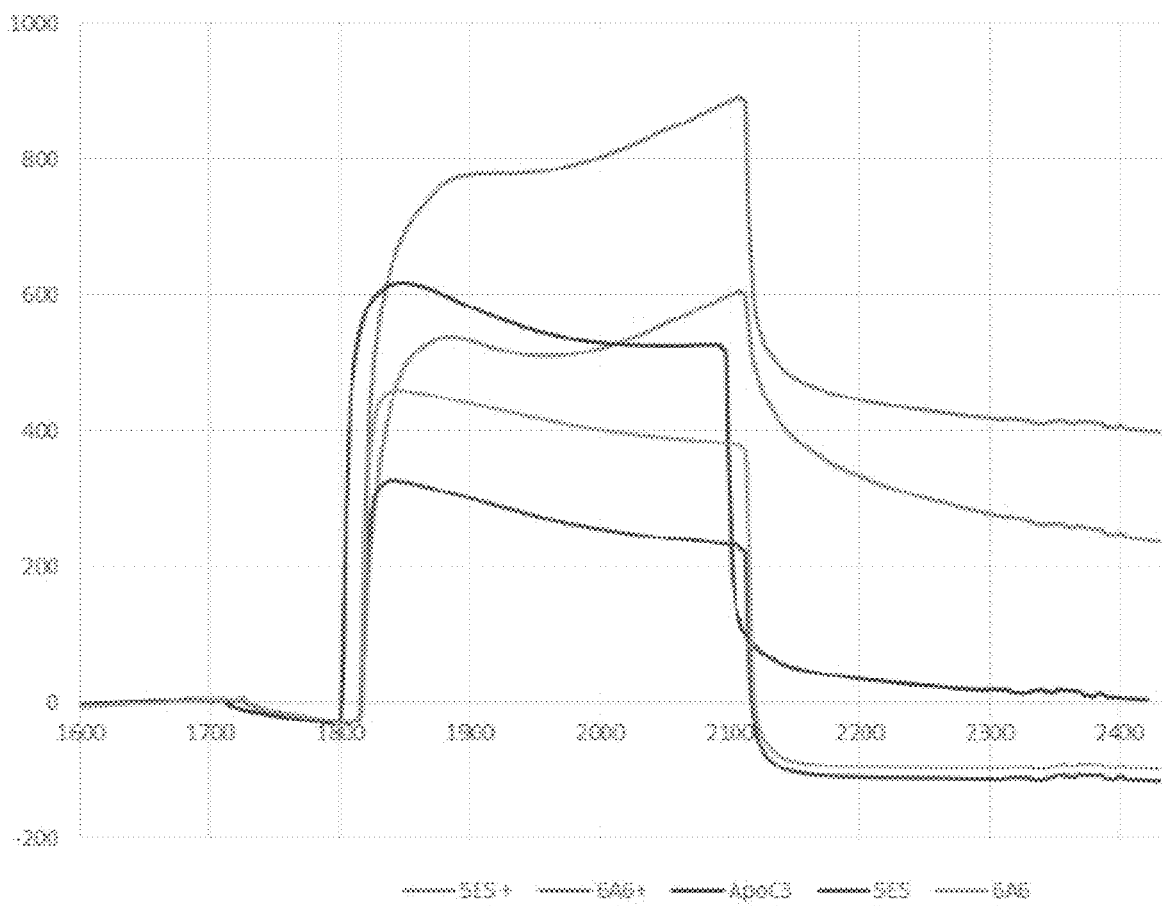

5E5 and 6A6, which did not compete with lipid for binding to ApoC3 in the ELISA assay, were also examined in this SPR-based assay system. As shown in FIG. 2B, ApoC3 injection in the presence of 5E5 or 6A6 led to an increase of binding signal, and the binding signal remained stronger upon buffer injection at t=2100 s than the signal of ApoC3 alone. This result suggested that an ApoC3-5E5 or ApoC3-6A6 complex was retained on the sensor chip through interaction with ApoC3-VLDL. Therefore, 5E5 and 6A6 did not compete for ApoC3 binding with lipid. Control samples of 5E5 or 6A6 alone without ApoC3 did not bind to the test surface.

3.3 SPR-Based Liposome Binding Assay

A second SPR-based lipid competition assay was performed to confirm whether the 14C7, 5E5 and 6A6 antibodies in the IgG1 format competed with lipid for ApoC3 binding. Briefly, DMPC liposomes were prepared by dissolving approximately 5 mg DMPC (Sigma) in chloroform in a glass vial to reach a concentration of 100 mg/ml. The glass vial was placed under vacuum for 3 hours to remove the chloroform, thereby allowing the DMPC to form a lipid film. 1 ml of resuspension buffer (20 mM Tris-HCl, 140 mM NaCl, pH 7.4) was added to the lipid film and vortexed vigorously until the film was removed from the walls. After 6 freeze thaw cycles (in liquid nitrogen), the suspension was extruded through a 100 nm polycarbonate membrane for 30 strokes to form liposomes. The liposomes were diluted 1:10 in HBS-N buffer. An L1 sensor chip was activated by injecting 10 µl of 100 mM NaOH at 10 µl/min, followed by 300 µl of HBS-N buffer at 150 µl/min. 20 µl of liposomes were injected at 2 µl/min to be immobilized on the activated chip surface. Subsequently, 20 µl of 100 mM NaOH was injected, followed by 10 µl of 100 µg/ml BSA. After washing the surface with HBS-N buffer, native human ApoC3 protein was injected at t=1800 s to form a lipsome-ApoC3 complex. The 14C7, 5E5, and 6A6 antibodies were then injected at t=4400 s.

Figure 2C:
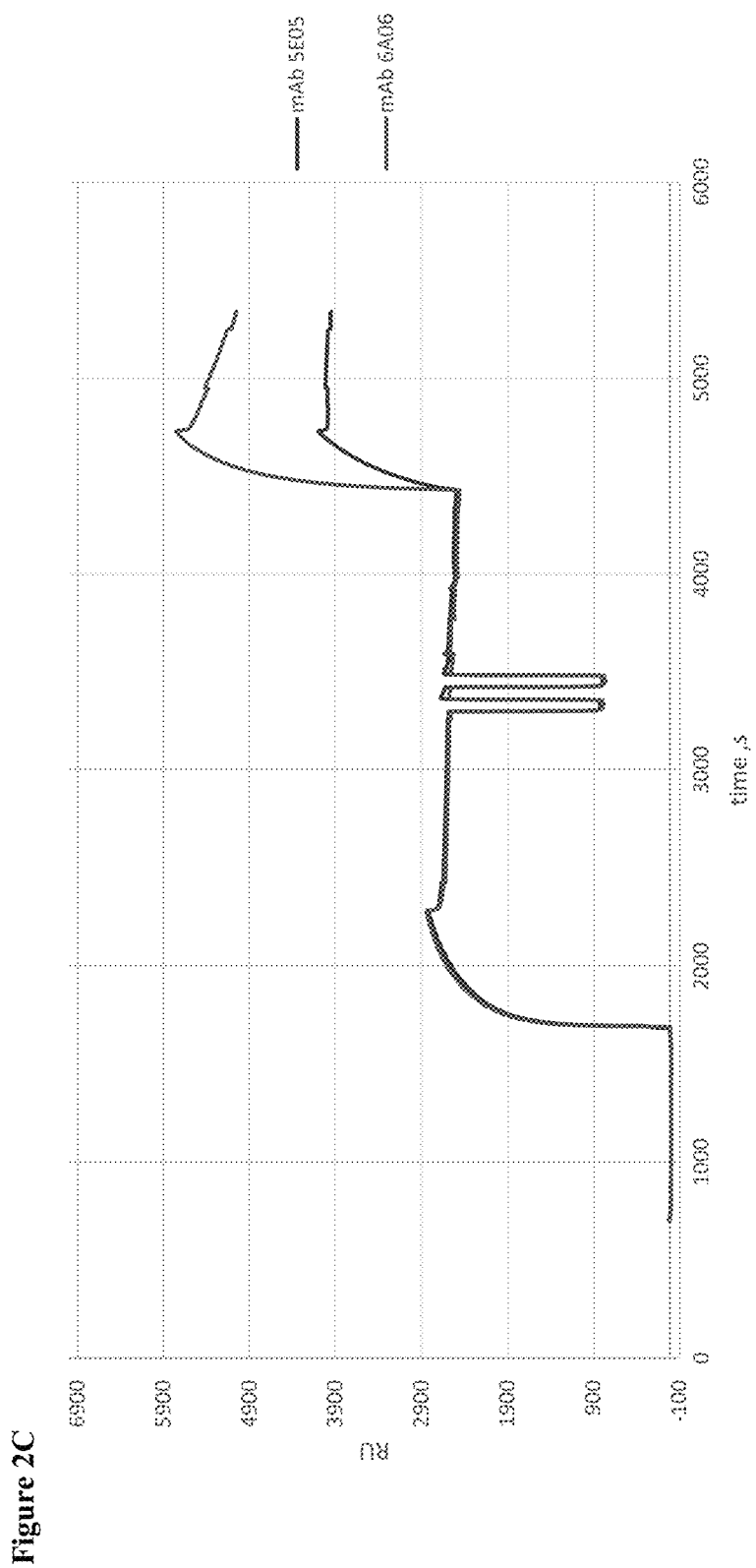

As shown in FIG. 2C, a larger complex was detected upon injection of the 5E5 and 6A6 antibodies, suggesting that these two antibodies were capable of binding to lipid-bound ApoC3 The 5E5 and 6A6 antibodies did not generate a signal in a control group wherein ApoA1 was substituted for ApoC3 (data not shown), indicating that they did not bind to the ApoA1 or DMPC liposome alone.

Example 4

Figure 3:
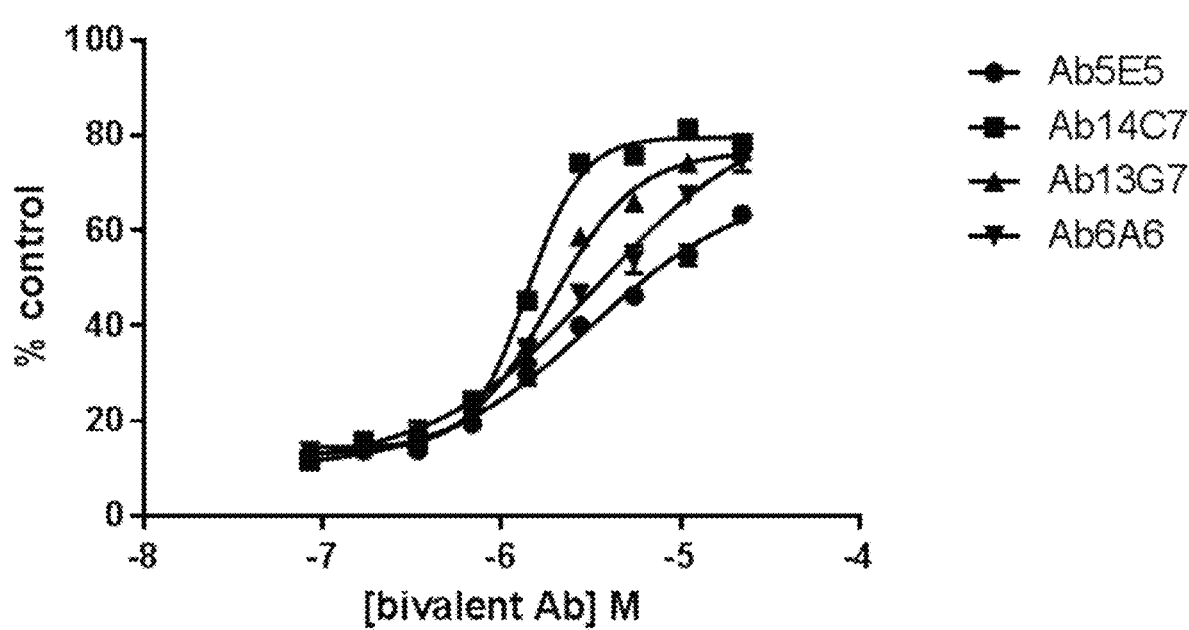
FIG. 3 is a graph showing that 14C7 and 13G7 attenuated the ability of ApoC3 to inhibit lipoprotein lipase (LPL) activity. 14C7, 13G7, 5E5 or 646 antibody was incubated with intralipid and purified ApoC3 protein. The production of non-esterified fatty acids (NEFA) was measured, and the percentages of produced NEFA as compared to NEFA production in the presence of ApoC3 but not an anti-ApoC3 antibody were plotted.

ApoC3-Mediated Lipoprotein Lipase (LPL) Inhibition Assay 4.1 Analysis of Modulation of LPL Activity This example describes characterization of anti-ApoC3 antibodies regarding their ability to attenuate ApoC3-mediated LPL inhibition. 14C7, 13G7, 5E5 and 6A6 antibodies were reformatted to the IgG1 form and were examined in an in vitro LPL activity assay. 14C7 and 13G7 attenuated ApoC3-mediated inhibition of LPL, and significantly increased the LPL activity in a dose-dependent manner (FIG. 3). The EC50 values for 14C7 and 13G7 were about 2 µM and 3 µM, respectively. Such attenuation was weaker and less significant with 5E5 or 6A6 antibodies, which have EC50 values greater than 5 µM.

4.2 Materials and Methods

A 20% intralipid emulsion (Santa Cruz Biotechnology; SC-215182) was washed 3 times by floatation at 15,000× g for 15 min at 10° C. with a 50 mM TRIS-HCl pH 8.0 buffer to remove excess phospholipids and other smaller lipid particles. At the end of the washing process, intralipid was estimated to be 10%. Intralipid was diluted 100-fold into an assay buffer composed of 50 mM TRIS-HCl pH 8.0, 150 mM NaCl, 2% BSA, 15 units/mL heparin. The assay was assembled in a V-bottom polypropylene plate (Falcon #353263) by the addition of 20 µL of intralipid containing test antibody, 20 µL of native ApoC3 protein purified from human serum (Athens Research and Technology) in assay buffer and 20 µL of LPL in assay buffer isolated from bovine milk. The final concentrations of intralipid, ApoC3 protein, and LPL in the assay buffer were 0.1%, 1.5 µM, and 30 nM, respectively. The assay was allowed to proceed for 30 minutes at 30° C., and was terminated by the addition of 100 µL Wako NEFA reagent A (999-34691; 995-34791) supplemented with 20 µM Orlistate. After 20 minutes at 30° C., 50 µL of Wako NEFA reagent B (991-34891; 993-35191) supplemented with 200 µM Amplex Red (AAT Bioquest) was added and the plate was incubated for 20 minutes at 30°

C. A 120 μL aliquot was transferred to a black 96-well plate (Costar #3915) and fluorescence was read at ex 560 nm/em 585 nm. Data was analyzed using 4-parameter logistic function (GraphPad Prism 6).

Example 5

Hepatocyte VLDL Uptake Assay 5.1 Analysis of Hepatocyte VLDL Uptake

Figure 4A:
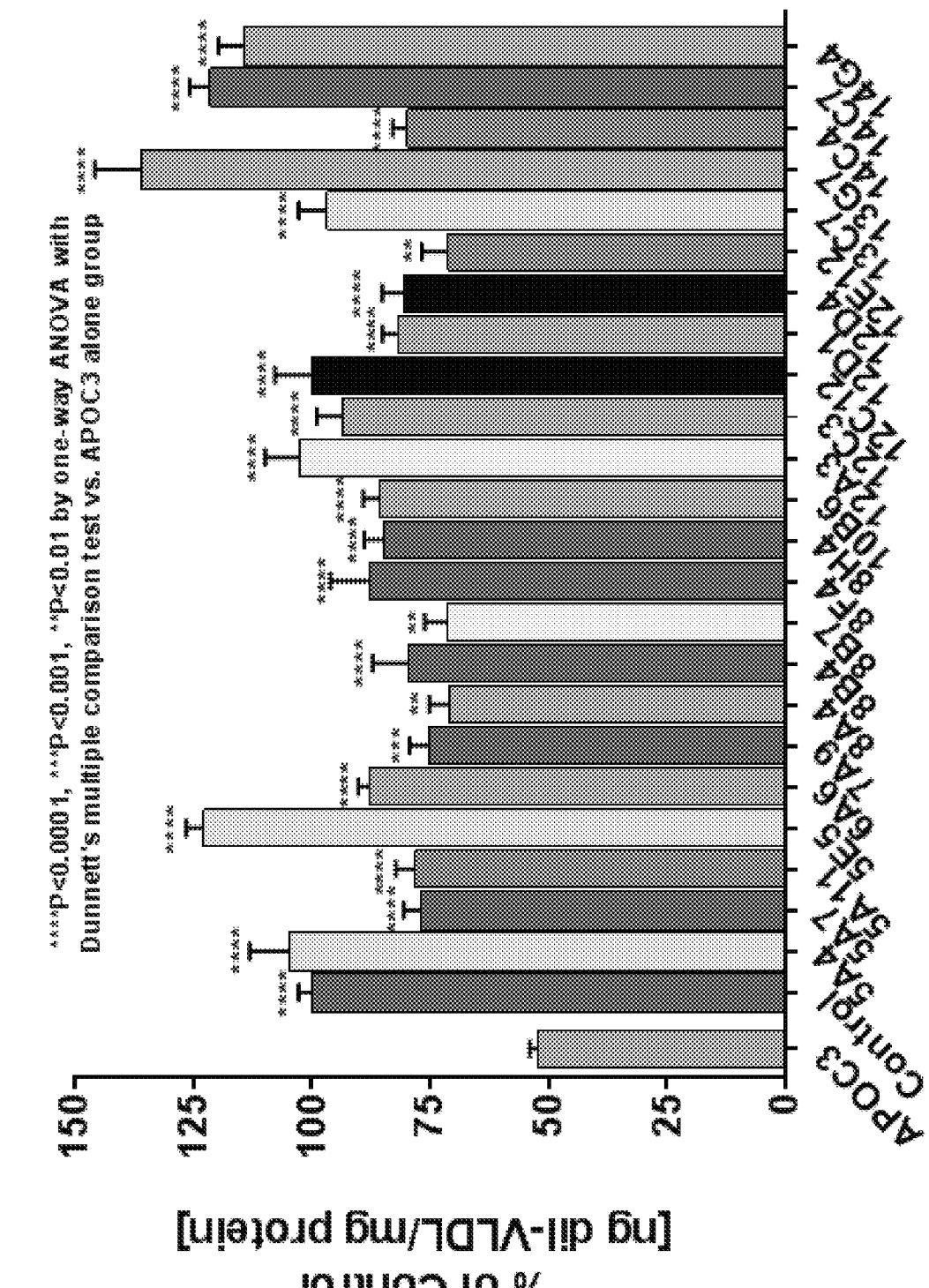
FIGS. 4A-4B are a set of graphs showing that certain anti-ApoC3 antibodies attenuated the ability of ApoC3 to inhibit very low density lipoprotein (VLDL) uptake by HepG2 cells (FIG. 4A), and certain anti-ApoC3 antibodies did not (FIG. 4B). HepG2 cells were incubated with DiI VLDL and purified ApoC3 either alone or in the presence of an anti-ApoC3 antibody as indicated. "Motavizumab" refers to a negative control group with motavizumab but no anti-ApoC3 antibody added. DiI VLDL, ingested by HepG2 cells were measured by fluorescence spectroscopy of the DiI dye.
Figure 4B:
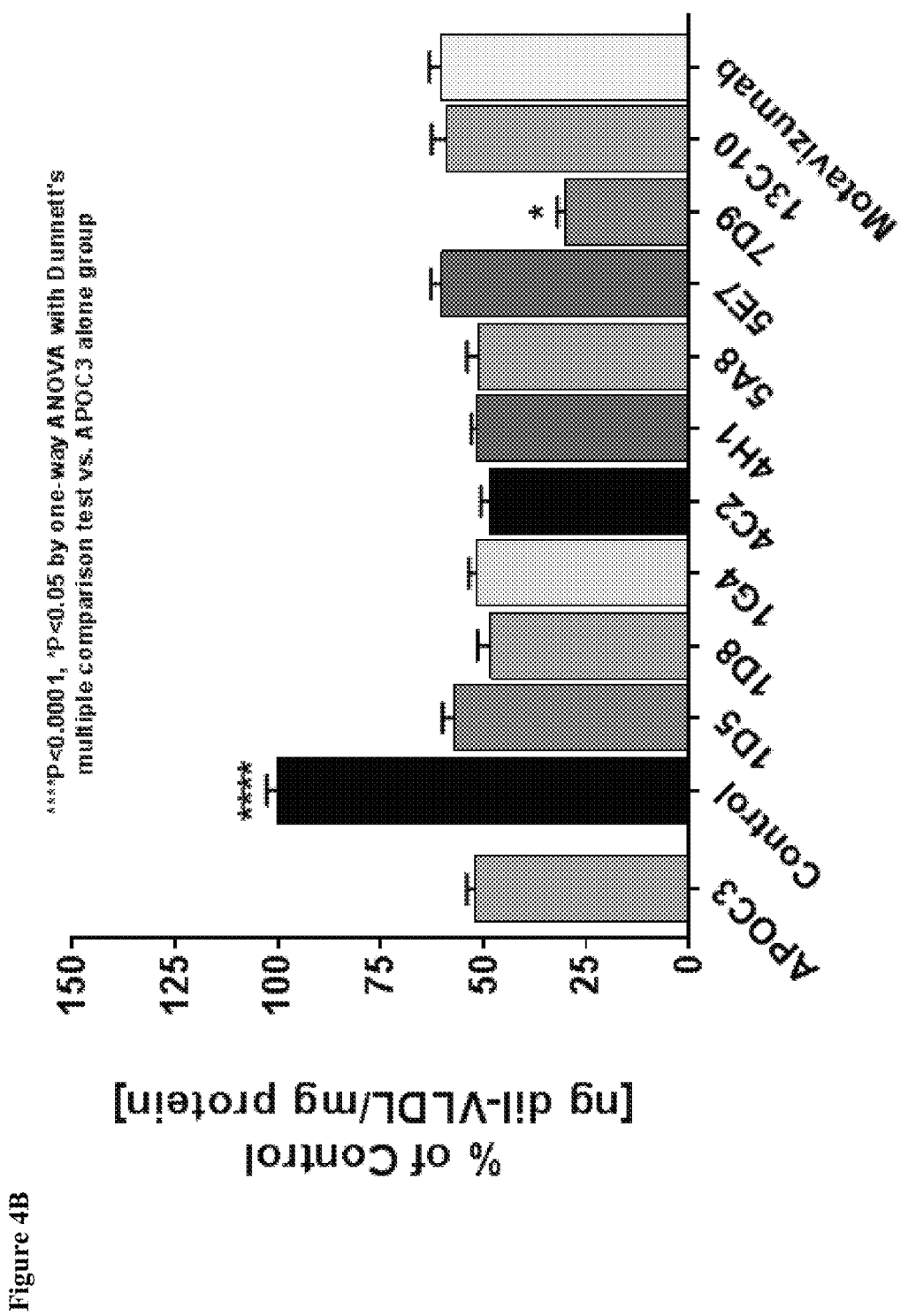

This example describes characterization of anti-ApoC3 antibodies regarding their ability to reverse the inhibition of hepatocyte VLDL uptake by ApoC3. As shown in FIG. 4, clones 5A4, 5A7, 5A11, 5E5, 6A6, 7A9, 8A4, 8B4, 8B7, 8F4, 8H4, 10B6, 12A3, 1203, 12C12, 12D1, 12D4, 12E12, 13C7, 13G7, 14C4, 14C7, and 14G4 increased VLDL uptake by HepG2 cells. The attenuation of the ability of ApoC3 to inhibit VLDL uptake can be quantified from the values in FIG. 4. The first bar labeled "ApoC3" indicates the level of VLDL uptake with purified ApoC3 added to the hepatocyte culture. The second bar labeled "control" indicates the level of VLDL uptake in the hepatocyte culture in the absence of exogenous ApoC3. Taking the value of the first bar as 0% inhibition and the value of the second bar as 100% inhibition, the attenuation of the ability of ApoC3 to inhibit VLDL uptake by 5A4, 5A7, 5A11, 5E5, 6A6, 7A9, 8A4, 8B4, 8B7, 8F4, 8H4, 10B6, 12A3, 12C3, 12C12, 12D1, 12D4, 12E12, 13C7, 13G7, 14C4, 14C7, and 14G4 is about 100%, 50%, 55%, 100%, 75%, 50%, 40%, 60%, 40%, 75%, 70%, 70%, 100%, 85%, 100%, 60%, 60%, 40%, 95%, 100%, 60%, 100%, and 100%, respectively (FIG. 4A). 5A7, 7A9 and 8B7 had the same VH and VL sequences. Clones 1D5, 1D8, 1G4, 4C2, 4H1, 5A8, 5E7, 7D9 and 13C10 did not attenuate the ability of ApoC3 to inhibit VLDL uptake by HepG2 cells (FIG. 4B).

5.2 Materials and Methods

HepG2 cells (ATCC HB-8065) were seeded on poly-d-lysine coated, 96-well tissue culture plates (Greiner Bio-One #655940) in 100 μL complete MEM (Life Technologies) supplemented with 10% FCS (Seradigm) and were cultured at 37° C. with 5% CO2. After 24 hours, the media was removed and the cell monolayer was washed once with 200 μL complete MEM supplemented with 0.0125% bovine serum albumin (Roche). 100 μL fresh medium of complete MEM supplemented with 0.0125% bovine serum albumin was added. After another 24 hours, the media was removed and replaced with 50 μL of a test mixture containing 3 μM ApoC3 (Athens Research and Technology) and 1.5 to 4 μM of test antibody (in the scFv-Fc format) in MEM supplemented with 0.0125% BSA. After 15-minute incubation at 37° C., 30 μg/mL ApoC3-depleted DiI VLDL (Kalen Biomedical, LLC # 770130-9) was added to the test mixture. After 4-hour incubation, the test mixture was removed and the cells were incubated with 100 μL 1% intralipid diluted in complete MEM for 20 minutes, 37° C. 5% CO2. The media was removed and cells were washed three times with 200 μL 37° C. DPBS (Life Technologies 14190-144). After washing, 100 μL isopropanol was added to each well and the plate was incubated at room temperature for 15 minutes with gentle shaking. A 75 μL aliquot was transferred to a black 96-well plate (VWR 89089-582) and fluorescence was measured (ex=520 nm; em=580). The amount of DiI-VLDL extracted from cells per unit volume isopropanol was determined from a DiI-VLDL standard curve. The remaining isopropanol was removed from the cell plate and 100 μL of lysis buffer (0.1 N NaOH, 0.1% SDS) was added to each well. After a minimum of 30 minute incubation, a 25 μL aliquot was used to quantify protein (Pierce BCA Protein Assay; Thermo Scientific #23225). The quantity of VLDL uptake into the cell was calculated as a ratio of DiI-VLDL to protein amount. Data was graphed using GraphPad Prism 6 and is reported as average +/−SEM. One-way ANOVA with multiple comparisons were calculated using GraphPad Prism 6.

Example 6

Cross-Species Reactivity Assay

This example describes characterization of anti-ApoC3 antibodies regarding their ability to cross-react with *Macaca fascicularis* (cynomologus monkey) ApoC3 (cynoApoC3) protein using a Biacore-based assay. As shown in FIG. 5A-5D, 14C7 (FIG. 5A), 5A7 (FIG. 5B), 5E5 (FIG. 5C) and 6A6 (FIG. 5D) in IgG1 format were all capable of binding to cynoApoC3, though their affinity to cynoApoC3 was lower than their affinity to huApoC3.

The SPR experiments were carried out using a Biacore 3000 instrument (GE Healthcare). Flow cells of CM5 sensor chips were coupled with the generated IgG formatted antibodies of 14C7, 5A7, 5E5 and 6A6 (~2000 RU) using the amine coupling chemistry. The coupling was performed using the adaptive immobilization Biacore protocol aiming 2000 RU as coating density, using 10 μg/ml antibody solutions in 10 mM sodium acetate buffer at pH 5.0. For all experiments the HBS-EP buffer at pH 7.4 was used as running and dilution buffer. 60 μl of human native ApoC3 or cynomologus monkey native ApoC3 protein preparations in the concentration range of 10 to 200 μg/ml were injected over all flow channels, followed by an off-rate wash at pH7.4 for 5 min. All injections were performed at a constant flow rate of 30 μl/min at 25° C. After the dissociation, the flow cell surfaces were regenerated by injecting 10 μl of 10 mM NaOH/1 M NaCl and 10 μl of 10 mM glycine at pH1.5. The resulting sensorgrams after blank channel subtraction were used to confirm cross-species reactivity and to evaluate affinity.

Example 7

Epitope Mapping of Anti-ApoC3 Antibodies 5E5, 6A6 and 14C7

7.1 Epitope Scanning of 5E5, 6A6 and 14C7

Figure 6A:
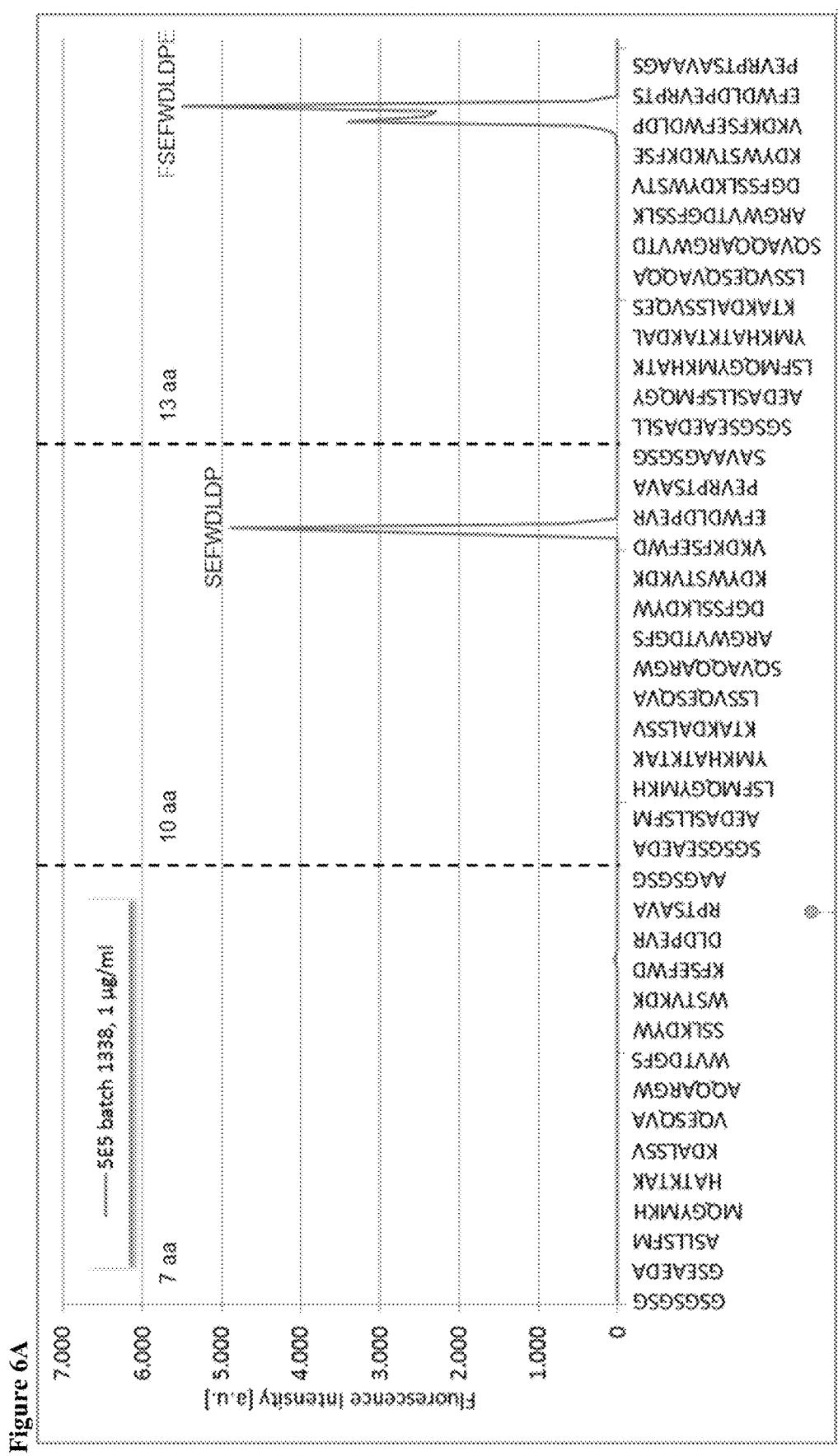
FIGS. 6A-6C are a set of graphs showing epitope mapping of 5E5 (FIG. 6A), 6A6 (FIG. 6B) and 14C7 (FIG. 6C). An array of cyclic ApoC3 peptides having 7, 10 or 13 amino acids was synthesized. Binding of the indicated anti-ApoC3 antibody with the peptides was measured, and intensity plots were generated according to the binding affinity. Amino acids contributing to antibody binding were identified and highlighted.

This example describes epitope scanning of 5E5, 6A6 and 14C7 antibodies. Llama antibody 5E5 was incubated with the ApoC3 peptide microarray at a concentration of 1 μg/ml, and the microarray was stained with secondary and control antibodies. Read-out at scanning intensifies of 7/7 (red/green) manifested very good signal-to-noise ratios, showing a strong and clear monoclonal response with two epitope-like spot patterns formed by adjacent 10 aa and 13 aa peptides with the consensus motif FSEFWDLDPE (SEQ ID NO: 3) (FIG. 6A).

Figure 6B:
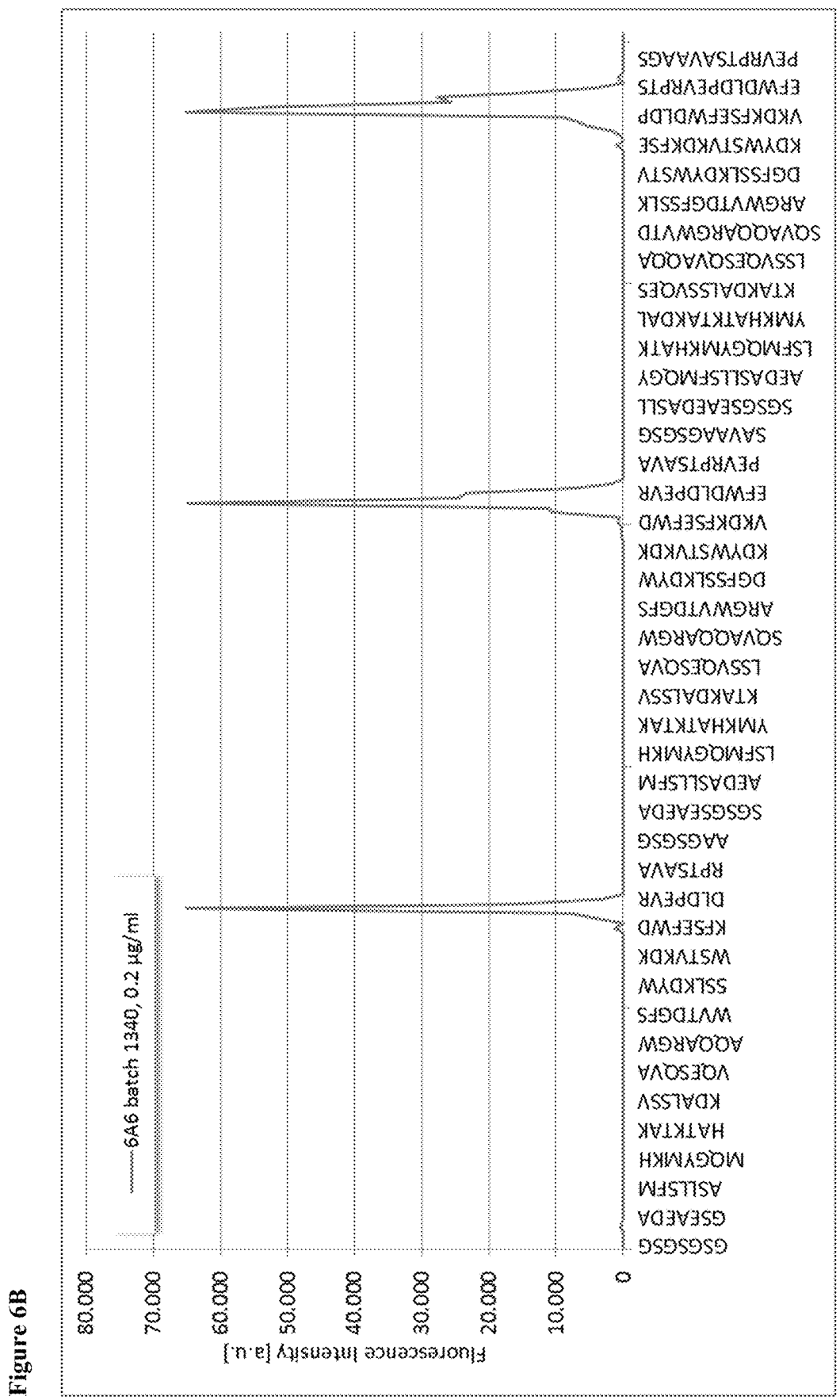
Figure 6C:
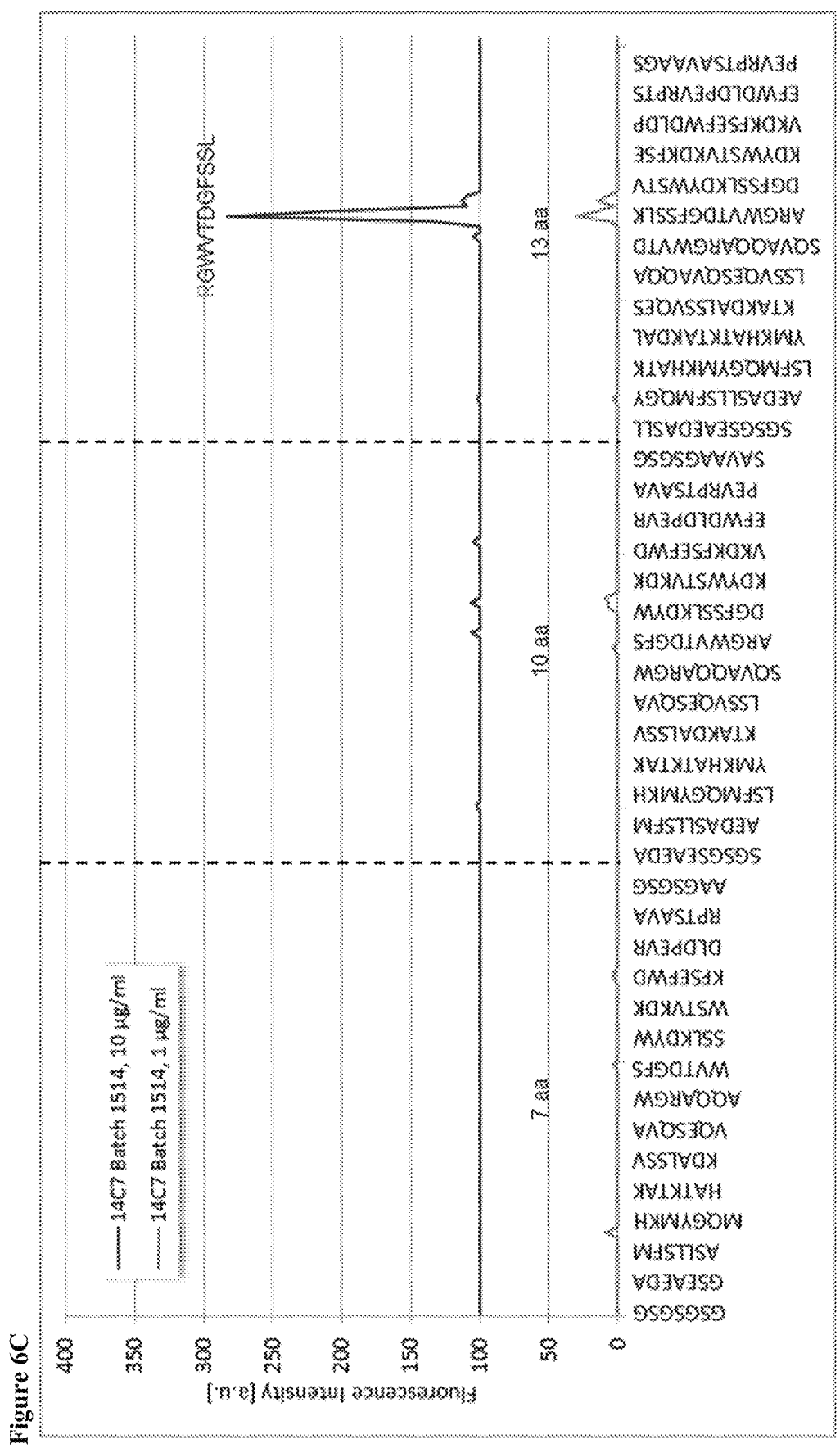

Llama antibody 6A6 was incubated with the ApoC3 peptide microarray at a concentration of 0.2 µg/ml, and the microarray was stained with secondary and control antibodies. Read-out at scanning intensities of 7/7 (red/green) manifested very good signal-to-noise ratios, showing a strong and clear monoclonal response with two epitope-like spot patterns formed by adjacent 10 aa and 13 aa peptides with the consensus motif FSEFWDLDPE (SEQ ID NO: 3) (FIG. 6B).

Amino acids L67 and P69 were moderately conserved; substitution of L67 by T or V, and substitution of P69 by T or S, were well-tolerated, while exchange by other amino acids resulted in approximately 50% loss in binding. Amino acid positions F61 and E63 were less conserved, but showed clear preference for wild type and few additional amino acids (E and Y in position F61; Y, P and A in position E63); exchange by other amino acids caused only minor decrease of spot intensities. Amino acid F64 was completely variable. Variable amino acid positions D59 and E70 apparently also showed a preference for the wild type amino acid, with a general and less specific preference for acidic amino acids D and E.

TABLE 6

Affinity of 5E5 to substituted ApoC3 peptides.

|   | D59 | K60 | F61 | S62 | E63 | F64 | W65 | D66 | L67 | D68 | P69 | E70 | V71 |
|---|---|---|---|---|---|---|---|---|---|---|---|---|---|
| A | 44.36 | 142.68 | 17.35 | 29.61 | 90.12 | 219.99 | 0.00 | 0.00 | 20.96 | 1.75 | 25.71 | 50.04 | 66.34 |
| C | 66.24 | 67.18 | 0.51 | 0.00 | 2.30 | 51.03 | 0.08 | 10.27 | 0.00 | 5.46 | 3.72 | 27.08 | 56.91 |
| D | 100.00 | 199.95 | 16.01 | 0.00 | 29.94 | 258.78 | 0.00 | 100.00 | 0.99 | 100.00 | 21.62 | 82.92 | 110.84 |
| E | 128.19 | 361.70 | 180.25 | 0.00 | 100.00 | 283.41 | 0.00 | 2.16 | 0.45 | 40.07 | 42.97 | 100.00 | 127.12 |
| F | 31.59 | 53.25 | 100.00 | 1.25 | 57.12 | 100.00 | 5.50 | 0.00 | 0.37 | 0.00 | 11.63 | 40.09 | 81.43 |
| G | 60.33 | 143.08 | 0.74 | 0.88 | 0.00 | 211.95 | 0.00 | 0.00 | 35.18 | 3.59 | 24.56 | 46.13 | 91.93 |
| H | 52.80 | 115.74 | 12.10 | 2.89 | 49.85 | 84.52 | 0.00 | 0.00 | 3.58 | 0.00 | 10.73 | 50.47 | 72.83 |
| I | 49.14 | 106.26 | 7.59 | 0.64 | 0.00 | 69.31 | 0.00 | 0.00 | 46.93 | 0.00 | 47.99 | 65.59 | 65.98 |
| K | 30.63 | 100.00 | 13.47 | 4.05 | 19.07 | 114.15 | 0.00 | 0.00 | 45.62 | 0.04 | 20.69 | 60.06 | 91.12 |
| L | 33.57 | 106.86 | 63.39 | 3.83 | 10.08 | 117.68 | 0.00 | 0.00 | 100.00 | 0.00 | 16.68 | 59.08 | 90.56 |
| M | 57.71 | 186.18 | 68.73 | 0.00 | 13.13 | 131.99 | 0.00 | 0.00 | 12.49 | 2.82 | 29.30 | 73.96 | 137.79 |
| N | 52.50 | 152.77 | 25.92 | 0.00 | 31.26 | 233.78 | 0.00 | 0.00 | 9.84 | 0.00 | 19.45 | 49.61 | 86.62 |
| P | 69.26 | 205.07 | 52.72 | 0.00 | 81.16 | 527.81 | 0.00 | 0.00 | 25.48 | 28.58 | 100.00 | 55.17 | 173.42 |
| Q | 68.34 | 178.48 | 75.61 | 1.13 | 32.38 | 129.80 | 0.00 | 0.00 | 3.99 | 0.96 | 24.26 | 67.97 | 86.76 |
| R | 43.33 | 111.73 | 2.77 | 1.45 | 2.19 | 73.66 | 0.02 | 0.17 | 15.39 | 0.00 | 20.11 | 35.75 | 57.33 |
| S | 57.72 | 173.90 | 22.57 | 100.00 | 47.86 | 366.80 | 0.00 | 0.00 | 36.52 | 0.17 | 86.87 | 55.24 | 74.14 |
| T | 94.94 | 177.11 | 40.34 | 215.08 | 0.00 | 467.47 | 0.00 | 0.00 | 167.80 | 0.65 | 113.22 | 83.00 | 96.74 |
| V | 43.34 | 100.56 | 20.16 | 30.48 | 4.20 | 116.72 | 17.87 | 0.00 | 84.76 | 0.00 | 55.17 | 57.01 | 100.00 |
| W | 56.76 | 41.90 | 15.66 | 0.00 | 9.57 | 88.50 | 100.00 | 0.00 | 1.45 | 0.00 | 5.36 | 35.41 | 68.72 |
| Y | 50.27 | 56.30 | 126.40 | 0.00 | 90.93 | 117.64 | 0.00 | 0.00 | 0.02 | 0.16 | 15.36 | 50.73 | 87.43 |

The first row denotes the amino acid positions in the wild-type ApoC3 peptide. The first column denotes specific amino acid substitutions.

Figure 5A:
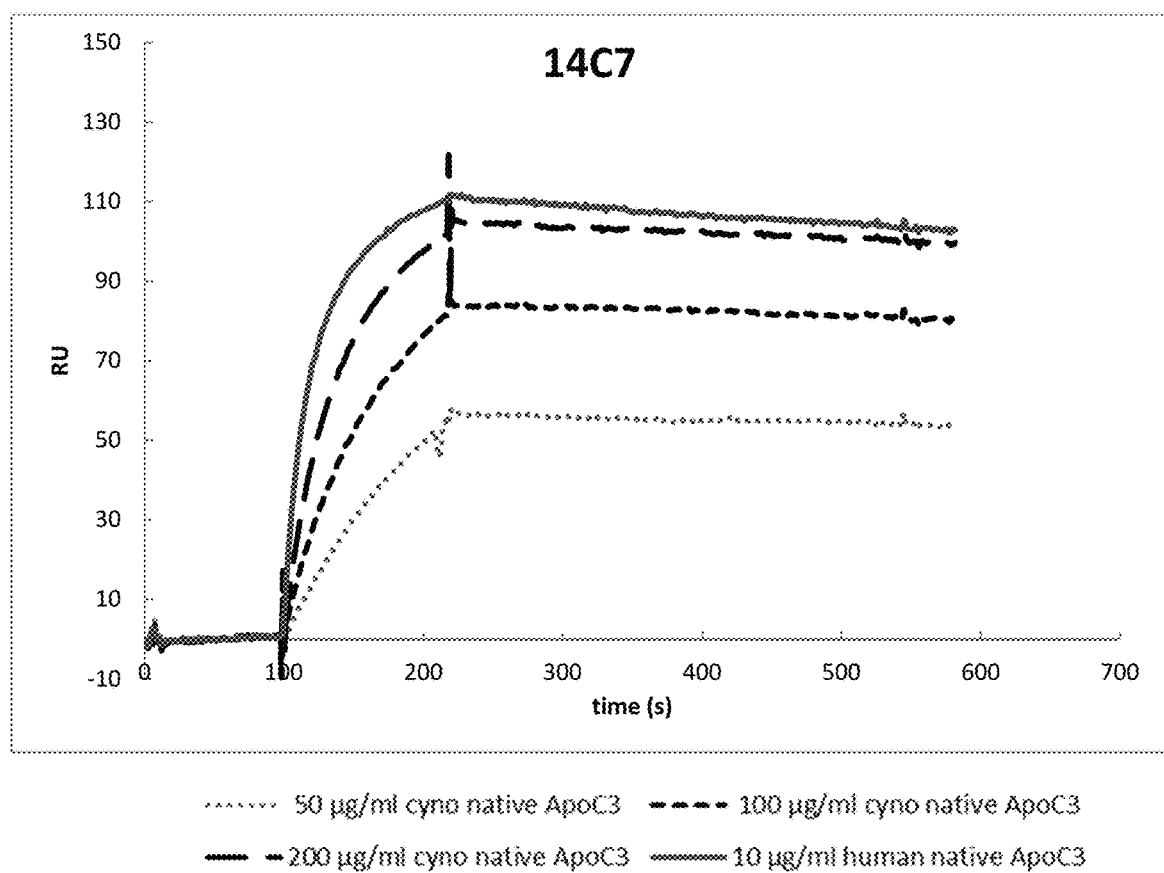
FIGS. 5A-5D are a set of graphs showing binding of 14C7 (FIG. 5A), 5A7 (FIG. 5B), 5E5 (FIG. 5C) and 6A6 (FIG. 5D) to human ApoC3 (huApoC3) or cvnomolgus monkey ApoC3 (cynoApoC3).
Figure 5B:
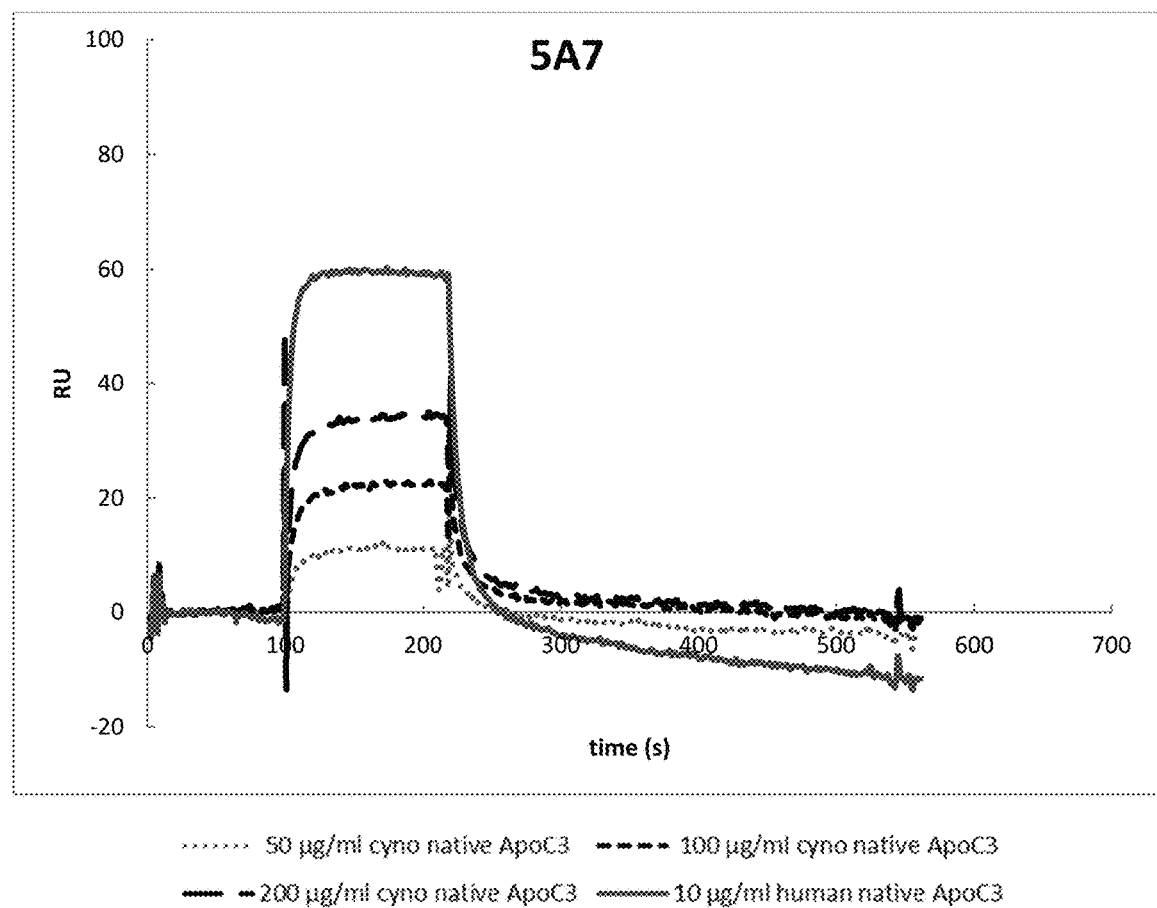
Figure 5C:
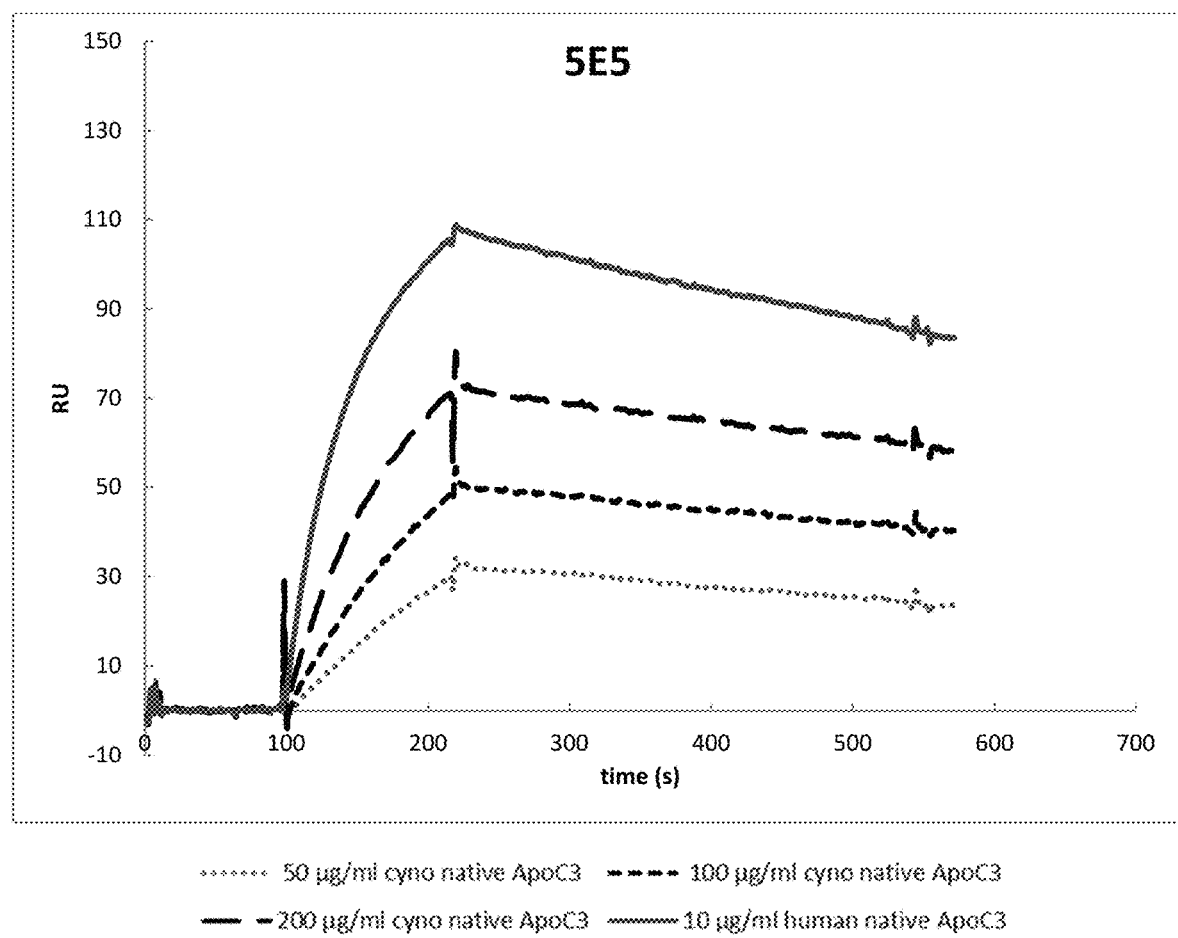
Figure 5D:
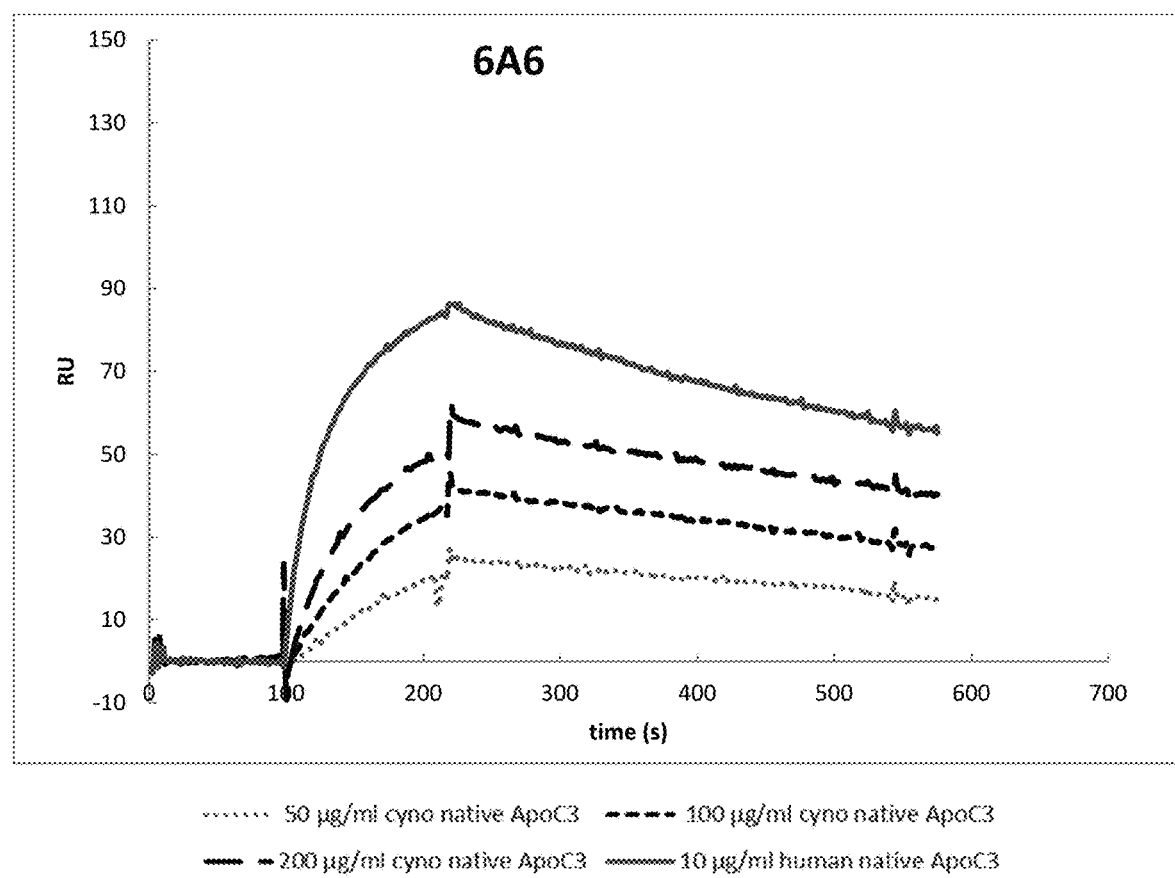

Llama antibody 14C7 was incubated with the ApoC3 peptide microarray at concentrations of 1 µg/ml and 10 µg/ml, and the microarray was stained with secondary and control antibodies. Read-out at scanning intensities of 7/7 (red/green) manifested good signal-to-noise ratios, showing a clear a monoclonal response with a single epitope-like spot pattern formed by adjacent 13 aa peptides with the consensus motif GWVTDGFSSLK (SEQ ID NO: 2) (FIG. 5C).

7.2 Epitope Substitution Scanning of 5E5, 6A6, and 14C7

The consensus motif FSEFWDLDPE (SEQ ID NO: 3) was further analyzed by substitution scanning to identify the amino acid residues that are critical to the interaction between the epitope and the 5E5 or 6A6 antibody. An array of 13 aa cyclic constrained peptides was synthesized. In each row of the array, a single amino acid residue in peptide DKFSEFWDLDPEV (SEQ ID NO: 44) was substituted, wherein the substituting residue was denoted by the column of the array.

The binding of 5E5 to the substitution array, as shown in Table 6 (affinity expressed as a percentage of binding to the wild-type ApoC3 peptide (SEQ ID NO: 44)) and in a substitution matrix (FIG. 7A), demonstrated that W65 and D66 of mature huApoC3 (SEQ ID NO: 1) were essential for binding of mAb 5E5 and did not tolerate exchange by any other amino acids. S62 and D68 of mature huApoC3 were also highly conserved; substitution of S62 by A or V, and substitution of D68 by E or P, caused decrease of spot intensities by ~60% or higher. Conservative substitution of S62 by T, however, resulted in doubling of spot intensities.

The binding of 6A6 to the substitution array, as shown in Table 7 (affinity expressed as a percentage of binding to the wild-type ApoC3 peptide (SEQ ID NO: 44)) and in a substitution matrix (FIG. 7B), demonstrated that E70 of mature huApoC3 (SEQ ID NO: 1) were essential for binding of mAb 6A6 and did not tolerate exchange by any other amino acids. D66 and D68 of mature huApoC3 were also highly conserved; conservative exchange by E caused a 80% decrease of spot intensities in position D66 and a 44% decrease in position D68, and replacement by other amino acids was not tolerated without complete loss in antibody binding. L67 was well conserved; substitution by 1 or T did not affect antibody binding, but exchange by V or M resulted in approximately 50% decrease in spot intensities. E63 was moderately conserved, but susceptible for conservative exchange by D; replacement by P even resulted in ~1.5 fold higher spot intensities, possibly due to a folding effect. W65 was also moderately conserved, but exchange by E, S, D and T led to increased spot intensities; substitution by other amino acids, however, caused at least a 45% decrease in antibody binding. F61 showed a clear preference for the wild type amino acid or for conservative exchange by Y, but was generally less conserved and susceptible for exchange by all other amino acids without a complete loss in binding to 6A6. S62 and P69 showed a certain preference for the wild type amino acids, but both positions were poorly conserved and tolerated a number of substitutions without any effect on antibody binding. F64 was completely variable. All other variable positions exhibited a clear preference for acidic amino acids D and E, possibly due to an ionic effect.

TABLE 7

Affinity of 6A6 to substituted ApoC3 peptides.

|   | D59 | K60 | F61 | S62 | E63 | F64 | W65 | D66 | L67 | D68 | P69 | E70 | V71 |
|---|---|---|---|---|---|---|---|---|---|---|---|---|---|
| A | 86.42 | 120.42 | 41.07 | 97.31 | 36.70 | 166.36 | 26.37 | 0.00 | 9.07 | 0.00 | 57.43 | 0.97 | 85.16 |
| C | 69.18 | 84.04 | 20.64 | 10.45 | 7.93 | 76.38 | 15.99 | 7.92 | 1.13 | 5.29 | 28.92 | 0.00 | 100.20 |
| D | 100.00 | 151.10 | 31.34 | 35.05 | 77.88 | 220.13 | 130.06 | 100.00 | 2.89 | 100.00 | 98.51 | 13.78 | 222.56 |
| E | 169.54 | 223.26 | 83.88 | 70.74 | 100.00 | 235.56 | 167.67 | 18.86 | 8.52 | 56.90 | 151.65 | 100.00 | 228.42 |
| F | 61.50 | 83.73 | 100.00 | 9.54 | 8.50 | 100.00 | 55.34 | 7.27 | 26.29 | 0.00 | 97.69 | 9.36 | 85.38 |
| G | 87.48 | 117.46 | 25.88 | 53.92 | 20.48 | 167.99 | 49.49 | 0.00 | 0.60 | 0.00 | 16.27 | 1.26 | 108.64 |
| H | 85.76 | 123.61 | 44.18 | 26.51 | 12.26 | 107.29 | 16.96 | 0.00 | 7.67 | 0.00 | 19.23 | 0.03 | 75.94 |
| I | 103.39 | 115.95 | 44.31 | 129.44 | 8.76 | 100.39 | 20.29 | 0.00 | 104.67 | 0.00 | 81.94 | 1.59 | 54.32 |
| K | 45.57 | 100.00 | 37.16 | 11.07 | 7.90 | 106.94 | 0.00 | 0.33 | 25.80 | 0.00 | 26.30 | 0.00 | 58.74 |
| L | 68.63 | 89.25 | 61.30 | 80.96 | 10.10 | 89.71 | 18.53 | 0.00 | 100.00 | 0.00 | 36.83 | 1.22 | 78.04 |
| M | 60.17 | 146.27 | 56.46 | 63.50 | 43.49 | 108.51 | 19.08 | 0.08 | 43.42 | 0.00 | 44.15 | 2.34 | 105.37 |
| N | 77.45 | 138.61 | 48.34 | 126.44 | 38.79 | 153.14 | 56.52 | 0.00 | 19.80 | 0.00 | 32.68 | 0.15 | 98.65 |
| P | 107.23 | 156.71 | 78.97 | 27.06 | 138.15 | 285.04 | 13.81 | 0.00 | 0.00 | 0.00 | 100.00 | 2.53 | 109.50 |
| Q | 95.04 | 139.83 | 64.50 | 110.76 | 46.31 | 133.47 | 38.33 | 0.00 | 25.68 | 0.00 | 28.19 | 2.10 | 81.39 |
| R | 70.18 | 105.31 | 35.63 | 37.21 | 5.31 | 79.08 | 7.71 | 0.00 | 22.62 | 0.66 | 17.43 | 0.00 | 47.50 |
| S | 87.47 | 155.61 | 39.23 | 100.00 | 35.22 | 196.16 | 131.50 | 0.00 | 26.51 | 0.57 | 75.63 | 1.05 | 84.72 |
| T | 101.48 | 148.75 | 56.29 | 138.96 | 35.92 | 214.93 | 104.59 | 0.00 | 100.22 | 0.69 | 118.29 | 1.55 | 94.50 |
| V | 65.08 | 106.12 | 46.96 | 93.60 | 12.98 | 85.96 | 23.96 | 0.00 | 56.47 | 0.00 | 68.32 | 0.27 | 100.00 |
| W | 78.11 | 78.57 | 32.94 | 4.78 | 1.91 | 69.55 | 100.00 | 0.00 | 1.26 | 0.00 | 13.69 | 2.84 | 59.19 |
| Y | 70.25 | 83.93 | 111.68 | 16.34 | 8.92 | 86.37 | 26.68 | 0.00 | 3.08 | 0.00 | 51.99 | 4.49 | 87.28 |

The first row denotes the amino acid positions in the wild-type ApoC3 peptide. The first column denotes specific amino acid substitutions.

The consensus motif GWVTDGFSSLK (SEQ ID NO: 2) was further analyzed by substitution scanning to identify the amino acid residues that are critical to the interaction between the epitope and the 14C7 antibody. An array of 13 aa cyclic constrained peptides was synthesized. In each row of the array, a single amino acid residue in peptide ARGWVTDGFSSLK (SEQ ID NO: 45) was substituted, wherein the substituting residue was denoted by the column of the array.

The binding of 14C7 to the substitution array, as shown in Table 8 (affinity expressed as a percentage of binding to wild-type ApoC3 peptide (SEQ ID NO: 45)) and in a substitution matrix (FIG. 7C), demonstrated that T44 and S49 of mature huApoC3 (SEQ ID NO: 1) were essential for binding of mAb 14C7 and did not tolerate exchange by any other amino acids without a complete or nearly complete loss in binding. Amino acids G41 and G46 were highly conserved; substitution of G41 by E, N or Q caused a decrease of spot intensities by ~70% or higher, whereas exchange of G46 by N was hardly tolerated and resulting in 90% reduced spot intensities. Amino acid positions F47 and L50 also exhibited a high degree of sequence conservation and tolerated only conserved exchange by Y (F47) or by other hydrophobic amino acids F and W (L50) with a remarkable decrease of spot intensities. Amino acid positions V43, D45 and K51 were also well conserved with a clear preference for the wild type amino acids and a certain tolerance particularly for conservative exchanges by Y, F and I (V43), A, E and K (D45) as well as by R (K51). These exchanges resulted in 30-55% reduction in spot intensity, while other amino acid exchanges were less tolerated. Replacement of V43 by Y, however, increased spot intensity by two fold. Amino acid positions W42 and 48S were poorly conserved or even variable; both positions were susceptible for only a number of amino acid exchanges, and exchange by F, S and T (W42) or by E (S48) even caused a two- to three-fold increase of spot intensity. Amino acid positions A39 and R40 were variable.

TABLE 8

Affinity of 14C7 to substituted ApoC3 peptides.

|   | A39 | R40 | G41 | W42 | V43 | T44 | D45 | G46 | F47 | S48 | S49 | L50 | K51 |
|---|---|---|---|---|---|---|---|---|---|---|---|---|---|
| A | 100.00 | 50.10 | 7.01 | 115.70 | 26.94 | 0.00 | 45.32 | 0.00 | 0.00 | 75.52 | 2.43 | 0.00 | 10.11 |
| C | 77.46 | 62.28 | 14.80 | 61.60 | 0.12 | 0.00 | 11.20 | 0.00 | 0.00 | 56.82 | 0.00 | 0.00 | 0.00 |
| D | 50.69 | 50.01 | 19.41 | 107.64 | 0.00 | 0.00 | 100.00 | 0.00 | 0.00 | 71.57 | 0.00 | 0.00 | 0.00 |
| E | 98.90 | 76.88 | 28.05 | 98.45 | 0.00 | 0.00 | 40.01 | 0.00 | 0.00 | 289.91 | 0.00 | 0.00 | 4.71 |
| F | 78.21 | 70.80 | 10.77 | 242.46 | 68.89 | 0.00 | 0.00 | 0.86 | 100.00 | 9.29 | 0.89 | 56.65 | 6.24 |
| G | 93.02 | 62.85 | 100.00 | 106.74 | 0.12 | 0.00 | 2.16 | 100.00 | 0.00 | 3.70 | 0.00 | 0.00 | 5.77 |
| H | 69.42 | 44.42 | 23.13 | 48.59 | 14.62 | 0.92 | 1.81 | 1.81 | 0.00 | 11.48 | 0.56 | 0.00 | 2.43 |
| I | 52.30 | 35.10 | 5.33 | 27.89 | 40.98 | 1.86 | 2.04 | 0.00 | 0.00 | 23.58 | 0.00 | 9.47 | 0.86 |
| K | 72.94 | 58.06 | 18.04 | 136.36 | 25.45 | 0.00 | 39.42 | 0.24 | 0.12 | 89.99 | 3.23 | 0.74 | 100.00 |
| L | 77.46 | 54.20 | 6.27 | 312.13 | 429.39 | 0.50 | 17.10 | 0.00 | 4.56 | 19.65 | 0.00 | 100.00 | 0.33 |
| M | 90.65 | 69.57 | 18.67 | 79.42 | 20.86 | 0.00 | 21.03 | 0.00 | 0.00 | 121.16 | 1.86 | 0.65 | 11.07 |
| N | 103.16 | 64.79 | 27.49 | 117.91 | 1.36 | 2.49 | 4.85 | 10.45 | 0.06 | 48.49 | 0.00 | 0.00 | 2.60 |
| P | 165.66 | 52.67 | 8.70 | 18.61 | 1.86 | 0.00 | 0.00 | 0.00 | 0.00 | 0.06 | 0.00 | 0.00 | 0.24 |
| Q | 103.54 | 85.76 | 27.11 | 93.13 | 7.49 | 0.00 | 21.01 | 0.00 | 0.00 | 46.80 | 0.33 | 0.12 | 5.47 |
| R | 89.37 | 100.00 | 19.38 | 140.98 | 15.12 | 0.00 | 20.09 | 0.30 | 0.00 | 34.50 | 0.74 | 0.00 | 57.41 |
| S | 81.39 | 54.67 | 18.70 | 204.26 | 1.54 | 1.12 | 20.83 | 0.00 | 0.00 | 100.00 | 100.00 | 0.00 | 27.46 |
| T | 88.69 | 38.69 | 9.44 | 185.67 | 9.94 | 100.00 | 8.67 | 0.00 | 0.00 | 88.35 | 6.21 | 0.00 | 17.46 |
| V | 75.95 | 57.50 | 8.76 | 48.29 | 100.00 | 4.26 | 1.21 | 0.00 | 0.06 | 45.32 | 0.59 | 0.74 | 3.85 |

TABLE 8-continued

Affinity of 14C7 to substituted ApoC3 peptides.

|   | A39 | R40 | G41 | W42 | V43 | T44 | D45 | G46 | F47 | S48 | S49 | L50 | K51 |
|---|---|---|---|---|---|---|---|---|---|---|---|---|---|
| W | 59.38 | 38.82 | 17.71 | 100.00 | 8.98 | 0.00 | 0.06 | 0.00 | 1.57 | 3.49 | 0.27 | 17.73 | 0.00 |
| Y | 40.48 | 37.52 | 6.27 | 148.73 | 230.30 | 0.00 | 0.00 | 0.00 | 67.71 | 5.83 | 0.00 | 0.38 | 0.00 |

The first row denotes the amino acid positions in the wild type ApoC3 peptide. The first column denotes specific amino acid substitutions.

7.3 Materials and Methods

The sequence of ApoC3 was elongated by neutral GSGSGSG (SEQ ID NO: 46) linkers at the C- and N-terminus to avoid tnincated peptides. The elongated sequence was translated into 7, 10 and 13 amino acid peptides with peptide-peptide overlaps of 6, 9 and 12 amino acids. After peptide synthesis via the Pepperchip® platform, all peptides were cyclized via a thioether linkage between a C-terminal cysteine side chain thiol group and an appropriately modified N-terminus. The resulting cyclic: ApoC3 peptide microarrays contained 252 different cyclic constrained peptides printed in duplicate (504 peptides spots) and were framed by additional HA control peptides (YPYDVPDYAG (SEQ ID NO: 112), 80 spots).

After 15 min pre-swelling in washing buffer and 30 min in blocking buffer, one of the ApoC3 peptide microarray copies was initially incubated with the secondary antibody goat anti-human IgG (Fc) DyLight680 at a dilution of 1:5000 and with control antibody mouse monoclonal anti-HA (12CA5) DyLight800 at a dilution of 1:2000 for 45 min at room temperature to analyze background interactions with the antigen-derived peptides. At scanning intensities of 7/7 (red/green), we did not observe any background interaction with both the secondary and the control antibody with the ApoC3 peptides even upon significant increase of brightness and contrast (see adjusted scan). The mouse monoclonal anti-HA (12CA5) DyLight800 control antibody gave rise to the expected well-defined HA control spot pattern framing the peptide microarray and validated the overall peptide microarray integrity and assay quality.

Pre-staining of one of the ApoC3 peptide microarrays was done with the secondary antibody goat anti-human IgG (Fe) DyLight680 (1:5000) and control antibody mouse monoclonal anti-HA (12CA5) DyLight800 (1:2000) to investigate background interactions of the secondary antibody with the antigen-derived peptides that could interfere with the main assays. Subsequent incubation of other ApoC3 peptide microarrays with antibody samples was followed by staining with secondary and control antibodies as well as read-out at scanning intensities of 7/7 (red/green). The additional HA peptides framing the peptide arrays were stained as internal quality control to confirm the assay quality and the peptide microarray integrity.

Quantification of spot intensities and peptide annotation were based on the 16-bit gray scale tiff files at scanning intensities of 7/7 that exhibit a higher dynamic range than the 24-bit colorized tiff files; microarray image analysis was done with PepSlide® Analyzer and summarized in the Excel files listed in Material and Methods. A software algorithm breaks down fluorescence intensities of each spot into raw, foreground and background signal, and calculates averaged median foreground intensities and spot-to-spot deviation of spot duplicates. Based on averaged median foreground intensities, an intensity map was generated and interactions in the peptide map highlighted by an intensity color code with red for high and white for low spot intensities. We tolerated a maximum spot-to-spot deviation of 40%; otherwise the corresponding intensity value was zeroed.

We further plotted averaged spot intensities of the assays with the antibody samples against the ApoC3 sequence from the N- to the C-terminus to visualize overall spot intensities and signal-to-noise ratios. The intensity plots were correlated with peptide and intensity maps as well as with visual inspection of the microarray scans to identify epitopes that were recognized by the antibody samples. Amino acids contributing to antibody binding were identified and highlighted.

Example 8

Reduction of Post-Prandial Triglyceride by Anti-ApoC3 Antibody 5E5

8.1 Production and Characterization of AAV8-huApoC3 Mouse Model

Figure 8A:
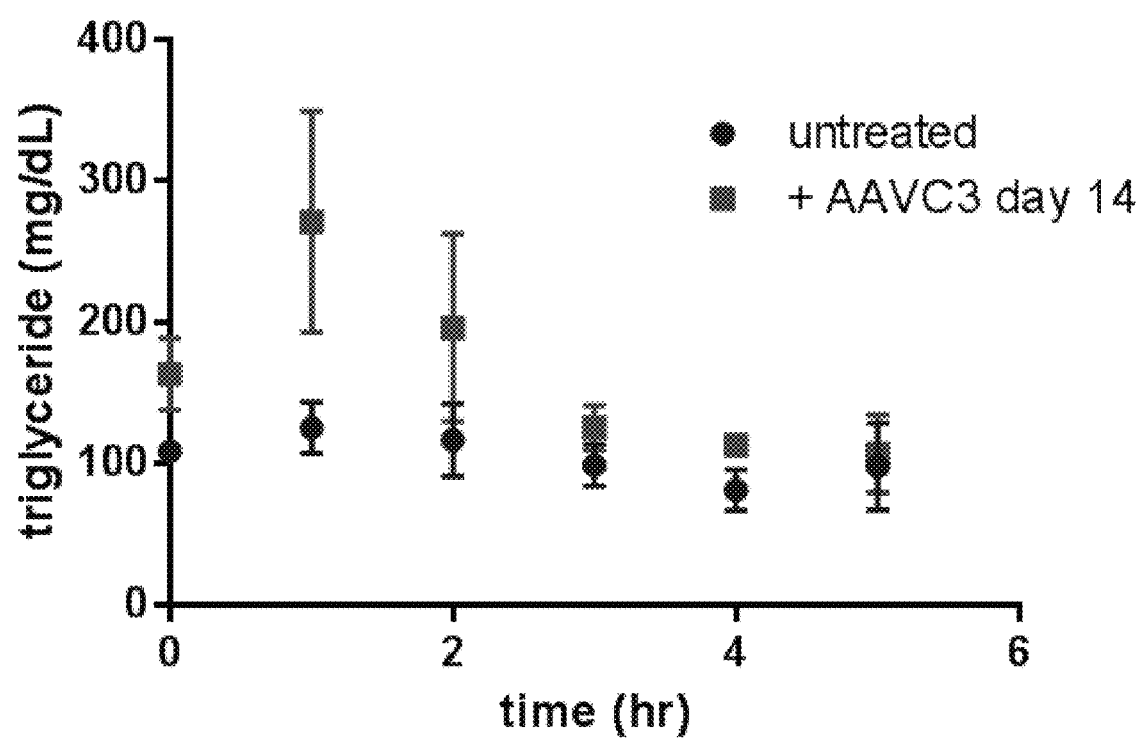
FIGS. 8A-8B are a set of graphs demonstrating the effect of huApoC3 overexpression on circulating post-prandial triglycerides in an AAV8-huApoC3 mouse model. Mice were infected with vehicle ("untreated") or $3\times10^{11}$ viral particles of AAV8-huApoC3 ("+AAVC3 day 14"). Serum triglyceride level after an olive oil challenge was higher in the AAV8-huApoC3 mice (FIG. 8A). The area under curve (AUC) of triglyceride level was increased by 38% with a p value of 0.0047 with unpaired T test (FIG. 8B).
Figure 8B:
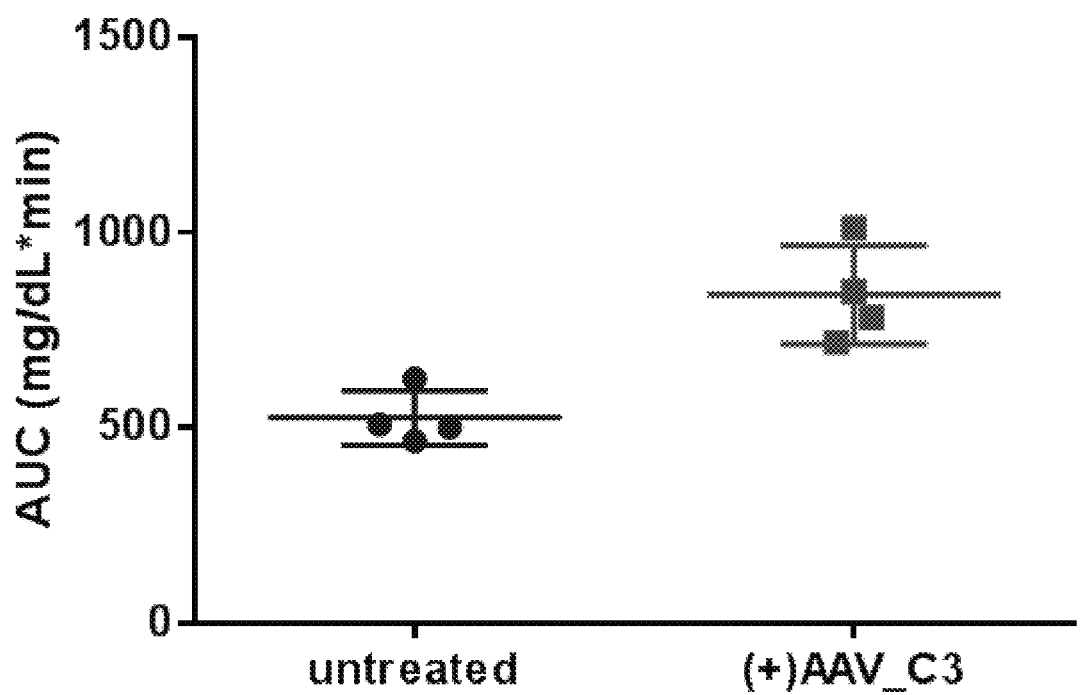

In this example, we first produced and characterized a mouse model expression human ApoC3. Mice (C57BL/6) were infected with $3 \times 10^{11}$ viral particles of an AAV8 vector harboring human ApoC3 gene or with vehicle control. 14 days after the infection, the mean serum huApoC3 level of the AAV8-huApoC3 mice was 5.7 µM. The circulating triglyceride level after a four-hour fasting was 163 mg/dL in these mice, compared to 109 mg/dL in the control mice (p=0.0065). To determine the impact of increased huApoC3 on the clearance of an oral lipid load, an oral dose of olive oil (10 µL per gram body weight) was given to the mice 14 days after the AAV or vehicle infection. Serum triglyceride levels were measured in a time course. The postprandial increase in triglyceride was higher in the AAV8-huApoC3 mice over the time course of the experiment (FIG. 8A), and the area under curve (AUC) of triglyceride level over time in the AAV8-huApoC3 mice was higher by 38% (p=0.0047 with unpaired T test) (FIG. 8B). Taken together, injection of $3 \times 10^{11}$ AAV8-huApoC3 viral particles led to impaired triglyceride clearance in mice and could serve as an animal model for characterizing anti-ApoC3 antibodies.

8.2 Characterization of 5E5 Effect on Postprandial Lipemia in the Mouse Model

Figure 9A:
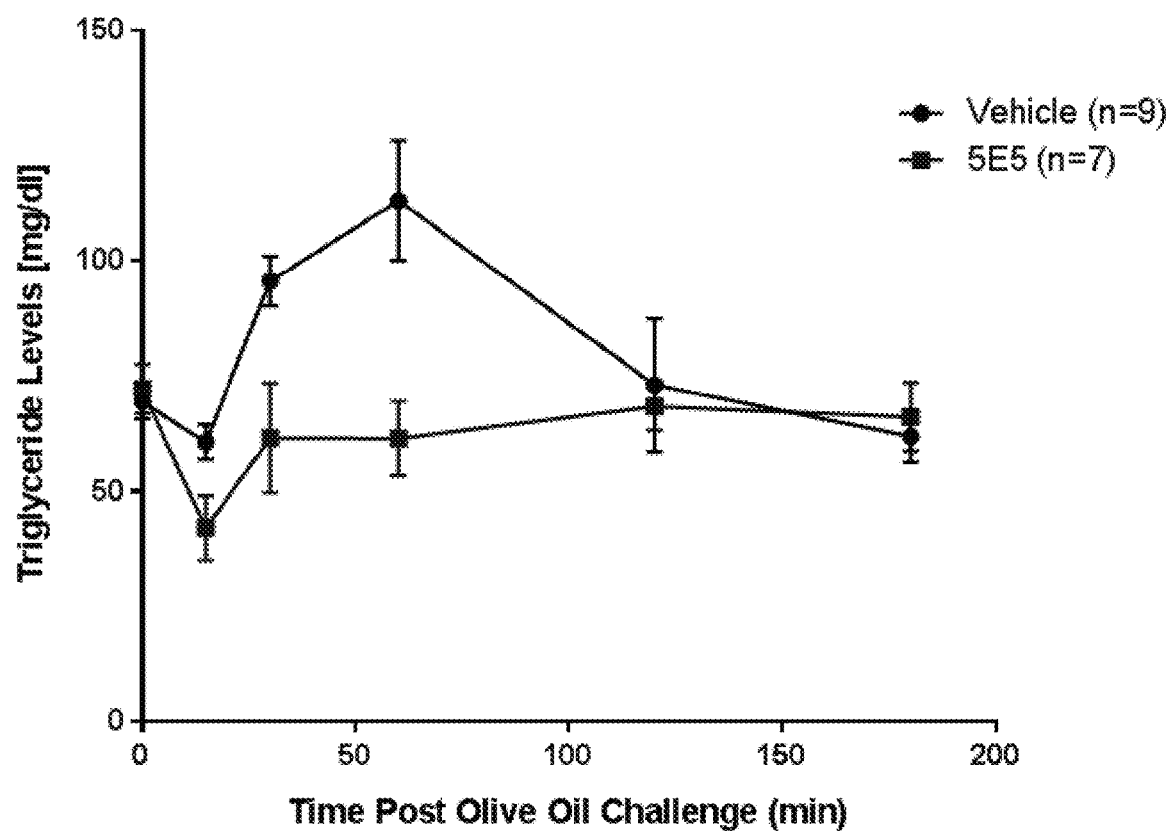
FIGS. 9A-9D are a set of graphs showing the post prandial triglyceride-lowering effect of 5E5. Vehicle or 5E5 antibody was administered to mice receiving $3\times10^{11}$ AAV8-huApoC3 viral particles. An oral dose of olive oil was given, and triglyceride levels were measured in a time course (FIG. 9A). The area under curve ("AUC") was reduced by about 25% with 5E5 administration as compared to vehicle control with a p value of 0.030 (FIG. 9B). Serum ApoC3 levels (FIG. 9C) and 5E5 antibody levels (FIG. 9D) were also measured in a time course.
Figure 9B:
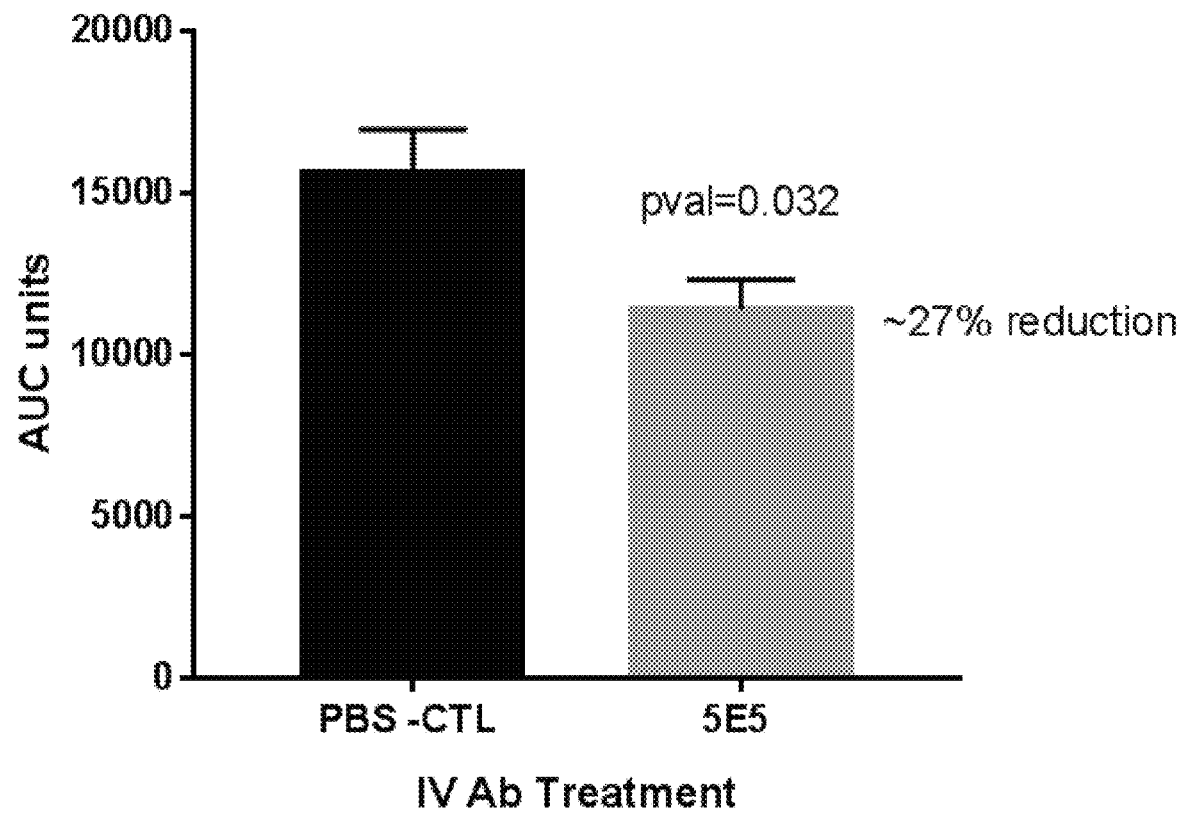
Figure 9C:
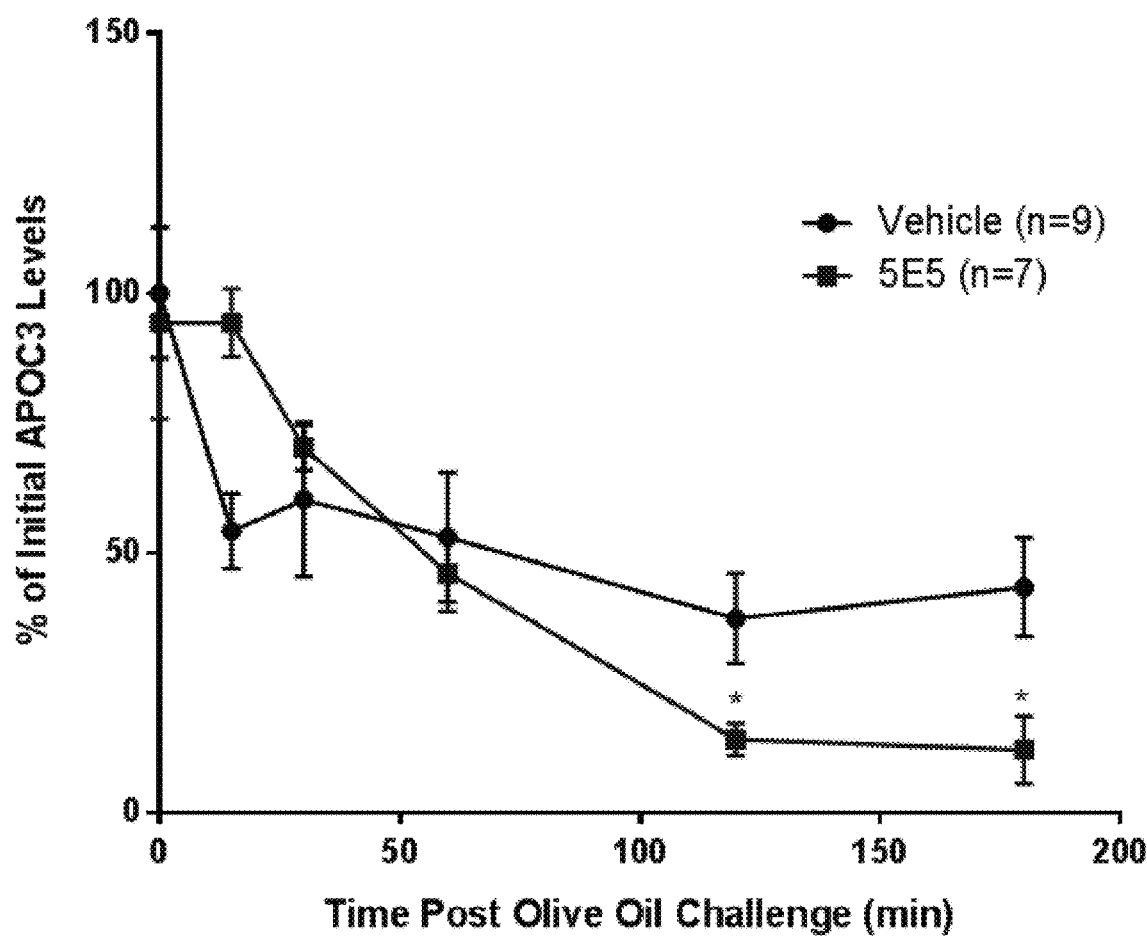

This example describes in vivo efficacy of mAb 5E5 in reducing post-prandial triglyceride in a mouse model. Mice receiving $3 \times 10^{11}$ AAV8-huApoC3 viral particles were used to characterize anti-ApoC3 antibody 5E5 in reducing postprandial triglyceride, which is absorbed from diet and packaged in chylomicrons. As shown in FIG. 9A administration of 5E5 antibody led to a significant reduction of postprandial surge of serum triglyceride. The increased level of post-prandial triglyceride was reduced to about zero, and the area under curve of triglyceride level over time was reduced by about 25% with a p value of 0.030 (FIG. 9B). The serum level of ApoC3 was significantly reduced in the presence of 5E5 2 hours and 3 hours after the olive oil challenge (FIG.

Figure 9D:
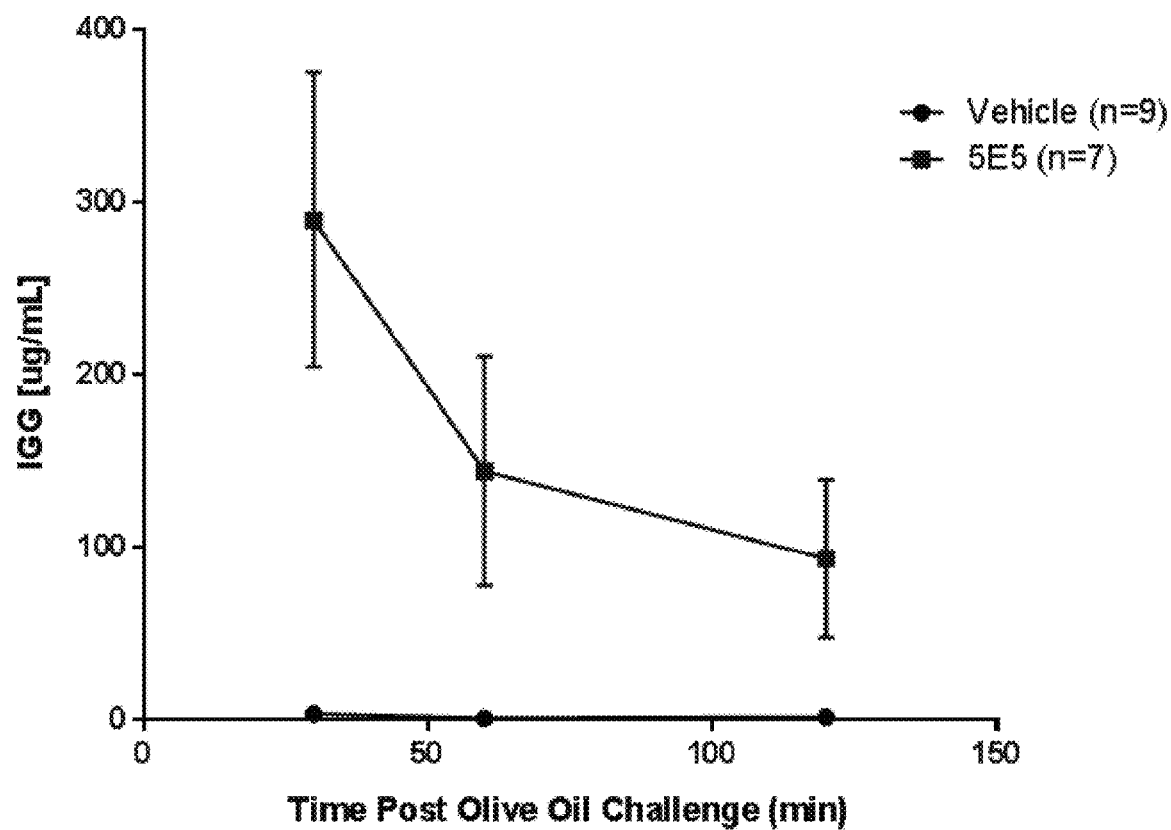
Figure 10A:
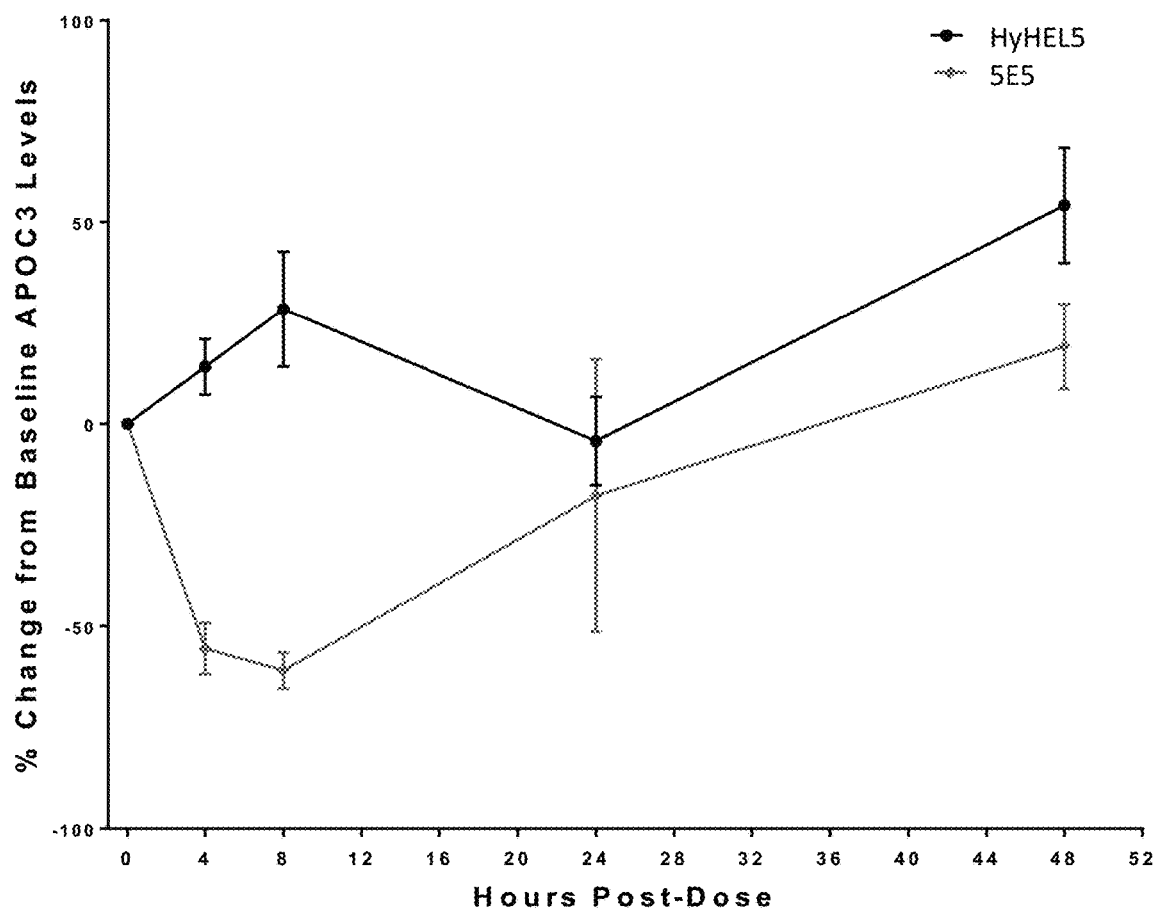
FIGS. 10A-10D are a series of graphs showing acceleration of ApoC3 and ApoB clearance from the blood after subcutaneous injection of the 5E5 and 6A6 antibody to mice expressing human ApoC3. An anti-hen egg lysosome human IgG1 antibody (HyHEL5) was used as an isotype control for 5E5 and PBS was used as vehicle control for 6A6.
Figure 10B:
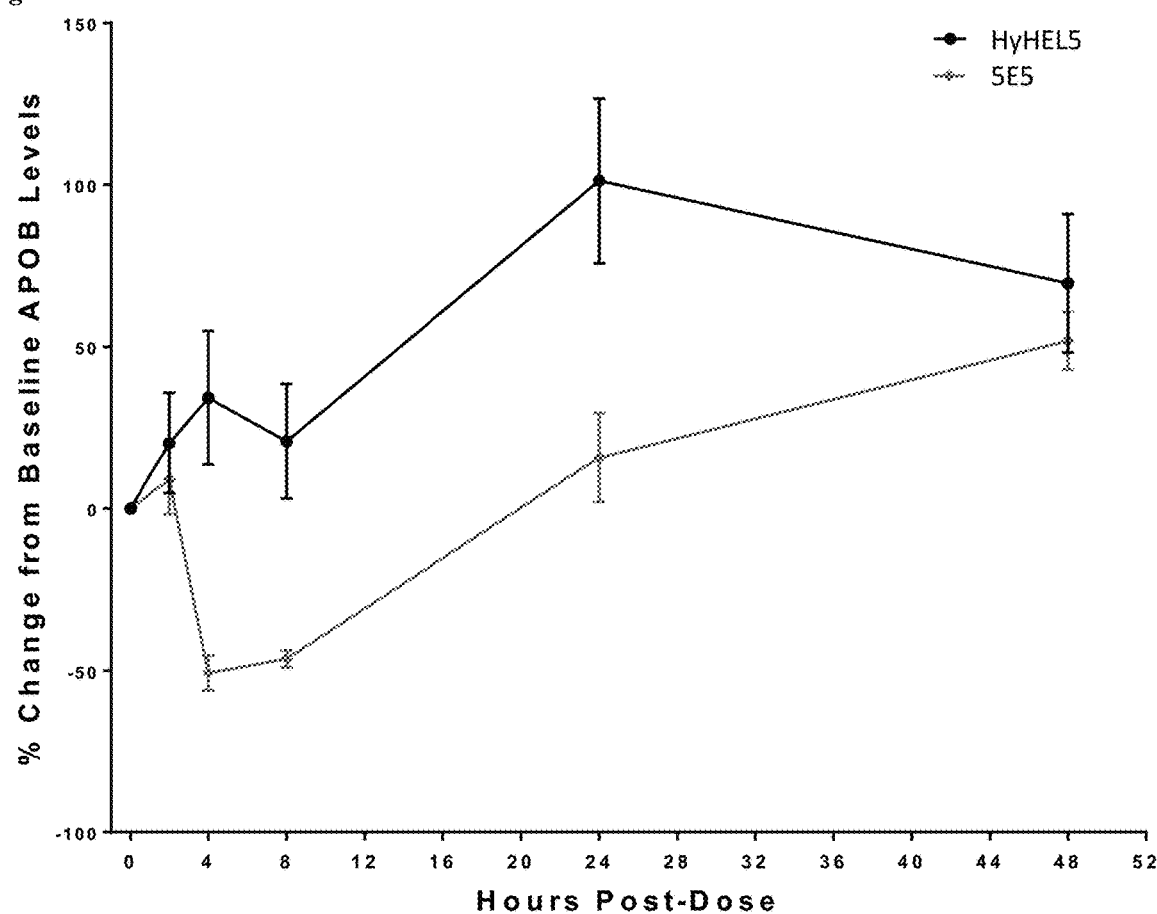
Figure 10C:
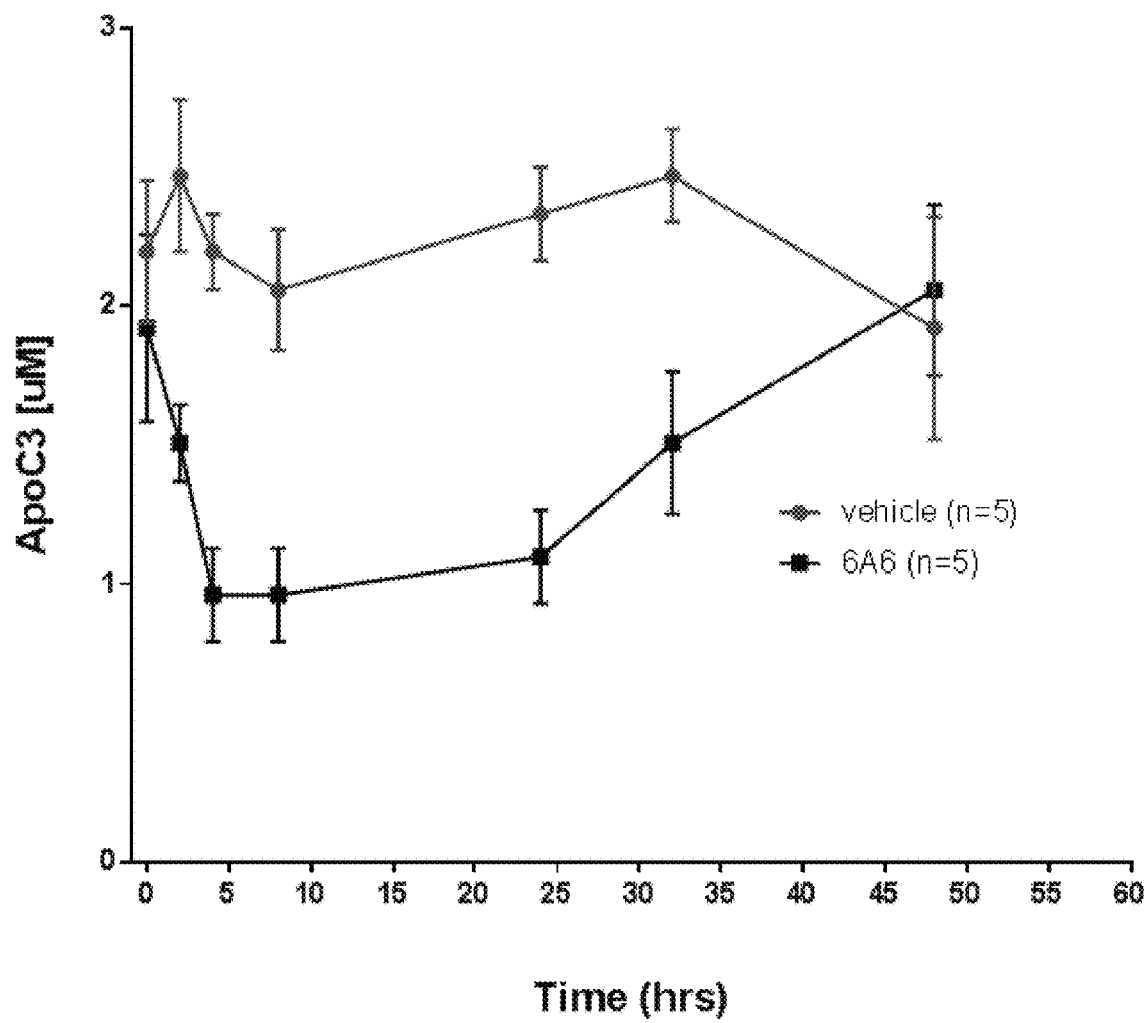
Figure 10D:
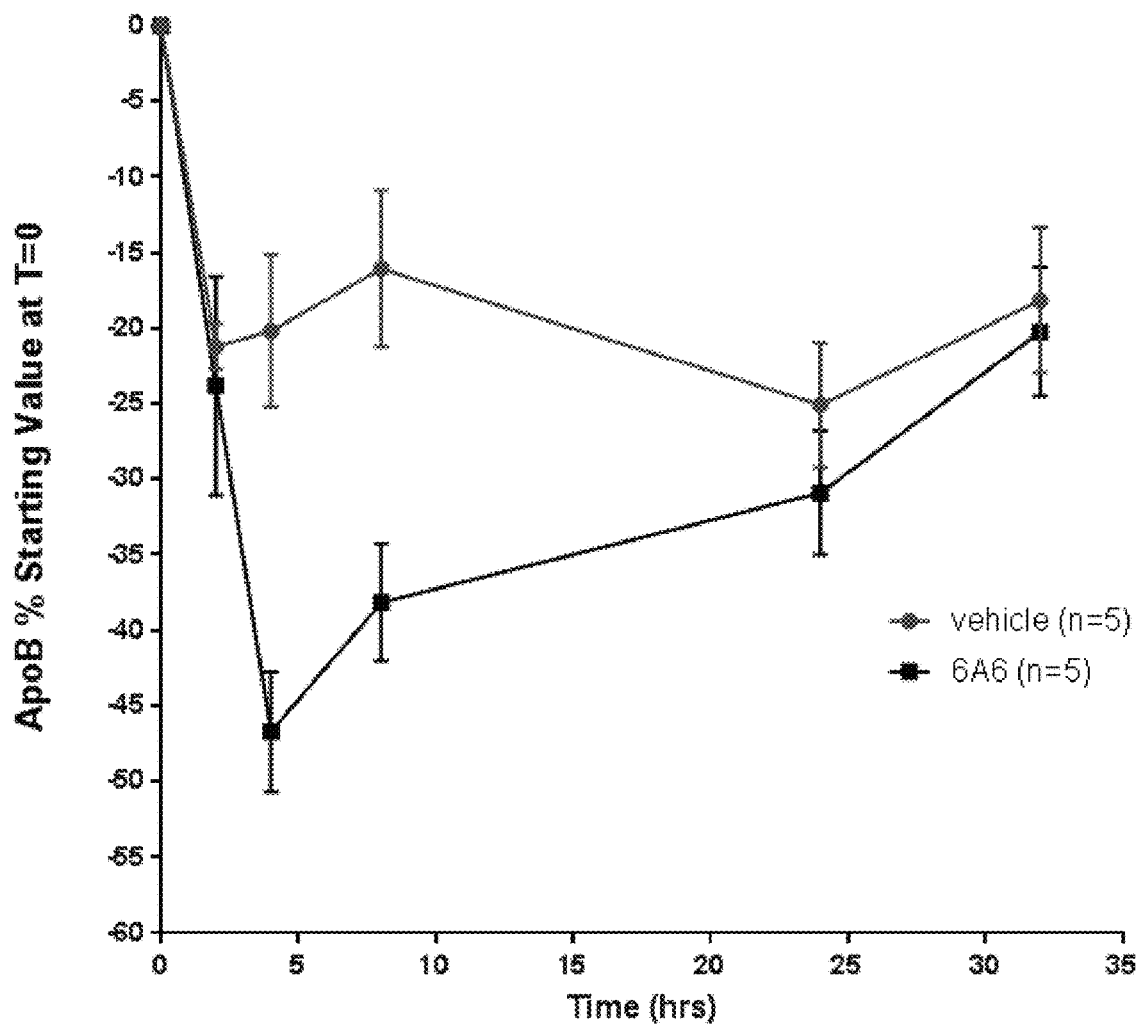

9C), whereas the serum level of 5E5 antibody itself declined slowly after the initial distribution phase (FIG. 9D).

8.3 Materials and Methods

The human AAV8-ApoC3 viral vector used in this example was obtained from RegenXbio (Rockville Md.). Twenty-four C57B16 male mice (Charles River) aged 60-63 days were maintained on a constant 12 hour light: 12-hour dark cycle with free access to water and ad libitum access to standard chow diet (Lab Diet; 5001). Twelve days following intraperitoneal administration of $3\times10^{11}$ viral particles per mouse, mice were retro-orbital sinus bled and placed into groups according to equivalent mean apoC3 levels. On day 14, mice were fasted for 6 hours and 25 µl of blood from retro-orbital sinus was collected to establish a triglycerides baseline. 25 mg/kg of 5E5 antibody in the IgG1 format was injected into the peritoneal cavity, followed immediately by a 250 µL oral bolus of olive oil (Sigma #01514). Mice were bled via retro-orbital sinus to determine levels of plasma triglycerides, ApoC3, and test antibody at 15, 30, 60, 120 and 240 minutes following olive oil challenge. Measured values were plotted as a function of time and area under the curve (AUC) for plasma triglyceride was calculated using GraphPad Prism. All animal studies were carried out in accordance with the recommendations in the Guide for the Care and Use of Laboratory Animals of the National Institutes of Health. All procedures were approved by the Institutional Animal Care and Use Committee of Vascumab. LLC.

Triglycerides were analyzed by incubating 5 µL of EDTA-plasma with 150 µL Thermo Scientific™ Triglycerides Reagent (TR22421) supplemented with 200 µM Amplex Red (AAT Bioquest) in a black 96-well plate (Costar #3915). After 10 minutes at 30° C., the plate was read (ex 560 nm; em 585 nm) and concentrations were calculated from a 4-parameter fit (Molecular Devices) of a glycerol standard curve.

ApoC3 levels were determined with a ELISA assay. A 96-well plate (Griener 655061) was coated overnight at 4° C. with 50 µL primary apoC3 antibody (Abcam rabbit polyclonal anti-human ApoC3 # ab21032) diluted in PBS. The plate was washed 4 times with 200 µL TBS-T, and blocked with 200 µL of blocking buffer (Pierce Clear Milk Blocker 37587 in PBS) for 90 minutes at 30° C. The blocking buffer was removed, and 50 µL of test sample diluted in blocking buffer was added and allowed to incubate for 2 hours at room temperature with rotation at 300 rpm. The plate was washed four times with 200 µL TBS-T, and 50 µL secondary antibody (Abeam goat polyclonal biotin-conjugate ApoC3 # ab21024) diluted in blocking buffer was added and allowed to incubate for 1 hour at room temperature with rotation at 300 rpm. The plate was washed once with TBS-T, and 50 µL SA-HRP (Abeam #34028) diluted 100-fold in PBS was added and allowed to incubate for 30 minutes at room temperature with rotation at 300 rpm. The plate was washed 4 times with 200 µL TBS-T, and developed with 80 µL TMB (Thermo Ultra-TMB ELISA #34028) followed by 50 µL 0.5 N HCL. Absorbance was read at 450 nm. The amount of ApoC3 in test wells was calculated from a 4-parameter fit of a standard curve (Molecular Devices) constructed using purified ApoC3 (Athens Research and Technology).

Levels of 5E5 antibody were determined with a ELISA assay. A 96-well plate (Griener #655061) was coated overnight at 4° C. with 50 µL primary IgG antibody (Fitzgerald 41-XG57 goat anti-human IgG Fc polyclonal) diluted in PBS. The plate was washed 4 times with 200 µL TBS-T, and blocked with 200 µL of blocking buffer consisting of 3% BSA (Roche BSA fraction V protease free #03 117 332 001) plus clear milk (Pierce Clear Milk Blocker #37587) in PBS for 90 minutes at 30° C. The blocking buffer was removed, and 50 µL of test sample diluted in blocking buffer was added and allowed to incubate for 2 hours at room temperature with rotation at 300 rpm. The plate was washed four times with 200 µL TBS-T, and 50 µL secondary antibody (Abeam goat anti-human IgG-Fc (biotin) polyclonal # ab97223) diluted in blocking buffer was added and allowed to incubate for 1 hour at room temperature with rotation at 300 rpm. The plate was washed once with TBS-T, and 50 µL SA-HRP (Abeam #34028) diluted 100-fold in PBS was added and allowed to incubate for 30 min at RT with rotation at 300 rpm. The plate was washed 4 times with 200 µL TBS-T, and developed with 80 µL TMB (Thermo Ultra-TMB ELISA #34028) followed by 50 µL 0.5 N HCL. Absorbance was read at 450 nm. The amount of IgG in test wells was calculated from a 4-parameter fit of a standard curve (Molecular Devices) constructed using the purified test antibody.

Example 9

Reduction of ApoC3 and ApoB by 5E5 and 646 Antibodies in a Mouse Model

Mice expressing human ApoC3 were generated and treated as described in Section 8.1. Twelve days after the AAV infection, blood samples were collected from retro-orbital sinus to establish baseline (T=0) human ApoC3 and mouse ApoB levels. The mice were then grouped such that all groups had similar mean ApoC3 levels at T0: A single dose of 25 mg/kg of the 5E5 antibody or a single dose of 20 mg/kg of the 6A6 antibody in the IgG1 format was administered to each mouse by injection into the dorsal subcutaneous space fourteen days after the initial AAV infection. Blood samples were collected from retro-orbital sinus 0, 2, 4, 8, and 24 hours after the administration of the test antibodies, and approximately every 2 days afterwards for 30 days. All animal studies were carried out in accordance with the recommendations in the Guide for the Care and Use of Laboratory Animals of the National Institutes of Health.

Plasma levels of human ApoC3 and mouse ApoB were determined with an ELISA assay. Specifically, a 96-well plate (Griener #655061) was coated overnight at 4° C. with 50 µL primary ApoC3 antibody (Abeam rabbit polyclonal anti-human ApoC3 # ab21032) or 50 µL primary ApoB antibody (Meridian Life Sciences goat polyclonal anti-human ApoB # K45253G) diluted in PBS. The plate was washed 4 times with 200 µL TBS-T, and blocked with 200 µL of blocking buffer (Pierce Clear Milk Blocker #37587 in PBS) for 90 minutes at 30° C. The blocking buffer was removed, and 50 µL of test sample diluted in blocking buffer was added and allowed to incubate for 2 hours at room temperature with rotation at 300 rpm. The plate was washed four times with 200 µL TBS-T, and 50 µL secondary ApoC3 antibody (Abeam goat polyclonal biotin-conjugate ApoC3 # ab21024) or secondary ApoB antibody (Meridian Life Sciences goat polyclonal biotin-conjugate ApoB48/100 # 34003G) diluted in blocking buffer was added and allowed to incubate for 1 hour at room temperature with rotation at 300 rpm. The plate was washed once with TBS-T, and 50 µL SA-HRP (Abeam # 64269) diluted 100-fold in PBS was added and allowed to incubate for 30 minutes at room temperature with rotation at 300 rpm. The plate was then washed 4 times with 200 µL TBS-T, and developed with 80 µL TMB (Thermo Ultra-TMB ELISA #34028) followed by 50 µL 0.5 N HCL. Absorbance was read at 450 nm. The amount of ApoC3 in test wells was calculated from a 4-parameter fit of a standard curve (Molecular Devices) constructed using purified ApoC3 (Athens Research and Technology). The amount of ApoB in test wells was calculated from a 4-parameter fit of a standard curve (Molecular Devices) constructed using mouse VLDL isolated by centrifugation (ApoB content is assumed to be 20% of total protein content).

As shown in FIG. 10 the 5E5 antibody (parts A and B) and the 6A6 antibody (parts C and D) similarly reduced the plasma levels of human ApoC3 and mouse ApoB for 1-2 days relative to the corresponding levels in the negative control groups. The plasma levels of ApoC3 were reduced by more than 50% 4-8 hours after the administration of the 5E5 and 6A6 antibodies (parts A and C). The plasma levels of ApoB were reduced by about 40-50% 4-8 hours after the administration of the 5E5 and 6A6 antibodies (parts B and D).

The invention is not to be limited in scope by the specific embodiments described herein. Indeed, various modifications of the invention in addition to those described will become apparent to those skilled in the art from the foregoing description and accompanying figures. Such modifications are intended to fall within the scope of the appended claims.

All references (e.g., publications or patents or patent applications) cited herein are incorporated herein by reference in their entirety and for all purposes to the same extent as if each individual reference (e.g., publication or patent or patent application) was specifically and individually indicated to be incorporated by reference in its entirety for all purposes.

Other embodiments are within the following claims.

What is claimed:

1. An isolated antibody that specifically binds to ApoC3, comprising a heavy chain variable region having complementarity determining regions CDRH1, CDRH2 and CDRH3, and a light chain variable region having complementarity determining regions CDRL1, CDRL2 and CDRL3, wherein CDRH1, CDRH2, CDRH3, CDRL1, CDRL2, and CDRL3 comprise the amino acid sequences set forth in SEQ ID NOs: 4, 5, 6, 73, 74, and 75; 7, 8, 9, 76, 77, and 78; 10, 11, 12, 79, 80, and 81; 13, 14, 15, 82, 83, and 84; 16, 17, 18, 85, 86, and 87; 19, 20, 21, 88, 83, and 89; 22, 23, 24, 90, 91, and 92; 25, 26, 27, 82, 93, and 94; 28, 29, 30, 95, 96, and 97; 16, 31, 32, 98, 99, and 100; 33, 34, 35, 101, 99, and 102; 25, 36, 37, 103, 104, and 105; 38, 39, 40, 82, 106, and 107; 41, 42, 43, 108, 109, and 110; 7, 8, 9, 111, 83, and 113; 47, 48, 49, 82, 114, and 115; 50, 51, 52, 116, 117, and 118; 53, 54, 55, 119, 120, and 121; 56, 57, 58, 122, 123, and 124; 59, 60, 61, 125, 83, and 126; 62, 63, 64, 127, 128, and 129; 65, 66, 67, 82, 114, and 130; 68, 69, 70, 131, 132, and 133; or 68, 71, 72, 124, 135, and 136, respectively.

2. An isolated antibody that specifically binds to ApoC3, the antibody comprising a heavy chain variable region and a light chain variable region, wherein the heavy chain variable region and the light chain variable region, respectively, comprise the amino acid sequences set forth in SEQ ID NOs: 137 and 161, 138 and 162, 139 and 163, 140 and 164, 141 and 165, 142 and 166, 143 and 167, 144 and 168, 145 and 169, 146 and 170, 147 and 171, 148 and 172, 149 and 173, 150 and 174, 138 and 175, 152 and 176, 153 and 177, 154 and 178, 155 and 179, 156 and 180, 157 and 181, 158 and 182, 159 and 183, or 160 and 151.

3. A pharmaceutical composition comprising the antibody of claim 1 and a pharmaceutically acceptable carrier.

4. A pharmaceutical composition comprising the antibody of claim 2 and a pharmaceutically acceptable carrier.

* * * * *